(12) United States Patent
Sun et al.

(10) Patent No.: US 8,874,273 B2
(45) Date of Patent: Oct. 28, 2014

(54) ANALYSIS ENGINE AND DATABASE FOR MANIPULATING PARAMETERS FOR FLUIDIC SYSTEMS ON A CHIP

(75) Inventors: Gang Sun, Cupertino, CA (US); Greg Harris, Longmont, CO (US); Andy May, San Francisco, CA (US); Kyle Self, San Jose, CA (US); Kevin Farrell, San Francisco, CA (US); Paul Wyatt, County Tipperary (IE)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 13/022,856

(22) Filed: Feb. 8, 2011

(65) Prior Publication Data

US 2012/0045087 A1 Feb. 23, 2012

Related U.S. Application Data

(62) Division of application No. 11/408,612, filed on Apr. 20, 2006, now Pat. No. 7,883,669.

(60) Provisional application No. 60/673,628, filed on Apr. 20, 2005.

(51) Int. Cl.
*G05B 21/00* (2006.01)
*G01N 35/00* (2006.01)
*G01N 15/14* (2006.01)
*B01L 3/00* (2006.01)

(52) U.S. Cl.
CPC ........ *G01N 35/0092* (2013.01); *G01N 15/1475* (2013.01); *B01L 3/5027* (2013.01)
USPC .......................................... 700/266; 422/502

(58) Field of Classification Search
USPC .......................................... 700/266; 422/502
See application file for complete search history.

(56) References Cited

U.S. PATENT DOCUMENTS

| | | | |
|---|---|---|---|
| 6,395,232 B1 | 5/2002 | McBride |
| 6,448,090 B1 | 9/2002 | McBride |
| 6,540,895 B1 | 4/2003 | Spence et al. |
| 6,885,982 B2 | 4/2005 | Harris et al. |
| 6,939,452 B2 | 9/2005 | Foret et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2003/0089605 A1* | 5/2003 | Timperman .................. 204/450 |
| 2004/0180377 A1 | 9/2004 | Manger et al. |
| 2004/0203055 A1 | 10/2004 | Kennedy et al. |
| 2004/0241748 A1 | 12/2004 | Ault-Riche et al. |
| 2005/0053952 A1 | 3/2005 | Hong et al. |
| 2005/0205005 A1 | 9/2005 | Hansen et al. |
| 2006/0163070 A1 | 7/2006 | Boronkay et al. |
| 2006/0172408 A1 | 8/2006 | Quake et al. |
| 2006/0211134 A1 | 9/2006 | Kennedy et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |

(Continued)

FOREIGN PATENT DOCUMENTS

| WO | WO 01/67369 A2 | 9/2001 |
|---|---|---|
| WO | WO 02/082047 | 10/2002 |
| WO | WO 03/085379 | 10/2003 |
| WO | WO 2004/089810 A2 | 10/2004 |
| WO | WO 2005/056813 | 6/2005 |
| WO | WO 2007/033385 A2 | 3/2007 |
| WO | WO 2007/044091 A2 | 4/2007 |
| WO | WO 2008/043046 A2 | 4/2008 |
| WO | WO 2009/100449 A1 | 8/2009 |
| WO | WO 2010/011852 A1 | 1/2010 |
| WO | WO 2010/017210 A1 | 2/2010 |
| WO | WO 2010/077618 A1 | 7/2010 |

*Primary Examiner* — Natalia Levkovich

(74) *Attorney, Agent, or Firm* — Kilpatrick Townsend & Stockton LLP

(57) ABSTRACT

Systems for managing workflows to perform chemical or biological reactions using microfluidic devices.

10 Claims, 66 Drawing Sheets

(56) References Cited

U.S. PATENT DOCUMENTS

| | | |
|---|---|---|
| 2008/0292504 A1 | 11/2008 | Goodsaid et al. |
| 2009/0018195 A1 | 1/2009 | Balagadde |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

\* cited by examiner

FIG. 3

Screen Plate Creation – Step 3

Review the Stock Solutions selected to create this Screen Pate. You may also add or remove Stock Solutions.

Selected Template
Template: SxPxB

Screen Creation Varibles

| Variable | Start |
|---|---|
| Salt | sodium acetate |
| Precipitant | 1,4-butanediol |
| Buffer | Various |

View/Modify Region
Region 1

| Variable | % Change | | Variation Method | Variation | | Units |
|---|---|---|---|---|---|---|
| | Start | End | | Start | End | |
| Salt – sodium acetate | 40 | 100 | Row Increment | 0.16 | 0.4 | M |
| Precipitant – 1,4-butanediol | 40 | 100 | Column Increment | 6 | 14 | %v/v |
| Buffer - Various | | | Constant | 8.6 | | pH |

[ < Back ] [ Next > ] [ Cancel ] [ Finish ]

FIG. 5

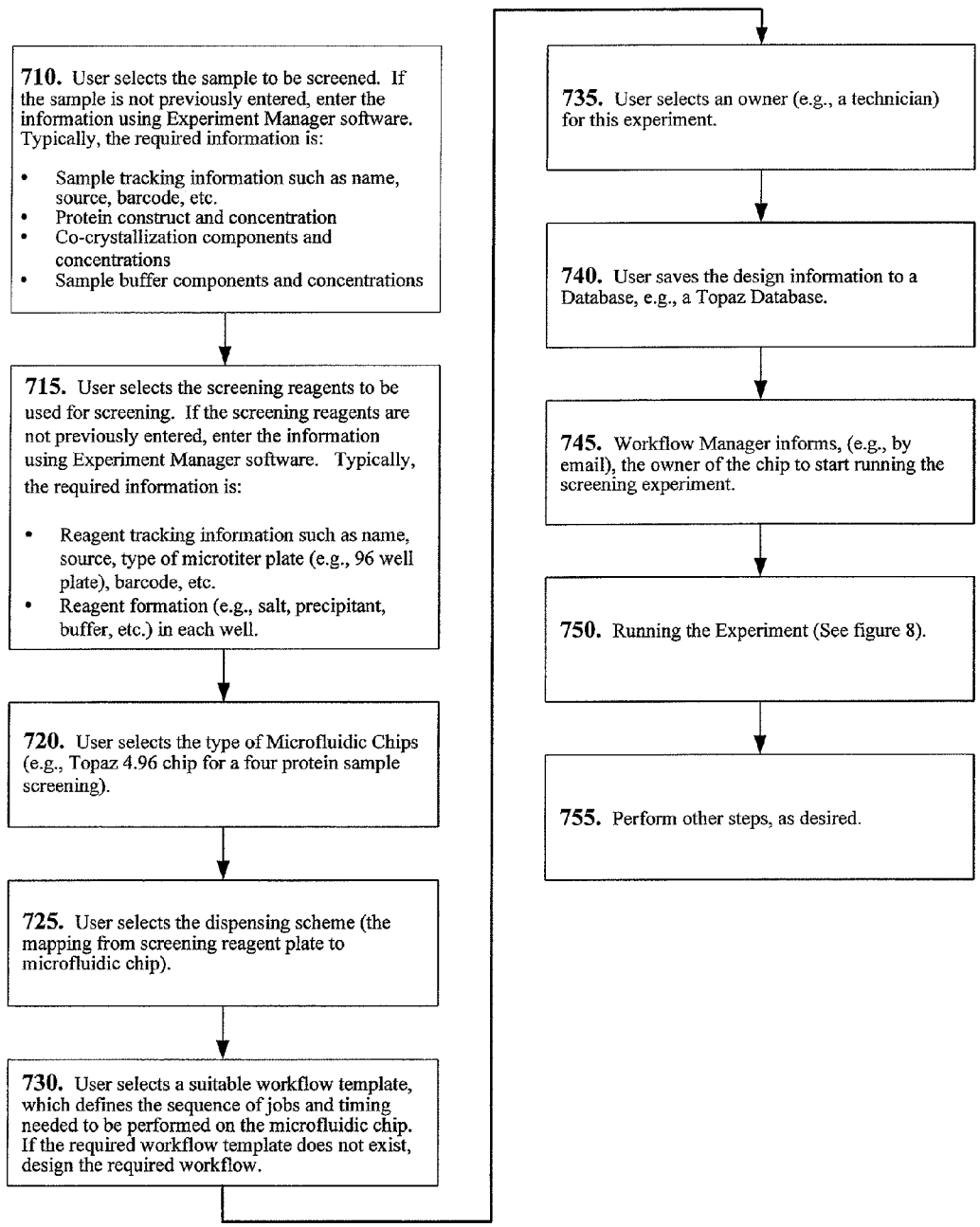
FIG. 7 - Experiment Design (Screening)

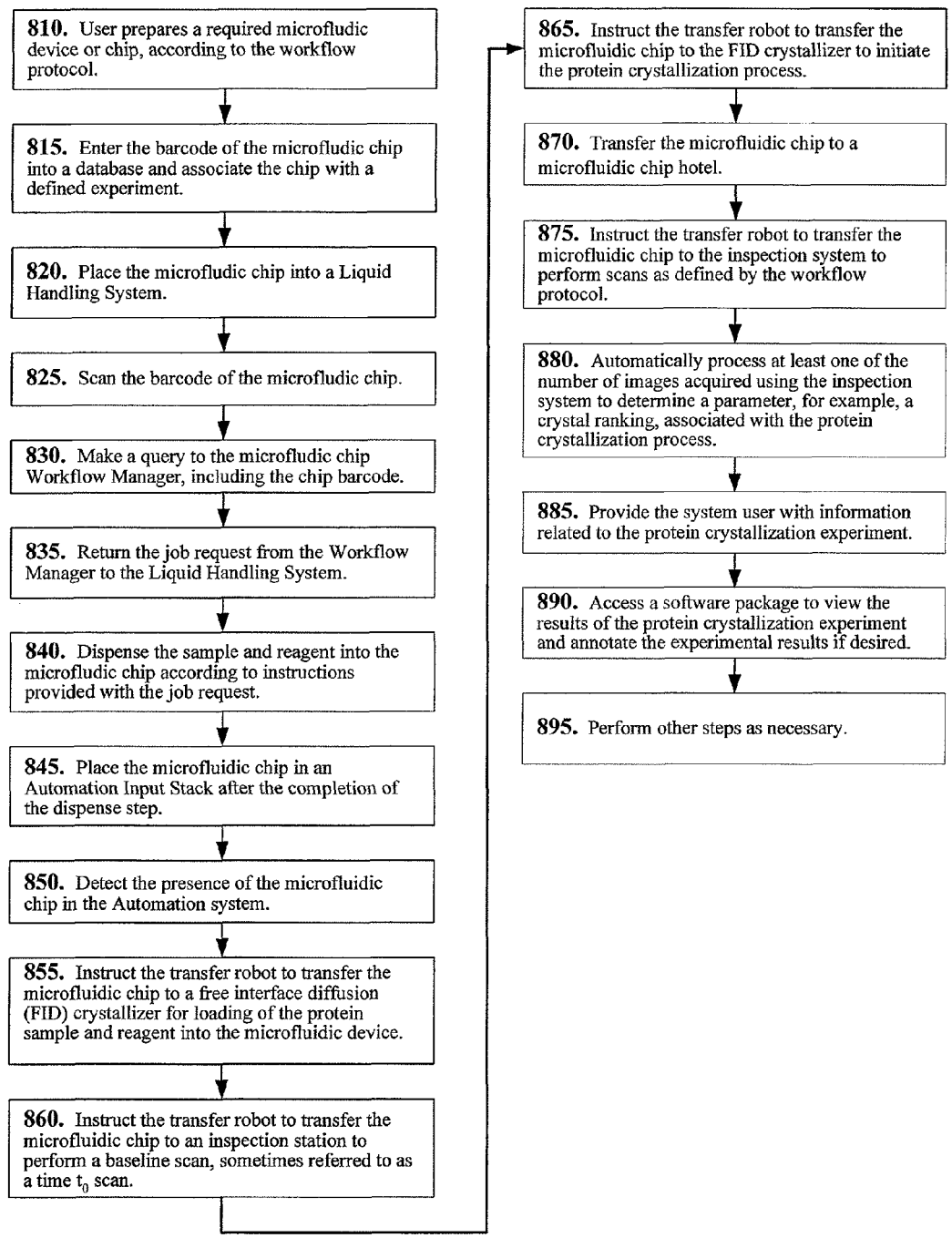
FIG. 8 - Running an Experiment

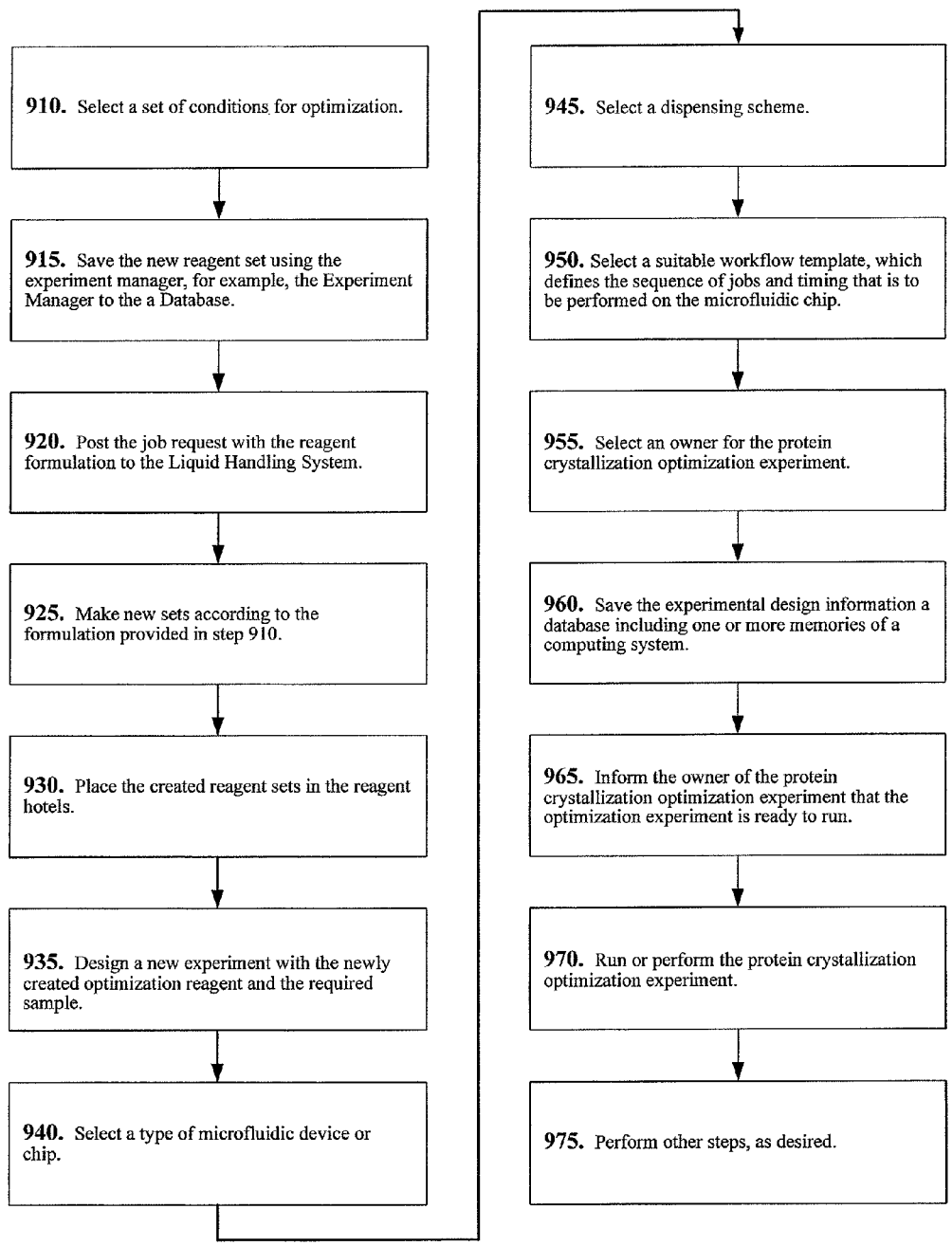
FIG. 9 - Experiment Design (Optimization)

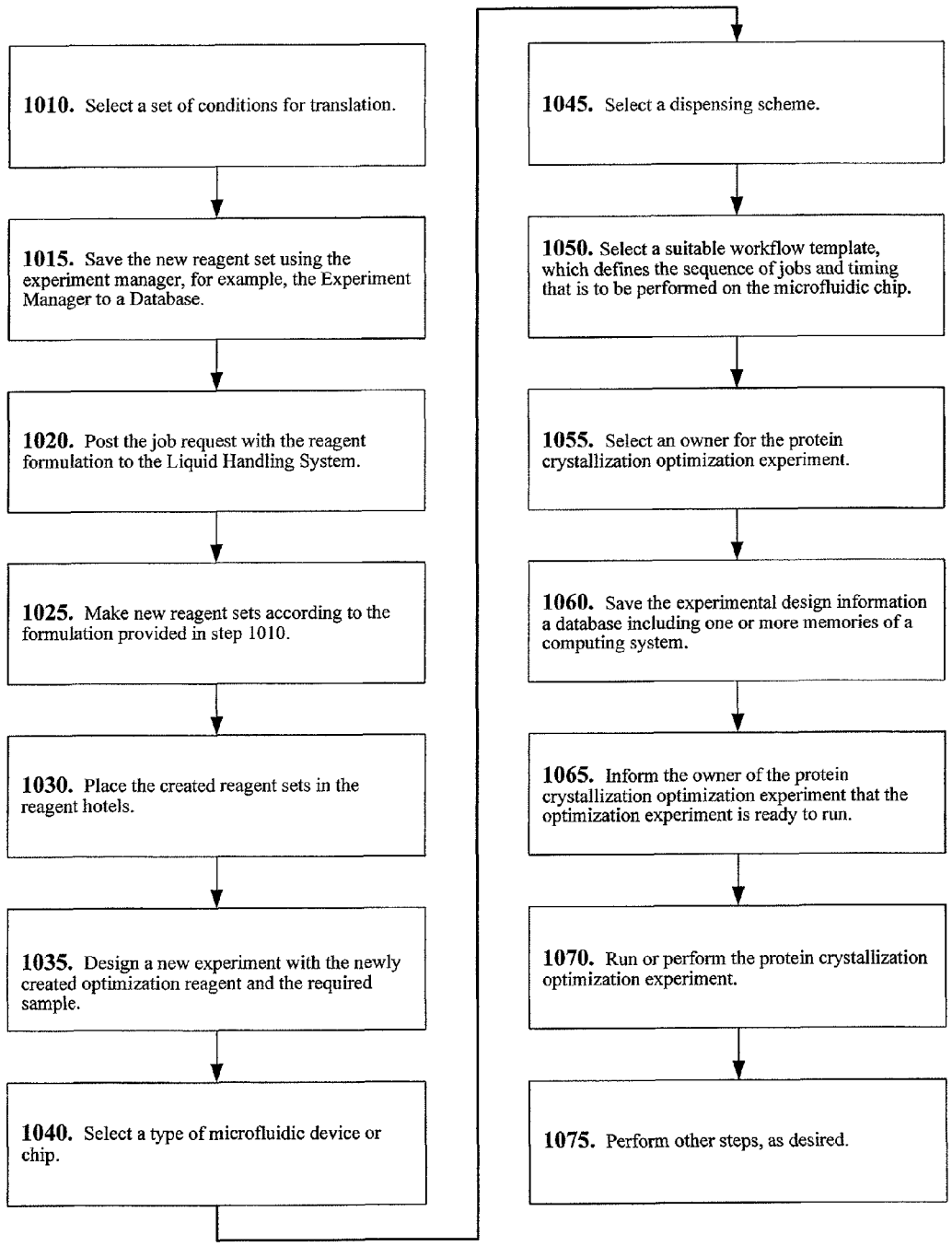
FIG. 10 - Experiment Design (Translation)

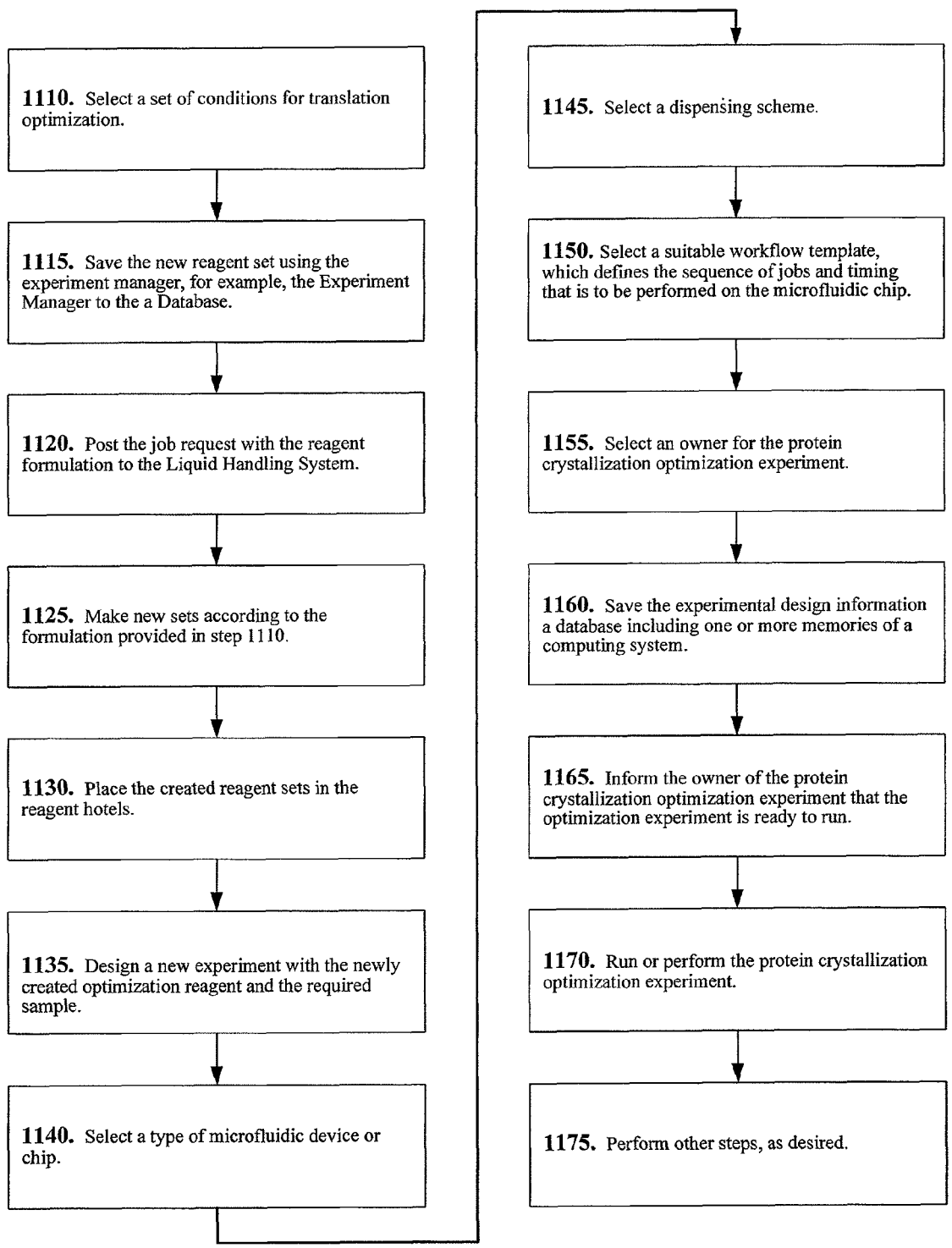
FIG. 11 - Experiment Design
(Translation Optimization)

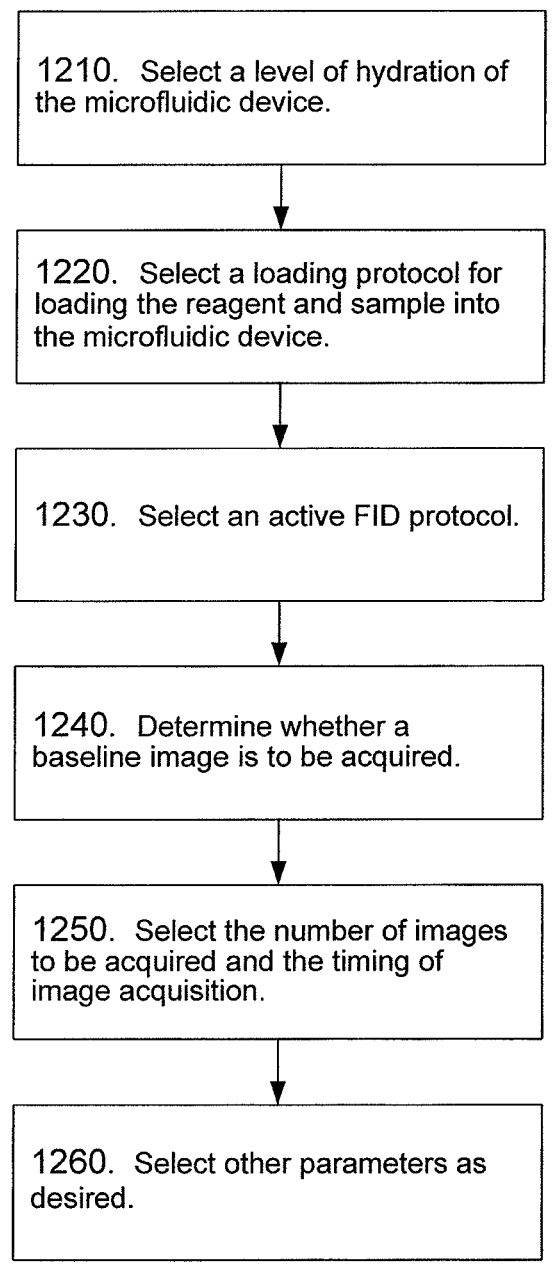
FIG. 12 - Workflow Template

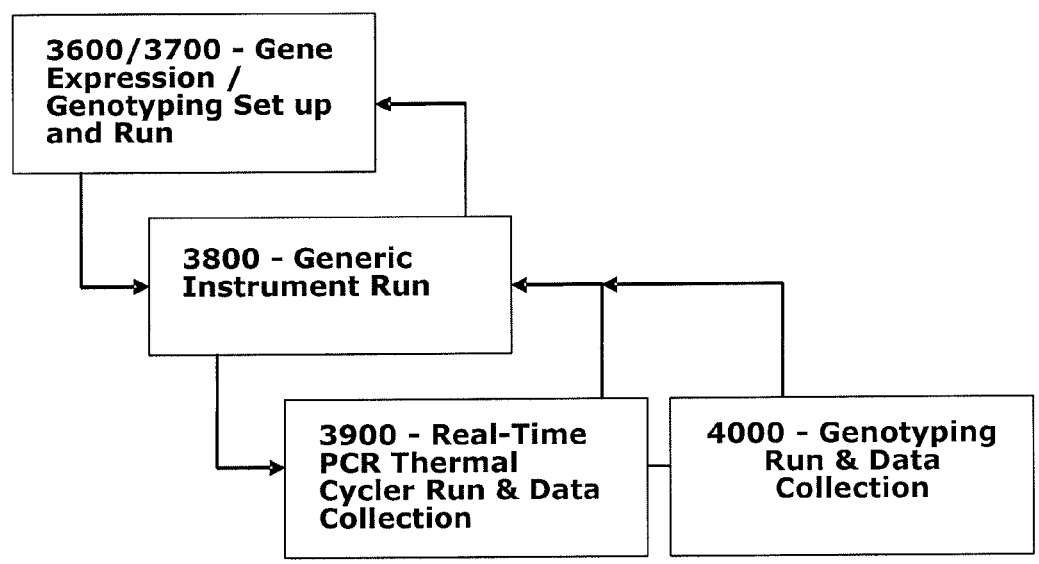
FIG. 35 - Gene Expression and Genotyping Experiments

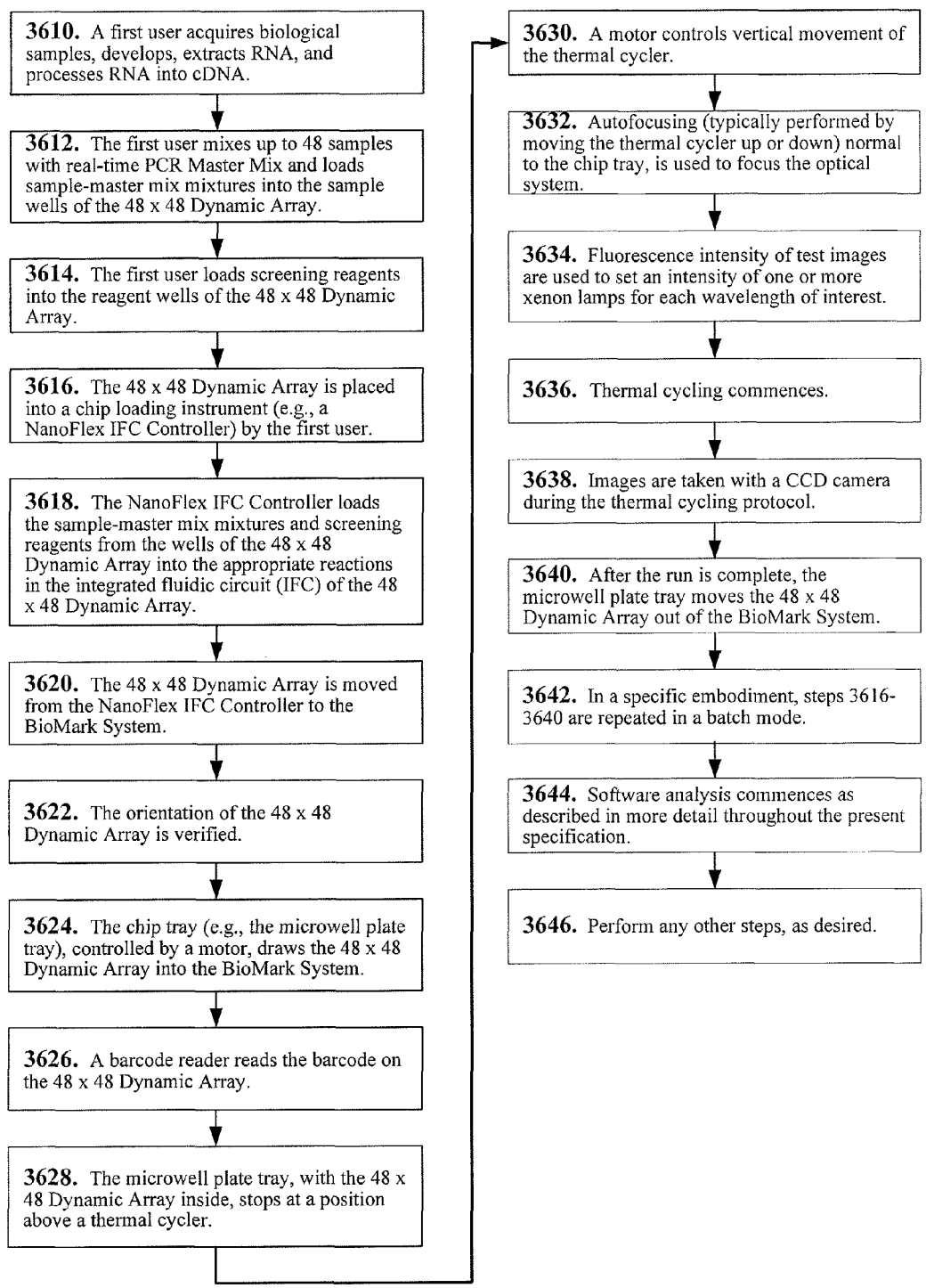
FIG. 36 - Gene Expression

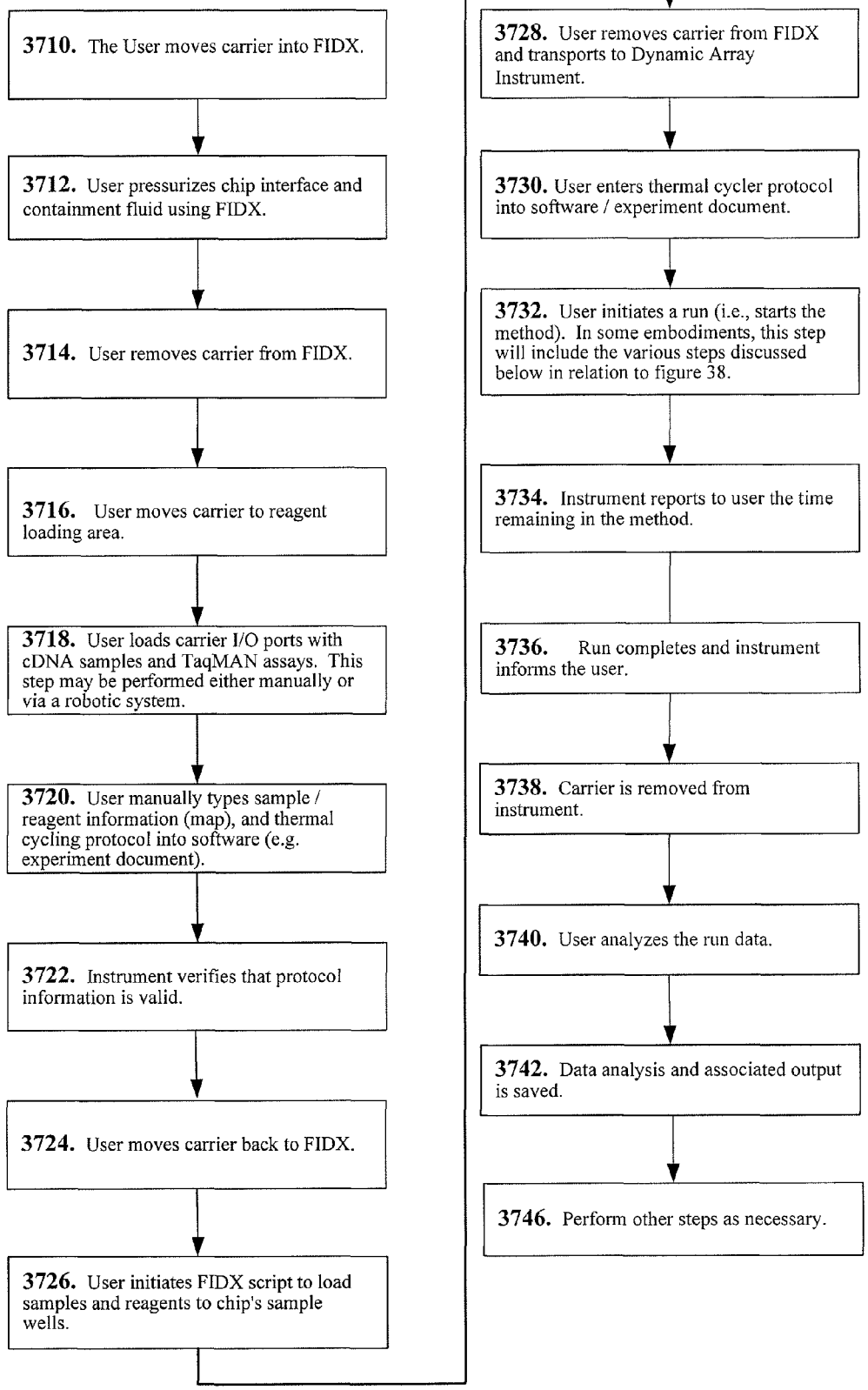
FIG. 37 - Gene Expression

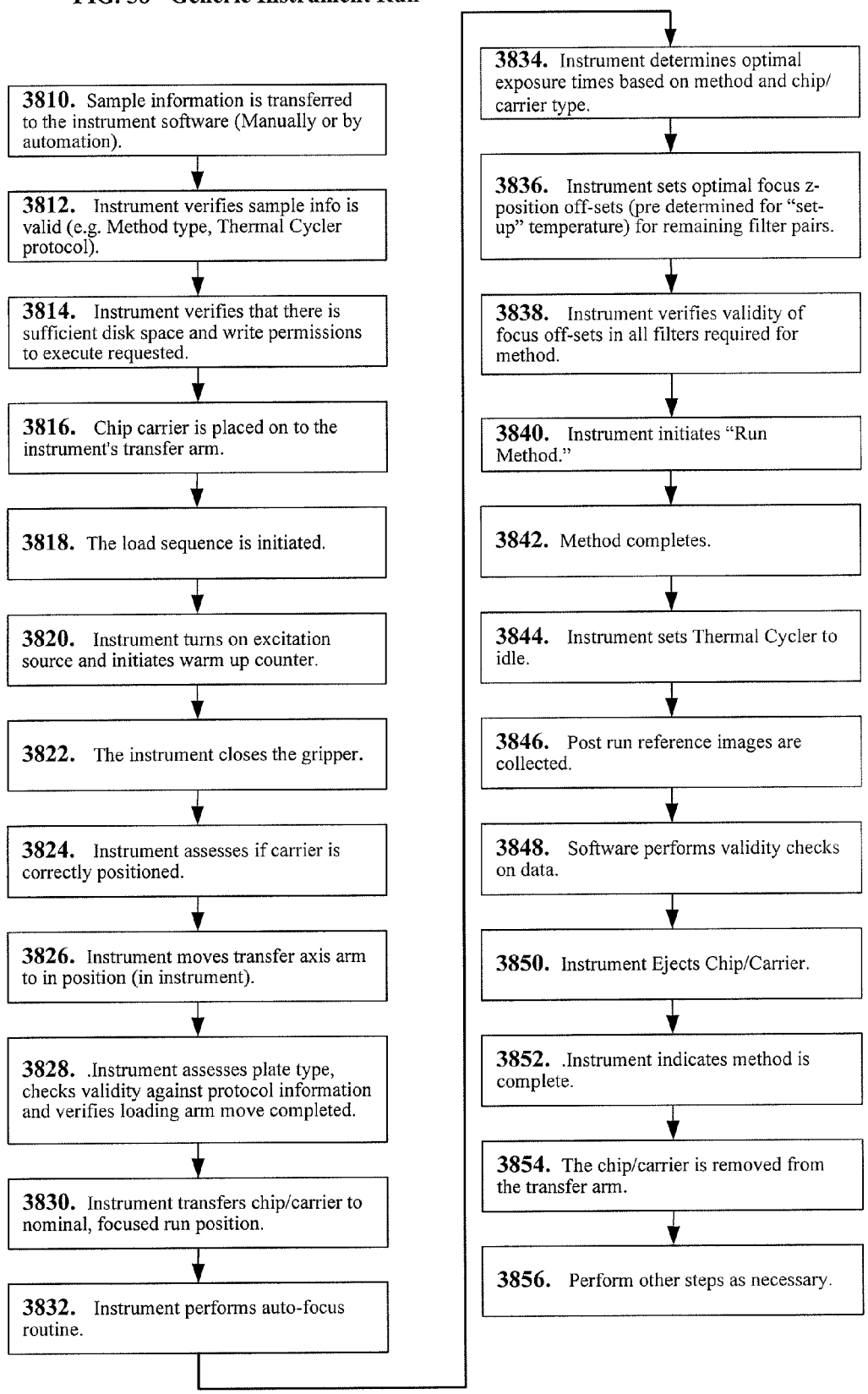
FIG. 38 - Generic Instrument Run

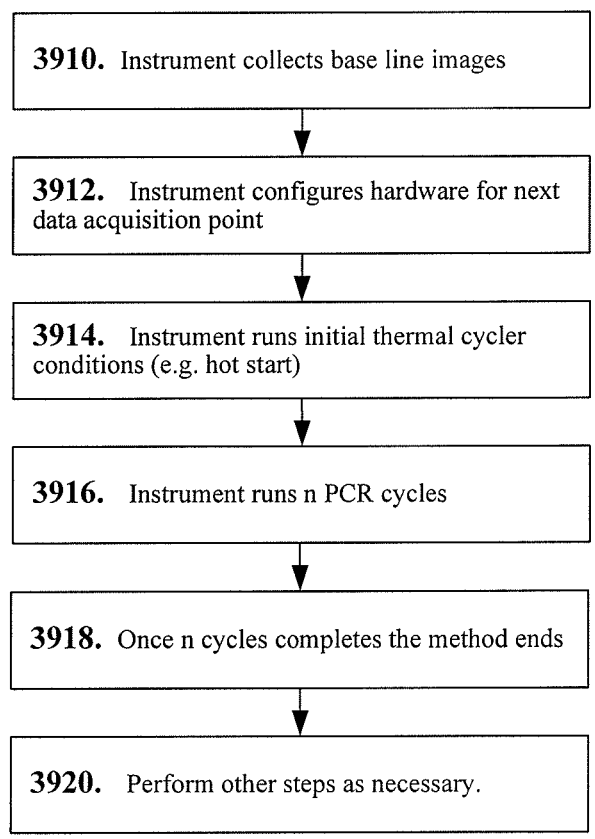
FIG. 39 - Real-Time PCR Thermal Cycling Run & Data Collection

FIG. 40 - Genotyping Run & Data Collection

4010. Instrument runs pre / post read thermal cycler condition

4012. Instrument configures hardware for next n data acquisition point

4014. Instrument initiates data collection sequence

4016. Instrument goes to step 4012 for next filter position / data point

4018. Instrument runs initial thermal cycler conditions (e.g. hot start)

4020. Instrument runs n PCR cycles

4022. Once n cycles completes the instrument collects the post PCR data

4024. Once the post run data is collected the method ends

4026. Perform other steps as necessary.

ANALYSIS ENGINE AND DATABASE FOR MANIPULATING PARAMETERS FOR FLUIDIC SYSTEMS ON A CHIP

CROSS-REFERENCES TO RELATED APPLICATIONS

This application is a division of Ser. No. 11/408,612, filed Apr. 20, 2006; which claims priority to U.S. Provisional Application No. 60/673,628, filed Apr. 20, 2005. The disclosures of Ser. Nos. 11/408,612 and 60/673,628 are hereby incorporated by reference herein for all purposes.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

Over the years, various fluid based processing techniques have been performed. Such processing techniques occur in both chemical and biological arts. Merely as an example, crystallization has been an important technique to the biological and chemical arts. Specifically, a high-quality crystal of a target can be analyzed by x-ray diffraction techniques to produce an accurate three-dimensional structure of the target. This three-dimensional structure information can then be utilized to predict functionality and behavior of the target.

In theory, the crystallization process is often simple to describe. For example, a target compound in pure form is dissolved in solvent. The chemical environment of the dissolved target material is then altered such that the target is less soluble and reverts to the solid phase in crystalline form. Such change in the chemical environment is typically accomplished by introducing a crystallizing agent that makes the target material less soluble, although changes in temperature and pressure can also influence solubility of the target material.

In practice however, forming a high quality crystal using conventional techniques is generally difficult, or sometimes impossible, requiring much trial and error and patience on the part of the researcher. A highly complex structure of even simple biological compounds often means that they are not amenable to forming a highly ordered crystalline structure. Therefore, a researcher must often be patient and methodical. The researcher also often experiments with a large number of conditions for crystallization, altering parameters such as reagents (e.g., type and concentration), sample concentration, solvent type, counter solvent type, temperature, and duration in order to grow a high quality crystal, if in fact a crystal can be grown at all. Additionally, conventional techniques are often difficult to use and monitor due to long processing times often associated with forming detecting, analyzing, crystal structures.

To overcome certain shortcomings with the conventional techniques, Hansen, et al., describe in PCT publication WO 02/082047, published Oct. 17, 2002 and herein incorporated by reference in its entirety for all purposes and the specific purposes disclosed therein and herein, a high-throughput system for screening conditions for crystallization of target materials, for example, proteins. The system is provided in a microfluidic device wherein an array of metering cells is formed by a multilayer elastomeric manufacturing process. Each metering cell comprises one or more of pairs of opposing chambers, each pair being in fluid communication with the other through an interconnecting microfluidic channel, one chamber containing a protein solution, and the other, opposing chamber, containing a crystallization reagent. Along the channel, a valve is situated to keep the contents of opposing chambers from each other until the valve is opened, thus allowing free interface diffusion to occur between the opposing chambers through the interconnecting microfluidic channel. As the opposing chambers approach equilibrium with respect to crystallization and protein concentrations as free interface diffusion progresses, it is hoped that the protein will, at some point, form a crystal. The microfluidic devices taught by Hansen et al. are have arrays of metering cells containing chambers for conducting protein crystallization experiments therein. Use of such arrays in turn provides for high-throughput testing of numerous conditions for protein crystallization which require analysis.

From the above, it is seen that improved techniques for processing and operating microfluidic chips are highly desired.

SUMMARY OF THE INVENTION

The present invention relates generally to systems and methods for managing workflow related to processing of one or more microfluidic devices. Microfluidic devices include a microfluidic chip or device. More particularly, the invention provides a system for automated preparation, processing, imaging, analysis, and control of microfluidic devices used to perform biological and chemical reactions including, for example, protein crystallization, polynucleotide amplification reactions, immunological reactions, chemical synthesis, genotyping, and the like. Merely by way of example, the techniques for microfluidic systems are applied to protein crystallization experiments using the TOPAZ™ BIOMARK™ and MATRIX™ systems of Fluidigm Corporation of South San Francisco, Calif., but it would be recognized that the invention has a much broader range of applicability. Examples of certain microfluidic devices and related systems and methods can be found in International Publication Numbers WO 03/085379 A3, WO 2004/089810 A2, PCT/US04/40864, and U.S. patent application Ser. No. 11/006,522, commonly assigned, and hereby incorporated by reference for all purposes.

In a specific embodiment of the present invention, a system for managing workflow related to processing of one or more microfluidic devices is provided. The system includes a processor device, a first database coupled to the processor device, and one or more process designs provided within a portion of the first database. The one or more process designs are associated with a respective process. The system also includes a microfluidic device comprising one or more well regions. Each of the well regions is capable of processing one or more of the process designs associated with the one or more respective processes. The system further includes an image acquisition device coupled to the processor device. The image acquisition device is spatially disposed to capture at least one image of a portion of at least one of the well regions of the microfluidic device. The image from the image acquisition device is in a first format and the at least one image of the portion of the at least one of the well regions may include a portion of an entity. Moreover, the system includes an image processing system coupled to the image acquisition device for processing the at least one image of the portion of the at least one of the well regions of the microfluidic device in the first format to a second format and a database management process coupled to the image processing system.

According to a specific embodiment, the client device is one of a plurality of client devices. In another specific embodiment, the client device is maintained in a private network. Moreover, in an embodiment, the first database and the second database are provided on a single database platform or are provided on multiple database platforms. In another embodiment, the well region is coupled to a movable valve member and the movable valve member is in communication with a driving fluid. In an alternative embodiment, the client device is selected from a personal computer, a paging device, a cellular phone, a laptop computer, a work station, or other remote computing entity. The system may also include an experimental manager process coupled to the one or more process designs. In a particular embodiment, the client device includes a user interface device. In another particular embodiment, the one or more process designs are experimental designs, for example, protein crystallization experimental designs.

The system also has an image acquisition device (e.g., CCD camera, CID camera, CMOS arrays, photographic devices) coupled to the processor device. The image acquisition device is spatially disposed to capture at least one image of a portion of at least one of the well regions of the microfluidic device. The image from the image acquisition device is in a first format, e.g., pixel domain. The image of the portion of the at least one of the well regions may include a portion of an entity, e.g., protein, polynucleotide (e.g., DNA or RNA), cell, chemical, living tissue. The system has an image processing system coupled to the image acquisition device for processing the at least one image of the portion of the at least one of the well regions of the microfluidic device in the first format to a second format, e.g., transform domain. The system also includes a database management process coupled to the image processing system and a second database coupled to the database management system. In a preferred embodiment, the second database is adapted to store an electronic representation of at least the one image in the second format. A publisher process is coupled to the second database. The publisher process is adapted to format information associated with the electronic representation of the one image in the second format. The publisher process is coupled to a world wide area network of computers, e.g., Internet. The system also has a client device (e.g., computer, work station, cell phone, laptop computer, PDA, pager) coupled to the publisher process through at least the world wide network of computers. The client device is adapted to allow the user of the one or more process designs to provide feedback to at least the decision making process of the one or more process designs.

In another specific embodiment, a database system for processing images provided in one or more well regions of a microfluidic device is provided. Each of the one or more well regions are arranged in a spatial orientation. The database system also includes an image capturing device coupled to the microfluidic device. The image capturing device is adapted to capture a plurality of images from at least one of the one or more well regions. Each of the plurality of images is captured in a first format. The database system additionally includes an image processing device operably coupled to the image capturing device to provide the plurality of images to the image processing device. The image processing device is adapted to process at least a first image and a second image derived from the plurality of images, the first image and the second image being in a second format, to determine at least a first feature information and a second feature information from the respective first image and the second image. The database system further includes a database storage device comprising a database management element. The database storage device is coupled to the image processing device and the database storage device is adapted to store at least the first feature information and the second feature information.

According to a particular embodiment, each of the one or more well regions are capable of holding a plurality of protein crystals to be imaged. In another embodiment, the first feature information includes a first fluorescent or chemiluminescent signal and the second feature information includes a second fluorescent or chemiluminescent signal. Moreover, in yet another embodiment, the first format and the second format are the same format. In a specific embodiment, the first format and the second format are a pixel format. In another specific embodiment, the first format is a pixel format and the second format is a transform format.

In yet another specific embodiment of the present invention, a computer program product for populating one or more databases with information related to an effect of a project is provide. In this embodiment, at least one structure associated with an entity is provided in a well region, the well region selected from a plurality of well regions in a spatial orientation. The computer program product includes code for receiving, from a user, a reagent and sample information related to the project. The computer program product additionally includes code for receiving, from the plurality of well regions, a well region at a time, one or more images of a plurality of objects resulting from an interaction involving a reagent. The computer program product further includes code for determining from the images of the plurality of objects a plurality of features of the plurality of objects. The computer program product further also includes code for populating a database with the plurality of features. Moreover, the computer program products includes code for publishing the plurality of features to the user, code for the user to modify the reagent and sample information, and a computer readable storage medium for holding the codes.

In an embodiment, the computer readable storage medium is provided in one or more locations. Additionally, in another embodiment, the codes are provided in one or more locations on the computer readable storage medium. In another embodiment, the codes are characterized as an executable computer code or codes. Furthermore, in a particular embodiment, the code for publishing is provided on a server.

In an alternative embodiment of the present invention, a system for performing one or more microfluidic processes is provided. The system includes an integrated fluidic device comprising a plurality of well regions and a plurality of control valves. At least one of the control valves is coupled to at least one of the well regions. The system also includes a workflow manager and a transfer robot adapted to transfer the integrated fluidic device between a plurality of stations in response to a series of instructions from the workflow manager. The system further includes a first station comprising a dispensing robot adapted to dispense at least one of a plurality of sample solutions and at least one of a plurality of reagents into the integrated fluidic device. The system additionally includes a second station including a fluidic controller unit adapted to actuate at least one of the plurality of control valves. Moreover, the system includes a third station comprising an inspection station adapted to acquire and process an image of at least a portion of one sample well selected from the plurality of sample wells of the integrated fluidic device. In some alternative embodiments, the system further includes a fourth station comprising an integrated fluidic device hotel.

In an embodiment, the one or more crystallization processes comprises an experiment. In another embodiment, the transfer robot is a track robot. Moreover, in a specific embodiment, the transfer robot includes an articulated arm.

In another alternative embodiment of the present invention, a method of designing a protein crystallization process is provided. The method includes selecting a sample to be screened during a screening process. According to the present invention, the sample is screened for protein crystallization activity. The method also includes selecting a plurality of screening reagents utilized during the screening process and selecting a particular type of microfluidic device from a plurality of microfluidic device types.

In a specific alternative embodiment, the method also includes selecting a dispense scheme that includes a mapping from a screening reagent plate to the selected particular type of microfluidic chip. The method additionally includes selecting a workflow template from a plurality of workflow templates, the workflow template including a work order sequence and a timing sequence for the protein crystallization process, selecting an owner for the protein crystallization process. The method further includes saving an electronic representation of information related to the previous steps of selecting in a design database. Moreover, the method includes notifying the owner of the protein crystallization process of a readiness for performing the protein crystallization process. In a particular embodiment, the method includes performing the protein crystallization process.

In some embodiments, the method includes entering sample information into an experiment manager database. In other embodiments, the sample information includes sample tracking information including name, source, and barcode identifier, protein construct and concentration, co-crystallization components and concentrations, and sample buffer components and concentrations. In another embodiment, the method includes entering screening reagent information into the experiment manager database. Additionally, in an embodiment, the screening reagent information includes reagent tracking information including reagent name, a source, type of microfluidic device, and reagent barcode identifier, expected reagent formation including salt, precipitant, and buffer. In a particular embodiment, the microfluidic device is a type of TOPAZ™ Chip. In another particular embodiment, the protein crystallization process is a protein crystallization experiment. In an embodiment, the method also includes entering a workflow template into the experiment manager database. In a specific embodiment, the workflow template includes at least one characteristic selected from a chip hydration level, a microfluidic device protocol including pressure level and loading time at which a reagent and a sample are loaded into the microfluidic device, an active free interface diffusion protocol including a time period during which an interface line is open, a flag related to acquisition of a time $t_0$ image, a number of images to be acquired, and a timing sequence for acquisition of the number of images. Moreover, in some embodiments, the owner of the protein crystallization process is a technician. In another embodiment, notifying is accomplished via e-mail, text message, voice mail, telephonic communication, and/or pager activation.

In yet another alternative embodiment of the present invention, a method of performing a process utilizing a microfluidic device is provided. The method includes preparing the microfluidic device according to a preselected workflow protocol. The method also includes providing at least one sample tube, a plurality of screening reagent sources, and at least one microfluidic device at an input stack. The method further includes transferring the at least one sample tube, the plurality of screening reagent sources, and the at least one microfluidic device to a dispensing robot. The method also includes dispensing at least one sample into the at least one microfluidic device and dispensing at least one screening reagent into the at least one microfluidic device. The method additionally includes transferring the at least one sample tube and the plurality of screening reagent sources to an output stack.

The method further includes transferring the at least one microfluidic device to a first station. In a particular embodiment, the first station is a free interface diffusion crystallizer. The first station is adapted to load the at least one sample and the at least one screening reagent into the at least one microfluidic device. Moreover, the method includes transferring the microfluidic device to an inspection workstation and acquiring a time $t_0$ image of the microfluidic device. The method additionally includes transferring the microfluidic device to a second station to initiate active free interface diffusion. In some embodiments, the second station is also a free interface diffusion crystallizer. The method also includes transferring the microfluidic device to a device hotel, which is a microfluidic device hotel in an embodiment according to the present invention. The method further includes transferring the microfluidic device to a third station (e.g., a free interface diffusion crystallizer) to terminate the active free interface diffusion process. In a specific embodiment, the first station, the second station, and the third station are free interface diffusion crystallizers.

In some embodiments, the crystallization parameter is a crystal ranking. Moreover, in other embodiments, the method further includes receiving an input from the user in response through the user interface.

Furthermore, the method includes transferring the microfluidic device to an inspection workstation. The method additionally includes acquiring an image of the microfluidic device at a second time and processing the image of the microfluidic device acquired at the second time to determine a crystallization parameter. The method further includes updating a database to include the crystallization parameter, notifying a user regarding the updating of the database, and providing a user interface to communicate the crystallization parameter to the user.

According to yet another alternative embodiment according to the present invention, a method of optimizing a protein crystallization experiment is provided. The method includes performing a first screening experiment related to protein crystallization using a first reagent set and producing a first set of experimental results. The method also includes determining a new reagent set based on the first reagent set and the first set of experimental results. The method further includes providing a plurality of stock solution tubes at an input stack. Each tube contains a particular stock solution. The method also includes providing an empty reagent plate at an input stack. The method additionally includes preparing the new reagent set on the reagent plate from the particular stock solutions contained in the stock solution tubes and transferring the plurality of stock solution tubes to an output stack. Moreover, the method includes preparing a microfluidic device according to a preselected workflow protocol. Furthermore, the method includes transferring the reagent plate from the input stack to a dispensing station and transferring the microfluidic device to the dispensing station. The method also includes selecting a dispense protocol that includes a mapping from the reagent plate to the microfluidic device and dispensing the new reagent set from the reagent plate to the microfluidic device utilizing the dispense protocol. Additionally, the method includes selecting a workflow template from a plurality of workflow templates. The workflow template includes a work order sequence and a timing sequence for the protein crystallization experiment. Further, the method includes selecting an owner for the protein crystallization experiment and saving an electronic representation of information related to the previous steps of selecting in a design database. The method also includes notifying the owner of the protein crystallization experiment of a readiness for performing the protein crystallization experiment and performing the protein crystallization experiment.

In a particular embodiment of the present invention, an automated system for processing one or more entities is provided. The system includes a platform and a robot device comprising a robot arm disposed on the platform. The robot arm is capable of accessing one or more work stations on the platform. Additionally, the robot is adapted to transfer one or more microfluidic devices from a first spatial location to a second spatial location. In this particular embodiment, the one or more microfluidic devices include one or more reaction chambers therein. The system additionally includes an input device coupled to the one or more work stations. The input device is adapted to receive one or more microfluidic devices from a user. The system also includes an output device coupled to one or more workstations. The output device is adapted to output the one or more microfluidic device to a user. Moreover, the system includes an image capturing workstation coupled between the input device and the output device. The image capturing workstation is adapted to capture one or more images of a portion of one or more reaction chambers and any contents therein of the microfluidic chip. The system further includes one or more ports coupled to one or more microfluidic devices. The one or more ports are adapted to provide one or more inputs into at least one of the reaction chambers. Moreover, the one or more ports are adapted to manipulate one or more processes being carried out in at least one of the reaction chambers in the one or more microfluidic devices.

In an embodiment, a chip hotel is coupled to the image capture device and is adapted to house one or more microfluidic devices therein in a predetermined environment. In a particular embodiment, the chip hotel is adapted to maintain a predetermined level of electromagnetic radiation. Moreover, in another embodiment, the one or more processes include a temporal element or a temperature element. Additionally, in an embodiment, the one or more ports is adapted to provide one or more fluids to the one or more microfluidic devices. In another embodiment, the robot device includes a track that is spatial disposed from a first spatial region to a second spatial region on the platform. In an embodiment, the system further includes a robot controller coupled to the robot device. The robot controller includes a plurality of input/output ports, each of the input/output ports being adapted to receive or transfer one or more electrical signals to operate the robot device. In some embodiments, the image capturing device includes a CCD device. In other embodiments, the system further includes a back end work station coupled between the input device and the output device.

In another particular embodiment, a graphical user interface device for a fluidic micro chip analysis system is provided. The graphical user interface device includes a first portion on a display comprising a representation of an array of well regions. The array of well regions includes a first axis, including a first set of indications. The array of well regions also includes a second axis, including a second set of indications. Each of the well regions in the array are capable of being addressed via at least one of the first indications and at least one of the second indications. The graphical user interface device also includes a second portion on the display comprising a list of entities. The list of entities are associated with at least one of the well regions in the array. Moreover, the list of entities are displayed upon a selection of the one of the well regions in the array.

In a particular embodiment, the first indications are numbered from 1 through N and the second indications are numbered from 1 through M. In another embodiment, the user interface also includes a third portion on the display indicating bar code information. In yet another embodiment, the user interface further includes a fourth portion on the display indicating an identifier. In some embodiments, the array of well regions includes at least one sample in one of the well regions. In other embodiments, the list of entities includes at least one entity. In a particular embodiment, the list of entities includes at least a result for at least one of the well regions.

In yet another particular embodiment, a method for displaying features on a graphical user interface device for a fluidic micro chip analysis system is provided. The method includes outputting on a first portion of a display a representation of an array of well regions. The array of well regions includes a first axis, including a first set of indications. The array of well regions also includes a second axis, including a second set of indications. Each of the well regions in the array is capable of being addressed via at least one of the first indications and at least one of the second indications. The method also includes outputting on a second portion of the display a list of entities. The list of entities is associated with at least one of the well regions in the array. Additionally, the list of entities is displayed upon a selection of the one of the well regions in the array.

In a specific embodiment, the list of entities includes one or more reagents. Moreover, in another embodiment, the array includes at least 96 well regions of a reagent plate. In some embodiments, the first portion and the second portion are displayed simultaneously. Moreover, in an embodiment, the first indications are numbered from 1 through N and the second indications are numbered from 1 through M. In another embodiment, the method further includes a third portion on the display indicating bar code information. In a particular embodiment, the method also includes a fourth portion on the display indicating an identifier.

According to one embodiment, the array of well regions includes at least one sample in one of the well regions. Additionally, in an embodiment, the list of entities includes at least one entity. In a particular embodiment, the list of entities includes at least a result for at least one of the well regions.

In an alternative particular embodiment according to the present invention, a method for displaying features on a graphical user interface device for a fluidic micro chip analysis system is provided. The method includes outputting on a first portion of a display a representation of an array of well regions. The array of well regions includes a first axis, including a first set of indications, and a second axis, including a second set of indications. Each of the well regions in the array is capable of being addressed via at least one of the first indications and at least one of the second indications. The method also includes outputting on a second portion of the display a list of entities. The list of entities is associated with at least one of the well regions in the array. The list of entities is displayed upon a selection of one of the one of the well regions in the array.

In some embodiments, the first portion, the second portion, and the third portion are displayed simultaneously. In other embodiments, the microfluidic chip includes a plurality of well regions and an input/output region. Moreover, in an embodiment, the list of addresses includes the first set of indications and the second set of indications. In a particular embodiment, the first set of indications is numbered from 1 through N and the second set of indications is numbered from 1 through M. Furthermore, in an embodiment, the first portion, the second portion, and the third portion are displayed concurrently with an operation process associated with the microfluidic chip. In a specific embodiment, the first portion and the second portion are different portions on the display. Moreover, in another embodiment, the array of well regions is associated with a microtiter plate.

In yet another alternative particular embodiment, a graphical user interface device for a fluidic micro chip analysis system coupled to a database is provided. The graphical user interface device includes a first portion provided on a display of a representation of an array of well regions. The array of well regions includes a first axis, including a first set of indications. The array of well regions also includes a second axis, including a second set of indications. Each of the well regions in the array is capable of being addressed via at least one of the first indications and at least one of the second indications. The graphical user interface device also includes a second portion provided on the display of a list of addresses. Each of the addresses is respectively associated with well regions in the array. The graphical user interface device further includes a third portion provided on the display of a representation of a microfluidic chip.

In a specific embodiment, the first portion, the second portion, and the third portion are displayed simultaneously. In another specific embodiment, the microfluidic chip includes a plurality of well regions and an input/output region. Moreover, in an embodiment, the list of addresses includes the first set of indications and the second set of indications. In another embodiment, the first set of indications is numbered from 1 through N and the second set of indications is numbered from 1 through M. In a particular embodiment, the first portion, the second portion, and the third portion are displayed concurrently with an operation process associated with the microfluidic chip. Additionally in some embodiments, the first portion and the second portion are different portions on the display. In an embodiment, the array of well regions is associated with a microtiter plate.

According to a particular embodiment according the present invention, a communications system is used to transmit information related to a protein crystallization process to a remote user. The communications system may include, for example, email, voice mail, instant messaging, paging, and/or SMS. In another embodiment, the microfluidic elastomeric process includes at least one of a protein crystallization process, a fluorogenic reaction process, or a chemiluminescent reaction process.

In another particular embodiment, methods and systems according to the present invention provide for the use of a database to manage information related to processes performed using microfluidic elastomeric chips. In some embodiments, the information is related to a protein crystallization process. In other embodiments, the information is related to at least one of a fluorogenic reaction process or a chemiluminescent reaction process.

In another alternative embodiment, a method for operating an imaging system for biological applications is provided. The method includes capturing one or more images, for example, of a portion of a protein crystal, in a pixel domain. The pixel domain is associated with a well region from a microfluidic chip. Moreover, the image in the pixel domain is captured using an image capturing device. The method also includes processing the one or more images in the pixel domain to derive information associated with the one or more images. In a specific embodiment, the information relates to crystallization process. The method further includes transferring a portion of the information associated with the one or more images to a remote client device. Merely by way of example, in a particular embodiment, the remote client device is a computer, work station, cell phone, laptop computer, PDA, or pager. According to an embodiment of the present invention, transferring occurs, in part, through a network of computers (e.g., the Internet).

In an embodiment, the information relates to a crystallization process and the one or more images includes a portion of a crystal from the crystallization process. In another embodiment, the information relates to at least one of a fluorogenic reaction process or a chemiluminescent reaction process and the one or more images includes images of at least one of a fluorescent chemical species or a luminescent chemical species. In other embodiments, the information relates to a process performed in a microfluidic elastomeric device. In some embodiments, the method further includes storing the information in a portion of a database, the database being coupled to the image capturing device. In a particular embodiment, the micro fluidic chip includes the well region coupled to a valve region and the valve region is coupled to one of a plurality of input and/or output ports.

In another embodiment, the method also includes using the portion of information for a drug discovery process. In a particular embodiment, the processing includes a publication process for the remote client device. In other embodiments, the processing includes converting the one or more images in the pixel domain to a second format to be transferred through the network of computers.

Numerous benefits are achieved using the present invention over conventional techniques. Some embodiments provide automated systems employing computer control to reduce the workload and increase the system efficiency for protein crystallization experiments. Additionally, the present invention provides an automated and/or semi-automated technique for processing one or more species in a microfluidic chip environment. Depending upon the embodiment, remote access may also be achieved in certain methods and systems. In other embodiments, the invention provides methods and systems that include partially or fully integrated computer based techniques including remote access, database systems and methods, and imaging techniques. Moreover, the present methods and systems may be integrated with other known and/or future methods and systems, including the CrystalMation™ product manufactured by RoboDesign International Incorporated of Carlsbad, Calif., the Crystal-Trak database application, also manufactured by RoboDesign International Incorporated, the Rhombix® Series manufactured by Kendro Laboratory Products, Inc. of Asheville, N.C., the RockMaker manufactured by Fommulatrix, Inc., of Waltham, Mass., and others. Depending upon the embodiment, one or more of these benefits may exist. These and other benefits have been described throughout the present specification and more particularly below.

Various additional objects, features and advantages of the present invention can be more fully appreciated with reference to the detailed description and accompanying drawings that follow.

BRIEF DESCRIPTION OF THE DRAWINGS

FIG. 3 is a simplified diagram illustrating a graphical user interface according to an embodiment of the present invention;

FIG. 5 is a simplified diagram illustrating a Screen Plate Creation graphical user interface according to an embodiment of the present invention;

FIG. 7 is a simplified flowcharts illustrating a method of designing an experiment according to an embodiment of the present invention;

FIG. 8 is a simplified flowchart illustrating a method of running an experiment according to an embodiment of the present invention;

FIG. 9 is a simplified flowchart illustrating a method of optimizing an experiment according to an embodiment of the present invention;

FIG. 10 is a simplified flowchart illustrating a method of translating an experimental design according to an embodiment of the present invention;

FIG. 11 is a simplified flowchart illustrating a method of optimizing a translation of an experimental design according to an embodiment of the present invention;

FIG. 12 is a simplified flowchart illustrating a workflow template according to an embodiment of the present invention;

FIG. 35 is a simplified flowchart illustrating a method of performing gene expression/genotyping experiments according to an embodiment of the present invention; and FIGS. 36-40 are simplified flowcharts illustrating operations performed according to exemplary embodiments of the present invention;

DETAILED DESCRIPTION OF SPECIFIC EMBODIMENTS

The invention provides systems and methods for managing workflow related to processing of one or more microfluidic devices, for example a system for automated preparation, processing, imaging, analysis, and control of microfluidic devices.

Figure 1:
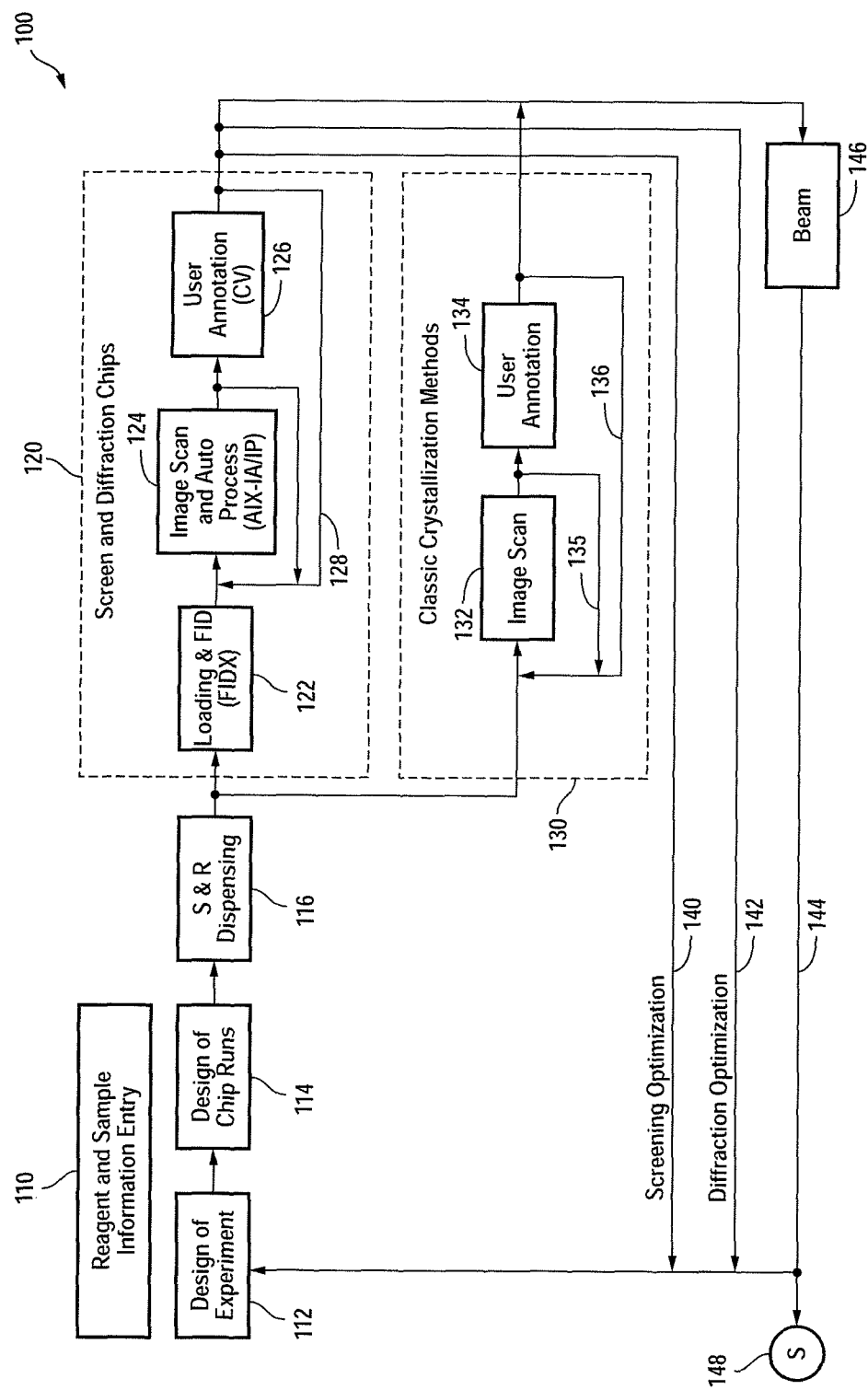
FIG. 1 is a simplified diagram illustrating a process workflow according to an embodiment of the present invention.

FIG. 1 is a simplified diagram illustrating a process workflow 100 according to an embodiment of the present invention. This diagram is merely an example of a process workflow, which should not unduly limit the scope of the claims herein. One of ordinary skill in the art would recognize many variations, modifications, and alternatives. As illustrated, the workflow process 100 is generally initiated by entering reagent and protein sample information in step 110. In some embodiments, the reagent and protein sample information if entered by a system user, although this is not required by the present invention. Additionally, experimental design information (step 112) and design of various chip runs (step 114) is performed according to embodiments of the present invention. As discussed more fully below with relation to FIG. 2 and the corresponding section of the detailed description, the experimental design information along with information regarding the designs for the various process runs are generally stored in an accessible database. Generally, a database is defined as one or more large structured sets of persistent data, usually associated with software to update and query the data. A simple database might be a single file containing many records, each of which contains the same set of fields where each field is a certain fixed width. A database is one component of a database management system.

In some embodiments of the present invention, various protein crystallization processes are referred to as protein crystallization experiments. This language is not intended to limit the scope of the claims herein, but to merely exemplify an application of the methods and systems provided according to embodiments of the present invention.

In step 116, the microfluidic device selected in step 114 is provided. Additionally, the protein sample and the reagent defined in step 114 are provided and dispensed into the microfluidic device or chip. In some embodiments, a screening chip is provided, the screening chip adapted for running a protein crystallization screening experiment. In other embodiments, a diffraction chip is provided, the diffraction chip adapted for running a protein crystallization diffraction experiment. Moreover, in yet other embodiments, other chips suitable for performing classic crystallization methods, for example, microtiter plates are provided and the protein sample and reagents are dispensed into such suitable chips. Additional details regarding the various microfluidic devices utilized in embodiments of the present invention will be provided throughout the present specification and more particularly below. In some embodiments, the dispensing step 116 includes dispensing of reagent solutions from stock reagent solutions into a reagent plate in order to prepare particular reagent solutions. However, as one of skill in the art will appreciate, this step is not required by the present invention.

Process 120 includes a number of individual steps related to certain microfluidic chips. In a particular embodiment of the present invention, the microfluidic chips are TOPAZ™ screening and/or TOPAZ™ diffraction chips or devices. Of course, other types of chips may also be used depending upon the specific embodiment. In step 122, the desired protein samples and reagent solutions are loaded into the selected microfluidic device and the device is placed in a free interface diffusion (FID) system. Generally, a FID system, such as the TOPAZ™ FID crystallizer (FIDX™), available from the present assignee, is utilized to intermix the protein sample and the reagents previously loaded into the microfluidic device, thereby producing crystals depending on the conditions. In a specific embodiment of the present invention, the FIDX is utilized at a screening stage of the process 100, during which a number of protein samples and reagents are combined in a screening process.

Image acquisition (IA) and image processing (IP) are performed in step 128. In some embodiments, these processes are performed using an automated image acquisition and processing system such as the TOPAZ™ AUTOINSPEX™ Workstation (AIX), available from the present assignee. In some embodiments, the image acquisition system includes an capturing device that is capable of capturing a single image of all reaction chambers concurrently or simultaneously. Thus, in contrast with step and repeat or stitching systems, images of an entire microfluidic device are collected at the same time, rather than in a sequential manner. Additional details regarding such systems are provided in "Method and System for Microfluidic Device and Imaging Thereof," published as International Patent Application No. WO2004/103563A2 filed May 20, 2004 and "Image Processing Method and System for Microfluidic Devices," listed under U.S. patent application Ser. No. 10/902,494, filed Jul. 28, 2004, commonly assigned, and hereby incorporated by reference for all purposes.

A system user is able to view and annotate experimental results in step 126 using software. In a specific embodiment of the present invention, software such as the TOPAZ™ AIX Software suite, including Crystal Vision software is used to view the experimental results and further annotate the experiments as desired. As illustrated by feedback look 128, after review of the experimental results, steps 124 and 126 may be repeated as desired. In some embodiments, a system user determines that additional images, for example, should be acquired and analyzed. Accordingly, feedback loop 128 is utilized to accomplish these objectives.

Upon the completion of the steps provided within process 120, feedback loop 140 is utilized in some embodiments to optimize the screening process. Experimental results produced in process 120 are utilized to redesign the experimental conditions in step 112, redesign the chip runs in step 124, and reinitiate the screening process. In alternative embodiments, only a portion of the experimental design or a portion of the chip run design, or both, are modified, depending on the particular application. Feedback loop 140 may be used once, twice, or more times, depending on the particular application and the results obtained during the screening runs.

In some embodiments, the screening process, generally combined with the screening optimization process, results in the production of crystals suitable for x-ray crystallography in step 146. As is well known to one of skill in the art, exposure of a crystal structure to a beam of x-rays, or other particles, may result in the production of diffraction patterns which are analyzed to determine the structure (step 148) of the particular crystal structure under examination. Accordingly, for screening processes which produce crystals amenable to x-ray or other diffraction studies, these studies may be performed (line 144), thereby generating information related to the crystal structure in step 148, completing the process 100.

Not only does process 120 provide for protein crystallization screening experiments, it additionally provides for protein crystallization diffraction experiments. Merely by way of example, crystals suitable for diffraction analysis are produced using TOPAZ™ diffraction microfluidic devices in an embodiment of the present invention. Typically, after the screening optimization process is performed, the experimental and chip run designs are modified at steps 112 and 114 and process 120 is repeated using diffraction chips. In a particular embodiment, after crystals have been obtained in the screening loop, the conditions are translated from nano-scale FID to micro-scale vapor diffusion techniques. Merely by way of example, large, diffraction-quality crystals are produced in a diffraction phase of process 120 using TOPAZ™ diffraction microfluidic devices using conditions determined during the translation process.

As discussed in relation to the screening process, feedback loop 128 is provided within process 120 for iteration on the image scanning and analysis process. Moreover, feedback loop 142 is provided for optimization of the diffraction chip experiments. Iteration in the larger feedback loop 142 provides for modification of design parameters, preferably leading to the production of diffraction-quality crystals. As discussed before, upon production of acceptable crystals, x-ray diffraction experiments (step 146) are utilized in a particular embodiment to generate structure information (step 148), terminating the workflow process 100.

Embodiments of the present invention are not limited to the production of diffraction-quality crystals through the use of TOPAZ™ diffraction chips. In alternative embodiments, process 130, including classic crystallization methods, such as vapor diffusion, are utilized to produce diffraction-quality crystals. In the vapor diffusion technique, a drop of water containing, for example, a protein sample, stabilizing buffers, precipitants, and/or crystallization reagents is allowed to equilibrate in a closed system containing a reservoir. The reservoir typically contains the same ingredients as the drop with the exception of the protein. The concentration of the materials in the reservoir is typically higher than the concentration in the drop so that water preferentially evaporates from the drop. Given the appropriate conditions, the evaporation will produce a gradual increase in protein and precipitant concentrations, resulting in the formation of protein crystals. Other crystal formation processes in addition to vapor diffusion are included in process 130 according to embodiments of the present invention.

Image scanning in step 132 and user annotation in step 134 are generally combined with feedback loops 135 and 136 in processes utilizing these crystallization methods. As illustrated in FIG. 1, feedback loop 142 is available for optimization of the crystallization methods illustrated by process 130. As discussed before, upon production of acceptable crystals, x-ray diffraction experiments (step 146) are utilized in a particular embodiment to generate structure information (step 148), terminating the workflow process 100. Although the above systems and methods for managing workflow have been described generally in relation to certain microfluidic devices such as, for example TOPAZ™, others can also be used. Other microfluidic devices that can be used in conjunction with the invention include devices designed to perform reactions including, but not limited to, polynucleotide hybridizations, PCR (polymerase chain reactions), immunological reactions such as ELISA reactions, signal amplifications, such as those called the INVADER™ system manufactured by Third Wave Technologies of 502 Rosa Rd., Madison, Wis. 5371-1256, digital amplifications, including, but not limited to, digital PCR, cell, tissue, microbe assays, crystal formation of non-organic materials, protein capture assays, including, quantitative and/or qualitative protein assays, cell and/or particle sorting, molecular sizing and/or sequencing, and the like. Of course, one of ordinary skill in the art would recognize many variations, alternatives, and modifications. An example of a system for automated protein crystallization using such a microfluidic chip can be found in more detail below.

Figure 2:
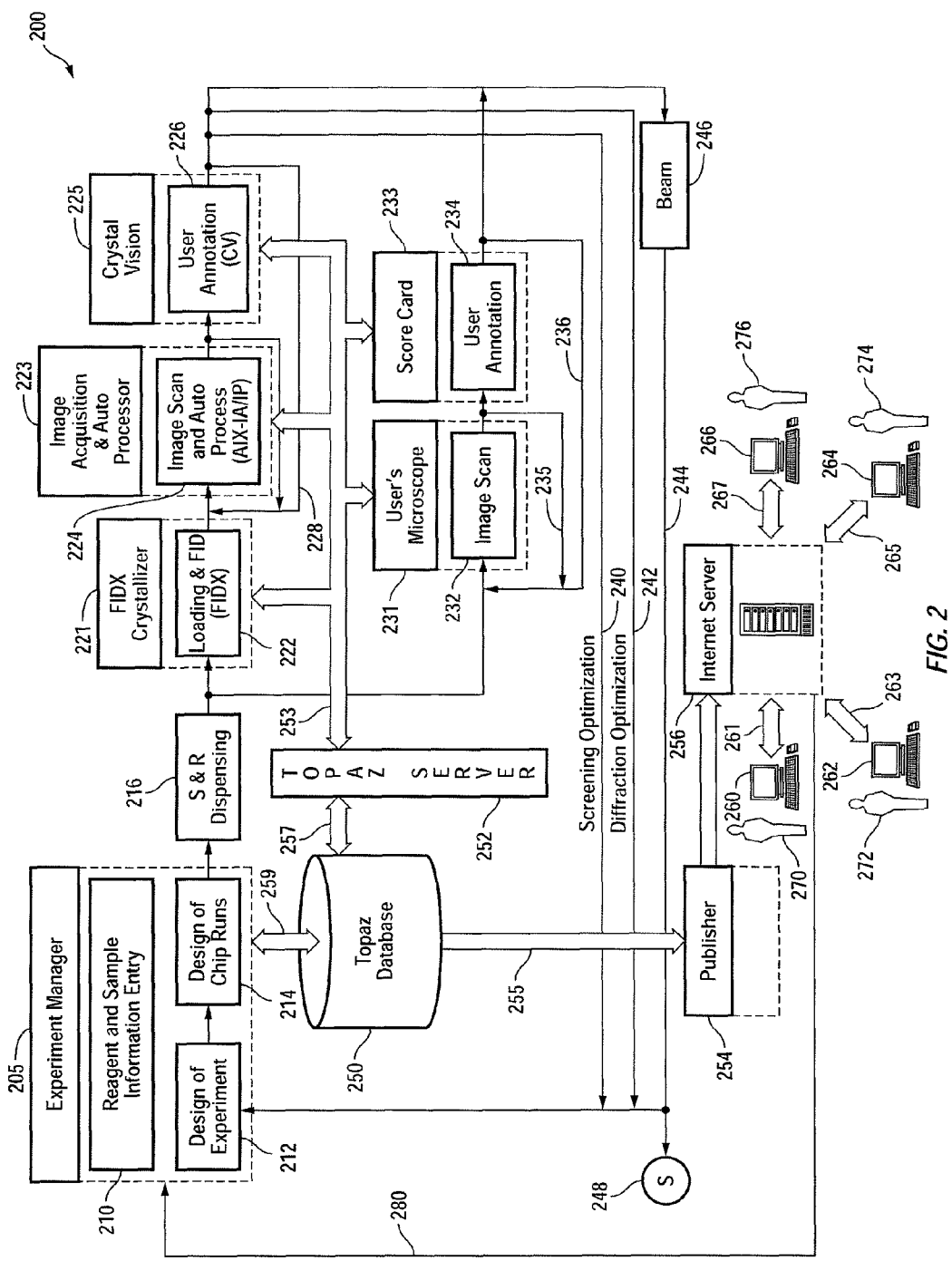
FIG. 2 is a simplified diagram illustrating an automated protein crystallization management system according to an embodiment of the present invention.

FIG. 2 is a simplified diagram illustrating an automated protein crystallization management system 200 according to an embodiment of the present invention. As illustrated in the figure, the various components utilized to perform steps of the workflow discussed in relation to FIG. 1 are provided. In some embodiments, the various software components provided in FIG. 2 are part of a TOPAZ™ Database Application Suite, although this is not required by the present invention. For example, an experiment manager 205 is provided that is utilized to enter, store, retrieve, modify, and process information provided as part of the reagent and sample information entry step 210, the design of the experiment in step 212, and the design of a chip run in step 214, reagent design, and data mining.

In a particular embodiment, the experiment manager is TOPAZ™ Experiment Manager software, available from the present assignee. In some embodiments, the experiment manager is contained in a first database, although this is not required by the present invention. In alternative embodiments, the experiment manager is provided as part of the database 250, discussed more fully below. In a particular embodiment, the experiment manager is the main graphical user interface (GUI) for the Database Application. Furthermore, the experiment manager interacts with the database 250 directly through data bus 259. In a specific embodiment, the database 250 is a Microsoft SQL or an MSDE server.

In a specific embodiment of the present invention as illustrated in FIG. 2, a number of applications are based on certain enhancements made to products available from the present assignee. For example, the FID crystallizer 221, the image acquisition and image processing system 223, and the Crystal Vision package 225 are coupled to perform protein crystallization experiments and exchange information with database 250 through server 252 as discussed in more detail below.

In step 216, the protein sample and reagent are dispensed into a microfluidic chip as discussed previously in preparation for a protein crystallization experiment. As illustrated in FIG. 2, the software included in various system components is shown. For example, software resident in the FID crystallizer 221, e.g., a TOPAZ™ FIDX, is utilized to perform the steps of loading a TOPAZ™ chip into the FIDX, opening appropriate valves in the TOPAZ™ chip to initiate FID, and closing appropriate valves as necessary to terminate the FID process (222). In like manner, software resident in the image acquisition and processing system 223 is adapted to automatically acquire and process images (step 224) of at least a portion of a microfluidic device. Using Crystal Vision software (225), for example, a user is able to annotate the experimental results in step 226. In a particular embodiment of the present invention, separate TOPAZ™ Image Acquisition and TOPAZ™ Auto Processor applications are provided as part of application 223.

Data bus 253 couples the FID crystallizer 221, the image acquisition and processing system 223, and the Crystal Vision software 225 to a server 252. In the embodiment illustrated in FIG. 2, the server is a Database Application Server (e.g., a TOPAZ™ Data Application Server, sometimes referred to as a TOPAZ™ Server), but this is not required by the present invention. In some embodiments, the server 252 is a hardware device, while in other embodiments, the server 252 is a database management process. For example, in an embodiment, the server is an interface layer between the database 250 and various software components, e.g., TOPAZ™ software components. In general, the database management process is a background application. One of ordinary skill in the art would recognize many variations, modifications, and alternatives. As illustrated in FIG. 2, the server 252 is coupled to database 250 by an additional data bus 257, although in an alternative embodiment, the server 252 and the database 250 are both coupled to data bus 253. Furthermore, database 250 is coupled to the experiment manager 205 through data bus 259, providing for two way communication between the database management process 252 and the experimental design phase of the protein crystallization process.

Data bus 253 provides for two way communication between the database management process 252 and the software driven processes utilized in the protein crystallization experiments. Accordingly, data utilized by the apparatus can be provided by the server or other pieces of equipment. Moreover, results and analysis produced by the apparatus are available to the system user through the server. Furthermore, commands to control facets of the protein crystallization processes may be generated at the server or other location and communicated to the apparatus through the data bus.

Merely by way of example, image acquisition and processing feedback loop 228 is utilized in a specific embodiment through communication over bus 253. After a first image acquisition and processing process is performed, the data is provided to the server 252 and the Crystal Vision software 225. A system user accesses the data through server 252 and determines that an additional image scan is appropriate. Communicating over bus 253, an instruction is provided to system 223 to acquire and process a second image, effectuating feedback through loop 228. This is merely a single example and one of ordinary skill in the art would recognize many variations, modifications, and alternatives.

As discussed in relation to FIG. 1, screening optimization is performed using feedback loop 240 and diffraction optimization is performed using feedback loop 242 in embodiments of the present invention. Moreover, database management process 252 and database 250 are utilized in some embodiments to track the iterations performed along these feedback loops.

Alternative crystallization methods, such as vapor diffusion, are utilized to produce diffraction-quality crystals as illustrated in FIG. 2. For example, software resident on a user's microscope 231 and crystal scoring programs interact with the microscope to collect and analyze images (step 232) of a protein crystal in an embodiment of the present invention. A user may record annotations related to the protein crystallization process in step 234 using the score card software 233 as illustrated. As with the information related to the screening and diffraction processes for microfluidic chips, data bus 253 provides for two way communication with the apparatus utilized in these alternative crystallization methods. Additionally, feedback loops 235 and 236 are provided as discussed in relation to FIG. 1. Diffraction-quality crystals, produced by screening or diffraction methods are subjected to analysis by system/method 246 and structure information is preferably ascertained at step 248.

In an embodiment of the present invention, the Score Card 233 is a software application adapted for a system user to manually enter the experimental conditions of the microfluidic device (chip) or of a classic crystallization method. As illustrated, the score card 233 interacts with the database 250 through the server 252. In a specific embodiment, the server 252 is a TOPAZ™ Database Application Server.

Not only is the database 250 coupled to the database management process 252 in FIG. 2, but it is additionally coupled to publisher 254. In a specific embodiment of the present invention, the publisher is utilized to extract data related to the protein crystallization process and transmit this data to a number of users 270, 272, 274, and 276 through computers 260, 262, 264, and 266. As illustrated in FIG. 2, the computers are coupled to internet server 256 through data links 261, 263, 265, and 267. In a particular embodiment of the present invention, the publisher is an application that generates experimental results as HTML files and publishes (e.g., copies) them to Internet Server 256. Thus, utilizing embodiments of the present invention, data resulting from the protein crystallization process is available for viewing by a wider audience without providing direct connections of the audience to the database 250.

Feedback loop 280 provides a link for users 270-276 to remotely interact with the Experiment Manager 205. Accordingly, embodiments of the present invention provide for automated control of protein crystallization experiments, remote publishing of the resulting experimental data and feedback based control of subsequent protein crystallization experiments. As illustrated, the users are provided with access to the Database as well as the Server, enabling remote analysis of experimental data and subsequent feedback. Merely by way of example, a user could view an experimental result in Crystal Vision, decide an additional image was beneficial, and instruct the AIX to perform an additional cycle. One of ordinary skill in the art would recognize many variations, modifications, and alternatives. Thus, through embodiments of the present invention, users are enabled to interact with, analyze, and control the protein crystallization experimental process at numerous stages of such processes.

In some embodiments of the present invention, a number of control features are within the control of the Database Application Suite. An example of such a system is discussed below in relation to FIG. 2. In particular embodiments, the sample and reagent dispensing function is provided separately from the Database Application Suite. In some of these particular embodiments, a user will follow the follow the dispensing instruction provided by the Experiment Manager in order to perform the sample and reagent dispensing functions. In other embodiments, the sample and reagent dispensing function is provided as a function under the control of the automated system, as illustrated in FIG. 9 below.

Figure 2A:
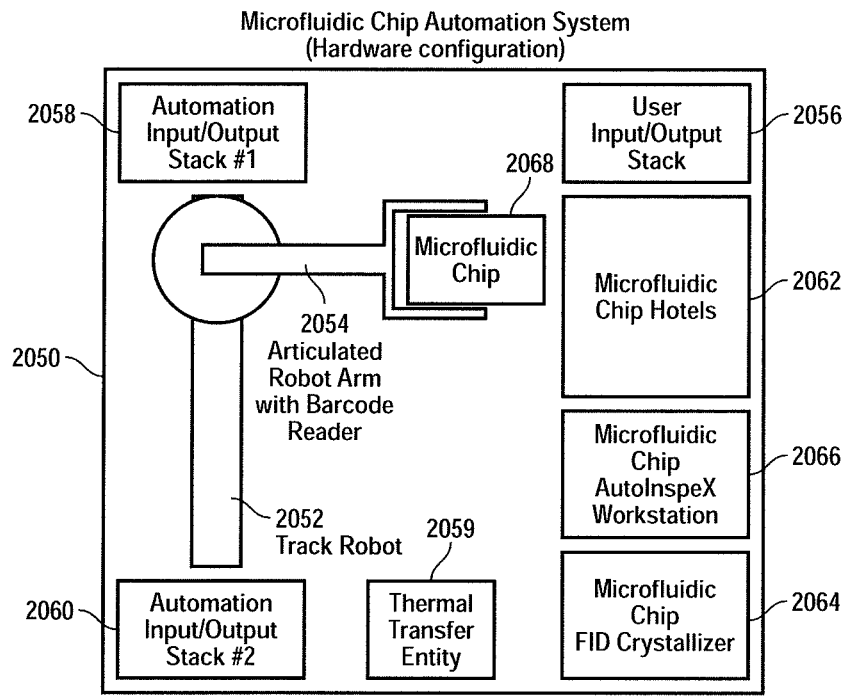
FIG. 2A is a simplified schematic diagram illustrating an automated protein crystallization system according to an embodiment of the present invention.

FIG. 2A is a simplified schematic illustration of an automated system for performing protein crystallization experiments according to an embodiment of the present invention. As illustrated in FIG. 2A, an automation table 2050 is provided to provide a stable base for a number of system components. In some embodiments according to the present invention, the entire automation table 2050 and all the items associated with the automated system are enclosed in an environmental enclosure, that provides, for example, temperature and humidity control for the automated system components. In alternative embodiments, partial control is provided by environmental enclosures that contain a portion of the system components that do not provide independent environmental control, for example, the track robot.

Track robot 2052 with articulated arm 2054 is located on the automation table 2050 and is adapted to provide automated transport operations between other system components on the automation table. Although FIG. 2A illustrates robot 2052 as a track robot, this is not required by the present invention. Other robots, including articulated robots or combination track/articulating robots, such as the CRS F3t Track Robot System, available from the Thermo Electron Corporation of Waltham, Mass.

In the embodiment illustrated in FIG. 2A, the automated system also comprises a number of input/output stacks adapted to store microfluidic devices or chips. In the embodiment illustrated in FIG. 2A, a User Input/Output Stack 2056 is provided. The User input/output stack is generally utilized for a user to transfer microfluidic chips to and from the Microfluidic Chip Automation system. For example, after reagent and samples have been loaded into microfluidic chips, the chips are placed in the user input/output stack by a robot, system operator, technician, or the like. Typically, a user is a technician, a system operator, and the like. Moreover, in one embodiment, two automation input/output stacks 2058 and 2060 are provided at two sides of the automation table. Generally, the Automation Input/Output stacks are used for transferring microfluidic chips between different portions of the automation system or between different automation systems (e.g., systems on different automation tables). Of course, one of skill in the art will appreciate that different numbers and arrangements of the input/output stacks may be used depending on the particular application.

FIG. 2A also illustrates a microfluidic Chip Hotel 2062 on the automation table. In some embodiments, the hotel is utilized to store chips before, during, and/or after FID experiments. Merely by way of example, the hotel stores chips in between analysis sessions using the AIX. Although FIG. 2A illustrates a microfluidic Chip Hotel, the present invention is not limited to chip hotels for microfluidic devices. In alternative embodiments, the hotel provides a controlled environment for storage of microtiter plates, trays, and the like.

A microfluidic chip FID Crystallizer (FIDX) 2064, a thermal transfer entity 2059, and a microfluidic chip AUTOIN-SPEX™ Workstation (AIX) 2066 are also provided as illustrated in FIG. 2A. As described previously, these system components are typically utilized in performing protein crystallization experiments.

In an embodiment of the present invention, the automated system is adapted to transfer a microfluidic chip 2068 between the user input/output stack, the automation input/output stacks, the Microfluidic Chip FIDX, the Microfluidic Chip AIX, and the Microfluidic Chip Hotel. A computer (not shown) is utilized to automate and control the operation of the system. In a specific embodiment of the present invention, the system is a protein crystallization experiment system. Merely by way of example, under computer control and through the use of the software described herein, a microfluidic chip may be transferred from one of the input/output stacks, processed through the FIDX, placed in the chip hotel for a predetermined period, and transferred to the AIX at a predetermined time. After automated processing, experimental results, communicated through the software and systems described herein, can be communicated to a remote user as described more fully below.

According to embodiments of the present invention, all of the aforementioned items are included in the system illustrated in FIG. 2A. In alternative embodiments, less than all the aforementioned items are provided. For example, in a specific embodiment, a single automation input/output stack is provided on the automation table. Moreover, other embodiments of the present invention are not limited to these items, but may include additional items as will be evident to one of skill in the art. Merely by way of example, processing and reading apparatus, in addition to or as a replacement for the FIDX and AIX are provided by some particular embodiments. In these particular embodiments, analysis of fluorescence, thermal, chemical, visual, or other properties are utilized in an automated manner to perform experiments of interest. Of course, one of ordinary skill in the art would recognize many variations, modifications, and alternatives.

The methods and systems provided according to the present invention will have a variety of uses. Merely by way of example, embodiments of the present invention provide a communications system used to transmit information related to a protein crystallization process to a remote user. In a specific embodiment, the communications system includes email, voice mail, instant messaging, paging, and/or SMS. Another embodiment according to the present invention provides systems and methods that use a database to manage information related to processes performed using microfluidic elastomeric chips, for example, information related to a protein crystallization process.

Figure 2B:
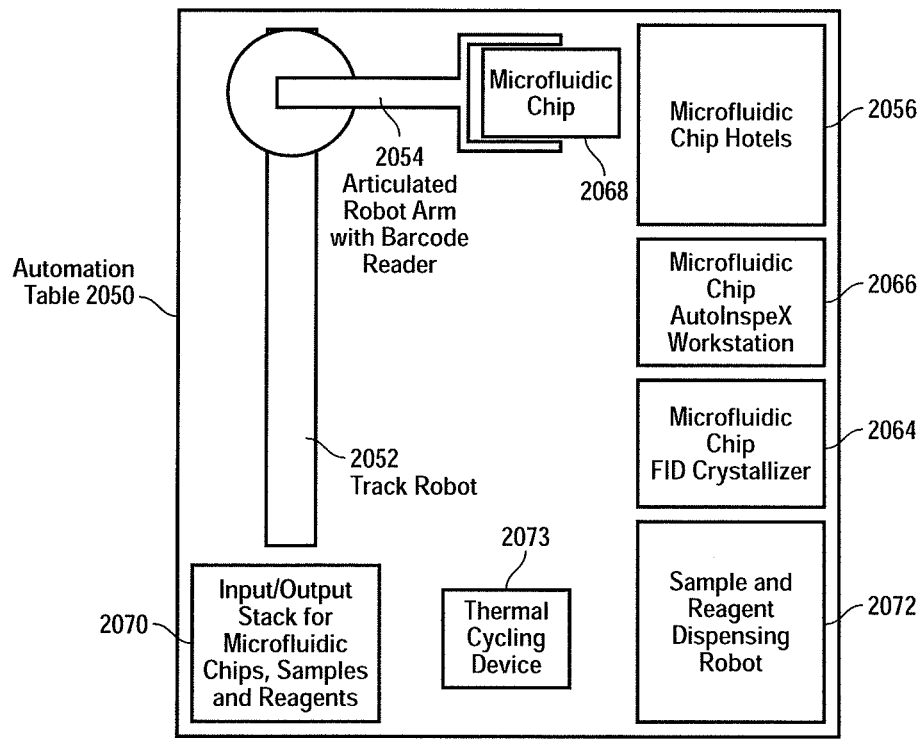
FIG. 2B is a simplified schematic diagram illustrating another automated protein crystallization system according to another embodiment of the present invention.

FIG. 2B is a simplified schematic diagram illustrating another automated protein crystallization system according to another embodiment of the present invention. As illustrated in FIG. 2B, selected components as illustrated in FIG. 2A are provided, along with a sample and reagent dispensing robot. Automation table 2050, track robot 2052 with articulated arm 2054 and an input/output stack for microfluidic chips, samples and reagents 2070 and thermal cycling device 2073 are provided according to an embodiment of the present invention. The platform is fabricated from a rigid material capable of maintaining the platform in a substantially stationary position, for example, with a spatial movement of less than about 1 millimeter when the robot device operates and moves the robot arm from a first spatial location to a second spatial location. The input/output stack provides temporary storage for both microfluidic chips, as well as a number of samples and reagents. The samples and reagents are utilized by the sample and reagent dispensing robot 2072 under computer control to dispense samples and reagents into appropriate chips. Therefore, the embodiment of the present invention illustrated in FIG. 2B provides the benefits available through the system illustrated in FIG. 2A and additionally provides for automated sample and reagent storage and dispense operations.

Figure 2C:
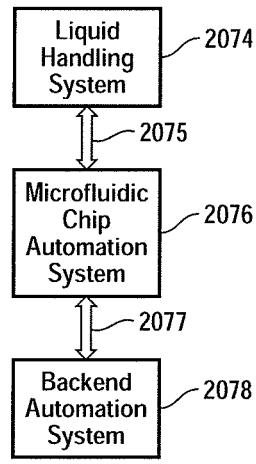
FIG. 2C is a simplified schematic diagram illustrating an automated protein crystallization experiment and analysis system according to an embodiment of the present invention.

FIG. 2C is a simplified schematic diagram illustrating an automated protein crystallization experiment and analysis system according to an embodiment of the present invention. As illustrated in FIG. 2C, a liquid handling system 2074, a Microfluidic Chip Automation System 1076, and a Backend Automation System 2078 are coupled to each other. In a specific embodiment, the Liquid Handling System 2074 comprises a reagent and sample storage, loading, and disposal system including a reagent and sample dispensing robot as illustrated in FIG. 2B. Moreover, in some embodiments, the Microfluidic Chip Automation System 2076 includes the elements shown in FIG. 2B. Thus, the system illustrated in FIG. 2C includes a number of sub-components in an integrated and automated manner. Furthermore, Backend Automation System 2078 generally includes methods and apparatus to automate the process of removing crystals from particular chips and performing analysis, including x-ray crystallography. As will be evident to one of skill in the art, computer hardware and software (not shown) will be utilized in various embodiments of the present invention to control the operation and interaction of the several systems illustrated in FIG. 2C.

Transfer sections 2075 and 2077 are provided in FIG. 2C. Transfer section 2075 is adapted to move a microfluidic device between the Liquid Handling System 2074 and the Microfluidic Chip Automation System 2076. In some embodiments, transfer section 2075 is operated under computer control to provide for automated motion of microfluidic devices from system to system. Transfer section 2077 is adapted to move a microfluidic device between the Microfluidic Chip Automation System 2076 and the Backend Automation System 2078. In some embodiments, transfer section 2077 is operated under computer control to provide for automated motion of microfluidic devices from system to system.

Figure 2D:
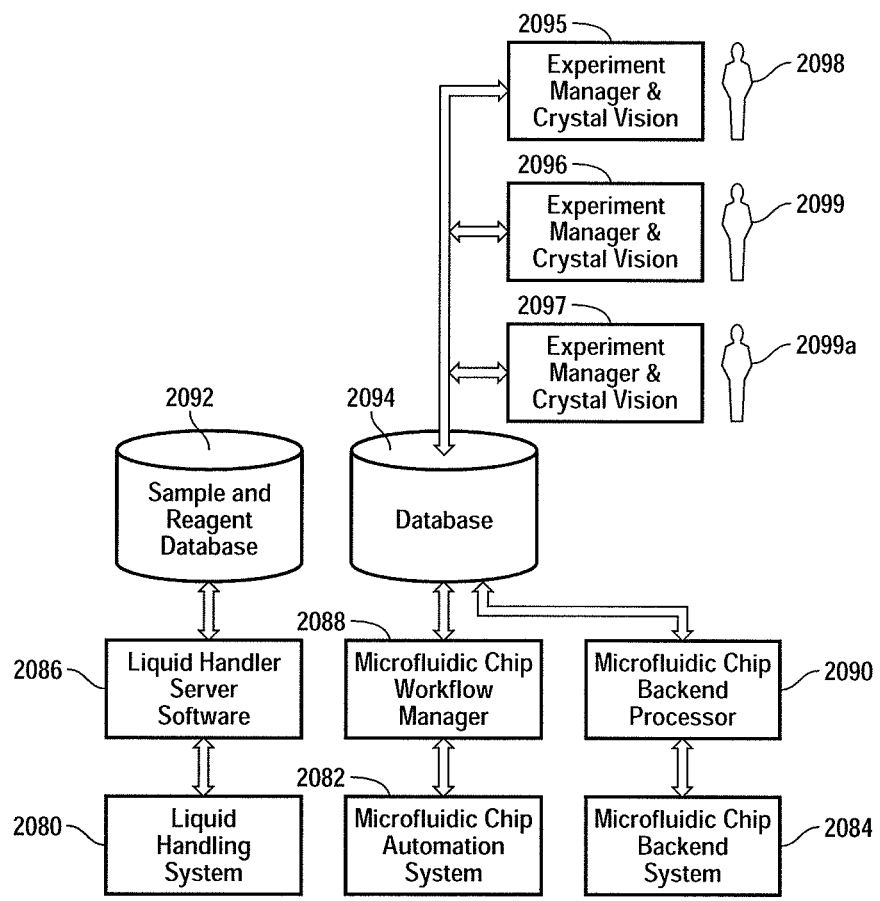
FIG. 2D is a simplified schematic diagram of system software according to an embodiment of the present invention.

FIG. 2D is a simplified schematic diagram of system software according to an embodiment of the present invention. As illustrated in FIG. 2D, a Liquid Handling System 2080, a Microfluidic Chip Automation System 2082, and a Backend System 2084 are provided and coupled to Liquid Handling Server Software 2086, a Microfluidic Chip Workflow Manager 2088, and a Microfluidic Chip Backend Processor 2090, respectively. The Liquid Handling Server Software is coupled to a Sample and Reagent Database 2092. The Microfluidic Chip Workflow Manager and the Microfluidic Chip Backend Processor are coupled to a Database 2094. In some embodiments of the present invention, the Sample and Reagent Database includes data utilized by the Liquid Handling Server Software to control and automate the Liquid Handling System. In general, elements 2086 and 2092 may be provided on one or more computers as appropriate to the particular application.

Experiment Manager and Crystal Vision software packages 2095, 2096, and 2097 are coupled to the Database 2094 as illustrated in FIG. 2D. As described previously, users 2098, 2099, and 2099a interact with the software control system utilizing one or more instances of Experiment Manager and Crystal Vision software. Referring back to FIG. 2, the functionality provided by the system described with respect to FIG. 2 is included in the embodiments illustrated in FIG. 2D, as well as additional functionality.

Figure 2E:
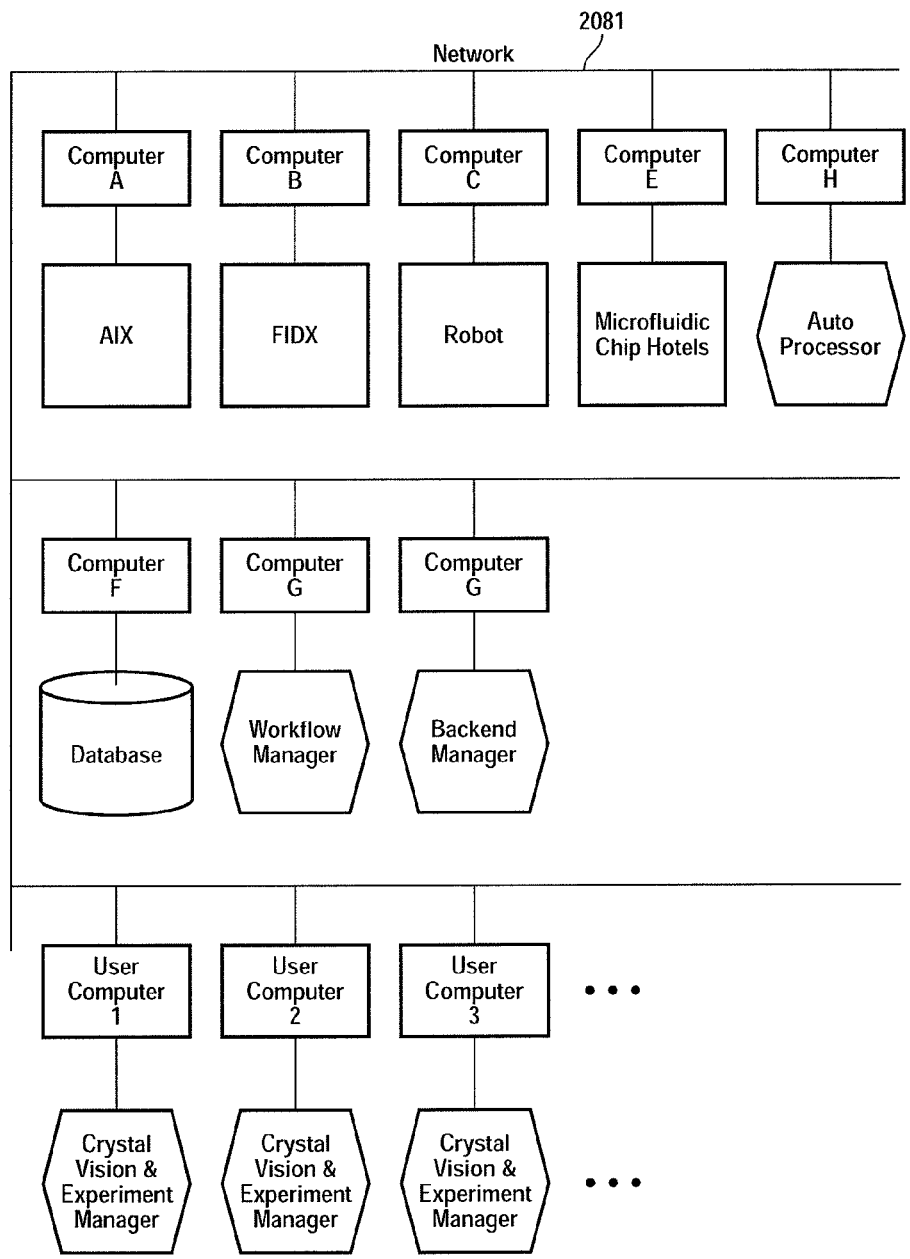
FIG. 2E is simplified schematic network diagram illustrating a computer network according to an embodiment of the present invention.

FIG. 2E is simplified schematic network diagram illustrating a computer network according to an embodiment of the present invention. As illustrated, one or more computers are utilized in an embodiment to control one or more hardware components. For example, referring to FIG. 2A, computers A and B are coupled to the AIX and the FIDX, respectively. Both computers A and B are coupled to a computer network 2081. Computers C and E are coupled to a robot, for example, the track robot with an articulated arm, and the Microfluidic Chip Hotels, respectively. Computers F and G are coupled to the Database and the Workflow Manager, respectively. As illustrated, computers C, E, F, and G are also coupled to the computer network 2081. Accordingly, according to embodiments of the present invention, the computer network 2081 provides for communication of data and control commands between various hardware and software components as described herein.

FIG. 2E also illustrates computer H coupled to an Auto Processor and computer G coupled to a Backend Processor. Accordingly, complete protein crystallization experimental systems, represented by the Auto Processor, are coupled to particular dedicated pieces of equipment and software in some embodiments of the present invention. Merely by way of example, the methods and systems provided by the embodiments of the present invention illustrated in FIG. 2E provide for combination of a number of FIDX systems as appropriate to a particular application. One of ordinary skill in the art would recognize many variations, modifications, and alternatives.

A number of user computers running the Experiment Manager and Crystal vision are also are coupled to the computer network as illustrated in FIG. 2E. As discussed in relation to FIG. 2, automated delivery of experimental conditions and information, as well as feedback processes adapted for the control, changing, and optimization of various experiments are provided by embodiments of the present invention.

Embodiments of the present invention provide a graphical user interface (GUI) through which users interact with the system. For example, an Experiment Manager, e.g., a TOPAZ™ Experiment Manager, is included in some embodiments as discussed in relation to FIGS. 1 and 2. The following section provides details related to the functionality of the Experiment Manager software and examples of methods of use and operation.

Figure 3:
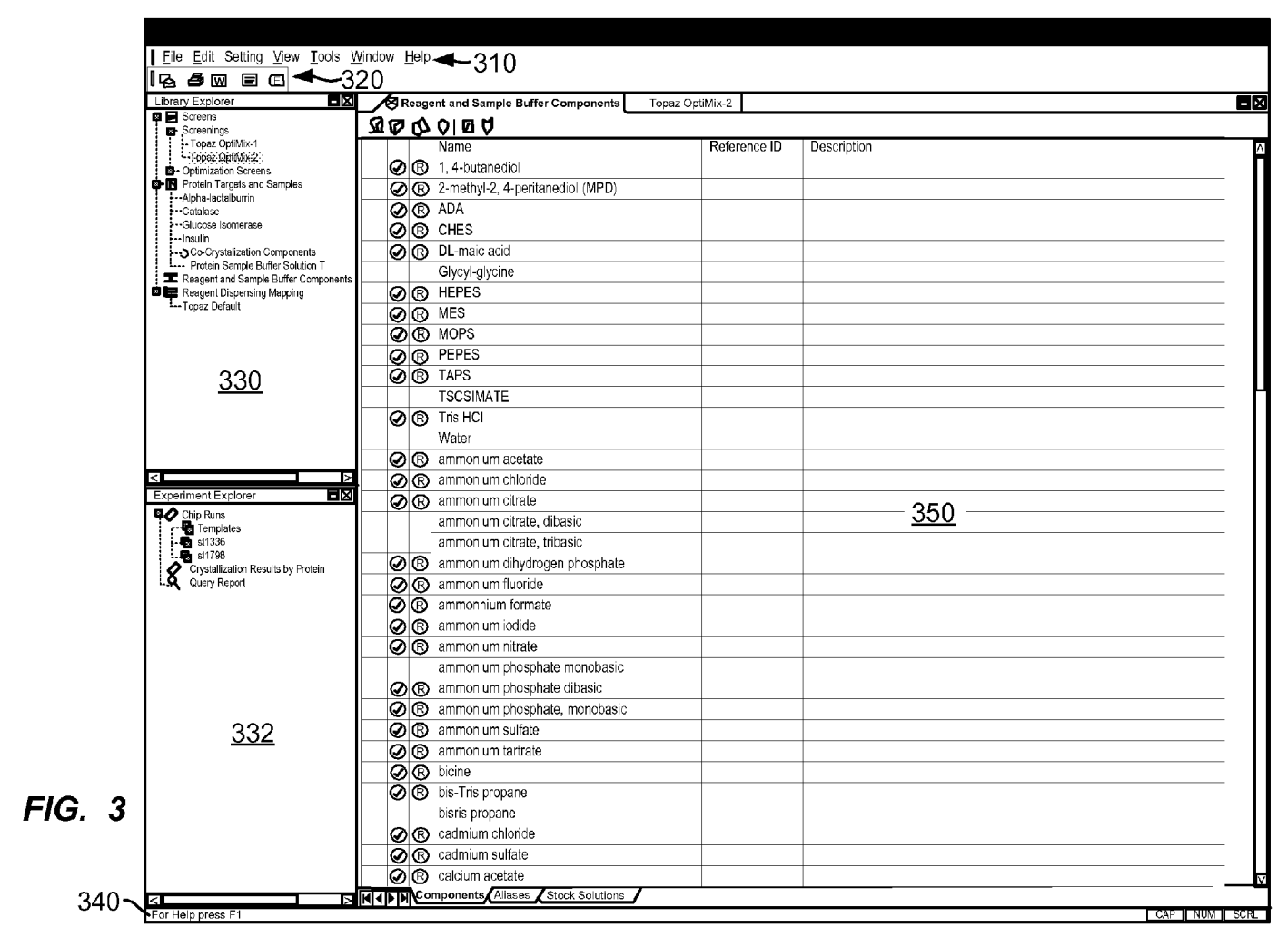

FIG. 3 is a simplified diagram illustrating a graphical user interface (GUI) according to an embodiment of the present invention. Depending upon the embodiment, the present GUI can be implemented using certain methods and systems described herein. As an example, the system and method can be those generally described above, although others may also be used, depending upon the specific embodiment. In general, the GUI layout includes a Menu Bar 310, a Tool Bar 320, a Library Explorer Panel 330 and an Experiment Explorer Panel 332, a Status Bar 340 and a Worksheet panel 350, as shown in FIG. 3, which illustrates a particular embodiment of the present invention. The following functions are provided by GUIs included within the scope of embodiments of the present invention.

Menu Bar 310—Top level menus include File, Edit, Settings, View, Tools, and Help. In some embodiments, each of the menus are pull-down menus activated by an input device, for example, a mouse or a touch screen, and include a number of menu items generally accessible through activation of the pull-down menus. In particular embodiments, the selection of a menu item will result in an action, whereas in other embodiments, the selection of a menu item, for example, a menu item followed by ellipsis ( . . . ), will result in generation of a pop-up window.

File
    Database Log-off
    New (allows a user to create a new item of Reagent set (also referred to as a screen), Target, Sample, and a Chip Run (Template and Ready-to-Run))
    Save (allows a user to save the current worksheet)
    Save As (allows a user to save the current worksheet as a different data file)
    The availability of this operation is dependent on the kind of worksheet. Additional details regarding worksheets are found in the worksheet specification below.
    Close (allows a user to close the current worksheet)
    Close All (allows a user to close all the opened worksheets)
    Import Chip Runs (allows a user to import Chip Runs from acquired outside database application)
    Export (allows a user to export the data in the current worksheet to a CSV file)
    History (allows a user to list the history of opened worksheet) The history may include when and who created the data and when and who last modified the data.
    Exit
Edit Menu
    Rename (allows the user to rename the currently selected item in the Explorer Panel if the data item is not referenced)
    Delete (allows a user to delete the currently selected item in the Explorer Panel if the data item is not referenced)
Setting Menu
    Classification Settings (Prompt the same dialog as the "Default Settings" in the Crystal Vision to define the User and Auto Classification settings)
    Generally, the Classification Settings are system wide, whereas the three settings below are user specific.
    Chip Run Result Worksheet Settings (Define the data reporting (e.g., what user and auto classification will be reported in a Chip Run result worksheet))
    Target Result Worksheet Settings (Define the data reporting (e.g., what user and auto classification will be reported in a Target result worksheet))
    Query Result Settings (Define what type of data will be reported)
View Menu
    Show/Hide Tool Bar
    Show/Hide Status Bar
    Refresh Current Worksheet
    Refresh Explorer
    Refresh All
Tools Menu
    Crystal Vision
    Windows Explorer
Window - List of the opened worksheets and the current worksheet
Help Menu
    About Experiment Manager...
    Fluidigm on the Web
    User Guide...

In alternative embodiments of the present invention, additional menus are provided, additional menus are provided in different orders, or one or more menus are removed without departing from the scope of the claims herein. Moreover, in certain embodiments, additional menu items are provided, additional menu items are provided in different orders, or one or more menu items are removed without departing from the scope of the claims herein.

Embodiments of the present invention further provide a toolbar and a status bar. The toolbar 320, as illustrated in FIG. 3, generally contains the most used operations defined under the menus. The status bar 340 generally contains information related to status and operation of the one or more programs. In an embodiment, the toolbar contains:

Toolbar
    File New
    File Save
    Export
Status Bar
    Current User
    Progress on the current operation
    Date and Time In alternative embodiments of the present invention, additional operations are provided on the toolbar, additional operations are provided in different orders, or one or more operations are removed without departing from the scope of the claims herein. Moreover, more than one toolbar is provided in certain embodiments, providing groupings of operations as appropriate to the particular application.

Moreover, in some embodiments, worksheet GUI guidelines are provided. In general, there are two types of worksheets: worksheets for data maintained by the system and worksheets for data maintained by the user. For an item, such as a component, displayed in the tabular form, there is preferably a column indicating whether the item is being referenced or not. For a dataset, such as a Reagent Set, there is preferably a field indicating whether the data is being referenced or not. In a specific embodiment, if the data is referenced, the attributes that can be modified by a user are limited (depending what is the data item). As described more fully below, the detailed specifications for the worksheets are defined item by item.

In an embodiment, the Worksheet for Data Maintained by the System includes: Reagent Components, Ligands, and Sample Components. Preferably, each of the worksheets contain the following: a table that contains the list of data items and a toolbar that contains tools for Creating, Removing, and Editing of a selected data item. The Worksheet for Data Maintained by the User essentially includes all items except the three described above.

Generally, a worksheet has the following generic form as illustrated in Table 1.

TABLE 1

Item Name: "ABC" (the name displayed in the Explorer panel)
High Level Item Attributes, such as ID, part number, vendor, and the like
Detailed descriptions for the sub items, such as component formulation for a reagent set, constructs for a target, and the like As illustrated in FIG. 3, in embodiments of the present invention, two explorers are provided. As illustrated the Library Explorer provides information on the library: (e.g., reagents, targets and samples) and the Experiment Explorer provides information related to the experimental results. Through selection of items in the Explorers, typically using a mouse or like input device, menus and sub-menus are opened, closed, and manipulated to display information, worksheets, input forms, output displays, and the like. The examples provided below are not the only explorer lists provided by the present invention, but are merely exemplary. In the Explorers illustrated in the figures, various examples of reagent sets or screens, targets, samples, and the like are shown for purposes of demonstration. Of course, the specific items presented in the Explorers according to embodiments of the present invention will depend on the particular applications.

Library Explorer 330—In an embodiment of the present invention, Library Explorer provides information related to the Reagent or Screens, Target and Sample. Merely by way of example the Library Explorer displays the following list in a specific embodiment of the present invention:

± Reagent Sets (icon)
    | -- Mix 1
    | -- Mix 2
    | -- Mix 3
    | -- Mix PEG
    | -- .....
± Design Templates (icon)
    | -- Optimization #1
    | -- Translation #1
    | -- .....
± Targets (icon)
    | -- alpha-lactalbumin
    | -- beta-lactoglobulin
    | -- catalase
    | -- glucose isomerase
    | -- .....
± Samples (icon)
    | -- alpha-lactalbumin #1
    | -- alpha-lactalbumin #2
    | -- catalase #1
    | -- .....
    | -- Ligands (icon)
    | -- Cofactors (icon)
± Sample Buffer Solution Templates (icon)
    | -- Buffer #1
    | -- Buffer #2
    | -- .....
± Reagent and Sample Buffer Components (icon)
± Dispensing Mapping (icon)
    | -- 96 reagent plate to TOPAZ ™ Screening Chip
    | -- 96 reagent plate to TOPAZ ™ Xray Chip
    | -- 96 reagent plate to 96 well
    | -- .....

In operating the system, when a user selects (i.e., double clicks) an item, the Experiment Manager software will display the information content of the item as a worksheet in the worksheet panel. The examples provided in the Library Explorer illustrate above are not intended to limit the present invention, but merely to provide examples of information accessible through the Library Explorer according to an embodiment of the present invention. Additional items can be added, removed, or the order in which the items are displayed can be changed without departing from the scope of the claims herein.

Utilizing the Library Explorer, a user may add a new Reagent Set, Target, Sample, and Dispensing Mapping if desired. If an item is not being referenced by another dataset, the user will be able to remove or modify an item from Reagent, Set, Target, Sample, and Dispensing Mapping. Once it is referenced by another dataset, a user can't remove the item. However, a user could perform limited modification to a referenced item. The limitation will be dependent on which item the user tries to modify, as will be explained below.

Experiment Explorer 332—In an embodiment of the present invention, the Experiment Explorer (sometimes also referred to as a Data Explorer) provides information related to the experiments performed using the automated system.

Merely by way of example the Experiment Explorer displays the following list in a specific embodiment of the present invention:

```
± Chip Runs (icon)
    | -- st001 (active icon)
    | -- st003 (active icon)
    | -- st004 (complete icon)
    | -- st005 (complete icon)
    | -- st006 (complete icon)
    | ...
    | -- st002 (Cancelled icon)
    | -- ± Templates (icon)
        | -- TOPAZ ™ #1
        | -- TOPAZ ™ #2
    | -- ± Ready-to-Run (icon)
        | -- st0010
        | -- st0011
± Crystallization Results by Targets
    | -- alpha-lactalbumin
    | -- beta-lactoglobulin
    | -- catalase
    | -- glucose isomerase
    | -- .....
± Query Reports
    | -- Mix 1 Query #1
    | -- Target Query #1
    | -- Target Query #2
    | -- .....
```

When a user selects (double clicks) an item, the Experiment Manager will display the information content of the item as a worksheet in the worksheet panel. As illustrated in FIG. 3, the Components item is selected and the Components information, for example, ComponentA and ComponentB, is displayed in the worksheet panel. The detailed specifications of the GUI contents when a user selects an item in the list are explained in the subsequent sub-sections below. The examples provided in the Experiment Explorer illustrate above are not intended to limit the present invention, but merely to provide examples of information accessible through the Experiment Explorer according to an embodiment of the present invention. Additional items can be added, removed, or the order in which the items are displayed can be changed without departing from the scope of the claims herein.

According to some embodiments of the present invention, a user may create, modify and delete a Template or Ready-to-Run chip run at any time. Additionally, users are also be able to delete a chip run as desired. In some embodiments, this deletion process involves the use of a Cancelled icon.

Reagent, Target, and Sample User Interface Specifications are provided by embodiments of the present invention as described below. With respect to the reagent set worksheet, when a user double clicks on a reagent set item in the Library Explorer, the Experiment Manager will display a Reagent Set Worksheet for the selected reagent set. In the reagent set worksheet, there will be two pages (tabs). The default one will display all the reagent set design information, and the second one will display a list of the physical reagent sets.

Figure 4:
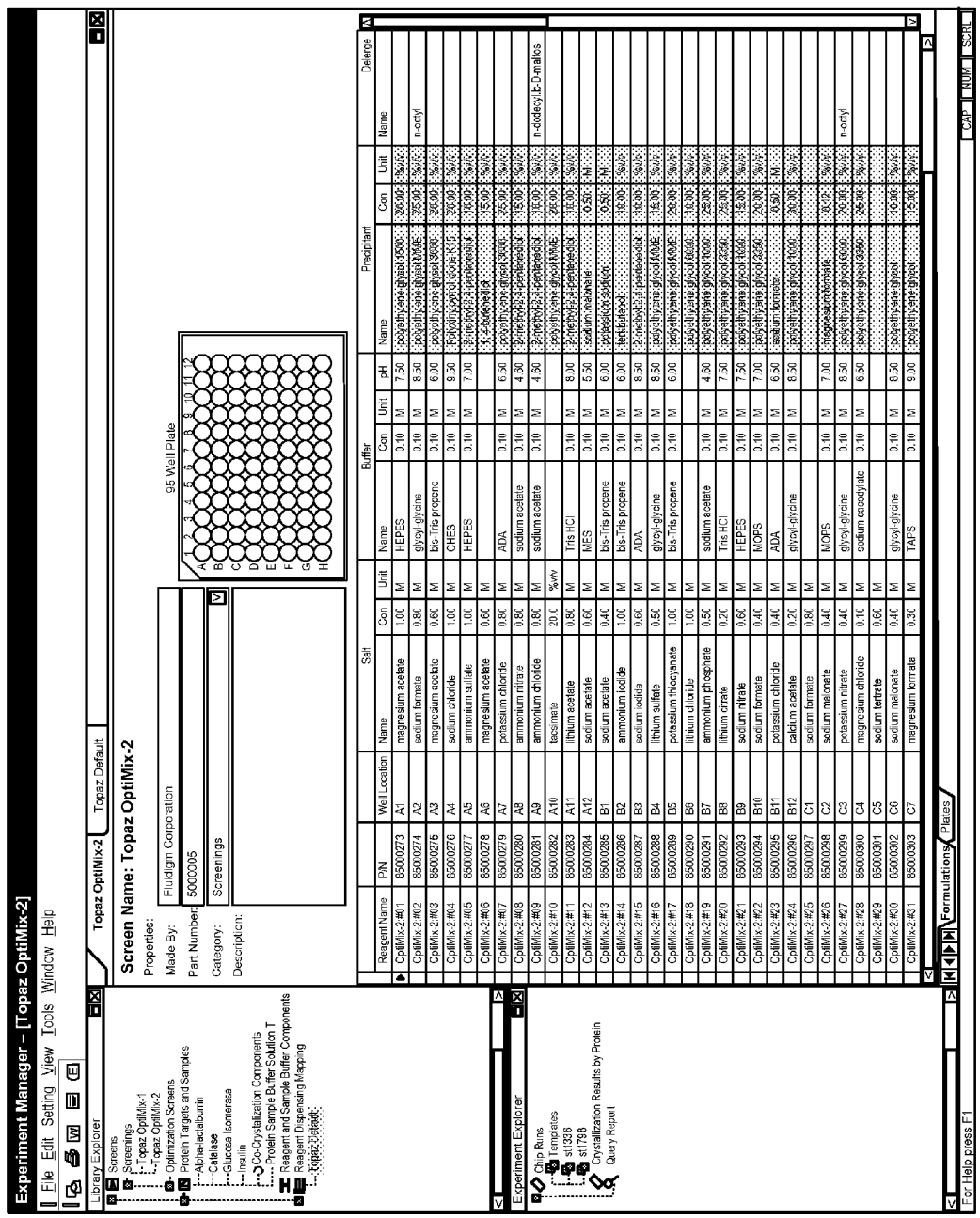
FIG. 4 is a simplified diagram illustrating a reagent graphical user interface according to an embodiment of the present invention.

FIG. 4 is a simplified diagram illustrating a reagent or screen user interface (UI) according to an embodiment of the present invention. As illustrated in FIG. 4, the layout for a reagent set design page according to an embodiment of the present invention is shown. In the reagent or screen UI shown, a table listing one or more of the reagent plates plus their attributes is displayed. Additionally, a Library and Experiment Explorer are provided as discussed above. In a specific embodiment, the reagent set design page includes a listing of all the reagent plates. Information regarding the reagent attributes is displayed in the UI, including the name, creation information, modification information, part number, vendor, and a description. Alternative embodiments, provide additional information, remove one or more information items, or present the information items in a different order without departing from the scope of the claims herein.

When a user selects a reagent plate (a row), the physical plate information will be displayed in a separate area and available for modification. A user will be able to add, remove, and modify a physical plate. Once a physical plate is reference by some other data, it can no longer be removed. There will be a generic reagent plate (default) for a given reagent set. The user cannot remove this item from the list. In a specific embodiment, if a reagent set does not include an information item, for example, Conductivity, Osmolality, or pH, that column will not be displayed. In other words, the column will be displayed only if there is data.

Depending upon the embodiment, the present methods and systems provide certain output formats, which are described in more detail below. Systems according to the present invention will also include Reagent and Sample Buffer Components Worksheets. When a user double clicks on the Reagent and Sample Buffer Components in the Library Explorer, the Experiment Manager will display the Reagent and Sample Buffer Components Worksheet. In some embodiments of the present invention, the Components Worksheet will provide a table displaying all the components used for all the reagent sets with the following attributes:

Name
Reference - If an item is referenced or is a standard name for alias(s), a reference icon will be shown.
Alias - If an item is referenced as a standard name for other alias, the standard name icon will be shown. If an item is an alias, an alias icon will be shown. If an item is not referred as the standard for an alias or it is not an alias, nothing is shown in the alias column.
Used for - The indication of whether the component is used for reagent and/or sample.
Reference ID
Description As will be evident to one of skill in the art, the attributes displayed in the worksheets are not limited to this list. In alternative embodiments, additional attributes are added, one or more attributes are removed, or one or more attributes are provided in a different order without departing from the scope of the claims herein.

A user will also be able to add a new component, remove a component (if it is not referenced), or modify a component by using the Reagent and Sample Buffer Components Worksheet. Additionally, in general, a user will be able to modify the Description, and Aliases. A user could also modify the name for the component if it is not being referenced. Additionally, a user will be able to sort on any column.

In a particular embodiment, an Aliases sub panel will display the aliases information for various components (Components Alias) with the format as illustrated in Table 2. A user will be able to add and remove an alias using this sub panel.

TABLE 2

| Standard Name | Alias |
| --- | --- |
| ABC | ABC-1 |
|  | ABC-2 |
|  | ABC-3 |
|  | ABC-4 |

TABLE 2-continued

| Standard Name | Alias |
|---|---|
| | ABC-5 |
| | ABC-6 |

Embodiments of the present invention provide a Component Stock Solution sub panel with a table displaying the list of Stock Solutions with the following attributes:

Part Number
Vendor
Component Name
Concentration
Concentration Unit
pH

As will be evident to one of skill in the art, a Stock Solution is a component solution that a user can purchase from a vendor. Each Stock Solution is associated with one component, and each component can have multiple Stock solutions (with different concentration and pH). As described in more detail throughout the specification, a user can use a software wizard to create a stock solution or import multiple stock solutions from, for example, a CSV file, as defined in the file format section.

Systems according to embodiments of the present invention will generally also include a Reagent Dispensing Mapping Worksheet. When a user double clicks on a Dispensing Mapping item in the Library Explorer, the Experiment Manager will display a Dispensing Mapping Worksheet. In a specific embodiment of the present invention, this worksheet displays the following items:

Attributes
Generally, there will be two sections or plates displayed, a Reagent Plate section and a Chip/Plate - Topaz section. In the reagent plate (source) and chip/plate (destination), the graphics will indicate whether a well is mapped (both in source and destination plate) or not. In a specific embodiment, all the wells in the destination chip/plate will be mapped. Additionally, there will typically be a list of well-to-well maps. When a user clicks on the list, the user will be able to see the wells highlighted in both the source and destination plates.

As will be evident to one of skill in the art, the items displayed in the worksheets are not limited to this list. In alternative embodiments, additional items are added, one or more items are removed, or one or more items are provided in a different order without departing from the scope of the claims herein.

The Dispensing Mapping Worksheet will operate as follows in a particular embodiment according to the present invention. A user will not be able to modify the name, reagent plate format, and chip run plate format once the dispensing mapping is referenced. The user can modify (e.g., correct a mistake) the mapping (well-to-well) after receiving a warning from the system. Generally, there are two modes in this worksheet: editing mode and view only mode. During operation in the view only mode, the user can only view the mapping information.

Systems according to embodiments of the present invention will generally also include a Target worksheet or UI that typically includes three display segments: Target Attributes; Constructs; and Samples. The Constructs segment will provide a list of constructs with their attributes. The user will be able to create, delete, and modify a construct through this UI. However, once a construct is referenced, it cannot be removed and user can only modify its sequence and description attributes. Additionally, there will be a default construct (full length) for each target. The construct attributes according to an embodiment of the present invention are:

Name: Full Length
Reference ID:
Sequence: Same as the target.
Description: Default construct for the target [name of the target].

A user will be able to modify the Reference ID and Description in some embodiments of the present invention. The full length construct cannot be deleted from the list in some embodiments of the present invention.

The samples segment of the Target worksheet will generally contain a list of all the samples that contain the target. In an embodiment, the display attributes are:

Name
Barcode ID
Construct

When a user selects (single clicks) on the sample tab in the protein target worksheet, a list of protein samples will be displayed that contain the protein target. Additional details are discussed in relation to the Sample worksheet below.

In an embodiment of the present invention, when a user double clicks on the Ligand in the Library Explorer, the Experiment Manager will display the Ligand Worksheet or UI. In the Ligand Worksheet, there will be a table displaying all the ligands currently in the system with the following attributes:

Name
Reference ID
Description

The user will also be able to add a new ligand, remove a ligand (if it is not referenced), or modify a ligand through this UI. The user will also be able to modify the Reference ID, and Description. The user could also modify the name for the ligand if it is not being reference.

When a user double clicks on the Cofactor in the Library Explorer, the Experiment Manager will display the Cofactor Worksheet or UI. In the Cofactor Worksheet, there will be a table displaying all the cofactors currently in the system with the following attributes:

Name
Reference ID
Description

The user will also be able to add a new cofactor, remove a cofactor (if it is not referenced), or modify a cofactor through this UI. The user will also be able to modify the Reference ID, and Description. The user could also modify the name for the cofactor if it is not being reference.

According to some embodiments, there will be two display sections for the Sample Buffer Solution Template Worksheet or UI. The first part of the UI displays: Buffer Solution Name and Description. The second part displays a list of the following attributes:

Component Name
Component Type
Component Concentration
Component Concentration Unit
Component pH.

The user will also be able to create a new buffer solution, remove a buffer solution (if it is not referenced), or modify a buffer solution by using this UI. The user will be able to modify the ID, and Description. A user will also be able to modify the name for the buffer solution if it is not being reference.

In some embodiments, the Sample Worksheet or UI will have three display segments: Sample Attributes; Constructs, Cofactor, and Ligand; and Sample Buffer Component. These segments include the following elements:

Sample Attributes
    Name
    Barcode ID
    Vendor (who made it)
    Part Number
    Description
    Number of constructs
    Number of cofactors
    Number of ligands
    Number of Components Constructs, Cofactor, and Ligand—A list displays the construct, cofactor and ligands with the following attributes:

Constructs
    Target Name/Construct Name
    Construct Concentration
    Construct Concentration Unit
Cofactor
    Cofactor Name
    Cofactor Concentration
    Cofactor Concentration Unit
Ligand
    Ligand Name
    Ligand Concentration
    Ligand Concentration Unit The graphic display for the Sample Worksheet will be similar to Table 3. Of course, one of ordinary skill in the art would recognize many variations, modifications, and alternatives.

TABLE 3

| Type | Name | Concentration | Unit |
|---|---|---|---|
| Target/Construct | Catalase/Full Length | 25 | mg/ml |
| Cofactor | ABC | 30 | mg/ml |
| Ligand | CDF | 50 | mg/ml |

Sample Buffer Component—The Sample Buffer Component will include the Sample Buffer Solution Template Name (if it exists) and a list of components with the following attributes:

Component Name
Component Type
Component Concentration
Component Concentration Unit
Component pH.

When a user creates a new sample, it can be created from, for example, a CSV file or it can be created by a new wizard. In an embodiment of the present invention, the wizard to create a new sample is constructed as follows:

Identifiers
    Name
    Barcode ID
    Vendor (who made it)
    Part Number
    Description
Targets
    Number of constructs
    Target Name
    Construct Name
    Construct Concentration
    Construct Concentration Unit
Ligands
    Number of Ligands
    Ligand Name
    Ligand Concentration
    Ligand Concentration Unit
Cofactors
    Cofactor Name
    Cofactor Concentration
    Cofactor Concentration Unit
Buffer Solution
    Select an existing buffer solution
Components
    Number of Components
    Component Name
    Component Type
    Component Concentration
    Component Concentration Unit
    Component pH If a user selects an existing sample buffer solution template, the information will be filled in automatically. In the Worksheet, the user will be able to manually enter all the required information. When a user selects the Target name, Construct name, Ligand Name, Cofactor Name and Component Name, there will be a dropdown list box for available for the specific data. When a user edits the Unit cell, there will be a dropdown list, but user will be able to add a new unit.

Embodiments of the present invention provide a Chip Run interface. A Chip Run Creation template is also provided, including the following information:

Chip run name (also used as Chip run template name)
Crystallization Method (e.g., TOPAZ ™, Vapor Diffusion) (Optional)
Chip Type (e.g. 1.96, 4.96, 8.96, X-ray chip or 96 microtiter plate) (Optional)
Reagent Set (Optional)
Reagent Dispensing Mapping (Optional)
Incubation Temperature (Optional)
Hydration Level (Optional)
Destination file location (Optional)
Number of scans and time (Optional)

A Chip Run Template may be created by using a wizard with the following steps:

Template Name
Crystallization Method (e.g., TOPAZ ™, Vapor Diffusion) (Optional)
Chip Type (e.g., TOPAZ ™ 1.96, 4.96, 8.96, X-ray chip or 96 microtiter plate) (Optional)
Reagent Set (Optional)
Reagent Dispensing Mapping (Optional)
Incubation Temperature (Optional)
Hydration Level (Optional)

-continued

Destination file location (Optional)
Number of scans or images and time (Optional)

Additionally, a Chip Ready-to-Run Template is created with the same information as found in the as the Chip Run Template, except that all the fields, except the number of scans and time, have to be defined. The Chip Ready-to-Run Template is created using a wizard with the following steps:

Initial Entries
    Chip Run Name
    Select a Chip Run Template (Optional)
    Owner of the Chip Run
Additional Entries
    Same as the steps in the Chip Run Template wizard, except that the user has to enter all the information with the exception of the Hydration level, which is still Optional.

If a Chip Run template is selected, a user will still guided through all the steps with the information pre-populated in some or all of the fields.

When a user double clicks on a Template item in the Experiment Explorer, a Chip Run template worksheet will be opened. All the Chip Run template information will be displayed and editable. The display format will follow the worksheet GUI guideline defined previously.

When a user double clicks on a Ready-to-Run item in the Experiment Explorer, a Chip Run Ready-to-Run worksheet will be opened. All the Chip Run Ready-to-Run information will be displayed and editable. The display format will follow the worksheet GUI guideline defined previously. Essentially, the Ready-To-Run and Template worksheets are the same, except the title of "Name" part. For the Template, it is "Chip Run Template Name.". For the Ready-To-Run, it is the "Chip Run Name." In this worksheet, a user will be able to save a Ready-to-Run to a HTML file or View the HTML file with the Internet Explorer (IE) and then print the HTML file with IE. The purpose for this HTML file is for user to follow the instructions to prepare and to run the chip.

When a user double clicks on an Active, Completed or Cancelled icon in the Experiment Explorer, a Chip Run worksheet will be opened. In a specific embodiment, this worksheet contains two display sections. The first section displays the complete chip run information defined in the "Chip Run Information." The second section displays the summary experiment results, presented in the format illustrated in Table 5.

The report settings are defined by the "Chip Run Worksheet" Settings. The Crystal A, Crystal B, and Crystal C are examples of user classification. The actual display will depend on the user classification defined in the database. The color of the circles (for user classification) or squares (for auto classification) will be determined from the classification settings defined in the Classification Setting.

A variety of operations are available using this worksheet. For example, a user will be able to sort on any column. When a user sorts the Result column, the sorting order will following the User Ranking defined by the Classification Setting. The user will also be able to print this work sheet (including both display sections). Other operations include:

Select a row and launch Crystal Vision for viewing the image for the given condition.

Select a Sample and open the Sample Worksheet.

Select a Reagent and open the Reagent Set Worksheet.

Select any number of rows and generated a query results (See Experiment Result Query for details).

According to embodiments of the present invention, the user will be able to select multiple chip runs in the Experiment Explorer, and then create a Multiple Chip Run worksheet. This worksheet displays a chip run summary result table defined as illustrated in Table 6.

TABLE 5

| Result | Chip Run | Crystallization Method | Sample | Reagent | Reagent Set | Day 1 | Day 2 | Day 3 | Day 5 | Day 7 | Overall | Started On | Duration |
|---|---|---|---|---|---|---|---|---|---|---|---|---|---|
| Crystal A | ST001 | Topaz Screening | SA1 | OptiMix 1: #1 | OptiMix 1 |  | 1 |  |  |  | 1 | Nov. 30, 2004 | 6 days |
| Crystal A | ST001 | Sitting Drop | SA2 | OptiMix 1: #2 | OptiMix 1 |  |  |  | 1 |  | 1 | Dec. 1, 2004 | 7 days |
| Crystal B | ST001 | Topaz Screening | SA1 | OptiMix 1: #3 | OptiMix 1 |  | 1 |  |  |  | 1 | Dec. 2, 2004 | 5 days |
| Crystal B | ST001 | Topaz Screening | SA1 | OptiMix 1: #4 | OptiMix 1 |  |  | 1 |  |  | 1 | Dec. 3, 2004 | 8 days |
| Crystal B | ST001 | Sitting Drop | SA3 | OptiMix 1: #5 | OptiMix 1 | 1 |  |  |  |  | 1 | Dec. 4, 2004 | 3 days |
| Crystal C | ST001 | Sitting Drop | SA4 | OptiMix 1: #6 | OptiMix 1 |  |  |  |  | 1 | 1 | Dec. 5, 2004 | 2 days |

TABLE 6

| Chip Run | Crystallization Method | Chip Type | Sample | Reagent Set | # of Auto Crystal | # of Crystal A | # of Crystal B | # of Crystal C | Started On | Duration (Days) |
|---|---|---|---|---|---|---|---|---|---|---|
| ST001 | TOPAZ ™ Screening | TOPAZ ™ 4.96 | SA1 | OptiMix1 | 3 | 2 | 0 | 0 | Nov. 1, 2004 | 6 |
| ST001 | Sitting Drop | TOPAZ ™ 4.96 | SA2 | OptiMix1 | 3 | 2 | 0 | 0 | Nov. 1, 2004 | 6 |
| ST001 | TOPAZ ™ Screening | TOPAZ ™ 4.96 | SA3 | OptiMix1 | 3 | 2 | 0 | 0 | Nov. 1, 2004 | 6 |
| ST001 | TOPAZ ™ Screening | TOPAZ ™ 4.96 | SA4 | OptiMix1 | 3 | 2 | 0 | 0 | Nov. 1, 2004 | 6 |
| ST002 | Sitting Drop | TOPAZ ™ 1.96 | SA5 | OptiMix2 | 4 | 1 | 3 |  | Nov. 1, 2004 | 7 |
| ST003 | Sitting Drop | Wall Plate | SA6 | OptiMix4 | 3 |  |  | 3 | Nov. 2, 2004 |  |

The report settings are defined by the "Chip Run Worksheet" Settings. The Crystal A, B, and C are examples of user classifications. The actual display will depend on the user classifications defined in the database. There can be additional User and System information reported, as defined by the Chip Run Worksheet Settings. The operations for this worksheet are the same as the ones defined in the Single Chip Run worksheet.

When a user double clicks on a Target result in the Experiment Explorer, a Target Result worksheet will be opened. This worksheet will contain two display sections. The first section displays the target information (without the constructs). The second section displays the crystallization results in the format illustrated in Table 7.

TABLE 7

| Target | Construct | Ligand | Cofacert | Sample | Reagent | Reagent Set | Crystallization Method | Crystal A At | Crystal B At | Crystal C At | Chip Run | Started On | Duration |
|---|---|---|---|---|---|---|---|---|---|---|---|---|---|
| BSGCAIR30322 | Full length |  |  | SA 1 | Reagent #1 | OptiMix 1 | Topaz Screening | 2.5 |  |  | ST001 | Nov. 11, 2004 | 6 days |
| BSGCAIR30322 | Full length |  |  | SA 2 | Reagent #1 | OptiMix 1 | Sitting Drop | 3.5 |  |  | ST004 | Nov. 12, 2004 | 7 days |
|  |  |  |  | ... |  |  | ... |  |  |  |  |  |  |
|  |  |  |  | ... |  |  | ... |  |  |  |  |  |  |

The report settings are defined by the "Target Result Worksheet" Settings. The Crystal A, B and C are examples of user classification. The actual display will depend on the user classification defined in the database. Operations for this worksheet include:

Sort on any column.
Print this worksheet (including both display sections).
Select a row and launch Crystal Vision for viewing the image for the given condition.
Select a Sample and open the Sample Worksheet.
Select a Construct and open the Target Worksheet.
Select a Ligand and open the Ligand worksheet.
Select a Cofactor and open the Cofactor worksheet.
Select a Reagent or a Reagent set and open the Reagent Set Worksheet.
Select a Chip run and open the Chip Run Worksheet.
User will be able to select any number of rows and generated a query results (See Experiment Result Query for details).

The user will be able to select multiple targets in the Experiment Explorer, and then create a Multiple Target worksheet. The multiple target worksheet displays the crystallization result table, which is identical to the table defined in the Single Target Worksheet. There will be multiple targets in the table.

Embodiments of the present invention provide for formatting of database query results. For example, when a user perform an experiment query through any mechanism, the following information will be displayed:

Sample Information
    Sample Name
    Sample Barcode ID (physical if any)
    Target(s)
    Construct(s)
    Construct Concentration(s)
    Construct Unit(s)
    Ligand(s)

-continued

Ligand Concentration(s)
    Ligand Unit(s)
    Cofactor (s)
    Cofactor Concentration(s)
    Cofactor Unit(s)
    Sample Component
        Component Name(s)
        Component Concentration(s)
        Component Unit(s)
        Component pH(s)
Reagent Information
    Reagent Name
    Reagent Set Name
    Reagent Plate Barcode ID (physical if any)
    Reagent pH
    Reagent Conductivity
    Reagent Osmolality
    Formulation
        Component Name(s)
        Component Concentration(s)
        Component Unit(s)
        Component pH(s)
Chip Run Information
    Chip run name (also used as Chip run template name)
    Chip Type (e.g., TOPAZ ™ 1.96, 4.96, 8.96, X-ray chip or 96 microtiter plate)

-continued

```
Crystallization Method (e.g., TOPAZ ™, Sitting Drop, Hanging
Drop, Microbatch and Other)
    Incubation Temperature
    Hydration Level
    FID Time
    Duration
Experiment Result
    User Classification #1 At (days)
    User Classification #2 At (days)
    User Classification #3 At (days)
    . . . (the number of User Classification will depend on the number of
    user classification available)
    Auto Crystal At (days)
```

In the "Query Result Settings" dialog, the user can customize the format with which data is reported. For example, a user can remove all the Chip Run information and the Sample Component information. Of course, depending on the particular application, a user will preferentially select the information to be displayed.

The Query Report Worksheet contains two display sections. The first part displays the report name, and Query criteria used for the query. The second part displays the experiment results for each conditions found. The table header will consist of three rows for the required display hierarchy. One operation provided is the ability to export the data to a CSV file.

For a predefined query, at the end of the query, as defined below, a query report worksheet will be generated. For example, a Reagent Set Data Analysis Wizard according to an embodiment of the present invention is provided as follows:

```
Select a reagent set.
Define the Chip Run criteria (AND relationship)
    Dates
    Targets
    Crystallization Method
    Experiment Parameter (FID, Hydration level, and incubation
    temperature)
Define the interested experiment results (User calls and Auto calls)
Find all the reagents meeting the criteria defined in Step #1.
Find all the chip runs containing the reagents found in Step #4 and also
meet the criteria in 2.
Define an Analysis Report Name. Default as "Untitled #1, . . .
Create a Query Report Worksheet.
```

In some embodiments, the last four steps are automatic, with no user intervention required.

Additionally, a Reagent Data Analysis Wizard according to an embodiment of the present invention is provided as follows:

```
Select a reagent or a number of reagents. Choose whether other reagents
with same composition but different concentration and pH will be search
or not.
Define the Chip Run criteria (AND relationship)
    Dates
    Targets
    Crystallization Method
    Experiment Parameter (FID, Hydration level, and incubation
    temperature)
Define the interested experiment results (User calls and Auto calls)
For all the reagents with same composition (precipitate and salt) but
with different concentration and pH if the option is chosen.
Find all the chip runs containing the reagents found in 4 and also meet
the criteria in 2.
Define an Analysis Report Name. Default as "Untitled #1, . . .
Create a Query Report Worksheet.
```

In some embodiments, the last four steps are automatic, with no user intervention required.

Additionally, a Component Data Analysis Wizard according to an embodiment of the present invention is provided as follows:

```
Select a component or a number of components.
Define the concentration range for each component. User can add pH
range as a constraint as well.
Define the Chip Run criteria (AND relationship)
    Dates
    Targets
    Crystallization Method
    Experiment Parameter (FID, Hydration level, and incubation
    temperature)
Define the interested experiment results (User calls and Auto calls)
For all the reagents containing the component(s).
Find all the chip runs containing the reagents found in 4 and also meet
the criteria in 2.
Define an Analysis Report Name. Default as "Untitled #1, . . .
Create a Query Report Worksheet.
```

In some embodiments, the last four steps are automatic, with no user intervention required.

Additionally, a Component Sub-Name Data Analysis Wizard according to an embodiment of the present invention is provided as follows:

```
Define a component sub-name.
Define the concentration range for the searched component(s). User can
add pH range as a constraint as well.
Define the Chip Run criteria (AND relationship)
    Dates
    Targets
    Crystallization Method
    Experiment Parameter (FID, Hydration level, and incubation
    temperature)
Define the interested experiment results (User calls and Auto calls)
For all the components containing the sub-name, and then find all the
reagents containing the components.
Find all the chip runs containing the reagents found in 4 and also meet
the criteria in 2.
Define an Analysis Report Name. Default as "Untitled #1, . . .
Create a Query Report Worksheet.
```

In some embodiments, the last four steps are automatic, with no user intervention required.

For a custom database query, the user will be able to:

```
Select a list attributes from reagent, target/construct, ligand, cofactor,
sample, and chip runs,
Define the criteria for each attribute
Define how to combine these attributes (AND or OR)
```

A Reagent Set Template Worksheet consists of three display sections, similar to a reagent set. The top left section describes the Reagent Template Attributes and includes:

```
Template Name
Number of Partitions
Attributes for Each Partition (concentration and pH changes for
component or component type)
Description
```

The top right section displays a 96 well plate graphics, such as the graphic illustrated in FIG. 5. The bottom section displays the dispensing scheme for the components as illustrated in Table 8. In a specific embodiment, Table 8 contains rows for 12 samples, but this is not required by the present invention.

TABLE 8

| Well | Component #1 | Component #2 | Component #3 | Water |
|---|---|---|---|---|
| A1 | 10 | 20 | 30 | 10 |
| A2 | | | | |
| A3 | | | | |
| A4 | | | | |

Additionally, a Reagent Set Template Creation Wizard according to an embodiment of the present invention is provided as follows:

Define the Template Name
Define the number of region, the size of each region and the location of each region.
Define the number of components or number of component types.
Iterate through each region, define the component or component type is used for each region, and how the concentration or pH changes required. The change can be linear or log.

Additionally, a Reagent Set Creation from a Reagent Set Design Template Wizard according to an embodiment of the present invention is provided as follows:

Identify the reagent components. The components can be defined from a crystallization condition.
Select a Reagent Set Design Template
Mapping the components to the components in the template. If the template is defined using component type, this step is not needed.
Find the Component Stock Solutions required for the components.
Calculate the dispensing from Component to reagent formulation.
Create a new reagent set.

Embodiments of the present invention provide for a variety of system settings. For example, classification settings are provided using the same dialog as the "Default Settings" in the Crystal Vision to define the User and Auto Classification settings. Additionally, Chip Run Result settings are provided to define the data reporting, including what user and auto classification will be reported in a Chip Run result worksheet. In this setting dialog, the user will be able to select the classification types, which will be used for both Single Chip Run and Multiple Chip Runs worksheets as follows:

Classification
  Crystal (Auto Classification)
  User Classification #1 (Say, Crystal A)
  User Classification #2 (Say, Crystal B)
  ...

For the Multiple Chip Run worksheet, additional Experiment Parameters, User information and System Information can be selected as follows. In some embodiments, the User Information and System Information are only provided for the Multiple Chip Runs Worksheet.

Experiment Parameter
  Incubation temperature
  Hydration level
  FID Time
User Information
  Owner of the chip Run
  Annotated by
  Approved by
  Status
System Information FID System Information
Imaging System Information The User Classifications are all the user classifications defined in the Classification Settings. The default setting is the Crystal of Auto Classification and all the User Classifications of Crystal Type.

Target Result Settings are provided to define the data reporting, including what user and auto classification will be reported in a Target result worksheet. In this setting dialog, user will be able to select the classification types and user information as follows Classification
  Crystal (Auto Classification)
  User Classification #1 (Say, Crystal A)
  User Classification #2 (Say, Crystal B)
  ...
User Information
  Owner of the chip Run
  Annotated by
  Approved by
  Status The default setting is the Crystal of Auto Classification and all the User Classifications of Crystal Type.

Query Result Settings are provided to define the type of data that will be reported in some embodiments of the present invention. There will be a list (tree view) with a "Check Box" for each item defined in the "Database Query Result Format" section.

A user may use the Import Chip Run function to import data acquired outside the Database Application. For example, data acquired during periods prior to the use of the Database Application by a user may be imported using this function. An Import Chip Run Wizard according to an embodiment of the present invention is provided as follows:

Select the import type: CSV file or Chip Run.

An Import Chip Run Wizard from, for example, a CSV file is also provided as follows:

Select a CSV file
Import all chip runs defined in the CSV file.

An Import Chip Run Wizard from Chip Run is further provided as follows:

Select a Chip Run - The wizard will automatically determine the number of samples required for the chip run from an experiment INE file.

In a specific embodiment of the present invention, if the sample does not exist in the database, the wizard will automatically create a sample. However, in this embodiment, the reagent set and the reagent dispensing mapping must already exist in the database. The number of samples defined will match the number of sample inlets in the chip run. If a user does not enter a sample for a given inlet, a blank sample will be created.

Preferably, the database will hold at least 4 million experiments (e.g., 10,000 4.96 chip runs) with system performance measured by the following metrics:

Response time for retrieving a data item in the Library Explorer will preferably be less than 1 second.
Response time for retrieving the crystallization result for a given chip run will preferably be 10 second or less for the response time.
Response time for retrieving the crystallization result for a given target will preferably be linearly related to the number of chip runs performed with the given target.

Additionally, users will be allowed to open multiple instances of the Experiment Manager on different computers at the same time. In an embodiment of the present invention, the Experiment Manager will use the first come/first served principle for the write access on any data. In some embodiments, an optimistic update (or protected) write model will be utilized. In this model, when data is opened, a time stamp will be created for the opening of the data, thereby noting the last time the data has been modified. Subsequently, when a write command is received, a comparison will be made between the time stamp for the open operation and the time stamp associated with the data at the time of the write operation. If the time stamps are equal (meaning the data has not been modified since the open operation), then the update will be accomplished. If the time stamps are not equal, then the data updating will not be performed, in order to not overwrite the modifications made since the open operation was performed. The same principle will be applied to other software components (e.g., software associated with the FID Crystallizer) as well. In general, only one Experiment Manager will have the write access to the Database at any one time.

FIG. 5 is a simplified diagram illustrating a Screen Plate Creation GUI according to an embodiment of the present invention. Information related to the reagents or screens is entered and provided in this GUI, including information related to salts, precipitants, and buffers. In a specific embodiment, the concentration variation for a particular salt, precipitant, and/or buffer is illustrated both graphically and numerically. As illustrated in FIG. 5, a color coded template 510 illustrates the variation of salt and precipitant concentration as a function of position over a plate. Section 520 of the GUI is utilized by a user to view and/or modify the variables in a particular region of the plate, for example Regions 1 through 4. The components of the selected salts, precipitants, and buffers are illustrated with the start and end percentage change, along with the actual variation measured in physical units.

Merely by way of example, section 520 illustrates the salt sodium acetate varying in concentration from 40% to 100% over a region as the salt concentration in a row is incremented from 0.16 M to 0.4 M. Likewise, the precipitant 1,4-butanediol is varied in concentration from 40% to 100% over the same region as the precipitant concentration in a column is incremented from 6 to 15% volume/volume. Selection of various regions in the GUI will provide for viewing and/or modification of the variables selected for that particular region.

Figure 6A:
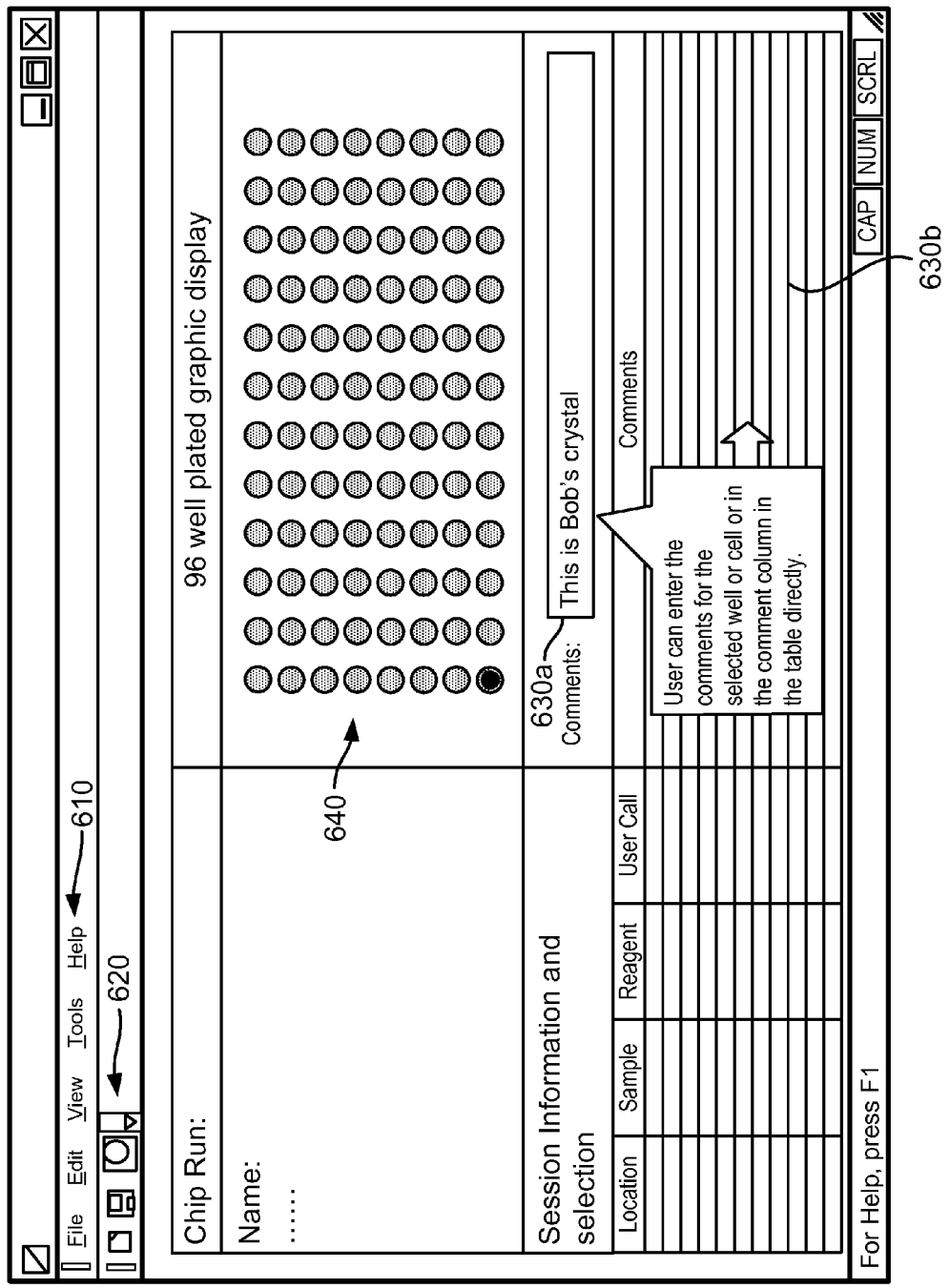
FIGS. 6A-6D are simplified diagrams illustrating additional graphical user interfaces according to an embodiment of the present invention.
Figure 6B:
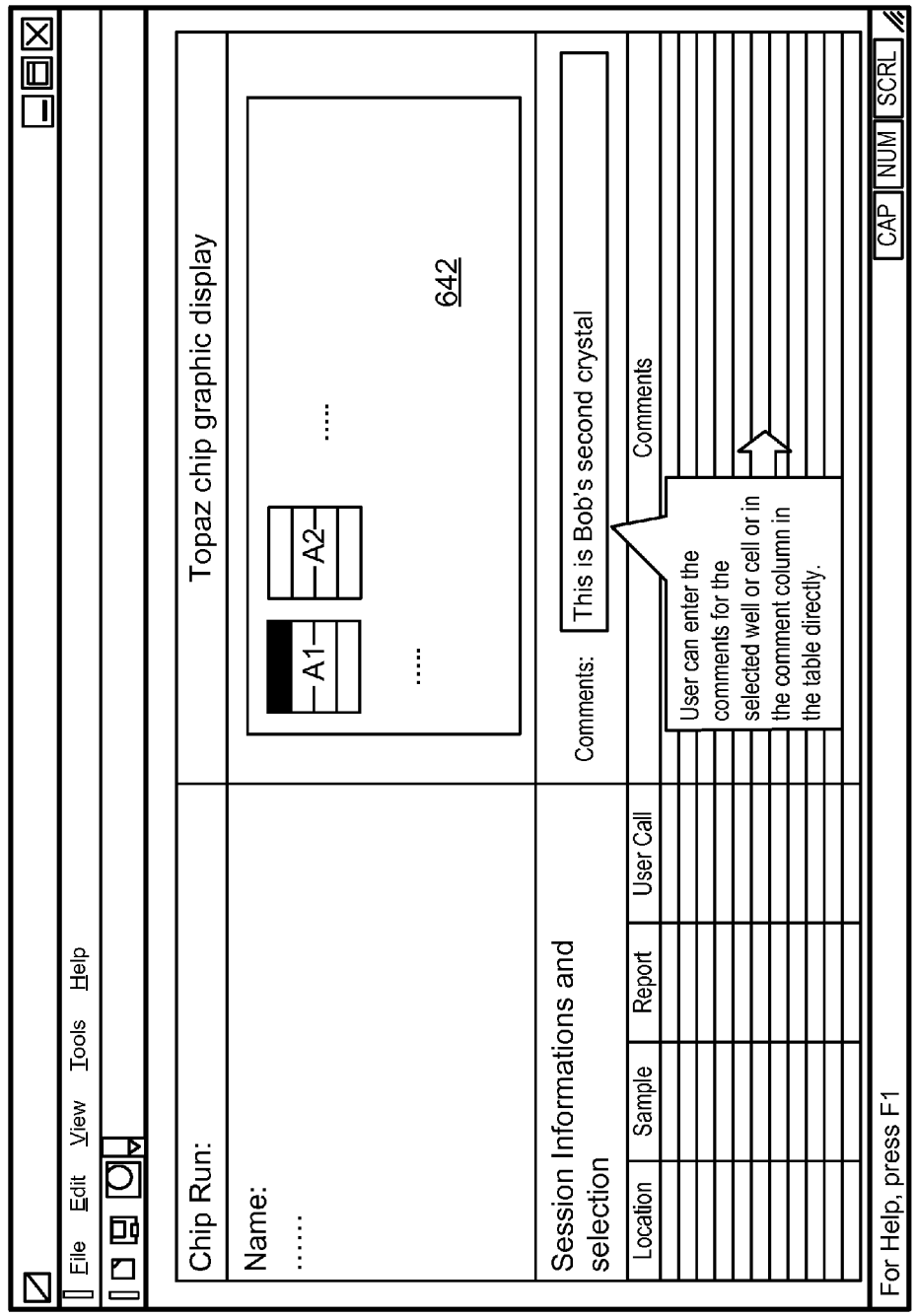

As discussed previously, embodiments of the present invention provide a Score Card utilizing a GUI. The following functional specifications and description of the Score Card, for example, a TOPAZ™ Score Card, is provided as an exemplary embodiment. As illustrated in FIGS. 6A and 6B, the figures are not drawn to scale, but merely represent the style of the GUI layout, not any particular dimensions associated with a specific GUI layout for the Score Card.

FIGS. 6A through 6D are simplified diagrams illustrating additional graphical user interfaces according to an embodiment of the present invention. FIG. 6A illustrates an example of a GUI layout for the Score Card according to an embodiment of the present invention. As illustrated, a menu 610, tool bar 620, and a graphic/annotation area 630 are provided. In the graphic/annotation area 630, a user can enter comments for a selected well or cell in the comment box 630a or in the table 630b directly. FIG. 6B illustrates an example of a GUI layout for an Overall Score Card for microfluidic chips, (e.g., TOPAZ™ Chips) according to an embodiment of the present invention. As illustrated, a number of TOPAZ™ Chips may be displayed on this Overall Score Card.

In the embodiment illustrated in FIGS. 6A and 6B, the Score Cards provide a number of menus 610. In alternative embodiments of the present invention, additional menus are provided, additional menus are provided in different orders, or one or more menus are removed without departing from the scope of the claims herein. Moreover, in certain embodiments, additional menu items are provided, additional menu items are provided in different orders, or one or more menu items are removed without departing from the scope of the claims herein.

In a specific embodiment of the present invention, the menus 610 include the following top level menus:

File
Edit
View
Tools
Help

The File menu includes the following functions according to an embodiment of the present invention:

Database Log-off
Open - Open a chip run from a microfluidic device Database
Save - Save the current chip run into one or more memories of a computing system
Export... - Export the data in the current worksheet to, for example, a CSV file.
Exit The Edit menu includes the following functions according to an embodiment of the present invention:

Create a New Session
Allow user to create a new "scan" session.
Clear
Clear All

The View menu includes the following functions according to an embodiment of the present invention:

Classification Settings...
Prompt the same dialog as the "Default Settings" in the Crystal Vision to view the User Classification Settings.
Show/Hide Tool Bar
Show/Hide Status Bar
Refresh The Tools menu includes the following functions according to an embodiment of the present invention:

Notepad
Paint Brush
Windows Explorer

The Help menu includes the following functions according to an embodiment of the present invention:

About Score Card...
Fluidigm on the Web
User Guide...

The toolbar 620 contains the most used operations defined under the menus. In a specific embodiment, the toolbar will contain:

File Open
File Save
Export

In some Score Cards, a status bar 650 contains the following information according to an embodiment of the present invention:

Current User
Date and Time

Referring to FIGS. 6A and 6B, the layout 642 and annotation 660 sections of the Score Card GUI are utilized as follows. When a user views a specific microfluidic chip, for example, a TOPAZ™ Chip, the well plate graphic 640 will be replaced by a microfluidic chip graphic layout 642 as illustrated in FIG. 6B. In some embodiments, the other elements in the Score Card GUI remain unchanged when the microfluidic graphic layout 642 replaces the 96 well graphic display 640.

In utilizing the Score Card, no explicit scan session is provided as in the Image Acquisition process. However, a user can still create a list of manual scan sessions in order to keep track of the experiment result over time. For example, a user can create a manual scan session on a per day basis, and examine the chip run and enter the crystallization of the chip run on a per day basis. Embodiments of the present invention provide for communicate between the Score Card and the Database 250 through the Database Application Server 252.

Figure 6C:
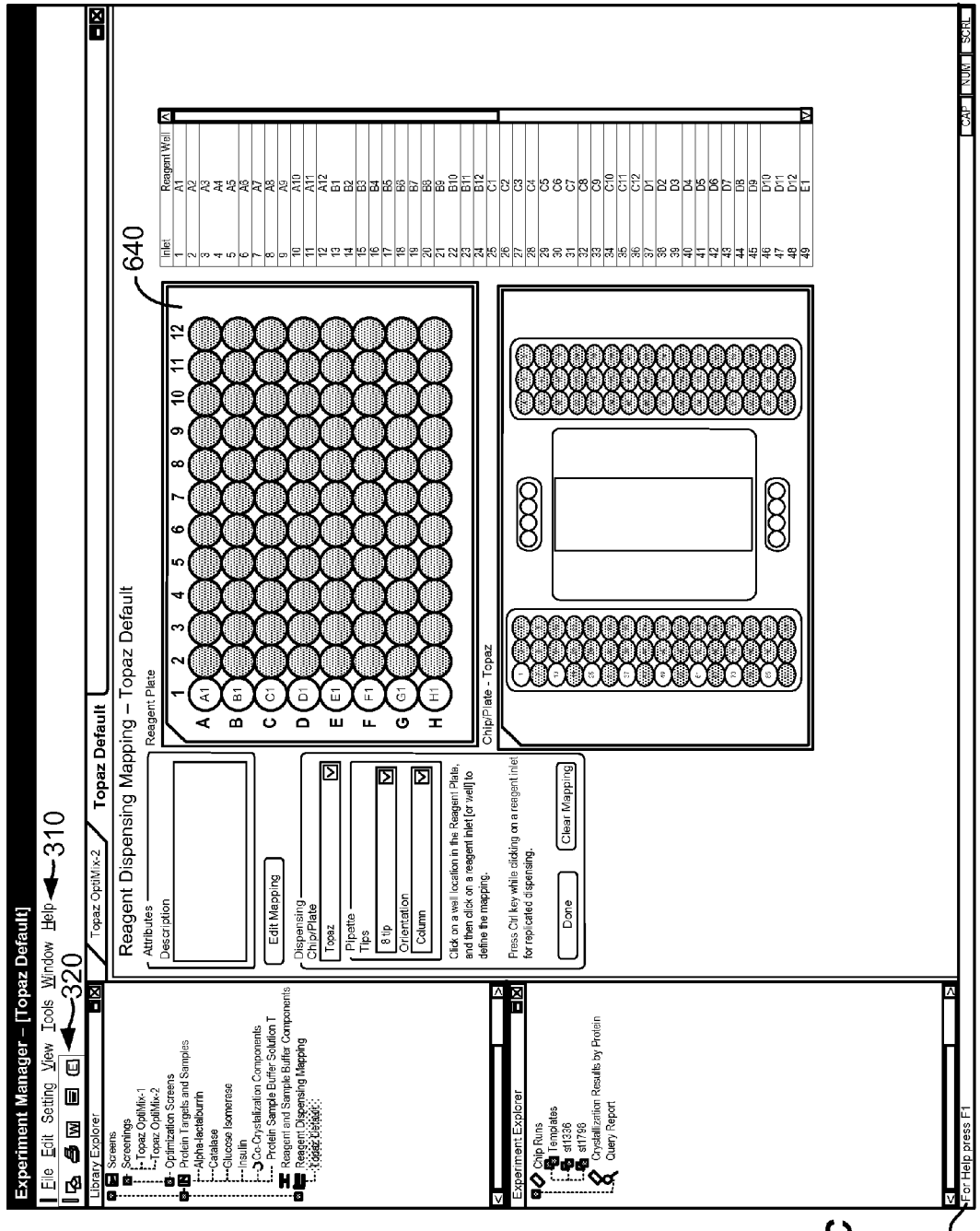

FIG. 6C is a simplified diagram illustrating an Experiment Manager GUI according to another embodiment of the present invention. In this GUI, a menu bar 610, a toolbar 620 and a status bar 650 are provided as discussed above. Additionally, a Library and Experiment Explorer are provided. In the worksheet area 640, a reagent dispensing mapping is illustrating, including a mapping for a reagent plate as well as a microfluidic chip, for example, a TOPAZ™ chip. Selection by a user of an inlet, for example, inlet 1, will result in the display of the reagent well, for example, reagent well A1, mapped to that inlet. The dispensing mapping may be both viewed and edited through this GUI by clicking on a well location in the Reagent Plate and then clicking on a reagent inlet (or well) to define the mapping.

Figure 6D:
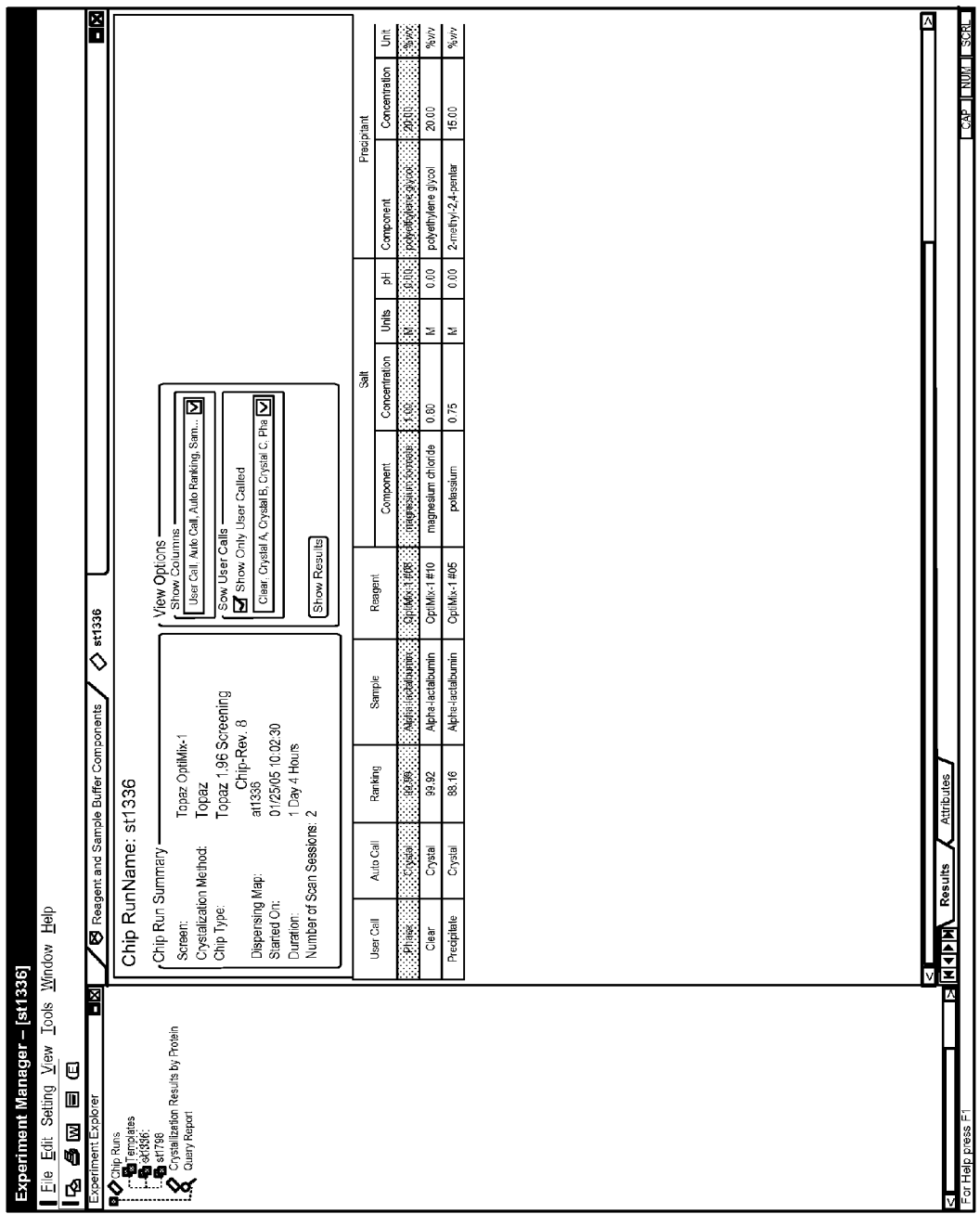

FIG. 6D is a simplified diagram illustrating an Chip Run GUI according to yet another embodiment of the present invention. The Results tab of the Chip Run Worksheet displays a variety of information related to the results of the Chip Run. In a specific embodiment, a Chip Run Results Summary section displays information including the reagent or screen name, the crystallization method, the chip type, and the Dispensing Map among other information. Moreover, a section including pull-down menus provides for the user to select the particular information that will be displayed using the interface. Protein crystallization process results, including crystal ranking along with information related to the conditions of the protein crystallization process (e.g., protein sample, reagent, components and concentration of the salt, and the like) are displayed for viewing by the user.

Embodiments of the present invention provide for enhancements to the FID Crystallizer (FIDX) as part of the Database Application. For example, a user is able to connect/disconnect the FIDX from the Database. One example of an operation provided by embodiments of the present invention is that when the FIDX is connected to the database, the user list will be provided by the database, not the local FID database.

Additionally, when the FIDX logs in to the Database and a user performs a Reagent and Sample loading process, the FIDX will perform a check to see whether the chip is already associated with a Chip Run or not as outlined in an embodiment according to the present invention by the following steps:

1. If yes, proceed to perform the loading and update the Database with the FID system information.
2. If no:
   Query the Database to get the "Ready-to-Run" list, and select a chip run from the list. If the chip run was not created in advance, ask the user to create a chip run for the chip.
   Go to 1.

After performing these steps, the chip will be associated with a Chip Run in the Database. After performing the FID, the FIDX will update the Database with the FID time and FID system information.

Due to the multi-tasking nature of the FIDX as provided in embodiments of the present invention, there is no explicit user login and logoff from Database. The FIDX will automatically perform a Database login just before a user starts the Loading and FID processes. Whether a user needs to enter his/her password will depend on the User Administration settings. The software will communicate with the Database through Database Application Server.

Embodiments of the present invention provide for enhancements to the Image Acquisition system as part of the Database Application. For example, a user is able to connect/disconnect the Image Acquisition software from the Database. One example of an operation provided by embodiments of the present invention is that when the Image Acquisition software is connected to the database, the user list will be provided by the database, not the local user ID list from the barcode identifier log.

Before an image scan is performed, the chip will already be associated with a Chip Run in the Database. Accordingly, a user will only need to input the chip barcode and the User ID. After the Scan is completed, the Image Acquisition software will automatically update the Chip Run with the information about the scan. The information will include:

Time of the Scan
Imaging System Information
Status of the Scan: Scanned.

Similar to the FIDX, for the Image Acquisition software, there is no explicit user login and logoff from Database. The Image Acquisition software will automatically perform a database login just before user starts the scan. Whether user needs to enter his/her password will depend on the User Administration settings. This software will communicate with the Database through the Database Application Server.

In some embodiments of the present invention, the Auto Processor, for example, a TOPAZ™ Auto Processor, is provided with enhancements as part of the Database Application. The user will be able to connect/disconnect the Auto Processor software from the database. When connected to the database, user has to login/off to/from the Database. This software will communicate with the Database through the Database Application Server.

In a specific embodiment, the Auto Processor will perform database information updating. After a section is processed, the Auto Processor will generally perform the following:

Perform a Database check to see whether the scan is defined in the Database or not.
If yes, update the Database with the following information:
  Scan:
    Auto Processor Software Version
    Status: Change to be Processed
  Diffusion Experiment:
    Ranking
    Auto Call In addition to other enhancements, Crystal Vision is provided with enhancements as part of the Database Application. In an embodiment, the user will be able to connect/disconnect the Crystal Vision software from the database. When connected to the database, user has to login/off to/from the Database. When the Crystal Vision connects to the Database, the File—Open command will explore the Chip Runs defined in the Database, instead of in the File system.

Moreover, the Crystal Vision software will perform a database information update function in an embodiment of the present invention. In performing this function, the following information regarding the chip run will be updated by the Crystal Vision software:

Annotated by:
Approved by:
Last Modified at:
User Calls, Flags for Review, and Comments of all diffusion experiments.

In some embodiments, there will be a mechanism for the Experiment Manager to instruct Crystal Vision to open a specific chip run and to initialize the display for a specific diffusion experiment. This can be accomplished through a Windows message. This software will communicate with the Database through the Database Application Server.

Embodiments of the present invention provide a Database Application Server 252 as illustrated in FIG. 2. In a particular embodiment, the Database Application Server is a COM server installed in the client computer.

In some embodiments of the present invention, as discussed in relation to FIG. 2, a Publisher (sometimes referred to as Database Publisher software) is provided. In a specific embodiment, the Publisher is a TOPAZ™ Database Publisher software package. In a particular embodiment of the present invention, the Database Publisher software is installed along with the Database in the same computer. The Database Publisher is a program utilized to publish the experimental results in a suitable format. In a particular embodiment, the experimental results are published as HTML forms, which are saved to a designated Web Server location.

The Publisher performs a variety of operations. These operations include HTML Report Generation. Merely by way of example, the HTML reports are generated in an embodiment of the present invention in three different report formats as follows:

Ready-To-Run Chip Runs Report - This report provides a list of chip runs that are in the Ready-To-Run state. The report is displayed in a HTML form. When a user clicks a chip run (e.g., presented as a hyperlink), the Publisher displays the details of the selected ready-to-run chip run in another HTML form, which is the same as the one defined in the section above regarding the Chip Run Ready-To-Run Worksheet. One purpose of this HTML form is for the user to view (and print out) the new chips to be run.
Chip Run Report - This report is an HTML table reporting the results of all the chip runs from specified dates, which is defined by the publisher setting dialog. The result format in this table is identical to the table of a multiple chip run worksheet.
Target Report - This report is an HTML table reporting all the results of all the targets, which is defined by the publisher setting dialog. The result format in this table is identical to the table of a multiple target worksheet.

The Publisher will generally have a series of user and system defined settings. For example, in a particular embodiment, there are three settings for the Publisher as follows:

Scheduler for report generation. The scheduler provides information related to the timing with which reports are generated (e.g. when reports are generated).
Chip Run Result Format and Period. The result format setting is identical to the result format setting for the chip run worksheet. In addition, a user can specify to report only those chip runs from certain period (e.g., last three months).
Target Result Format. The result format setting is identical to the result format setting for the target worksheet. In addition, user can specify to report only those chip runs from certain period (e.g., last three months).

The Database User Administrator software is installed along with the Database in the same computer. This is a program to manage users in relation to database access. This program will manage the following user information, as discussed previously in relation to the Database.

User Full Name
  User Description
  User Login Name
  User Password
  Access Right. In some versions, only full access rights are supported.
  Status (either Active or Inactive)

Generally, the program performs a variety of operations including the following:

Add a new user with required attributes.
    Remove a user if it is not referenced.
    Change the attributes of a user.

Moreover, there will be a setting indicating whether it is necessary for a user to enter his/her password when logging in to the Database for each of the following applications:

Experiment Manager
    FID Crystallizer

Image Acquisition
Crystal Vision
Score Card

Embodiments of the present invention provide a number of possible System Configurations. In a specific embodiment, the Database Application supports both a Microsoft SQL server and an MSDE Server. The MSDE server is the default configuration for Database Application, and the user is provided with means to upgrade to an SQL server.

Several operating systems are compatible with embodiments of the present invention. Operating systems for the database include:

Windows 2003 Server for Microsoft SQL Server
Windows XP + SP2 for Microsoft MSDE Server
Windows 2000 + SP4 for Microsoft MSDE Server Additionally, operating systems for all the Software Applications include:

Windows 2003 Server - Compatible with the following Applications:
   Experiment Manager
   User Administrator
   Auto Processor
   Crystal Vision
Windows 2000 + SP4 (Compatible with all Applications)
Windows XP + SP2 (Compatible with all Applications)

In some operating systems, a Start Menu is provided. In these operating systems, the program listing is provided in the Start Menu as:

Start →
  All Programs →
    Fluidigm →
      Experiment Manager
      Publisher
      User Administrator
      Score Card
      FID Crystallizer
      Image Acquisition
      Auto Processor
      Crystal Vision Embodiments of the present invention provide Recommended System Configurations. For the Experiment Manager Application, the recommended desktop display has a pixel count greater than or equal to 1280×1024 pixels. The recommended display font is a normal font (96 dpi). The minimum requirement for certain embodiments of the present invention is a desktop display with a pixel count greater than or equal to 1024×768 pixels with a normal display font (96 dpi). The recommended process is an Intel® Pentium® 4 (1.5 GHz) or higher. The recommended available hard disk storage space is 2 GB of free memory.

For the Score Card Application, the recommended system configuration is the same as for the Experiment Manager. For the Database, the recommended system configuration is an Intel® Pentium® 4 processor (1.5 GHz) or higher and 200 GB of available hard disk space.

Embodiments of the present invention provide an application configuration for the automated system, which has been described herein. In a specific embodiment, the configuration includes the following elements:

Database Computer:
  Database User Administrator
  Publisher (scheduled running during the off-hours)
  Microsoft SQL or MSDE server + Database.
Chip Run Storage and Processing Computer:
  Microfluidic Chip Auto Processor (scheduled running daily during the off-hours)
  All the Microfluidic Chip Runs (image data).
  Crystal Vision (Optional)
FIDX Computer:
  FIDX Crystallizer
  Experiment Manager (Optional). The primary use case for Experiment Manager on this computer is to design chip runs. It is not designed as a general purpose data analysis and query station due to the ergonomic setup of the laptop.
AIX Computer:
  Image Acquisition
  Experiment Manager (Optional)
  Crystal Vision (Optional)
Application Computer(s):
  Experiment Manager (Optional)
  Crystal Vision (Optional)
  Score Card (Optional)

In some embodiments, the applications and chip run data are both placed on the Database computer. In other embodiments, which are provided for applications characterized by heavy network traffic, the applications and chip run data are separated and stored on the Database Computer as well as one or more separate computers.

In general, an installation procedure will be followed when installing the software. When the installation procedure is started, the user is presented with a choice of which applications the user intends to install or uninstall. Typically, there are two installation CD, for example, TOPAZ™ Database Installation CDs. In a specific embodiment, the first CD is a TOPAZ™ Database CD, including the following software components:

Microsoft MSDE Server
TOPAZ ™ Database
TOPAZ ™ User Administrator
TOPAZ ™ Publisher
TOPAZ ™ Database Application Server Generally, all of the above software components will be installed automatically. Additionally, in this specific embodiment, the second CD is a TOPAZ™ Database Application CD, including the following software components:

TOPAZ ™ Experiment Manager
TOPAZ ™ Score Card

Embodiments of the present invention provide an Automated System for Protein Crystallization. The system comprises a number of components, including:

Microfluidic Chips
Microfluidic Chip FID Crystallizer (FIDX)
Microfluidic Chip AutoInspeX Workstation (AIX)
Transfer Robot
Barcode reader
Microfluidic Chip Hotel
Microfluidic Chip User Input/Output
Microfluidic Chip Automation Input/Output
Microfluidic Chip Auto Processor
Crystal Vision Software
Microfluidic Chip Experiment Manager
Microfluidic Chip Workflow Manager ---
Microfluidic Chip Database Server
Computers connected by network
---

Some embodiments of the present invention include all of the aforementioned items, whereas others include less than all the aforementioned items. Moreover, embodiments of the present invention are not limited to these items, but may include additional items as will be evident to one of skill in the art. Moreover, in some embodiments, TOPAZ™ chips, available from the present assignee are utilized, although this is not required by the present invention. In some embodiments, other microfluidic devices are utilized as part of a protein crystallization process, or other microfluidic process.

Merely by way of example, another embodiment of the Automated System provided according to the methods and systems of the present invention comprises the aforementioned elements along with items from a liquid handling automation system. Some purposes of the liquid handling automation system are to automate the process for moving the sample, reagents, or stock solution from storage (chemical hotels) to the dispensing robot; creating a new reagent set from stock solutions; transferring reagents from reagent tubes to at least one microtiter plate; and dispensing the sample and reagent to the microfluidic chip. In some embodiments, the liquid handling automation system is provided by a third party. Elements of the liquid handling automation system include:

---
Reagent and Sample Dispensing Robot
Reagent and sample hotels
Robot
Reagent and sample database (generally provided by a third party)
---

Moreover, in yet other embodiments of the present invention, the Automated System, for example, an Automated TOPAZ™ System, comprises the aforementioned elements (including the liquid handling automation system) along with items from a Backend automation system. Some purposes for the backend automation system are to extract the physical data (such as crystals) from the microfluidic chips and place the completed chip into storage or trash bins. Embodiments of the backend automation system include:

---
Microfluidic Chip Backend Software Controller
Robotics for sample extraction from microfluidic chips
---

Now that a general method and system have been described, certain information is provided and utilized to perform, for example, protein crystallization experiments according to embodiments of the present invention. As an example, the following information hierarchy including a variety of fixed and variable parameters is utilized in a specific embodiment of the present invention. Such fixed and variable parameters will assist the reader to understand the various embodiments contained herein. Of course, these parameters are merely examples and should not unduly limit the scope of the claims herein. One of ordinary skill in the art would attach the broadest meaning to such parameters using ordinary meaning, although certain variations may be used depending upon the embodiment of the present invention.

In some embodiments, this information is provided in an automated system such as the ones illustrated in FIGS. 2 through 2E. As an example, the information would be stored in a database such as, for example, the Database 250 as also illustrated in FIG. 2. Accordingly, it is accessible by the Server 252, a database management process in some embodiments, which is coupled to various system hardware and software elements, for example, the Experiment Manger, the FIDX, the AIX, and the Crystal Vision software. Further details of each of the information categories utilized in embodiments of the present microfluidic system are described throughout the present specification and more particularly below. As noted below, such categories are not intended to unduly limit the scope of the claims herein.

---
Information Hierarchy

1) Reagent Plate
   a) Reagent Set
      i) Reagent
         (1) Component Formulation
            (a) Component
2) Dispense Mapping
3) Sample
   a) Construct Formulation
      i) Construct
         (1) Target
   b) Ligand Formulation
4) Ligand
   a) Cofactor Formulation
      i) Cofactor
   b) Component Formulation
      i) Component
5) Chip/Plate Run
   a) Sample
   b) Reagent Set
   c) Reagent Dispense Mapping
   d) Scan Session
      i) Diffusion Experiment Result
6) Program Settings
7) Users
---

Although the general parameters have been described above, such parameters of the information hierarchy can be further sub-divided as explained below. The following parameter definitions and elements are not intended to limit the claimed invention, but to merely provides examples of various parameters utilized in embodiments of the present invention.

As an example, in some embodiments, a reagent set contains the design information for a set of reagents contained in a well plate.

The attributes of the reagent set according to an embodiment include:

---
Name
Part Number
Vendor
Description
Plate Format (e.g., a 96 well plate format in a specific embodiment).
List of the Reagents
---

Moreover, generally a reagent plate is used to track the physical reagent user purchased from a vendor or made internally. The reagent plate according to an embodiment may include:

---
Barcode ID
Lot number
Made on
Description
---

The reagent contains the design information for a reagent. Its attributes according to an embodiment include:

```
Name
Part Number
Vendor
Description
pH
Conductivity
Osmolality
Component and its formulation
```

The dispense mapping describes how the reagents in a reagent plate are dispensed (mapped) to a chip run plate. The dispense mapping according to an embodiment includes:

```
Name
Description
Reagent Plate Format (i.e., source)
Chip Run Plate Format (i.e., destination)
Dispensing Tip format (e.g., 1, 2, 4, or 8 tips)
Mapping between wells in reagent plate and chip run plate. In some
embodiments, one reagent well is mapped to multiple chip run wells.
```

In specific embodiments, the sample, construct formulation, construct, target ligand and component are specified. Generally, the construct formulation describes a construct formula in a sample. Additionally, the ligand formulation typically describes a ligand formula in a sample. Moreover, the cofactor formulation usually describes a cofactor formula in a sample. For example, these items are specified according to an embodiment by the following attributes:

```
Sample
    Name
    Barcode ID or identifier
    Vendor (i.e., who produced the sample)
    Part Number
    Description
    A list of constructs and their formulation
    A list of ligands and their formulation
    A list of components and their formulation.
Construct Formulation
    Construct Name
    Concentration
    Concentration Unit
Construct
    Construct Name
    Target Name
    Reference ID
    Sequence
    Description
    URL
Target
    Name
    Reference ID
    Sequence
    Description
    URL
Ligand Formulation and Ligand
    Ligand
    Concentration
    Concentration Unit
Ligand
    Name
    Reference ID
    Description
Cofactor Formulation
    Cofactor
    Concentration
    Concentration Unit
```

```
    Cofactor
        Name
        Reference ID
        Description
```

In other embodiments, the sample and reagent components are specified. The component formulation is the component formula in a reagent. These items according to an embodiment include the following attributes.

```
Component Formulation
    Component
    Component Type
    Concentration
    Concentration Unit
    pH
Component
    Name
    Reference ID
    Description
    Alias
Component Stock Solution
    Part Number
    Vendor
    Component Name
    Concentration
    Concentration Unit
    pH
```

Additionally, information related to a chip run, in which protein crystallization processes are performed using microfluidic chips according to an embodiment of the present invention, the scan session, in which multiple images are acquired and processed to analyze one or more chip runs according to an embodiment of the present invention, and results, such as diffusion experiment results, are provided by embodiments of the present invention. Of course, there can be other processes used according to embodiments of the present invention. According to some embodiments of the present invention, the chip run, scan session, and diffusion experiment results, according to some embodiments, include the following attributes.

An example of an overall chip run according to a specific embodiment is provided below:

```
Chip Run
    Chip run name (also used as Chip run template name)
    Chip Type (e.g., TOPAZ ™ 1.96, 4.96, 8.96, X-ray chip or 96
    microtiter plate)
    Crystallization Method (e.g., TOPAZ ™, Sitting Drop, Hanging Drop,
    Microbatch and Other)
    Chip barcode
    Experiment Parameters
        Incubation Temperature
        Hydration Level
        FID Time
    Sample and Reagent
        Sample(s)
        Reagent Set
        Reagent Dispensing Mapping
    Scan Sessions and Times
        Destination file location
        Number of scans and time (Design)
        Number of scans and time (Actual)
        Start Time (Ideally, it is the time at the start of FID).
        Duration (from Start to the last image scan)
```

-continued

```
Loading and FID
    FID System ID for Loading
    FID Bay ID for Loading
    Loaded by (User ID)
    FID System ID for FID
    FID Bay ID for FID
    FID by (User ID)
    FID Software Version
User History
    Owner of the Chip Run
    Annotated by
    Approved by
Status (one of the following)
    Ready-to-Run
      Active
      Completion
    Description
Scan Session
    Scan Time
    Scan by (User ID)
    Imaging System ID
    Image System Software Version
    Status. One of the following:
      Scan Completed
      Auto Classified
    Auto Processor Version
Diffusion Experiment (DE) Result
    DE Number
    Reagent Inlet
    Sample Inlet
    Auto Ranking Score
    Auto Classification ID
    User Classification ID
    User Comment
    Image File URL
```

According to embodiments of the present invention, a number of program settings are provided. The program settings according to a specific embodiment can be systems settings, display formats, and the like. As an example, the Database contains a list of user classification with the following attributes. In a particular embodiment, these attributes are the same as the ones defined in Crystal Vision. Moreover, in some embodiments, the user classification (annotation) settings provide settings for how to create data reports and other operations. The program settings according to an embodiment of the present invention include the following:

```
        Classification Name
        Classification Type (Crystal, Ranked or Other)
        User Ranking
        Color
        Hot Key
```

According to other embodiments, user information is provided and stored. The user information includes parameters that uniquely and specifically identifies a particular user of the present methods and systems according to specific embodiments. As an example, the Database generally contains a list of users with the following attributes according to an embodiment of the present invention:

```
User Full Name
User Description
User Login Name
User Password
Access Right. In some embodiments, only full access rights are supported.
Status (either active or inactive)
```

FIG. 7 is a simplified flowchart illustrating a method of designing an experiment according to an embodiment of the present invention. In the embodiment illustrated in FIG. 7, a method for designing a protein crystallization experiment to screen protein samples is outlined. Although certain details of the method are also provided according to the flow diagram illustrated by FIG. 7, this figure is not intended to unduly limit the scope of the claims herein. One of ordinary skill in the art would recognize many variations, alternatives, and modifications.

Select the sample to be screened (710). In some embodiments, this step is performed by a system user. In an alternative embodiment, the sample information is entered into experiment manager software if the sample information has not been previously entered into the experiment manager software. Merely by way of example, the sample information may be entered using experiment management software such as TOPAZ™ Experiment Manager software, available from the present assignee. In some embodiments, the information entered into the experiment management software is sample tracking information, such as sample name, source, barcode identifier, and the like. Additionally, in some embodiments, the protein construct and concentration, the co-crystallization components and concentrations, and sample buffer components and concentrations are entered.

Select the screening reagents to be used for screening (715). In some embodiments, this step is performed by a system user. In a particular embodiment, the screening reagent information is entered into the experiment manager software if the screening reagent information has not been previously entered into the experiment manager software. Merely by way of example, the screening reagent information may be entered using experiment management software such as TOPAZ™ Experiment Manager software, available from the present assignee. In some embodiments, the information entered into the experiment management software includes reagent tracking information, such as reagent name, source, type of microfluidic plate, barcode identifier, and the like. In a particular embodiment, the type of microfluidic plate is a microtiter plate (e.g., a 96 well plate). Additionally, in some embodiments, reagent formation information for each well (e.g., salt, precipitant, buffer and the like) is also entered into the experiment manager software.

Select a type of microfluidic device or chip (720). In some embodiments, this step is performed by a system user. In a specific embodiment, TOPAZ™ chips, available from the present assignee are selected. Merely by way of example, a TOPAZ™ 1.96 chip or a TOPAZ™ 4.96 chip, providing formats that screen one or four protein samples, respectively, against 96 reagents, are selected in a particular embodiment of the present invention.

Select a dispensing scheme (725). In some embodiments, this step is performed by a system user. Generally, the dispensing scheme includes a mapping from a screening reagent plate to the microfluidic chip, for example, the TOPAZ™ chip.

Select a suitable workflow template, which defines the sequence of jobs and timing that is to be performed on the microfluidic chip (730). In some embodiments, this step is performed by a system user. In some embodiments, the workflow template is defined, as discussed in relation to FIG. 12 if the suitable workflow template does not already exist.

Select an owner for the protein crystallization experiment (735). In some embodiments, this step is performed by a system user. Moreover, in an embodiment, the owner is, for example, a technician.

Save the experimental design information a database (740). In a particular embodiment, the database is a database provided as part of a TOPAZ™ System available from the present assignee.

Inform the owner of the protein crystallization experiment that the screening experiment is ready to run (745). In some embodiments, a workflow manager is utilized to inform the owner. In specific embodiments of the present invention, the owner is notified by e-mail, pager, SMS, instant messenger (IM), voice mail, and the like.

Run or perform the protein crystallization experiment (750). Additional details regarding the running of the experiment are provided below in relation to the discussion of FIG. 8.

Perform other steps, as desired (755).

It should be appreciated that the specific steps illustrated above provide a particular method of designing a process (sometimes an experimental process) according to an embodiment of the present invention. Other sequence of steps may also be performed according to alternative embodiments. For example, alternative embodiments of the present invention may perform the steps outlined above in a different order. Moreover, the individual steps illustrated by this method may include multiple sub-steps that may be performed in various sequences as appropriate to the individual step. Furthermore, additional steps may be added or removed depending on the particular applications. One of ordinary skill in the art would recognize many variations, modifications, and alternatives. Further details of methods and resulting structures of the present microfluidic system have been described throughout the present specification and more particularly below.

FIG. 8 is a simplified flowchart illustrating a method of running an experiment according to an embodiment of the present invention.

Prepare a microfluidic chip (810). Merely by way of example, in some embodiments, the microfluidic chip is a TOPAZ™ chip, for example, a TOPAZ™ 1.96 chip or a TOPAZ™ 4.96 chip, providing formats that screen one or four protein samples, respectively, against 96 reagents. Moreover, in an embodiment this step is performed by a system user. In a specific embodiment, the microfluidic chip is prepared according to a workflow protocol defined during the experimental design process, as discussed in relation to FIG. 7.

Enter the barcode of the microfluidic chip, into a database and associate the chip with a defined experiment or process (815). In some embodiments, the microfluidic chip is a TOPAZ™ chip and this step is performed by a system user. Moreover, in other embodiments, the experiment is defined as illustrated in relation to FIG. 7.

Place the microfluidic chip into a Liquid Handling System (820). In some embodiments, this step is performed by a system user. Liquid Handling Systems are described in additional detail throughout the present specification.

Scan the barcode of the microfluidic device (825). In some embodiments, this step is performed automatically by the Liquid Handling System using appropriate hardware and software.

Make a query to the Workflow Manager, the query including the chip barcode (830). In some embodiments, the Workflow Manager is a TOPAZ™ Workflow Manager. Moreover, in other embodiments, this step is performed by the Liquid Handling System through a standard software communication protocol, such as SOAP (Simple Object Access Protocol)).

Return the job request from the Workflow Manager to the Liquid Handling System (835). In a particular embodiment, the job request instructs the Liquid Handling System with respect to what samples and reagents are required and how to dispense them into the microfluidic chip, for example a TOPAZ™ Chip.

Dispense the sample and reagent into the microfluidic chip according to instructions provided with the job request (840). In some embodiments, this step is performed automatically by the Liquid Handling System using appropriate hardware and software.

Place the microfluidic chip in an Automation Input Stack after the completion of the dispense step (845). In some embodiments, this step is performed automatically by the Liquid Handling System using appropriate hardware and software.

Detect the presence of the microfluidic chip in the Automation system (850). In some embodiments, this step is performed automatically by the Automation system by a process of scanning the barcode associated with the microfluidic device.

Instruct the transfer robot to transfer the microfluidic chip to a free interface diffusion (FID) crystallizer for loading of the protein sample and reagent into the microfluidic device (855). In a specific embodiment, the FID crystallizer is a TOPAZ™ FID crystallizer (FIDX) available from the present assignee. Moreover, in some embodiments, this step is performed by a Workflow Manager.

Instruct the transfer robot to transfer the microfluidic chip to an inspection station to perform a baseline scan, sometimes referred to as a time $t_0$ scan (860). Baseline scans are performed at various stages depending on the particular application. As one of skill in the art will appreciate, acquiring a baseline image enables techniques to reduce background noise, among other reasons. For example, in a specific embodiment, the time $t_0$ scan is acquired before an experiment is begun by loading the reagent and sample into the wells on the chip but not opening the valves to allow for diffusion of the reagents and samples. In this specific embodiment, the image is acquired before the FID process begins. Of course, other embodiments acquire the baseline scan at other stages depending on the particular application. In some embodiments, the instructions are provided by the Workflow Manager. In a specific embodiment, the inspection station is a TOPAZ™ AUTOINSPEXT™ Workstation (AIX), available from the present assignee. In some embodiments, this step is an optional step as baseline scans or images are not utilized.

Instruct the transfer robot to transfer the microfluidic chip to the FID crystallizer to initiate the protein crystallization process (865). In a specific embodiment, the FID crystallizer is the TOPAZ™ FIDX and valves present on a TOPAZ™ chip are controlled to release the sample and the reagent and initiate the FID process. As one of skill in the art will appreciate, in some cases, the FID process results in the formation of a crystal in the well region of the microfluidic chip. In the present specification, references to a well region or well regions include, but are not limited to chambers, micro-chambers, channels, micro-channels, reaction chambers, and the like.

Transfer the microfluidic chip to a microfluidic chip hotel (870). In some embodiments, the instructions are provided by the workflow manager. Depending on the length of time designed for the FID process, along with the status of other tasks performed by the protein crystallization experiment system, it may be desirable to store the microfluidic chips in a chip hotel. The chip hotel provides control of the temperature and humidity environment surrounding the microfluidic chip, among other parameters. In some embodiments, this is an optical step as the microfluidic chip remains in the FID crystallizer during the duration of the FID process. In some embodiments, the system will transfer the microfluidic chip to the FID crystallizer to terminate the FID process. According to an embodiment of the present invention, in process flows in which the microfluidic device is stored in the microfluidic chip hotel, the workflow manager instructs the transfer robot to transfer the microfluidic chip to the FID crystallizer. In a specific embodiment, the FID crystallizer is the TOPAZ™ FIDX and valves present on a TOPAZ™ chip are controlled to load and manipulate the sample and the reagent for the protein crystallization processes, and also to terminate the FID process.

Instruct the transfer robot to transfer the microfluidic chip to the inspection system to perform scans as defined by the workflow protocol (875). In a specific embodiment, the inspection station is a TOPAZ™ AUTOINSPEX™ Workstation (AIX), available from the present assignee and a number of images are acquired and processed at time intervals defined by the workflow protocol. In other embodiments, results from initial measurements made using the inspection system are analyzed to determine the time intervals for subsequent image acquisition and/or processing.

Automatically process at least one of the number of images acquired using the inspection system to determine a parameter, for example, a crystal ranking, associated with the protein crystallization process (880). In some embodiments, one or more parameters are determined and stored in a database, thereby updating the database. In a particular embodiment, the database is a database provided as part of the TOPAZ™ System, for example, a TOPAZ™ database.

Provide the system user with information related to the protein crystallization experiment (885). In some embodiments, the system user is provided with this information by a server coupled to the inspection system, for example, a TOPAZ™ database server. Moreover, in a specific embodiment, the information includes the crystal ranking determined in the previous step.

Access a software package to view the results of the protein crystallization experiment and annotate the experimental results if desired (890). In some embodiments, the system user uses the TOPAZ™ AIX Software suite, including Crystal Vision software to view the experimental results and further annotate the experiments as desired.

Perform other steps as necessary (895).

According to embodiments of the present invention, after performing the aforementioned steps, the system user may pursue a variety of options according to this method. For example, the user may desire to continue the protein crystallization experiment, acquiring and processing additional images of portions of the microfluidic chip. As will be evident to one of skill in the art, the comparison of images acquired as a function of time may yield additional information related to the protein crystallization process. Additionally, the user may select an option in which another screening process is initiated, using the workflow protocol defined separately. Moreover, based on the information communicated in step 885, the user may desire to perform an optimization experiment. Furthermore, the user may select to perform a translation experiment, utilizing a microfluidic diffraction chip such as the TOPAZ™ Chip, a classic method, (e.g. Sitting Drop, Hanging Drop, and Microbatch), and the like.

It should be appreciated that the specific steps illustrated in steps 1 through 14 provide a particular method of running an experiment according to an embodiment of the present invention. Other sequence of steps may also be performed according to alternative embodiments. For example, alternative embodiments of the present invention may perform the steps outlined above in a different order. Moreover, the individual steps illustrated by this method may include multiple sub-steps that may be performed in various sequences as appropriate to the individual step. For example, the step of acquiring and processing an image may contain sub-steps, such as the alignment and focusing of optical elements. Furthermore, additional steps may be added or removed depending on the particular applications. One of ordinary skill in the art would recognize many variations, modifications, and alternatives. Further details of methods and resulting structures of the present microfluidic system have been described throughout the present specification and more particularly below.

FIG. 9 is a simplified flowchart illustrating a method of optimizing an experiment according to an embodiment of the present invention.

Select a set of conditions for optimization (910). In some embodiments of the present invention, this step is performed by a system user. In an embodiment of the present invention, an experiment manager, for example a TOPAZ™ Experiment Manager creates a new reagent set using standard experiment methodology.

Save the new reagent set using the experiment manager, for example, the TOPAZ™ Experiment Manager to the Database (915). In an embodiment, the reagent set is saved in one or more memories of a computing system. Next, place a job request with a Workflow Manager. In a specific embodiment, the Workflow Manager is a TOPAZ™ Workflow Manager.

Post the job request with the reagent formulation to the Liquid Handling System (920). In some embodiments, this step is performed by the Workflow Manager.

Make new sets according to the formulation provided in step 910 (925). In some embodiments, this step is performed automatically by the Liquid Handling System using appropriate hardware and software.

Place the created reagent sets in the reagent hotels (930). In some embodiments, this step is performed automatically by the Liquid Handling System using appropriate hardware and software.

Design a new experiment with the newly created optimization reagent and the required sample (935). In some embodiments, this step is performed in parallel with the reagent preparation and delivery steps, but this is not required by the present invention. In some embodiments of the present invention, this step is performed by a system user.

Select a type of microfluidic device or chip (940). In some embodiments, this step is performed by a system user. In a specific embodiment, TOPAZ™ chips, available from the present assignee are selected. Merely by way of example, a TOPAZ™ 1.96 chip or a TOPAZ™ 4.96 chip, providing formats that screen one or four protein samples, respectively, against 96 reagents, are selected in a particular embodiment of the present invention.

Select a dispensing scheme (945). In some embodiments, this step is performed by a system user. Generally, the dispensing scheme includes a mapping from an optimization reagent plate to the microfluidic chip, for example, the TOPAZ™ chip.

Select a suitable workflow template, which defines the sequence of jobs and timing that is to be performed on the microfluidic chip (950). In some embodiments, this step is performed by a system user. In some embodiments, the workflow template is defined, as discussed in relation to FIG. 12 if the suitable workflow template does not already exist.

Select an owner for the protein crystallization optimization experiment (955). In some embodiments, this step is performed by a system user. Moreover, in an embodiment, the owner is, for example, a technician.

Save the experimental design information a database including one or more memories of a computing system (960). In a particular embodiment, the database is a database provided as part of a TOPAZ™ System available from the present assignee.

Inform the owner of the protein crystallization optimization experiment that the optimization experiment is ready to run (965). In some embodiments, a workflow manager is utilized to inform the owner. In specific embodiments of the present invention, the owner is notified by e-mail, pager, SMS, instant messenger (IM), voice mail, and the like.

Run or perform the protein crystallization optimization experiment (970). Additional details regarding the running of the optimization experiment are provided above in relation to the discussion of FIG. 8.

Perform other steps, as desired (975).

FIG. 10 is a simplified flowchart illustrating a method of translating an experiment according to an embodiment of the present invention.

Select a set of conditions for translation. In some embodiments of the present invention, this step is performed by a system user. In an embodiment of the present invention, an experiment manager, for example an Experiment Manager creates a new reagent set using a standard translation protocol or a TOPAZ™ specific translation protocol. Merely by way of example, in a specific embodiment, the Experiment Manager is a TOPAZ™ Experiment Manager.

Save the new reagent set using the experiment manager, for example, the TOPAZ™ Experiment Manager to a Database (1015). In an embodiment, the reagent set is saved in one or more memories of a computing system. Next, place a job request with a Workflow Manager. In a specific embodiment, the Workflow Manager is a TOPAZ™ Workflow Manager.

Post the job request with the reagent formulation to the Liquid Handling System (1020). In some embodiments, this step is performed by the Workflow Manager.

Make new sets according to the formulation provided in step 1010 (1025). In some embodiments, this step is performed automatically by the Liquid Handling System using appropriate hardware and software.

Place the created reagent sets in the reagent hotels (1030). In some embodiments, this step is performed automatically by the Liquid Handling System using appropriate hardware and software.

Design a new experiment with the newly created optimization reagent and the required sample (1035). In some embodiments, this step is performed in parallel with the reagent preparation and delivery steps, but this is not required by the present invention. In some embodiments of the present invention, this step is performed by a system user.

Select a type of microfluidic device or chip (1040). In some embodiments, this step is performed by a system user. In a specific embodiment, TOPAZ™ chips, available from the present assignee are selected. Merely by way of example, a TOPAZ™ 1.96 chip or a TOPAZ™ 4.96 chip, providing formats that screen one or four protein samples, respectively, against 96 reagents, are selected in a particular embodiment of the present invention.

Select a dispensing scheme (1045). In some embodiments, this step is performed by a system user. Generally, the dispensing scheme includes a mapping from an optimization reagent plate to the microfluidic chip, for example, the TOPAZ™ chip.

Select a suitable workflow template, which defines the sequence of jobs and timing that is to be performed on the microfluidic chip (1050). In some embodiments, this step is performed by a system user. In some embodiments, the workflow template is defined, as discussed in relation to FIG. 12 if the suitable workflow template does not already exist.

Select an owner for the protein crystallization optimization experiment (1055). In some embodiments, this step is performed by a system user. Moreover, in an embodiment, the owner is, for example, a technician.

Save the experimental design information a database including one or more memories of a computing system (1060). In a particular embodiment, the database is a database provided as part of a TOPAZ™ System available from the present assignee.

Inform the owner of the protein crystallization optimization experiment that the optimization experiment is ready to run (1065). In some embodiments, a workflow manager is utilized to inform the owner. In specific embodiments of the present invention, the owner is notified by e-mail, pager, SMS, instant messenger (IM), voice mail, and the like.

Run or perform the protein crystallization optimization experiment (1070). Additional details regarding the running of the translation experiment are provided above in relation to the discussion of FIG. 8.

Perform other steps, as desired (1075).

FIG. 11 is a simplified flowchart illustrating a method of translation optimization for an experiment according to an embodiment of the present invention.

Select a set of conditions for translation optimization (1110). In some embodiments of the present invention, this step is performed by a system user. In an embodiment of the present invention, an experiment manager, for example an Experiment Manager creates a new reagent set using a standard translation optimization protocol. Merely by way of example, in a specific embodiment, the Experiment Manager is a TOPAZ™ Experiment Manager.

Save the new reagent set using the experiment manager, for example, the TOPAZ™ Experiment Manager to a Database (1115). In an embodiment, the reagent set is saved in one or more memories of a computing system. Next, place a job request with a Workflow Manager. In a specific embodiment, the Workflow Manager is a TOPAZ™ Workflow Manager.

Post the job request with the reagent formulation to the Liquid Handling System (1120). In some embodiments, this step is performed by the Workflow Manager.

Make new sets according to the formulation provided in step 1110 (1125). In some embodiments, this step is performed automatically by the Liquid Handling System using appropriate hardware and software.

Place the created reagent sets in the reagent hotels (1130). In some embodiments, this step is performed automatically by the Liquid Handling System using appropriate hardware and software.

Design a new experiment with the newly created optimization reagent and the required sample (1135). In some embodiments, this step is performed in parallel with the reagent preparation and delivery steps, but this is not required by the present invention. In some embodiments of the present invention, this step is performed by a system user.

Select a type of microfluidic device or chip (1140). In some embodiments, this step is performed by a system user. In a specific embodiment, TOPAZ™ chips, available from the present assignee are selected. Merely by way of example, a TOPAZ™ 1.96 chip or a TOPAZ™ 4.96 chip, providing formats that screen one or four protein samples, respectively, against 96 reagents, are selected in a particular embodiment of the present invention.

Select a dispensing scheme (1145). In some embodiments, this step is performed by a system user. Generally, the dispensing scheme includes a mapping from an optimization reagent plate to the microfluidic chip, for example, the TOPAZ™ chip.

Select a suitable workflow template, which defines the sequence of jobs and timing that is to be performed on the microfluidic chip (1150). In some embodiments, this step is performed by a system user. In some embodiments, the workflow template is defined, as discussed in relation to FIG. 12 if the suitable workflow template does not already exist.

Select an owner for the protein crystallization optimization experiment (1155). In some embodiments, this step is performed by a system user. Moreover, in an embodiment, the owner is, for example, a technician.

Save the experimental design information a database including one or more memories of a computing system (1160). In a particular embodiment, the database is a database provided as part of a TOPAZ™ System available from the present assignee.

Inform the owner of the protein crystallization optimization experiment that the optimization experiment is ready to run (1165). In some embodiments, a workflow manager is utilized to inform the owner. In specific embodiments of the present invention, the owner is notified by e-mail, pager, SMS, instant messenger (IM), voice mail, and the like.

Run or perform the protein crystallization translation optimization experiment (1170). Additional details regarding the running of the translation optimization experiment are provided above in relation to the discussion of FIG. 8.

Perform other steps, as desired (1175).

FIG. 12 is a simplified flowchart illustrating a workflow template according to an embodiment of the present invention.

Select a level of hydration for the microfluidic device (1210).

Select a loading protocol for loading the reagent and sample into the microfluidic device or chip (1215). Generally, the loading protocol will include information As one of skill in the art will appreciate, in some embodiments of the present invention, this step is dependent on the type of microfluidic device selected for the protein crystallization experiment.

Select an active FID protocol (1220). Typically, the active FID protocol includes a length of time during which the interface line is open, among other variables.

Determine whether a baseline (time $t_0$) image is to be acquired (1225). In some embodiments, no baseline image is acquired and this determination is made in this step.

Select the number of images to be acquired and the timing with which this number of images is to be acquired (1210).

Select other parameters as desired (1230).

According to embodiments of the present invention, there are multiple examples of protein crystallization experiments that are run utilizing the Database Application Suite. Some of these experiments involve multiple software components, while others will only involve one component. One of ordinary skill in the art would recognize many variations, modifications, and alternatives. Additionally, some of these examples of using methods and systems according to embodiments of the present invention do not constitute performance of entire experiments, but merely portions or sub-elements thereof.

As a first example, a method for forming a reagent set according to an embodiment of the present invention is provided by the following process flow. As described more fully below, a reagent set formed according to embodiments of the present invention may be used in performing protein crystallization experiments as will be evident to one of skill in the art.

Figure 13:
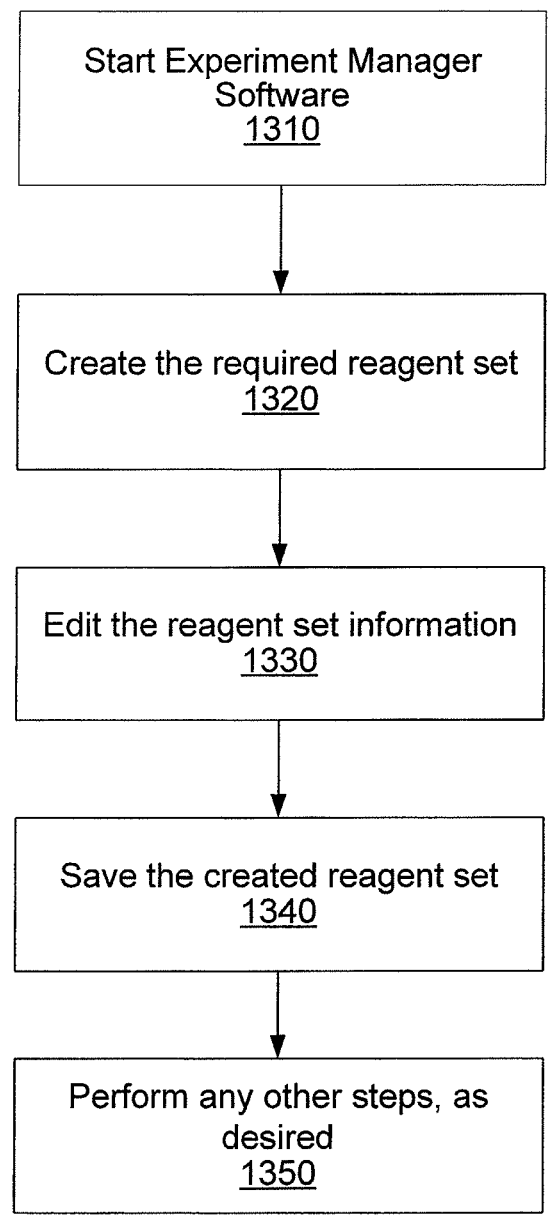
FIGS. 13-26 are simplified flowcharts illustrating operations performed according to exemplary embodiments of the present invention.

FIG. 13 is a simplified flowchart illustrating operations performed according to an exemplary embodiment of the present invention. Accordingly, the reference numerals in the following process flow refer to FIG. 13.

1310. Start Experiment Manager Software if desired on an automated system, which has been described herein.

1315. Create the required reagent set by importing the reagent set using for example, a comma separated values (CSV) file, provided by a first entity. In some embodiments of the present invention, the first entity is Fluidigm Corporation ("Fluidigm").

1320. Edit the reagent set information, if desired, including adding or removing and/or modifying any of the reagents in the reagent set, to form a desired reagent set by a second entity or user of the edited reagent set.

1325. Save the created reagent set into one or more memories of a computing system.

1330. Perform any other steps, as desired.

As shown, above, the above steps can be used to form a reagent set according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 14:
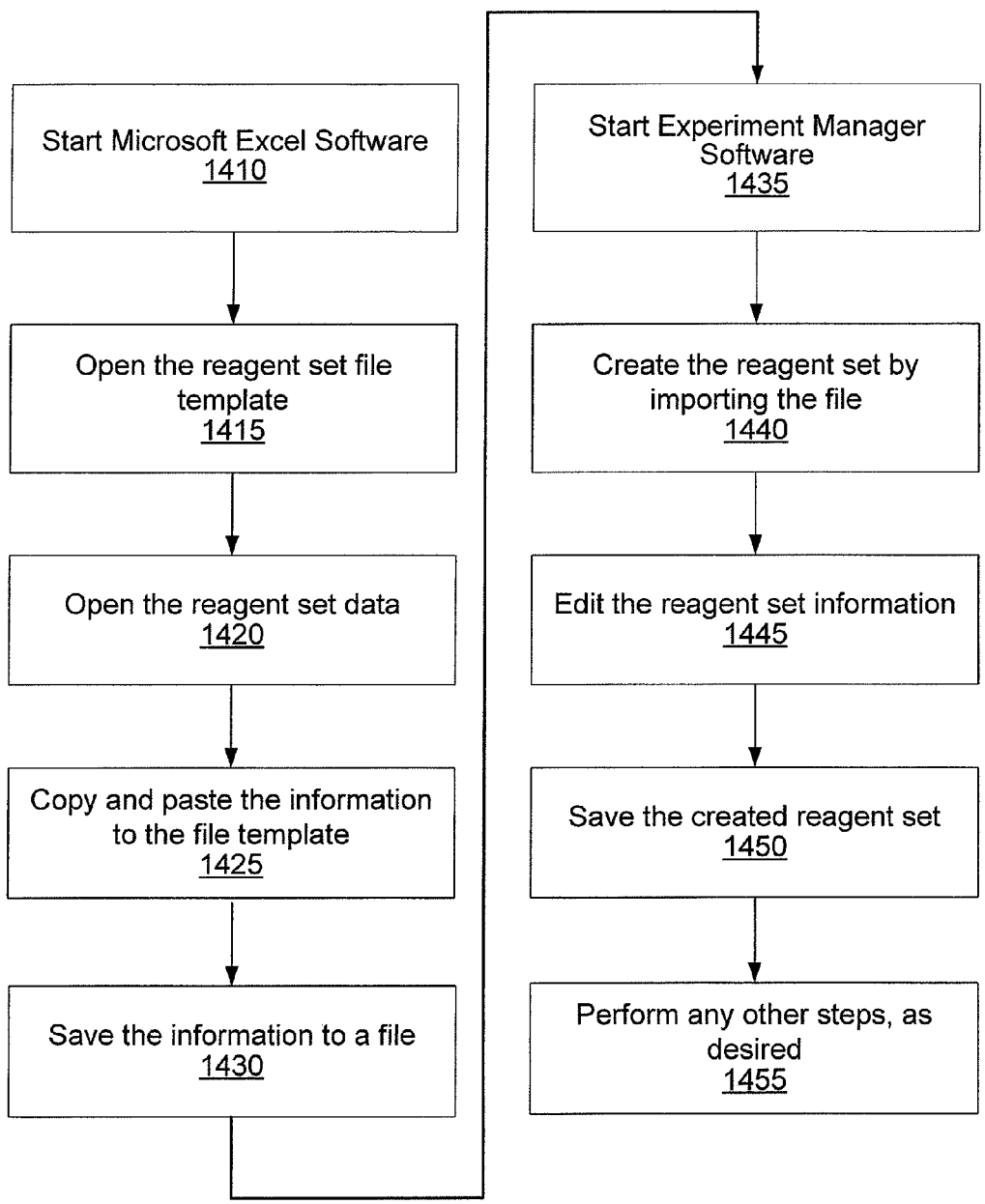

As a second example, a method for forming a new non-Fluidigm reagent set according to an embodiment of the present invention is provided by the following process flow. FIG. 14 is a simplified flowchart illustrating operations performed according to an exemplary embodiment of the present invention. Accordingly, the reference numerals in the following process flow refer to FIG. 14.

1410. Start Microsoft Excel software on an automated system, which has been described herein.

1415. Open the reagent set using for example, a CSV file template provided by a first entity. In some embodiments, the first entity is Fluidigm.

1420. Open the reagent data set provided by a third party vendor or a reagent data set created, for example, internally.

1425. Copy and paste the desired reagent data information to the CSV file template provided by the first entity.

1430. When finished with the copy and paste operation, save the reagent data information to a CSV file stored in one or more memories of a computing system.

1435. Start Experiment Manager Software if desired on an automated system, which has been described herein.

1440. Create the required reagent set by importing the newly created CSV file.

1445. Edit the reagent set information, if desired, including adding or removing and/or modifying any of the reagents in the reagent set, to form a desired reagent set by a second entity or user of the edited reagent set.

1450. Save the created reagent set into one or more memories of a computing system.

1455. Perform any other steps, as desired.

As shown, above, the above steps can be used to form a non-Fluidigm reagent set according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 15:
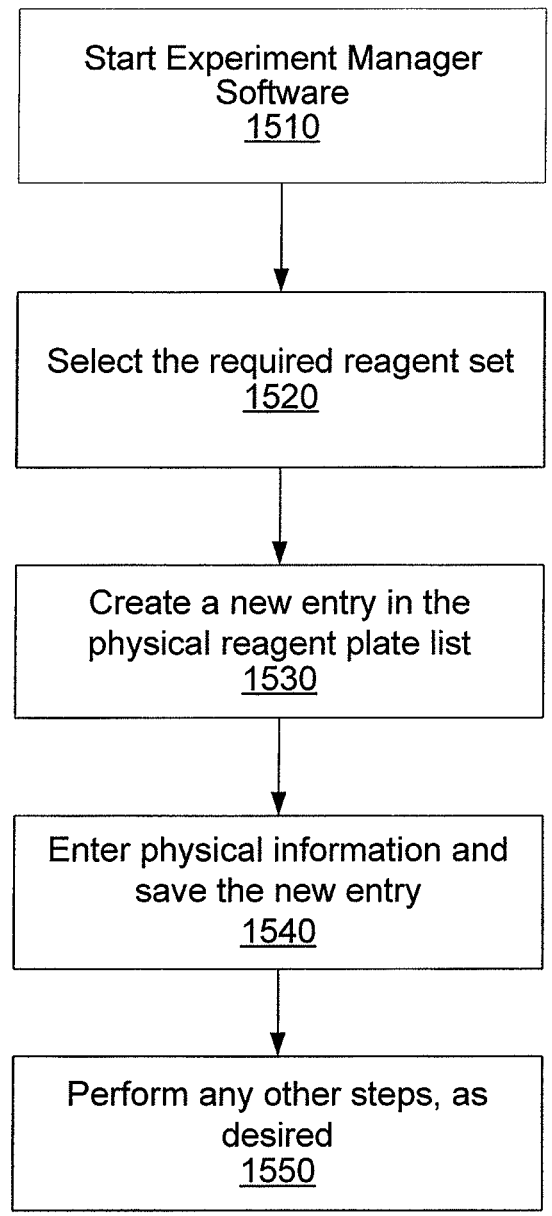

In a third example, a method of adding a physical reagent plate according to an embodiment of the present invention is provided by the following process flow. In general, a precondition for this example is that the reagent set (i.e., design information for the reagent set) for the physical reagent plate is already stored in the database. FIG. 15 is a simplified flowchart illustrating operations performed according to an exemplary embodiment of the present invention. Accordingly, the reference numerals in the following process flow refer to FIG. 15.

1510. Start Experiment Manager Software if desired on an automated system, which has been described herein.
    1520. Select the reagent set for the physical reagent plate.
    1530. Create a new entry in the physical reagent plate list.
    1540. Enter the barcode identifier, batch number, and other physical information for the new entry and then save the new entry into one or more memories of a computing system.
    1550. Perform any other steps, as desired.

As shown, above, the above steps can be used to add a physical reagent plate according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 16:
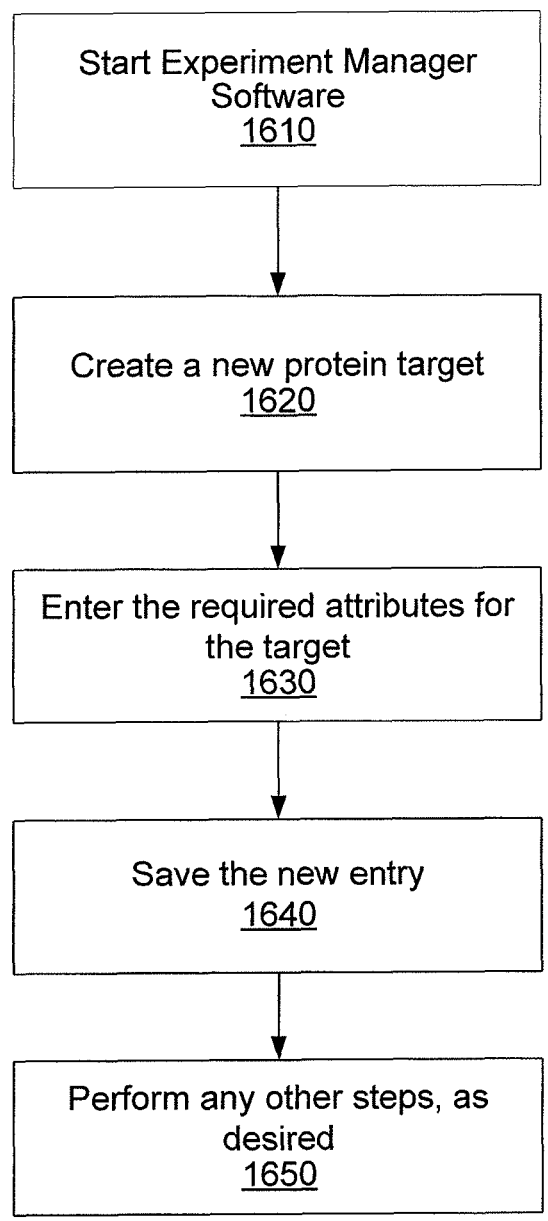

As a fourth example, a method for forming a new protein target according to an embodiment of the present invention is provided by the following process flow. FIG. 16 is a simplified flowchart illustrating operations performed according to an exemplary embodiment of the present invention. Accordingly, the reference numerals in the following process flow refer to FIG. 16.

1610. Start Experiment Manager Software if desired on an automated system, which has been described herein.
    1620. Create a new protein target.
    1630. Enter the required attributes for the target.
    1640. Save the new entry into one or more memories of a computing system.
    1650. Perform any other steps, as desired.

As shown, above, the above steps can be used to form a new protein target according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 17:
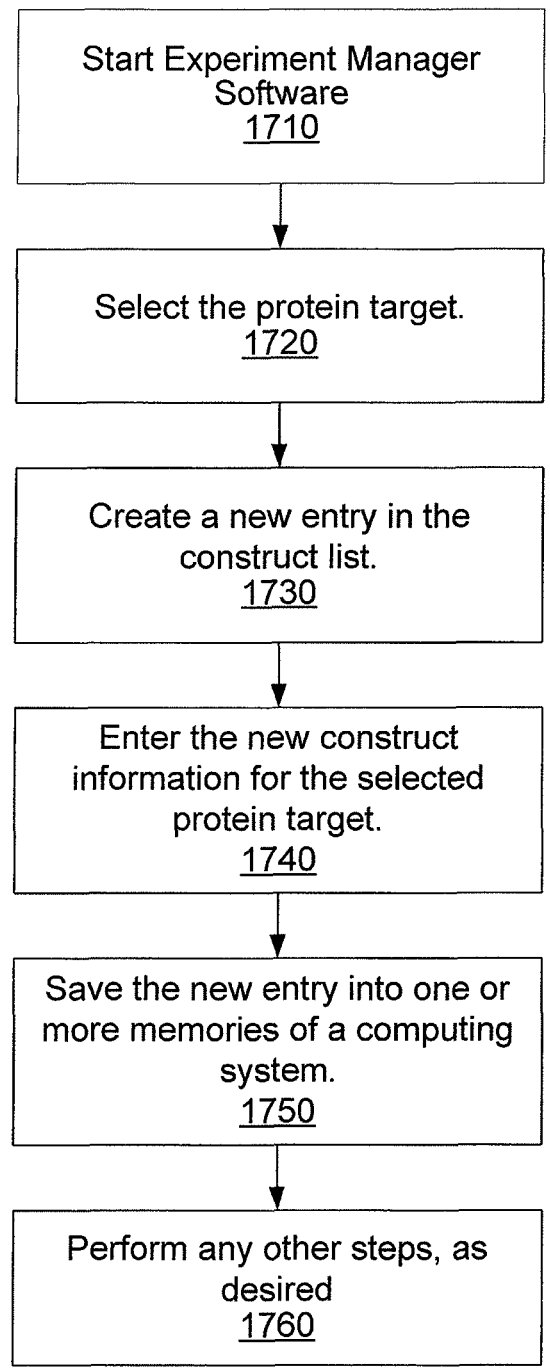

As a fifth example, a method of forming a new protein construct according to an embodiment of the present invention is provided by the following process flow. Generally, a precondition for this process is that the protein target for the new construct is already created and stored in the Database. Merely by way of example, the method of forming a new protein target discussed in relation to the fourth example is used in a specific embodiment of the present invention. Typically, there is a default construct (full length) for each protein target. FIG. 17 is a simplified flowchart illustrating operations performed according to an exemplary embodiment of the present invention. Accordingly, the reference numerals in the following process flow refer to FIG. 17.

1710. Start Experiment Manager Software if desired on an automated system, which has been described herein.
    1720. Select the protein target.
    1730. Create a new entry in the construct list.
    1740. Enter the new construct information for the selected protein target.
    1750. Save the new entry into one or more memories of a computing system.
    1760. Perform any other steps, as desired.

As shown, above, the above steps can be used to form a new protein construct according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 18:
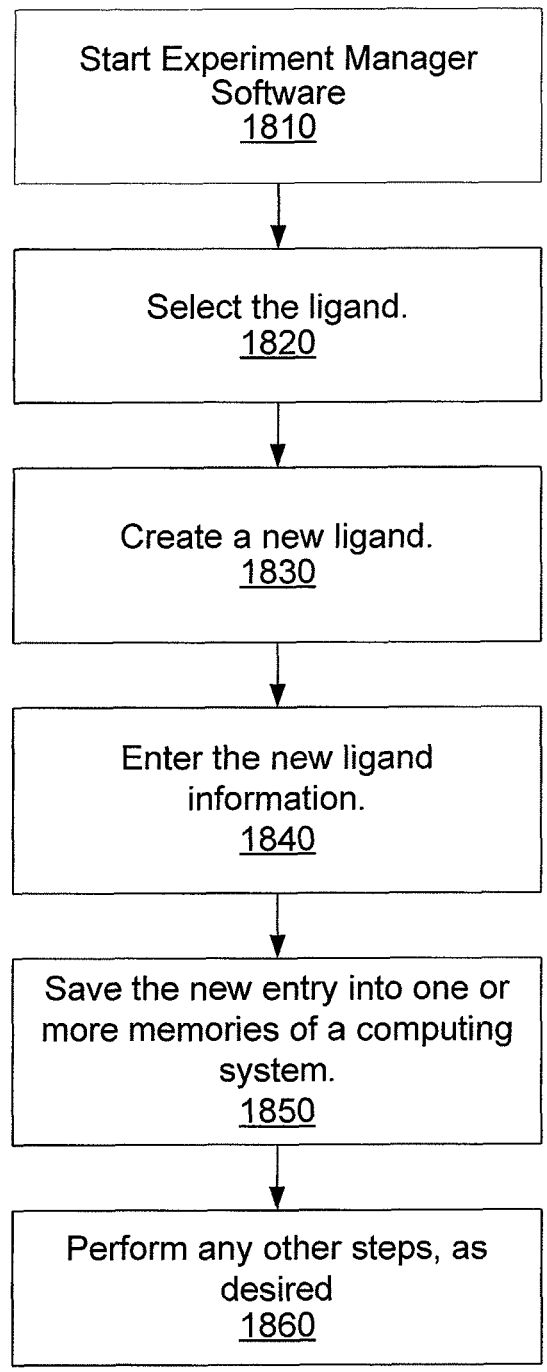

In a sixth example, a method of forming a new ligand according to an embodiment of the present invention is provided by the following process flow. FIG. 18 is a simplified flowchart illustrating operations performed according to an exemplary embodiment of the present invention. Accordingly, the reference numerals in the following process flow refer to FIG. 18.

1810. Start Experiment Manager Software if desired on an automated system, which has been described herein.
    1820. Select the ligand.
    1830. Create a new ligand.
    1840. Enter the new ligand information.
    1850. Save the new entry into one or more memories of a computing system.
    1860. Perform any other steps, as desired.

As shown, above, the above steps can be used to form a new ligand according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 19:
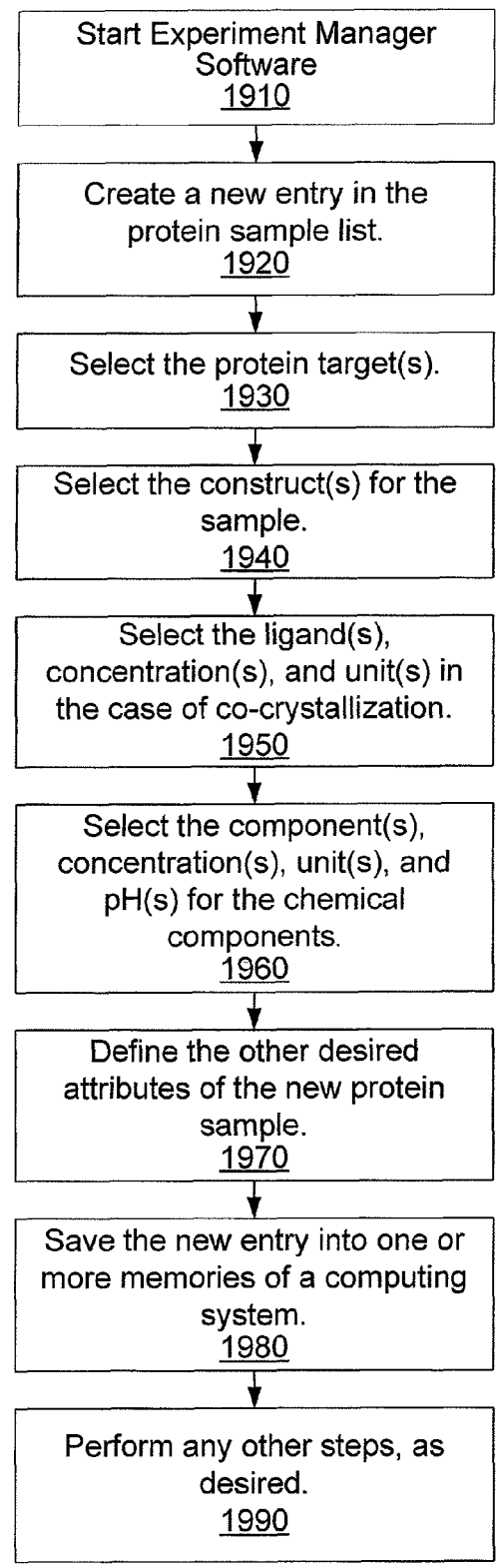

In a seventh example, a method of forming a new protein sample according to an embodiment of the present invention is provided by the following process flow. Typically, the protein target(s), construct(s), ligand(s), and buffer(s) for the new protein sample are already created and stored in the Database. FIG. 19 is a simplified flowchart illustrating operations performed according to an exemplary embodiment of the present invention. Accordingly, the reference numerals in the following process flow refer to FIG. 19.

1910. Start Experiment Manager Software if desired on an automated system, which has been described herein.
    1920. Create a new entry in the protein sample list.
    1930. Select the protein target(s).
    1940. Select the construct(s) for the sample.
    1950. Select the ligand(s), concentration(s), and unit(s) in the case of co-crystallization.
    1960. Select the component(s), concentration(s), unit(s), and pH(s) for the chemical components.
    1970. Define the other desired attributes of the new protein sample.
    1980. Save the new entry into one or more memories of a computing system.
    1990. Perform any other steps, as desired.

As shown, above, the above steps can be used to form a new protein sample according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 20:
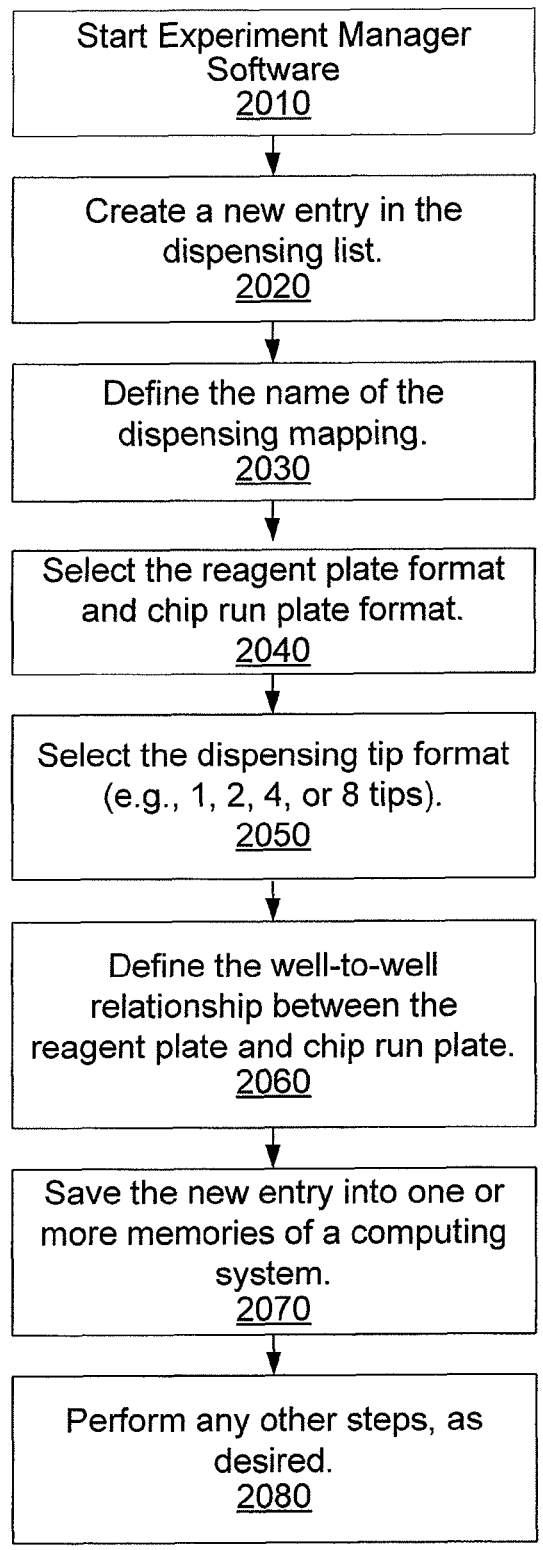

In an eighth example, a method of forming a new dispensing mapping according to an embodiment of the present invention is provided by the following process flow. FIG. 20 is a simplified flowchart illustrating operations performed according to an exemplary embodiment of the present invention. Accordingly, the reference numerals in the following process flow refer to FIG. 20.

2010. Start Experiment Manager Software if desired on an automated system, which has been described herein.
2020. Create a new entry in the dispensing list.
2030. Define the name of the dispensing mapping.
2040. Select the reagent plate format and chip run plate format.
2050. Select the dispensing tip format (e.g., 1, 2, 4, or 8 tips).
2060. Define the well-to-well relationship between the reagent plate and chip run plate.
2070. Save the new entry into one or more memories of a computing system.
2080. Perform any other steps, as desired.

As shown, above, the above steps can be used to form a new dispensing mapping according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 21:
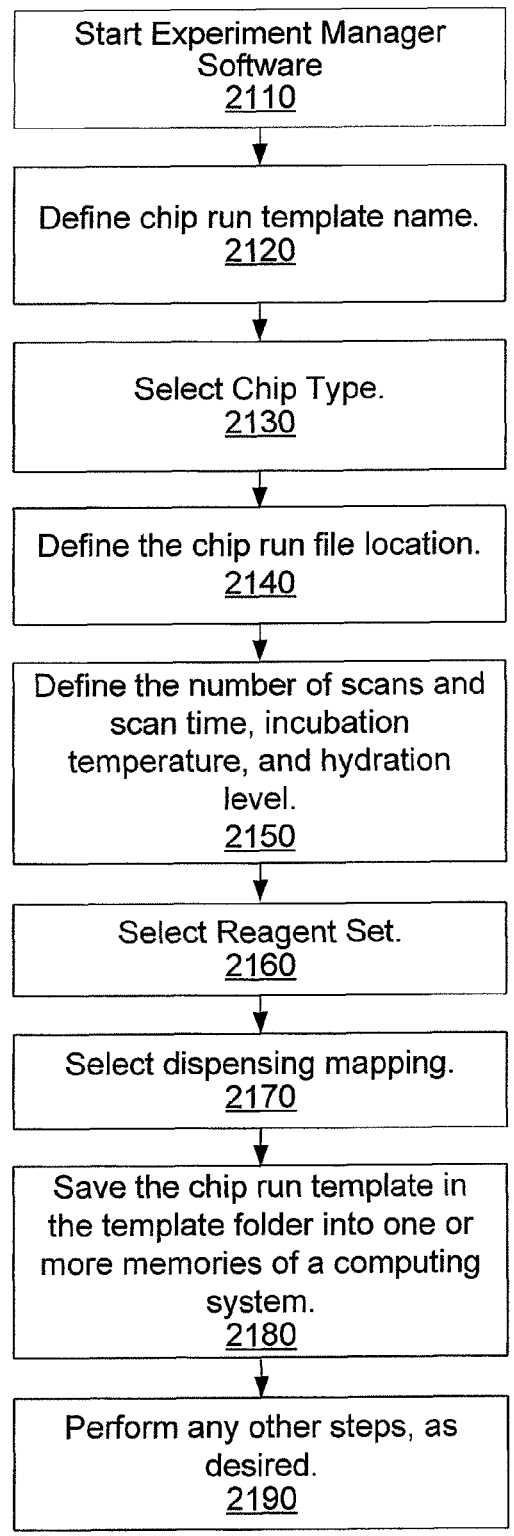

In a ninth example, a method of forming a new chip run template according to an embodiment of the present invention is provided by the following process flow. Generally, a precondition for this process is that the reagent set, protein sample(s), and the dispensing mapping are already created and stored in the Database. FIG. 21 is a simplified flowchart illustrating operations performed according to an exemplary embodiment of the present invention. Accordingly, the reference numerals in the following process flow refer to FIG. 21.

2110. Start Experiment Manager Software if desired on an automated system, which has been described herein.
2120. Define chip run template name.
2130. Select Chip Type. In some embodiments, this step is optional.
2140. Define the chip run file location. In some embodiments, this step is optional.
2150. Define the number of scans and scan time, incubation temperature, and hydration level. In some embodiments, these steps are optional.
2160. Select Reagent Set. In some embodiments, this step is optional.
2170. Select dispensing mapping. In some embodiments, this step is optional.
2180. Save the chip run template in the template folder into one or more memories of a computing system.
2190. Perform any other steps, as desired.

As shown, above, the above steps can be used to form a new chip run template according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 22:
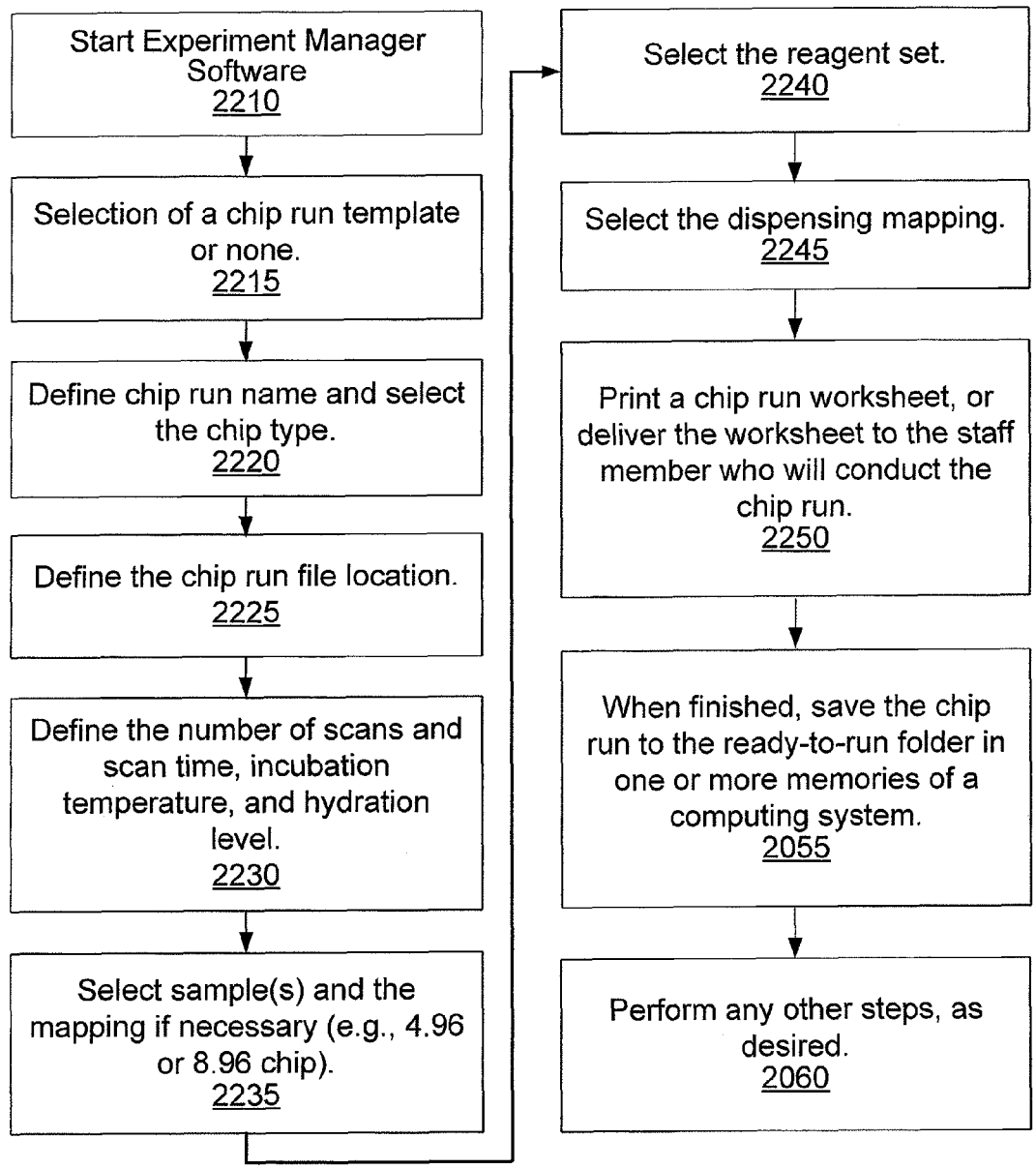

In a tenth example, a method of forming a chip run in the ready-to-run list according to an embodiment of the present invention is provided by the following process flow. Generally, a precondition for this process is that the reagent set, protein sample(s), and the dispensing mapping are already created and stored in the Database. FIG. 22 is a simplified flowchart illustrating operations performed according to an exemplary embodiment of the present invention. Accordingly, the reference numerals in the following process flow refer to FIG. 22.

2210. Start Experiment Manager Software if desired on an automated system, which has been described herein.
2215. Selection of a chip run template or none.
2220. Define chip run name and select the chip type.
2225. Define the chip run file location.
2230. Define the number of scans and scan time, incubation temperature, and hydration level.
2235. Select sample(s) and the mapping if necessary (e.g., 4.96 or 8.96 chip)
2240. Select the reagent set.
2245. Select the dispensing mapping. Merely by way of example, the dispensing mapping is created using the method discussed in relation to the eighth example above.
2250. Print a chip run worksheet or deliver, for example, through email or other communication means, the worksheet to the staff member who will conduct the chip run. The worksheet will generally be in a Hyper Text Markup Language (HTML) format.
2255. When finished, save the chip run to the ready-to-run folder in one or more memories of a computing system.
2260. Perform any other steps, as desired.

As shown, above, the above steps can be used to form a chip run in the ready-to-run list according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 23:
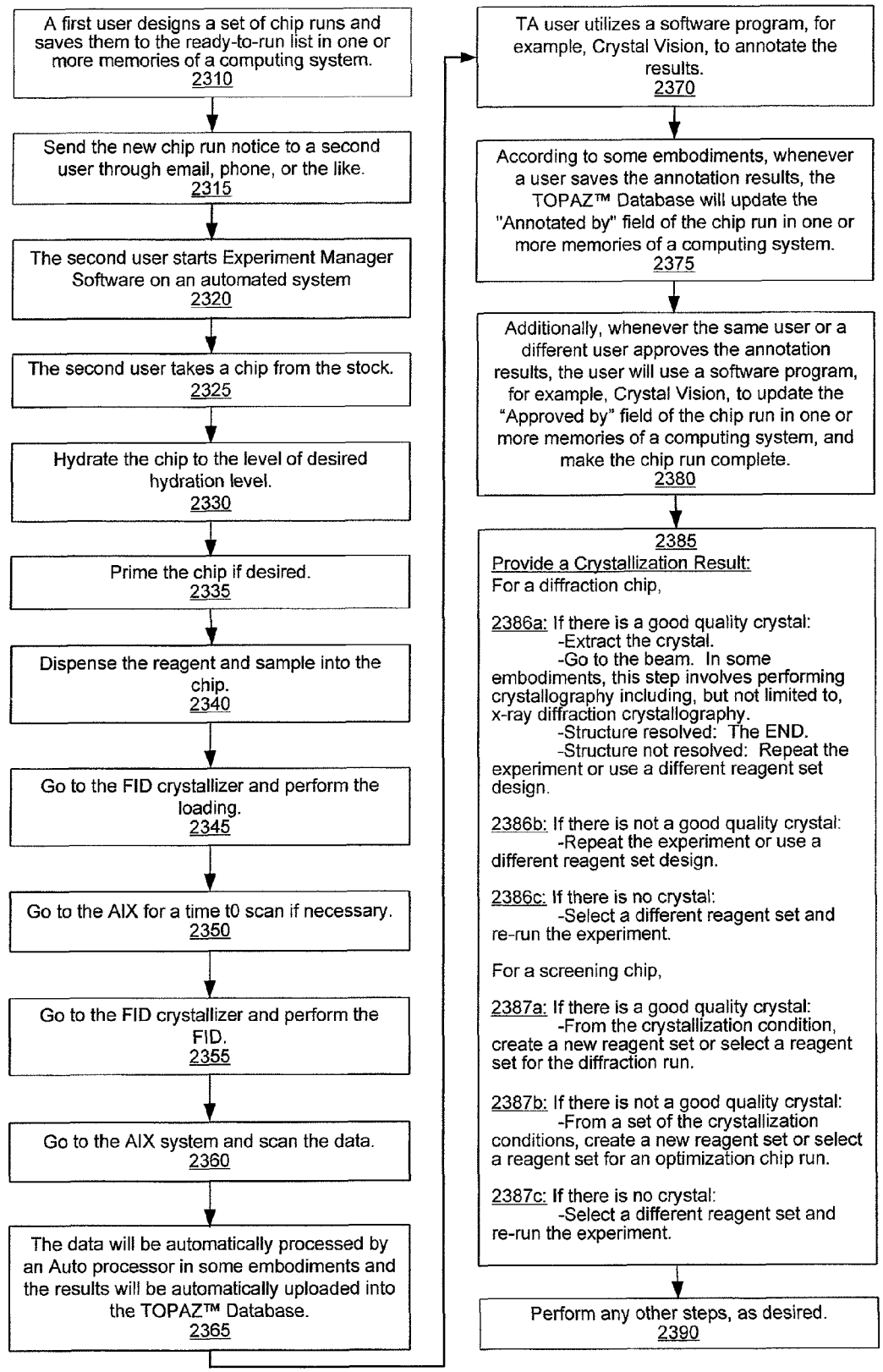

In an eleventh example, a method for running a microfluidic chip run utilizing a designed chip run according to an embodiment of the present invention is provided by the following process flow. Generally, as a precondition, the designed chip run is already created as discussed in relation to the tenth example. FIG. 23 is a simplified flowchart illustrating operations performed according to an exemplary embodiment of the present invention. Accordingly, the reference numerals in the following process flow refer to FIG. 23.

2310. A first user designs a set of chip runs and saves them to the ready-to-run list in one or more memories of a computing system (see the tenth example for creating a chip run in the ready-to-run list).
2315. Send the new chip run notice to a second user through email, phone, or the like.
2320. The second user starts Experiment Manager Software on an automated system, which has been described herein. The second user uses the Experiment Manager or Internet Explorer to find the details of the new chip run and optionally print the work order.
2325. The second user takes a chip from the stock. In some embodiments, this step is not a TOPAZ™ database function, but is performed off-line by a technician or other system operator.
2330. Hydrate the chip to the level of desired hydration level. In some embodiments, this step is not a TOPAZ™ database function.
2335. Prime the chip if desired. Generally, this is a FID function and in some embodiments, no database information exchange is needed.
2340. Dispense the reagent and sample into the chip.
2345. Go to the FID crystallizer and perform the loading. Typically, at the same time, the FID software will ask the user to:
Associate this chip to a chip run in the Ready-to-Run list.

Enter the physical information for the Sample and Reagent Plate

Additionally, typically, the FID will update the Database with system information.

2350. Go to the AIX for a time $t_0$ scan if necessary. Since the chip run information is already stored in the Database, the AIX will automatically update the chip run information if a time $t_0$ scan is performed. The chip run is generally identified by the barcode identifier.

2355. Go to the FID crystallizer and perform the FID. The FID will update the database with FID time and system information.

2360. Go to the AIX system and scan the data. AIX will update the information for this chip run in the Database.

2365. The data will be automatically processed by an Auto processor in some embodiments and the results will be automatically uploaded into the Database.

2370. A user utilizes a software program, for example, Crystal Vision, to annotate the results.

2375. According to some embodiments, whenever a user saves the annotation results, the Database will update the "Annotated by" field of the chip run in one or more memories of a computing system.

2380. Additionally, whenever the same user or a different user approves the annotation results, the user will use a software program, for example, Crystal Vision, to update the "Approved by" field of the chip run in one or more memories of a computing system, and make the chip run complete.

2385. Provide a Crystallization Result:

For a diffraction chip,

2386a. If there is a good quality crystal:
Extract the crystal.
Go to the beam. In some embodiments, this step involves performing crystallography including, but not limited to, x-ray diffraction crystallography.
Structure resolved: The END.
Structure not resolved: Repeat the experiment or use a different reagent set design.

2386b. If there is not a good quality crystal:
Repeat the experiment or use a different reagent set design.

2386c. If there is no crystal:
Select a different reagent set and re-run the experiment.

For a screening chip,

2387a. If there is a good quality crystal:
From the crystallization condition, create a new reagent set or select a reagent set for the diffraction run.

2387b. If there is not a good quality crystal:
From a set of the crystallization conditions, create a new reagent set or select a reagent set for an optimization chip run.

2387c. If there is no crystal:
Select a different reagent set and re-run the experiment.

2390. Perform any other steps, as desired.

As shown, above, the above steps can be used to run a microfluidic chip run utilizing a designed chip run according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 24:
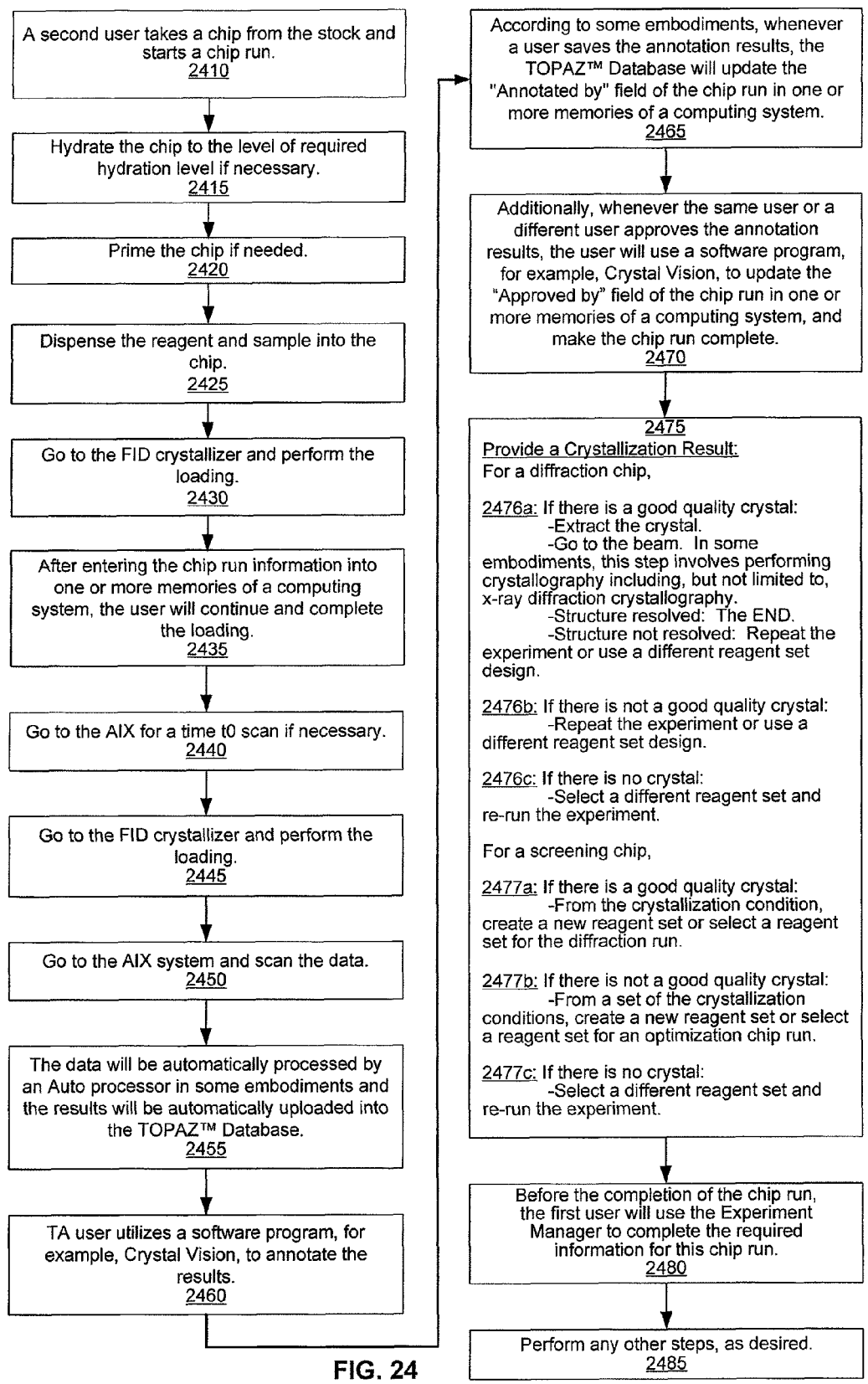

As a twelfth example, a method for running a microfluidic chip run without a designed chip run according to an embodiment of the present invention is provided by the following process flow. FIG. 24 is a simplified flowchart illustrating operations performed according to an exemplary embodiment of the present invention. Accordingly, the reference numerals in the following process flow refer to FIG. 24.

2410. A second user takes a chip from the stock (generally not a TOPAZ™ database function) and starts a chip run.

2415. Hydrate the chip to the level of required hydration level if necessary (not a TOPAZ™ database function).

2420. Prime the chip if needed (generally a FID function, but no database information exchange needed).

2425. Dispense the reagent and sample into the chip.

2430. Go to the FID crystallizer and perform the loading. Since there is no chip run in the "Ready-to-Run" list, the second user will generally have to create a new chip run on the fly in the FID software. To create a new chip run, a user generally has to enter the following information into one or more memories of a computing system:

---
Chip Run Name
Chip Type
Crystallization Method
Reagent Set and Reagent Plate (Optional)
Dispensing Mapping (Optional)
Sample (Optional)
---

2435. After entering the chip run information into one or more memories of a computing system, the user will continue and complete the loading.

After completion of 2435, additional steps as provided by steps 2350 to 2385 in the eleventh example are followed.

2480. Before the completion of the chip run, in a specific embodiment of the present invention, the first user will use the Experiment Manager to complete the required information for this chip run.

2485. Perform any other steps, as desired.

As shown, above, the above steps can be used to run a microfluidic chip run without a designed chip run according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 25:
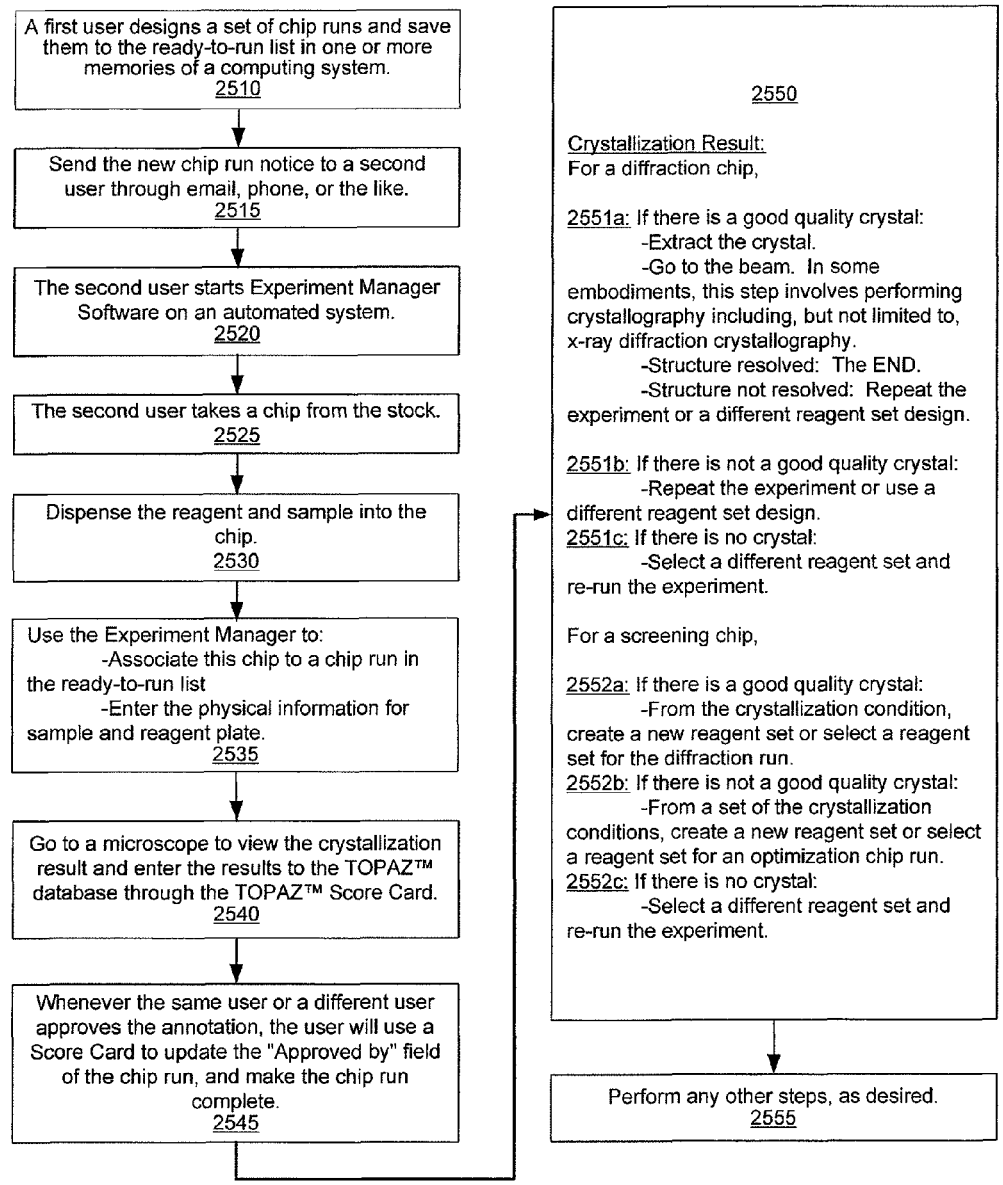

As a thirteenth example, a method for running a chip run using a classic crystallization method with a designed chip run according to an embodiment of the present invention is provided by the following process flow. Generally, a precondition for this method is that the chip run is already created and stored in one or more memories of a computing system as discussed in relation to the tenth example. FIG. 25 is a simplified flowchart illustrating operations performed according to an exemplary embodiment of the present invention. Accordingly, the reference numerals in the following process flow refer to FIG. 25.

2510. A first user designs a set of chip runs and save them to the ready-to-run list in one or more memories of a computing system (see tenth example for creating a chip run in the ready-to-run list).

2515. Send the new chip run notice to a second user through email, phone, or the like.

2520. The second user starts Experiment Manager Software on an automated system, which has been described herein. The second user uses the Experiment Manager or Internet Explorer to find the details of the new chip runs and print the work order.

2525. The second user takes a chip from the stock (generally not a TOPAZ™ database function).

2530. Dispense the reagent and sample into the chip.

2535. Use the Experiment Manager to:
Associate this chip to a chip run in the ready-to-run list.
Enter the physical information for sample and reagent plate 2540. Go to a microscope to view the crystallization result and enter the results to the database through the Score Card, for example, a TOPAZ™ Score Card. Generally, whenever the user saves the annotation results, the database will update the "Annotated by" field of the chip run.

2545. Whenever the same user or a different user approves the annotation, the user will use a Score Card to update the "Approved by" field of the chip run, and make the chip run complete.

2550. Crystallization Result:
For a diffraction chip,
2551a. If there is a good quality crystal:
Extract the crystal.
Go to the beam. In some embodiments, this step involves performing crystallography including, but not limited to, x-ray diffraction crystallography.
Structure resolved. The END.
Structure not resolved. Repeat the experiment or a different reagent set design.
2551b. If there is not a good quality crystal:
Repeat the experiment or use a different reagent set design.
2551c. If there is no crystal:
Select a different reagent set and re-run the experiment.
For a screening chip,
2552a. If there is a good quality crystal:
From the crystallization condition, create a new reagent set or select a reagent set for the diffraction run.
2552b. If there is not a good quality crystal:
From a set of the crystallization conditions, create a new reagent set or select a reagent set for an optimization chip run.
2552c. If there is no crystal:
Select a different reagent set and re-run the experiment.

2555. Perform any other steps, as desired.

As shown, above, the above steps can be used to run a chip run using a classic crystallization method with a designed chip run according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Figure 26:
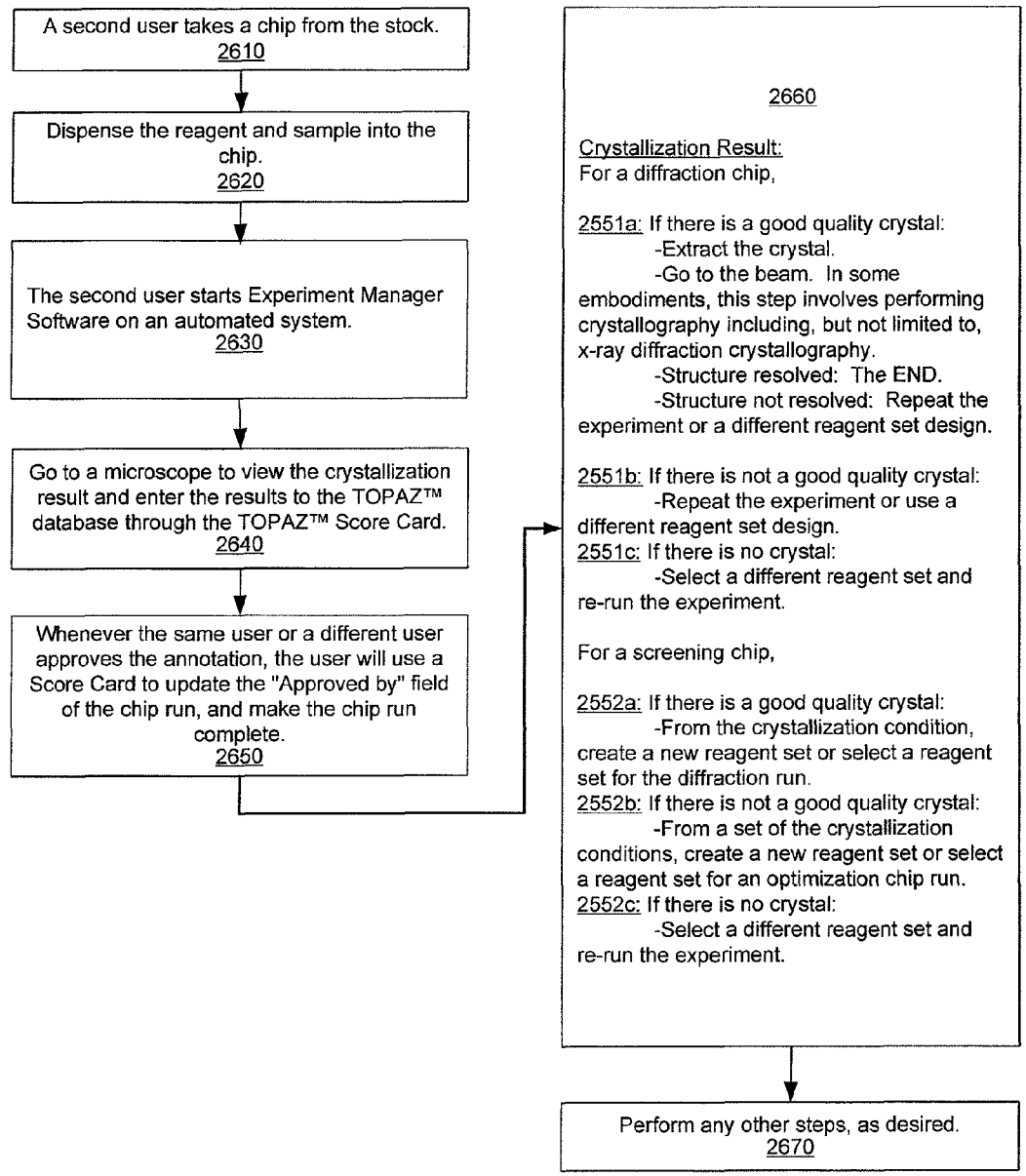

As a fourteenth example, a method for running a chip run using a classic crystallization method without a designed chip run according to an embodiment of the present invention is provided by the following process flow. FIG. 26 is a simplified flowchart illustrating operations performed according to an exemplary embodiment of the present invention. Accordingly, the reference numerals in the following process flow refer to FIG. 26.

2610. A second user takes a chip from the stock.
2620. Dispense the reagent and sample into the chip.
2630. The second user starts Experiment Manager Software on an automated system, which has been described herein. Start Experiment Manager Software if desired on an automated system, which has been described herein. Use the Experiment Manager to create a new chip run, and then associate the reagent plate and sample information with the new chip run.
Associate this chip to a chip run in the Ready-to-Run list.
Enter the physical information for the Sample and the Reagent Plate.
After completion of 3, additional steps as provided by steps 2540 to 2550 in the thirteenth example are followed.
2670. Perform any other steps, as desired.

As shown, above, the above steps can be used to run a chip run using classic crystallization method without a designed chip run according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

In certain embodiments, the disclosed invention encompasses a system for managing workflow related to processing of one or more microfluidic devices including devices that perform polynucleotide amplifications, immunological reactions, chemical synthesis or degradation reactions, or any chemical or biochemical, organic or inorganic reaction that provides a visibly detectable reaction product.

Microfluidic devices for performing polynucleotide amplifications are disclosed, for example, in U.S. Patent Application Publication No. 2003/0138829, U.S. Patent Application Publication No. 2005/0129581, and U.S. Patent Application Publication No. 2005/0214173, all of which are hereby incorporated by reference for all purposes.

Such devices may comprise one or more elastomeric layers made by multilayer soft lithography having the plurality of microfluidic channels and reaction chambers/sites that may be defined and isolated by the actuation of one or more elastomeric valves. Such devices are described in detail by Unger et al. (2000) Science 288:113-116, in U.S. patent application Ser. No. 09/605,520, filed Jun. 27, 2000, in U.S. patent application Ser. No. 09/724,784, filed Nov. 28, 2000, and in PCT publication WO 01/01025, all of which are hereby incorporated by reference for all purposes.

In certain embodiments, a microfluidic device for performing polynucleotide amplifications may include a heat exchange element via which heat is exchanged between the reaction chambers and a thermocycler. A heat exchange element may comprise a plate or surface having a higher thermal conductivity and/or a lower thermal heat capacity than the surrounding material of which the microfluidic device is fabricated. For instance the body of the microfluidic device may be made substantially of an elastomeric polymer such as PDMS, and the heat exchange element may be made of silicon or a semiconductor material or a metal such as steel, aluminum or copper. The heat exchange element may be sized, shaped and placed in contact with the body of the microfluidic device such that heat energy may be readily exchanged with the reaction chambers when in use. In certain preferred embodiments the heat exchange element is integrally fabricated into the structure of the microfluidic device, for example as a plate integrated into the bottom portion of the device wherein one side of the plate is in contact with the bottom surface of the microfluidic device and the other side is exposed so as to be available to be contacted with a complementary thermocycler plate.

In certain embodiments, the disclosed invention encompasses a system for managing workflow related to processing of one or more microfluidic devices for which the microfluidic device comprises one or more well regions, each of the well regions being capable of processing one or more of the process designs associated with the one or more respective processes; and wherein the process encompasses a PCR reaction.

In various preferred embodiments, one or more channels within the microfluidic device is a blind flow channel. Such a blind flow channel may include a region that functions as a reaction site. Certain such devices include a flow channel formed within an elastomeric material, and a plurality of blind flow channels in fluid communication with the flow channel, with a region of each blind flow channel defining a reaction site. The device can also include one or more control channels overlaying and intersecting one or more of the blind flow channels. The devices can optionally further include a plurality of guard channels formed within the elastomeric material and overlaying the flow channel and/or one or more of the reaction sites. The guard channels are designed to have fluid flow therethrough to reduce evaporation from the flow channels and reaction sites of the device. Additionally, the devices can optionally include one or more reagents deposited within each of the reaction sites.

In certain devices a single flow channels is in fluid communication with multiple blind flow channels branching from the flow channel. In some instances the flow channels are interconnected with one another. In other devices, however, the plurality of flow channels are isolated from each other such that fluid introduced into one flow channel cannot flow to another flow channel, and each flow channel comprises an inlet at one or both ends into which fluid can be introduced.

In certain embodiments, the architecture of the flow channels and sample channels is such that the device enables every possible pairwise combination of a number of reagents and a number of samples. For example for samples S1 and S2 and reagents R1 and R2, the architecture facilitates the separate and uncontaminated mixing of sample and reagent to produce combinations: R1S1, R2S1, R1S2 and R2S2.

Other embodiments encompass a device in which a reagent for conducting a reaction is immobilized. The reagent mat be a reagent for conducting a nucleic acid amplification reaction such as a primer, polymerase and one or more nucleotides.

In certain embodiments, the disclosed invention encompasses a system for managing workflow related to processing of one or more microfluidic devices including devices that perform immunological reactions.

Microfluidic devices for performing immunological reactions are disclosed, for example, in U.S. Patent Application Publication No. 2004/0072278 and U.S. Patent Application Publication No. 2004/0180377, both of which are hereby incorporated by reference for all purposes. Such devices are usable to conduct immunological experiments and assays such as qualitative and quantitative immunological assays including ELISA reactions.

Microfluidic devices for use with the invention include devices with the ability to conduct many simultaneous experiments with no cross-talk between the antibodies. Cross-talk is eliminated by physically isolating each primary and secondary antibody in the panel. Each primary antibody is delivered through a separate primary delivery channel, into a reaction chamber. These reaction chambers are then flowed through with a sample containing the target antigen, and then flowed through with a second antibody which is also separate and delivered via a second inlet.

The isolation and separate delivery of the secondary antibody to the reception chambers is fundamental to eliminating potential cross-talk between all antibodies in the panel. Current systems combine the secondary antibodies into a single cocktail which is used to flood the assay cambers. This cocktail may contain antibodies that will cross-talk with other antibodies (e.g. secondary antibodies may bind non-specifically with primary antibodies). This cross-talk problem requires users to employ the very laborious process of screening individual pairs of antibodies against one another to determine cross-talk and therefore identify the "poor quality" antibodies that produce the false positives.

The devices of the invention, for example, may be used as an analytical tool to determine whether a particular target protein or peptide of interest is present or absent in a sample. Such devices may also be used to detect the presence or amount of antibodies in a sample.

The devices may be utilized to test for the presence or quantity of particular pathogen, or for the presence or quantity of proteins, peptides or antibodies associated with such pathogens (e.g., viruses, bacteria or fungi). Such applications would provide a quick, efficient, accurate, sensitive, and inexpensive screening method useful in public health and counter-bio-terrorism applications. The invention may also be used to detect protein and non-protein agents, poisons and toxins (such as abrin, ricin and modeccin etc), and nerve agents, e.g., the "G" agents (such as tabun, soman, sarin, and cyclosarin) and the "V" agents, such as VX. Such devices could also be used for identification purposes (e.g., paternity and forensic applications). Such devices could also be utilized to detect or characterize specific proteins or antibodies correlated with particular diseases or genetic disorders such as diabetes, cancer, and the like.

Alternatively, the devices can be used to perform combinatorial synthetic chemistry or immunology, preparing a large number of combinations simultaneously.

According to some embodiments of the present invention, microfluidic devices provided herein provide reaction chambers characterized by small predetermined volumes. Merely by way of example, some devices provide chambers with a volume of about 25 µl and less. In a particular, embodiment, chambers with a volume of less than about 1 µl to about 1 nl are provided. The throughput of systems utilizing reaction chambers characterized by these small predetermined volumes is higher than conventional systems. Moreover, as described throughout the present specification, numerous combinations of samples and reagents are scanned using embodiments of the present invention.

Moreover, embodiments of the present invention provide microfluidic devices characterized by reduced spatial and temporal variation compared to conventional devices. For example, some microfluidic device provided herein reduce spatial variation as a result on the reduced spatial dimensions of the microfluidic devices in comparison to conventional microtiter plates. Accordingly, temperature variations across the chambers present in the microfluidic device are reduced, enabling increased accuracy in performing PCR processes. Additionally, these reduced spatial dimensions result in a decrease in temporal variations, as reactions are initiated and terminated within a smaller time window than achieved using conventional techniques such as microtiter plates. One of ordinary skill in the art would recognize many variations, modifications, and alternatives.

Matrix Design

A. General

Devices utilizing the matrix design generally have a plurality of vertical and horizontal flow channel that intersect to form an array of junctions. Because a different sample and reagent (or set of reagents) can be introduced into each of the flow channels, a large number of samples can be tested against a relatively large number of reaction conditions in a high throughput format. Thus, for example, if a different sample is introduced into each of M different vertical flow channels and a different reagent (or set of reagents) is introduced into each of N horizontal flow channels, then M×N different reactions can be conducted at the same time. Typically, matrix devices include valves that allow for switchable isolation of the vertical and horizontal flow channels. Said differently, the valves are positioned to allow selective flow just through the vertical flow channels or just through the horizontal flow channels. Because devices of this type allow flexibility with respect to the selection of the type and number of samples, as well as the number and type of reagents, these devices are well-suited for conducting analyses in which one wants to screen a large number of samples against a relatively large number of reaction conditions. The matrix devices can optionally incorporate guard channels to help prevent evaporation of sample and reactants.

B. Exemplary Designs and Uses

Figure 27:
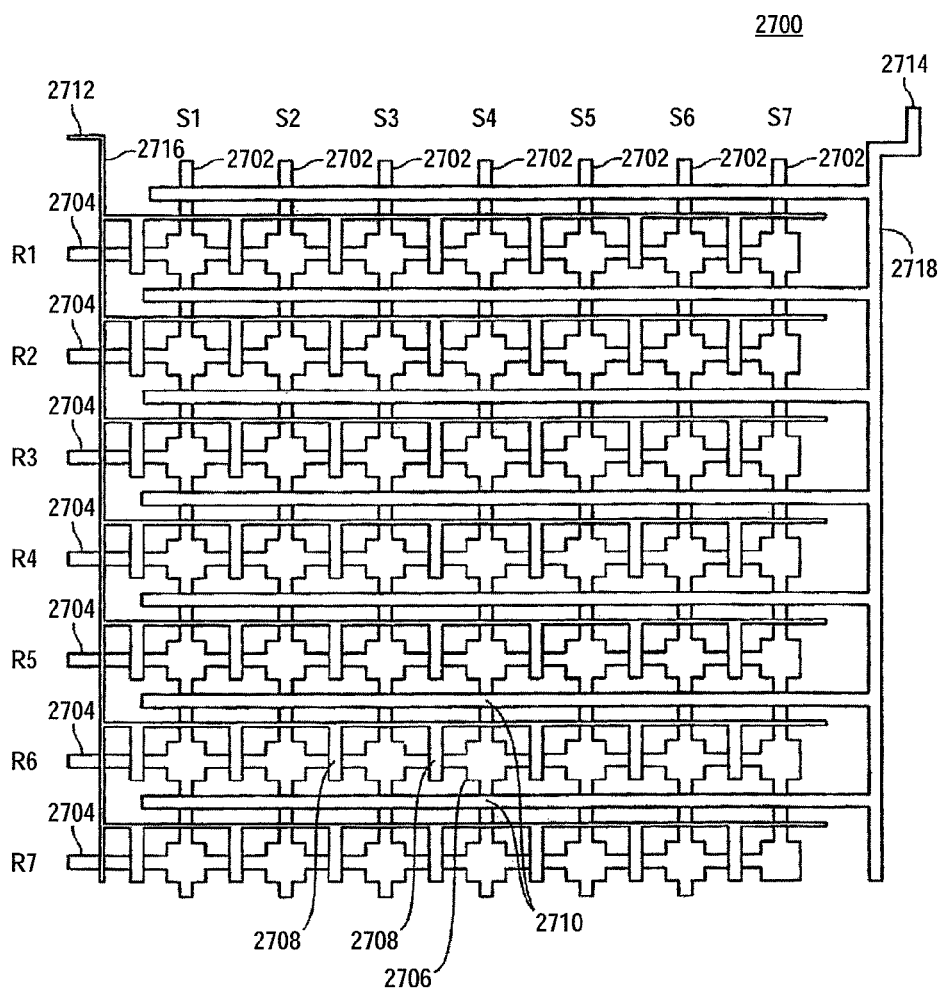
FIG. 27 is a schematic representation of an exemplary device with a matrix design of intersecting vertical and horizontal flow channels.

FIG. 27 provides an illustration of one exemplary matrix device. This device 2700 comprises seven vertical flow channels 2702 and seven horizontal flow channels 2704 that intersect to form an array of 49 different intersections or reaction sites 2706. This particular device thus enables seven samples to be reacted with seven different reagents or sets of reagents. Column valves 2710 that regulate solution flow in the vertical direction can be controlled by control channels 2718 that can all be actuated at a single inlet 2714.

Similarly, row valves 2708 regulate solution flow in the horizontal direction; these are controlled by control channels 2716 that are actuated by a single control inlet 2712. As shown in FIG. 27, the control channels 2716 that regulate the row valves 2708 vary in width depending upon location. When a control channel 2716 crosses a vertical flow channel 2702, the control channel 2716 is sufficiently narrow that when it is actuated it does not deflect into the vertical flow channel 2702 to reduce substantially solution flow therethrough. However, the width of the control channel 2716 is increased when it overlays one of the horizontal flow channels 2704; this makes the membrane of the control channel sufficiently large to block solution flow through the horizontal flow channel 2704.

In operation, reagents R1-R7 are introduced into their respective horizontal flow channels 2704 and samples S1-S7 are injected into their respective vertical flow channels 2702. The reagents in each horizontal flow channel 2704 thus mix with the samples in each of the vertical flow channels 2702 at the intersections 2706, which in this particular device are in the shape of a well or chamber. Thus, in the specific case of a nucleic acid amplification reaction, for example, the reagents necessary for the amplification reaction are introduced into each of the horizontal flow channels 2704. Different nucleic acid templates are introduced into the vertical flow channels 2702. In certain analyses, the primer introduced as part of the reagent mixture that is introduced into each of the horizontal flow channels 104 might differ between flow channels. This allows each nucleic acid template to be reacted with a number of different primers.

Blind Channel Designs

A. General

Devices utilizing a blind channel design have certain features. First, the devices include one or more flow channels from which one or more blind channels branch. As indicated above, the end region of such channels can serve as a reaction site. A valve formed by an overlaying flow channel can be actuated to isolate the reaction site at the end of the blind channel. The valves provide a mechanism for switchably isolating the reaction sites.

Second, the flow channel network in communication with the blind channels is configured such that all or most of the reaction sites can be filled with a single or a limited number of inlets (e.g., less than 5 or less than 10). The ability to fill a blind flow channel is made possible because the devices are made from elastomeric material. The elastomeric material is sufficiently porous such that air within the flow channels and blind channels can escape through these pores as solution is introduced into the channels. The lack of porosity of materials utilized in other microfluidic devices precludes use of the blind channel design because air in a blind channel has no way to escape as solution is injected.

A third characteristic is that one or more reagents are non-covalently deposited on a base layer of elastomer during manufacture (see infra for further details on the fabrication process) within the reaction sites. The reagent(s) are non-covalently attached because the reagents are designed to become dissolved when sample is introduced into the reaction site. To maximize the number of analyses, a different reactant or set of reactants is deposited at each of the different reaction sites.

Certain blind channel devices are designed such that the reaction sites are arranged in the form of an array.

Thus, in those blind channel devices designed for conducting nucleic acid amplification reactions, for example, one or more of the reagents required for conducting the extension reaction are deposited at each of the reaction sites during manufacture of the device. Such reagents include, for example, all or some of the following: primers, polymerase, nucleotides, cofactors, metal ions, buffers, intercalating dyes and the like. To maximize high throughput analysis, different primers selected to amplify different regions of DNA are deposited at each reaction site. Consequently, when a nucleic acid template is introduced into the reaction sites via inlet, a large number of extension reactions can be performed at different segments of the template. Thermocycling necessary for an amplification reaction can be accomplished by placing the device on a thermocycling plate and cycling the device between the various required temperatures.

The reagents can be immobilized in a variety of ways. For example, in some instances one or more of the reagents are non-covalently deposited at the reaction site, whereas in other instances one or more of the reagents is covalently attached to the substrate at the reaction site. If covalently attached, the reagents can be linked to the substrate via a linker. A variety of linker types can be utilized such as photochemical/photolabile linkers, themolabile linkers, and linkers that can be cleaved enzymatically. Some linkers are bifunctional (i.e., the linker contains a functional group at each end that is reactive with groups located on the element to which the linker is to be attached); the functional groups at each end can be the same or different. Examples of suitable linkers that can be used in some assays include straight or branched-chain carbon linkers, heterocyclic linkers and peptide linkers. A variety of types of linkers are available from Pierce Chemical Company in Rockford, Ill. and are described in EPA 188,256; U.S. Pat. Nos. 4,671,958; 4,659,839; 4,414,148; 4,669,784; 4,680,338, 4,569,789 and 4,589,071, and by Eggenweiler, H. M, Pharmaceutical Agent Discovery Today 1998, 3, 552. NVOC (6 nitroveratryloxycarbonyl) linkers and other NVOC-related linkers are examples of suitable photochemical linkers (see, e.g., WO 90/15070 and WO 92/10092). Peptides that have protease cleavage sites are discussed, for example, in U.S. Pat. No. 5,382,513.

B. Exemplary Designs and Uses

Figure 28:
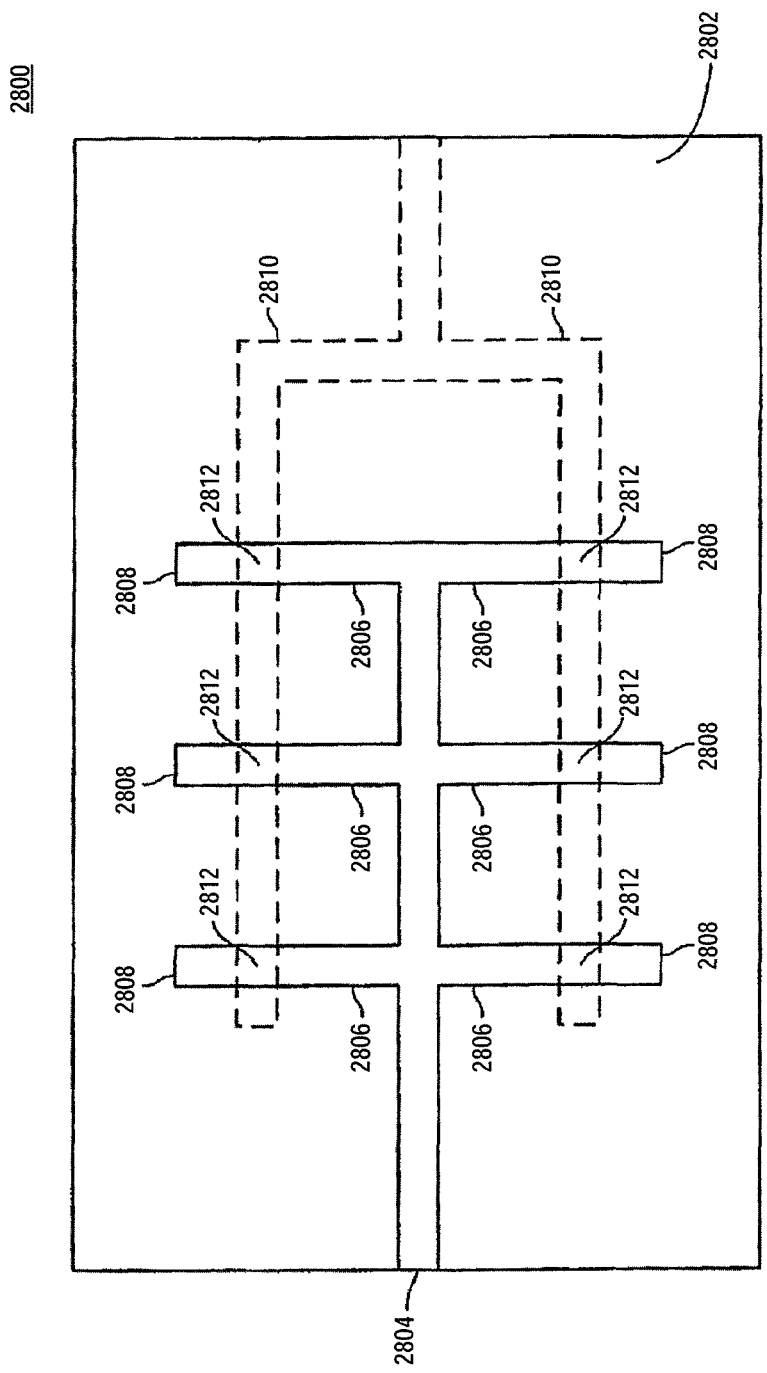
FIG. 28 is a plan view of an exemplary blind channel device.

FIG. 28 is a simplified plan view of one exemplary device utilizing the blind channel design. The device 2800 includes a flow channel 2804 and a set of branch flow channels 2806 branching therefrom that are formed in an elastomeric substrate 2802. Each branch flow channel 2806 terminates in a reaction site 2808, thereby forming an array of reaction sites. Overlaying the branch flow channels 2806 is a control channel 2810 that is separated from the branch flow channels 2806 by membranes 2812. Actuation of control channel 2810 causes membranes 2812 to deflect into the branch flow channels 2806 (i.e., to function as a valve), thus enabling each of the reaction sites 2808 to be isolated from the other reaction sites.

Operation of such a device involves injecting a test sample into flow channel 2804 with solution subsequently flowing into each of branch channels 2806. Once the sample has filled each branch channel 2806, control channel 2810 is actuated to cause activation of valves/membranes 2812 to deflect into branch channels 2806, thereby sealing off each of reaction sites 2808. As the sample flows into and remains in reaction sites 2808, it dissolves reagents previously spotted at each of the reaction sites 2808. Once dissolved, the reagents can react with the sample. Valves 2812 prevent the dissolved reagents at each reaction site 2808 from intermixing by diffusion. Reaction between sample and reagents are then detected, typically within reaction site 2808. Reactions can optionally be heated as described in the temperature control section infra.

Example 1

Signal Strength Evaluations

I. Introduction

The purpose of this set of experiments was to demonstrate that successful PCR reactions can be conducted with a microfluidic device of the design set forth herein with signal strength greater than 50% of the Macro TaqMan reaction.

II. Microfluidic Device

Figure 29A:
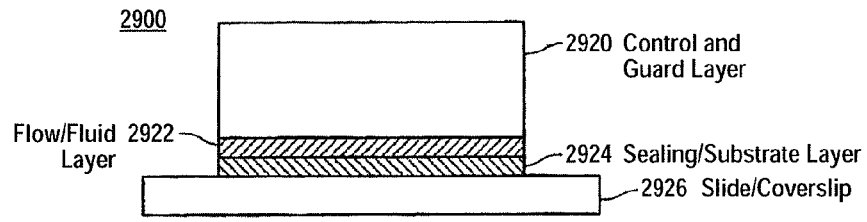
FIGS. 29A and 29B respectively are a cross-sectional view and a schematic diagram of another hybrid type microfluidic device and represents the type of device used to conduct experiments according to embodiments of the present invention.

A three layer microfluidic device, fabricated using the MSL process, was designed and fabricated for conducting the experiments described in the following example; FIG. 29A shows a cross-sectional view of the device. As shown, the device 2900 includes a layer 2922 into which is formed the flow channels. This fluid layer 2922 is sandwiched between an overlaying layer 2920 that includes the control and guard layers and an underlying sealing layer 2924. The sealing layer 2924 forms one side of the flow channels. The resulting three-layer structure is affixed to a substrate 2926 (in this example, a slide or coverslip), which provides structural stiffness, increases thermal conductivity, and helps to prevent evaporation from the bottom of microfluidic device 2900.

Figure 29B:
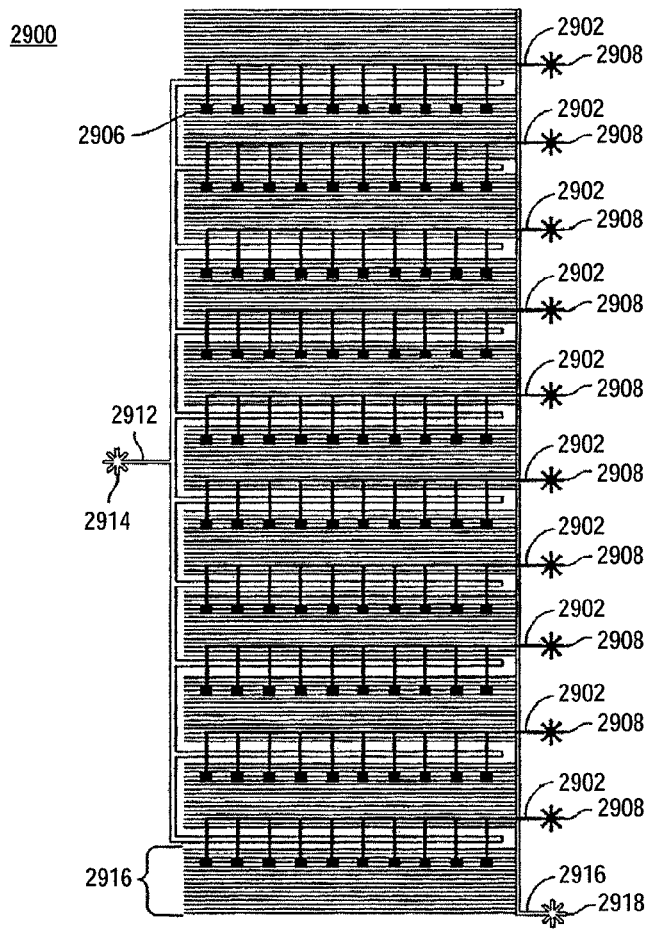

FIG. 29B shows a schematic view of the design of the flow channels in flow layer 2922 and of the control channels and guard channel in control/guard layer 2920. Device 2900 consists of ten independent flow channels 2902, each with its own inlet 2908, and branching blind channels 2904, each blind channel 2904 having a 1 nl reaction site 2906. Device 2900 contains a network of control lines 2912, which isolate the reaction sites 2906 when sufficient pressure is applied. A series of guard channels 2916 are also included to prevent liquid from evaporating out of the reaction sites 2906; fluid is introduced via inlet 2918.

II. Experimental Setup

A PCR reaction using 13-actin primers and TaqMan probe to amplify exon 3 of the β-actin gene from human male genomic DNA (Promega, Madison Wis.) was conducted in device 2900. The TaqMan reaction consists of the following components: 1× TaqMan Buffer A (50 mM KCl, 10 mM Tris-HCl, 0.01M EDTA, 60 nM Passive Reference 1 (PR1), pH 8.3); 3.5-4.0 mM MgCl; 200 nM dATP, dCTP, dGTP, 400 nM dUTP; 300 nM β-actin forward primer and reverse primer; 200 nM FAM-labeled β-actin probe; 0.01 U/μl AmpEraseUNG (Applied Biosystems, Foster City, Calif.); 0.1-0.2 U/μl DyNAzyme (Finnzyme, Espoo, Finland); 0.5% Triton-x-100 (Sigma, St. Louis, Mo.); 0.8 μg/μl Gelatin (Calbiochem, San Diego, Calif.); 5.0% Glycerol (Sigma, St. Louis, Mo.); deionized $H_2O$ and male genomic DNA. The components of the reaction were added to produce a total reaction volume of 25 μl. Negative controls (Control) composed of all the TaqMan reaction components, except target DNA were included in each set of PCR reactions.

Once the TaqMan reaction samples and Control were prepared, they were injected into microfluidic device 2900 by using a gel loading pipet tip attached to a 1 ml syringe. The pipet tip was filled with the reaction samples and then inserted into the fluid via 2908. The flow channels 2902 were filled by manually applying backpressure to the syringe until all the entire blind channels 2904 and reaction sites 2906 were filled. Control lines 2912 were filled with deionized water and pressurized to 15-20 psi after all of the samples were loaded into the flow lines 2902, 2904. The pressurized control lines 2912 were actuated to close the valves and isolate the samples in the 1 nl wells 2906. The guard channels 2916 were then filled with deionized water and pressurized to 5-7 psi. Mineral oil (15 μl) (Sigma) was placed on the flatplate of a thermocycler and then the microfluidic device/coverglass 2900 was placed on the thermocycler. Micro fluidic device 2900 was then thermocycled using an initial ramp and either a three-step or two-step thermocycling profile:

1. Initial ramp to 95° C. and maintain for 1 minute (1.0° C./s to 75° C., 0.1° C./sec to 95° C.).
2. Three step thermocycling for 40 cycles (92° C. for 30 sec., 54° C. for 30 sec., and 72° C. for 1 min) or;
3. Two step thermocycling for 40 cycles (92° C. for 30 seconds and 60° C. for 60 sec.)

MicroAmp tubes (Applied Biosystems, Foster City, Calif.) with the remaining reaction mixture, designated Macro TaqMan reactions to distinguish them from reactions performed in the microfluidic device, were placed in the GeneAmp PCR System 9700 (Applied Biosystems, Foster City, Calif.) and thermocycled in the 9600 mode. The Macro TaqMan reactions served as macroscopic controls for the reactions performed in the micro fluidic device. The thermocycling protocol was set to match that of the microfluidic device, except that the initial ramp rate was not controlled for the Macro TaqMan reactions.

Once thermocycling was completed, the control and guard lines were depressurized and the chip was transferred onto a glass slide (VWR, West Chester, Pa.). The chip was then placed into an Array WoRx Scanner (Applied Precision, Issaquah, Wash.) with a modified carrier. The fluorescence intensity was measured for three different excitation/emission wavelengths: 475/510 nm (FAM), 510/560 nm (VIC), and 580/640 nm (Passive Reference 1 (PR1)). The Array Works Software was used to image the fluorescence in the micro fluidic device and to measure the signal and background intensities of each 1 nl well. The results were then analyzed using a Microsoft Excel file to calculate the FAM/PR1 ratio for β-actin TaqMan reactions. For conventional Macro TaqMan, positive samples for target DNA were determined using calculations described in the protocol provided by the manufacturer (TaqMan PCR Reagent Kit Protocol). The signal strength was calculated by dividing the FAM/PR1 ratio of the samples by the FAM/PR1 ratio of the controls. A successful reaction was defined as a sample ratio above the 99% confidence threshold level.

III. Results

Initially, AmpliTaq Gold (Applied Biosystems, Foster City, Calif.) was used in TaqMan reactions and FAM/PR1/Control ratios of 1.5-2.0 were produced, compared to Macro TaqMan reaction ratios of 5.0-14.0. Although results were positive, increased signal strength was desired. Therefore, the AmpliTaq Gold polymerase was substituted with DyNAzyme polymerase due to its increased thermostability, proofreading, and resistance to impurities. The standard Macro TaqMan DyNAzyme concentration of 0.025 U/μl was used in the microfluidic experiments. This polymerase change to DyNAzyme produced FAM/ROX/Control ratios of 3.5-5.8. The signal strength was improved, but it was difficult to achieve consistent results. Because it is know that some proteins stick to PDMS, the concentration of the polymerase was increased and surface modifying additives were included. Two increased concentrations of DyNAzyme were tested, 8×(0.2 U/μl) and 4×(0.1 U/μl) the standard concentration for Macro TaqMan, with 100 pg or 10 pg of genomic DNA per nl in the micro fluidic device. Gelatin, Glycerol, and 0.5% Triton-x-100 were added to prevent the polymerase from attaching to the PDMS.

The microfluidic TaqMan reaction ratios range from 4.9-8.3, while the Macro TaqMan reactions range from 7.7-9.7. Therefore, the signal strength of the TaqMan reactions in chip is up to 87% of the Macro TaqMan reactions. There was no significant difference between 4× or 8× DyNAzyme. The results demonstrate that PCR reactions can be done with greater than 50% signal strength, when compared to the Macro TaqMan reactions, in the microfluidic devices. The results have been consistent through at least four attempts.

Example 2

Verification of PCR by Gel Electrophoresis

I. Introduction

As an alternative method to prove amplification of DNA was occurring in the microfluidic device, an experiment to detect PCR product by gel electrophoresis was performed. PCR reactions compositions were as described in Example 1, except the TaqMan probe was omitted and the β-actin forward primer was conjugated to FAM.

II. Procedure

A. Microfluidic Device

Figure 30:
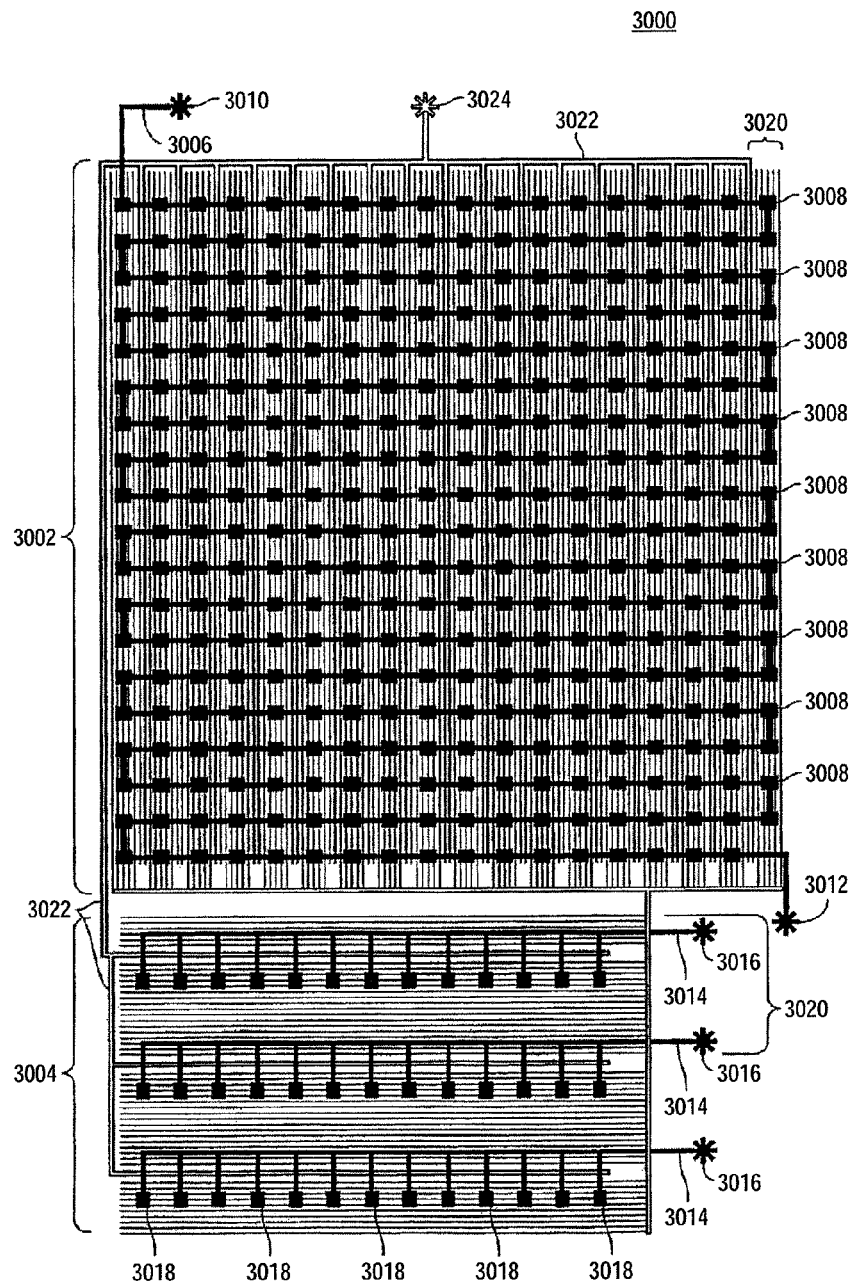
FIG. 30 is a schematic diagram of the microfluidic device used for experiments according to another embodiment of the present invention.
Figure 31A:
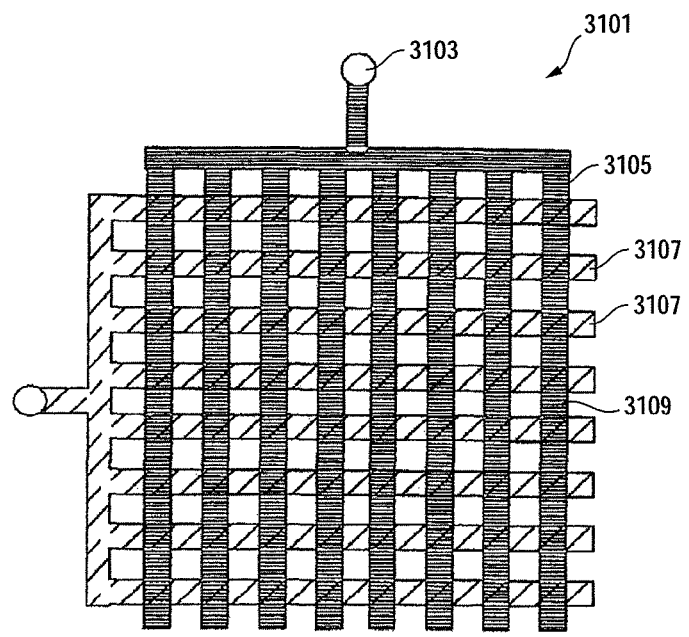
FIGS. 31A-31D depict two preferred designs of a partitioning microfluidic device in a valve off and valve actuated state.
Figure 31B:
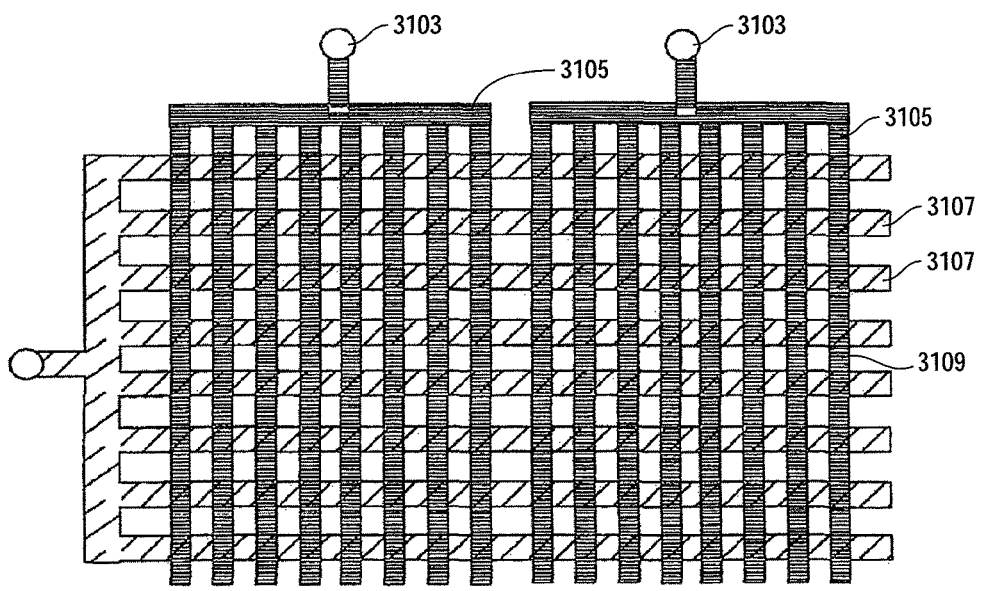
Figure 31C:
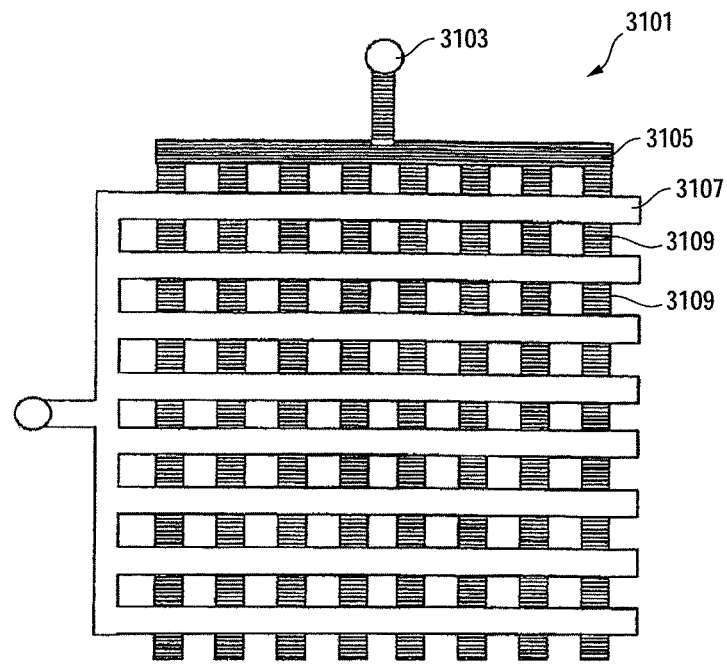
Figure 31D:
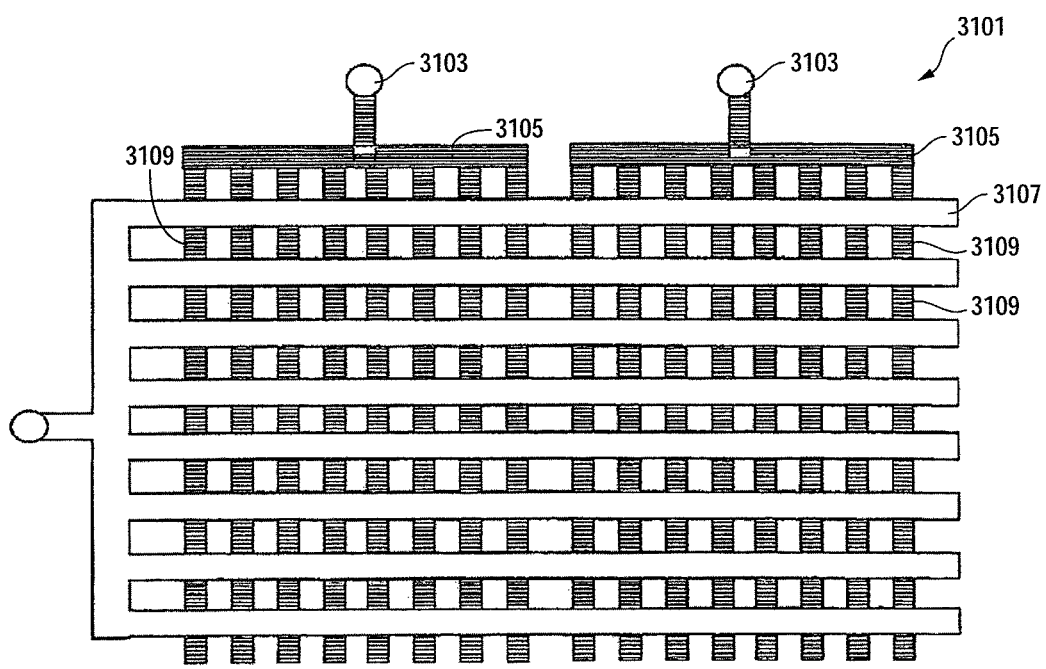

A three layer microfluidic device, fabricated using the MSL process, was designed and fabricated for conducting the experiments described in this example; FIG. 30 shows a schematic view of the design. The device 3000 generally consists of a sample region 3002 and a control region 3004. Sample region 3002 contains three hundred and forty-one 1 nl reaction sites 3008 represented by the rectangles arrayed along flow channel 3006, which includes inlet via 3010 and outlet via 3012. Control region 3004 contains three control flow channels 3014 each containing ten 1 nl reaction sites 3018, also represented by the rectangles and an inlet via 3016. A network of control lines 3022 isolate each reaction site 3008, 3018 when sufficient pressure is applied to inlet via 3024. A series of guard channels 3020 are included to prevent liquid from evaporating out of the reaction sites 3008, 3018. The device is a three-layer device as described in Example 1 (see FIG. 29A). The entire chip is placed onto a coverslip.

B. Experimental Setup

Microfluidic device 3000 was loaded and thermocycled using the 3 temperature profile described in Example 1. The remaining reaction sample was thermocycled in the Gene-Amp 9700 with the same thermocycling profile as for microfluidic device 3000. The reaction products were recovered after thermocycling was completed. To recover the amplified DNA, 3 μl of water was injected into sample input via 3006 and 3-4 μl of product were removed from outlet via 3012. The reaction products from device 3000 and the Macro reaction were treated with 2 μl of ExoSAP-IT (USB, Cleveland, Ohio), which is composed of DNA Exonuclease I and Shrimp Alkaline Phosphatase, to remove excess nucleotides and primers. The Macro product was diluted from 1:10 to 1:106. The product from device 3000 was dehydrated and resuspended in 4 μl of formamide.

III. Results

Both products, along with negative controls were analyzed, on a polyacrylamide gel. FIG. 30 shows the gel electrophoresis results. The appropriate size DNA band of 294 base pairs in length was observed.

The products from the Macro reactions are shown on the left hand side of the gel and correspond to about 294 base pairs, the expected size of the β-actin PCR product. The negative controls lack the PCR product. Similarly, the product derived from the device gave the expected β-actin PCR product. Therefore, target DNA was amplified in the micro fluidic device.

Example 3

Massive Partitioning

The polymerase chain reaction (PCR) has become an essential tool in molecular biology. Its combination of sensitivity (amplification of single molecules of DNA), specificity (distinguishing single base mismatches) and dynamic range ($10^5$ with realtime instrumentation) make it one of the most powerful analytical tools in existence. We demonstrate here that PCR performance improves as the reaction volume is reduced: we have performed 21,000 simultaneous PCR reactions in a single microfluidic chip, in a volume of 90 pL per reaction and with single template molecule sensitivity.

FIGS. 31A-31D depict a single bank and dual bank partitioning microfluidic device where multilayer soft lithography (MSL) (1), was used to create elastomeric microfluidic chips which use active valves to massively partition each of several liquid samples into a multitude of isolated reaction volumes. After injection of the samples into inlet 3103 which is in communication with branched partitioning channel system 3105 of microfluidic device 3101 (FIG. 31B), 2400 90 pL volumes 3109 of each sample are isolated by closing valves 3107 spaced along (FIG. 31D) simple microfluidic channels. The chip device is then thermocycled on a flat plate thermocycler and imaged in a commercially available fluorescence reader.

Figure 32:
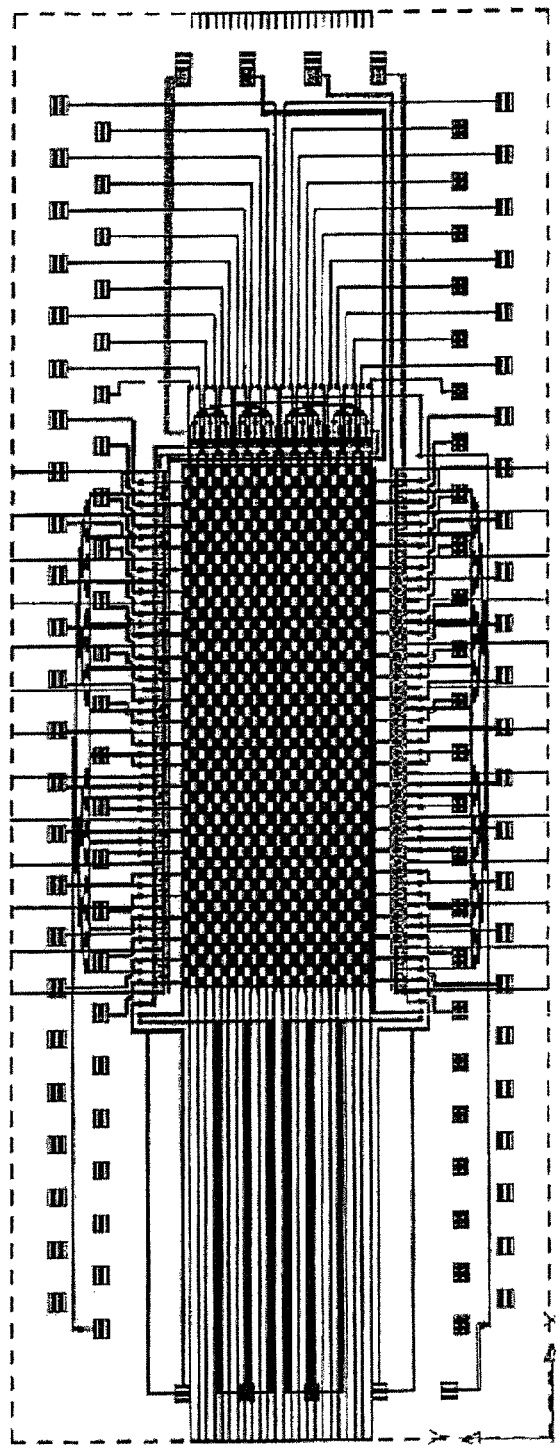
FIG. 32 is a schematic drawing of one "immunochip" embodiment of the device having 24 sample inputs and 24 primary antibody inputs, and 24 secondary antibody inputs.

FIG. 32 is a schematic drawing of one "immunochip" embodiment of the device having 24 sample inputs and 24 primary antibody inputs, and 24 secondary antibody inputs. Additional disclosure related to immunochip embodiments of the present invention are provided in U.S. Provisional Patent Application No. 60/716,823, entitled "Microfluidic Devices for Performing Immunological Assays," filed on Sep. 13, 2005, and incorporated herein by reference for all purposes.

Figure 33:
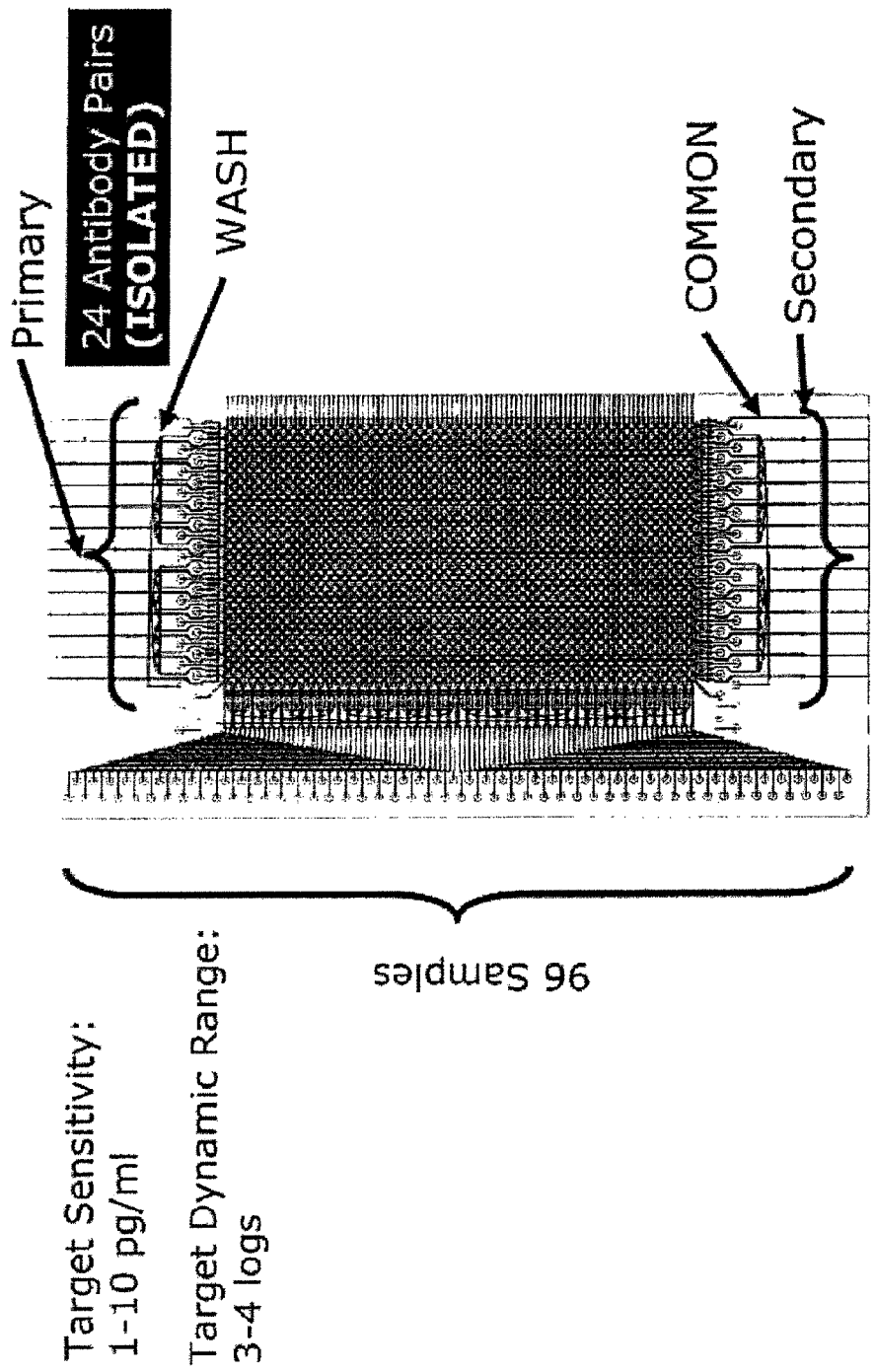
FIG. 33 is a schematic drawing of another embodiment of the device having 96 sample inputs and 24 primary antibody inputs, and 24 secondary antibody inputs.

FIG. 33 is a schematic drawing of another embodiment of the device having 96 sample inputs and 24 primary antibody inputs, and 24 secondary antibody inputs.

Figure 34:
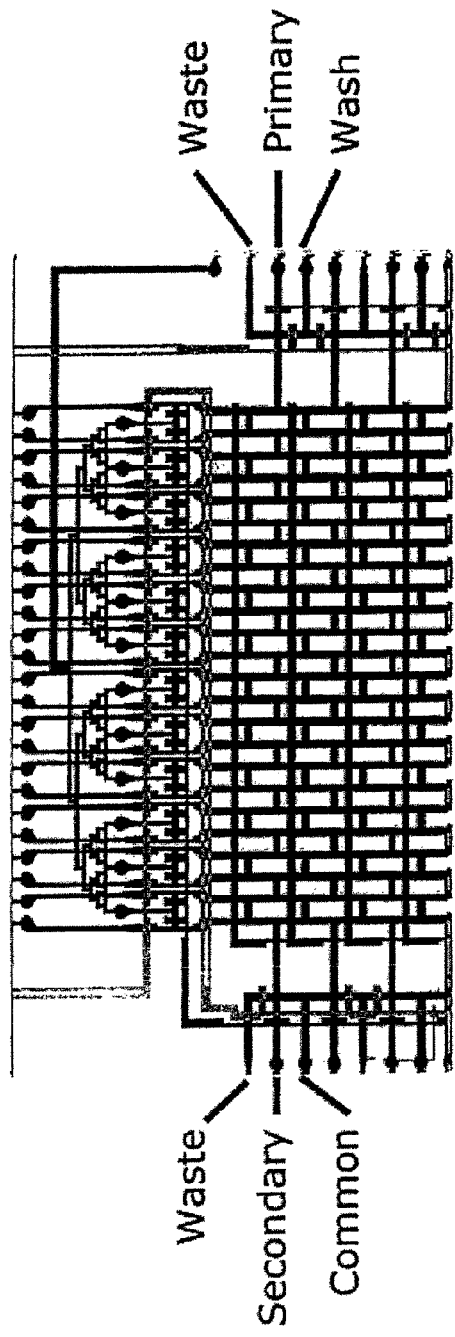
FIG. 34 is a schematic drawing showing a magnified section of an embodiment the device.

FIG. 34 is a schematic drawing showing a magnified section of an embodiment the device. The primary inlet is the inlet through which the primary antibody is introduced. The secondary is the inlet through which the secondary antibody is introduced. The wash inlet is the inlet through which washing solution is introduced. The two waste outlets are the outflows through which the excess reactant fluid (of any kind) is expelled. In use, the blocking solution is flowed through the lumens of the chip via the common inlet. The primary antibody solution is then introduced through the primary inlet and flows through the lumens of the chip and through the reaction chambers. A wash solution is then flowed through all the lumens and chambers to remove unbound primary antibody. The secondary antibody solution is introduced through the secondary inlet and flows through the lumens of the chip and through the reaction chambers. Another wash solution is then flowed through all the lumens and chambers to remove unbound secondary antibody. The enzyme solution is then introduced, followed by another washing step, followed by the substrate solution, followed by a final wash step. A signal is thus produced and measured.

According to embodiments of the present invention, in addition to protein crystallization experiments, there are multiple examples of other fluorogenic reactions, chemiluminescent reactions, colorimetric reactions, and radiometric reactions that are run utilizing the Database Application Suite. Some of these experiments involve multiple software components, while others will only involve one component. One of ordinary skill in the art would recognize many variations, modifications, and alternatives. Additionally, some of these examples of using methods and systems according to embodiments of the present invention do not constitute performance of entire experiments, but merely portions or sub-elements thereof.

FIG. 35 is a simplified flowchart illustrating a method of performing gene expression/genotyping experiments according to an embodiment of the present invention. As shown in FIG. 35, several different experiments may be performed in a sequential and/or recursive manner according to embodiments of the present invention.

FIGS. 36-40 are simplified flowcharts illustrating operations performed according to exemplary embodiments of the present invention.

As a first example, a method for using a Dynamic Array, for example a 48×48 element array, for gene expression analysis according to an embodiment of the present invention is provided by the following process flow. FIG. 36 is a simplified flowchart illustrating operations performed according to an exemplary embodiment of the present invention. Accordingly, the reference numerals in the following process flow refer to FIG. 36.

3610. A first user acquires biological samples, develops, extracts RNA, and processes RNA into cDNA. In some embodiments, this is an optional step. Additionally, the first user develops screening reagents (e.g., TaqMan assays).

3612. The first user mixes up to 48 samples with real-time PCR Master Mix and loads sample-master mix mixtures into the sample wells of the 48×48 Dynamic Array. In some embodiments, this step is performed manually by hand-pipetting, whereas in other embodiments, this step is performed automatically with automated liquid handling workstations. One of ordinary skill in the art would recognize many variations, modifications, and alternatives.

3614. The first user loads screening reagents into the reagent wells of the 48×48 Dynamic Array. In some embodiments, this step is performed manually by hand-pipetting, whereas in other embodiments, this step is performed automatically with automated liquid handling workstations.

3616. The 48×48 Dynamic Array is placed into a chip loading instrument (e.g., a NanoFlex IFC Controller) by the first user. In some embodiments, a FIDX™ is utilized for this step.

3618. The NanoFlex IFC Controller loads the sample-master mix mixtures and screening reagents from the wells of the 48×48 Dynamic Array into the appropriate reactions in the integrated fluidic circuit (IFC) of the 48×48 Dynamic Array. According to an embodiment of the present invention, a chip-specific computer script controls this loading operation.

3620. The 48×48 Dynamic Array is moved from the NanoFlex IFC Controller to the BioMark System. In a particular embodiment, this step involves placing the 48×48 Dynamic Array in a chip tray such as a microwell plate tray).

3622. The orientation of the 48×48 Dynamic Array is verified.

3624. The chip tray (e.g., the microwell plate tray), controlled by a motor, draws the 48×48 Dynamic Array into the BioMark System.

3626. A barcode reader reads the barcode on the 48×48 Dynamic Array. According to embodiments of the present invention, each barcode contains a unique number to identify the 48×48 Dynamic Array as well as the chip type (e.g. 48×48 Dynamic Array, digital array, and the like).

3628. The microwell plate tray, with the 48×48 Dynamic Array inside, stops at a position above a thermal cycler.

3630. A motor controls vertical movement of the thermal cycler. The motor moves the thermal cycler up until a vacuum seal between the thermal block and an IHS (integrated heat spreader) of the 48×48 Dynamic Array is detected.

3632. Autofocusing (typically performed by moving the thermal cycler up or down) normal to the chip tray, is used to focus the optical system.

3634. Fluorescence intensity of test images are used to set an intensity of one or more xenon lamps for each wavelength of interest.

3636. Thermal cycling commences. According to embodiments of the present invention, protocols are pre-programmed or entered prior to the run.

3638. Images are taken with a CCD camera during the thermal cycling protocol. The one or more xenon lamps, excitation filter wheel, emission filter wheel, thermal cycler, CCD camera, and computer are synchronized in an embodiment in order to properly collect images on all wavelengths of interest.

3640. After the run is complete, the microwell plate tray moves the 48×48 Dynamic Array out of the BioMark System.

3642. In a specific embodiment, steps 3616-3640 are repeated in a batch mode. In exemplary embodiments, batch mode operation is performed provided that multiple 48×48 Dynamic Arrays were set up in steps 3612 and 3614 and that automation is in place for the steps that are external to the BioMark System.

3644. Software analysis commences as described in more detail throughout the present specification.

3646. Perform any other steps, as desired.

As shown, above, the above steps can be used to use a Dynamic Array for gene expression analysis according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

As a second example, a Matrix Instrument is used to set up and run a Dynamic Array Gene Expression experiment. Various numbers of reaction chambers (e.g., 48×48 or 96×96) are provided herein. Preferably, a number of initial conditions are provided prior to running the gene expression experiment. These initial conditions may include: the Instrument System is installed; the Instrument System is calibrated; the Instrument System is powered up and warmed up; the FIDX™ System is installed; and the user has prepared cDNA and assays; the user has designed the experiment. FIG. 37 is a simplified flowchart illustrating operations performed according to an exemplary embodiment of the present invention. Accordingly, the reference numerals in the following process flow refer to FIG. 37.

3710. The User moves carrier into FIDX.

3712. User pressurizes chip interface and containment fluid using FIDX.

3714. User removes carrier from FIDX.

3716. User moves carrier to reagent loading area.

3718. User loads carrier I/O ports with cDNA samples and TaqMAN assays. This step may be performed either manually or via a robotic system.

3720. User manually types sample/reagent information (map), and thermal cycling protocol into software (e.g. experiment document).

3722. Instrument verifies that protocol information is valid.

3724. User moves carrier back to FIDX.

3726. User initiates FIDX script to load samples and reagents to chip's sample wells.

3728. User removes carrier from FIDX and transports to Dynamic Array Instrument. Instrument records barcode information.

3730. User enters thermal cycler protocol into software/experiment document.

3732. User initiates a run (i.e., starts the method). In some embodiments, this step will include the various steps discussed below in relation to FIG. 38.

3734. Instrument reports to user the time remaining in the method.

3736. Run completes and instrument informs the user.

3738. Carrier is removed from instrument.

3740. User analyzes the run data.

3742. Data analysis and associated output is saved.

3746. Perform other steps as necessary.

As shown, above, the above steps can be used to use a Dynamic Array for gene expression analysis according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Various alternatives and variations are provided according to embodiments of the present invention. Merely by way of example, in an alternative embodiment, at one or more of the steps, a robotic system is utilized to perform the various operations. In another embodiment, at step 3718, barcode information is read from carrier by a robotic system and transferred to software. Moreover, at step 3720, the sample and thermal cycler protocol information may be automatically transferred to software/experiment document via the robotic system or barcode. If, at step 3722, invalid thermal cycler protocol is entered, the instrument reports the error to the user, requests a valid protocol, and then returns to step 3720. In another alternative embodiment, at step 3738, operating in a batch mode, the carrier is removed and the next carrier is loaded. Then the run returns to step 3710. As yet another alternative for batch mode operation, at step 3738, the system will determine, based on the time remaining in the currently running method, when to initiate processing of the next experiment plate. Merely by way of example, this determination may be made with 60 minutes remaining in current run. Generally, after completion of a run, the carrier is removed and the instrument is maintained in an idle state.

According to embodiments of the present invention, considerations related to the user interface and data analysis options are provided as described more fully throughout the present specification. These considerations include the data output format, data persistence, loading, mapping, and displaying of sample information, among others. One of ordinary skill in the art would recognize many variations, modifications, and alternatives.

As a third example, a generic instrument run with a carrier is performed according to embodiments of the present invention. Preferably, a number of initial conditions are provided prior to running the generic instrument experiment. These initial conditions may include: the Instrument System is installed; the Instrument System is calibrated; the Instrument System is powered up and warmed up; the user has a chip/carrier loaded with a sample and ready for the instrument run, the thermal cycler is at an idle state, and the command to load the sample and run the instrument has been initiated. FIG. 38 is a simplified flowchart illustrating operations performed according to an exemplary embodiment of the present invention. Accordingly, the reference numerals in the following process flow refer to FIG. 38.

3810. Sample information is transferred to the instrument software (Manually or by automation). This preferably includes loading map, assay type, chip carrier type, run protocol.

3812. Instrument verifies sample info is valid (e.g. Method type, Thermal Cycler protocol).

3814. Instrument verifies that there is sufficient disk space and write permissions to execute requested.

3816. Chip carrier is placed on to the instrument's transfer arm.

3818. The load sequence is initiated.

3820. Instrument turns on excitation source and initiates warm up counter.

3822. The instrument closes the gripper.

3824. Instrument assesses if carrier is correctly positioned.

3826. Instrument moves transfer axis arm to in position (in instrument).

3828. Instrument assesses plate type, checks validity against protocol information and verifies loading arm move completed.

3830. Instrument transfers chip/carrier to nominal, focused run position. In an embodiment, this step includes a number of sub-steps:

3830a. z-stage moves Cycler up to "hand-off" z position

3830b. Instrument registers carrier against gripper datum location

3830c. Instrument releases gripper

3830d. Instrument verifies that vacuum vent valve is closed

3830e. Instrument applies vacuum to chuck/carrier interface

3830f. Instrument verifies that vacuum is established

3830g. Instrument moves Cycler to nominal focus z position (specific to Chip type)

3830h. Instruments sets Thermal Cycler to "set-up" temperature (e.g. 20° C.)

3832. Instrument performs auto-focus routine. In an embodiment, this step includes a number of sub-steps:

3832a. Instrument moves Excitation and Emission filter wheels to correct filter position for focus (Uses passive reference dye channel)

3832b. Instrument determines best exposure time for focus ("Good" signal/no saturation)

3832c. Instrument moves z stage up and down±n steps and takes images every "m" steps 3832d. Instrument evaluates images to determine best focus z position for passive reference channel 3832e. Instrument verifies focus position validity 3834. Instrument determines optimal exposure times based on method and chip/carrier type.

3836. Instrument sets optimal focus z-position off-sets (predetermined for "set-up" temperature) for remaining filter pairs.

3838. Instrument verifies validity of focus off-sets in all filters required for method.

3840. Instrument initiates "Run Method." For Gene Expression, the process described in relation to FIG. 39 is utilized in some embodiments including Real-Time PCR Thermal Cycler Run & Data Collection. For Genotyping, the process described in relation to FIG. 40 is utilized in some embodiments, including Genotyping Run & Data Collection.

3842. Method completes.

3844. Instrument sets Thermal Cycler to idle.

3846. Post run reference images are collected.

3848. Software performs validity checks on data.

3850. Instrument Ejects Chip/Carrier. In an embodiment, this step includes a number of sub-steps:

3850a. Instrument turns off vacuum pump

3850b. Instrument opens vacuum vent valve

3850c. Instrument waits/confirms vacuum is vented

3850d. Instrument lowers cycler to "down" z-position

3850e. Instrument closes vacuum vent valve

3850f. Instrument engages gripper on chip/carrier

3850g. Instrument verifies chip/carrier is positioned correctly

3850h. Instrument moves transfer axis arm to out position

3850i. Instrument verifies move is complete

3850j. Instrument releases gripper

3852. Instrument indicates method is complete.

3854. The chip/carrier is removed from the transfer arm.

3856. Perform other steps as necessary.

As shown, above, the above steps can be used to use a Dynamic Array for gene expression analysis according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

Various alternatives and variations are provided according to embodiments of the present invention. Merely by way of example, in an alternative embodiment, at one or more of the steps, automation accessories are utilized to perform the various operations. Moreover, in various embodiments, at step 3830, focus optimization is performed manually, at step 3812, if the assay method validity fails, the instrument informs user of specific error and T.U.C.E., at step 3814, if there is not enough disk space/no read write permission, the instrument informs user of specific error and T.U.C.E., at step 3824, if the Chip/carrier is positioned incorrectly, the instrument informs user of specific error and T.U.C.E., and at step 3828, if the Chip/carrier type does not match Assay method type, the instrument informs user of specific error and T.U.C.E. Furthermore in some embodiments, at step 3828, if the transfer arm move failed, the instrument retries the movement in step 3826 once and then proceeds, otherwise the instrument informs user of specific error and T.U.C.E., at step 3830(f), if vacuum is not established, the instrument informs user of specific error and T.U.C.E., at step 2832(e), if the instrument focus position is not valid, the instrument retries once (goes to 2830(f)), else informs user of specific error and T.U.C.E., and at step 3838, if the focus z-position off-sets are not valid, the instrument informs user of specific error and T.U.C.E. Additionally, in other embodiments, at step 3848, if the instrument determines errors with data, the user is informed of specifics and operation proceeds to step 3850, at step 3850(c), if vacuum is not released, the instrument proceeds to step—Instrument goes to 3850(a); at step 3850(g), if the chip/carrier is not positioned correctly, the instrument retries once (goes to 3850(d)), else informs user of specific error and T.U.C.E., at step 3850(i), if the transfer arm did not complete eject move, the instrument retries once (goes to 3850(h)), else informs user of specific error and T.U.C.E.

In an alternative embodiment, dosimeter operation is provided. In this alternative embodiment, pre-set or calibrated information is included for each instrument and for each excitation filter position. This information includes dose monitor setup information (e.g. gain resistor, selectable), which is stored in a computer-readable file, such as an .ini file, during instrument calibration.

Generally, several steps are used to obtain and store dose reading for all cases. These steps are implemented by modifying image acquisition steps. (e.g., steps 3912 and 3916 as described in relation to FIG. 39 below; and step 4014 as described in relation to FIG. 40 below). The steps to obtain and store dose reading for all cases include:

a. Prepare dose monitor: at same step as camera reset/arm (discharge capacitor, select range resistor, and the like).

b. Start integration/sampling before excitation shutter commanded to open.

c. End integration/sampling after excitation shutter commanded to close.

d. Read out from dose monitor (NI analog read).

e. Discharge the dose monitor (in case discharge time helps).

f. Log the dose monitor readout with other parameters in CaptureLog.txt.

According to embodiments of the present invention, the dose monitor is utilized during exposure setting (once per image type: see step 3834 in FIG. 38). This operation may include evaluating the dose reading for under/over-saturation and reselecting the dose range if needed. Presumably, this will entail re-acquiring an image (or prompting for a new "Test Capture") if the range needs changing. Also, as a possible alternative to providing a baseline image as described below, the dose monitor value may be stored as a basis for normalizing this image type for this run. The dose monitor may also be utilized to collect baseline images at start and end of protocol (see step 3910 discussed in relation to FIG. 39 below and step 3846 in relation to FIG. 38. Moreover, the dose monitor may be utilized during cycling, in particular at each acquisition. Generally, during analysis, the dose reading is retrieved for a baseline image (e.g. 20° C. pre-run image) and for each well, after ripping and background subtraction, the signal value is scaled by the ratio of the baseline dose to the current image's dose.

After the above process is complete, the transfer arm is in the "out" position, the chip/carrier is removed, and the instrument is idle. In general, the Universal Thermal Cycler protocol for Gene Expression should be considered and Real Time Display is provided as described more fully throughout the present specification. In relation to step 3814, for a batch process, the check should include disk space and write permissions for the entire batch, not just the first plate. Moreover, at step 3834, exposure times are dependent on assay/chemistry type, bench time, chip type, thermal protocol, chip quality, and the like. In an embodiment, at step 3838, the "Run method" will generate additional experiments specific to gene Expression, DID, Immunoassay, and the like. One of ordinary skill in the art would recognize many variations, modifications, and alternatives.

According to embodiments of the present invention, the sample information required by the instrument at the start of a run to meet necessary traceability and validity requirements is determined. Moreover, 24 hour walk away automation function is provided herein and analysis is performed and integrated with the instrument control packages as described more fully throughout the present specification. Additionally, an exposure time selection methodology is provided by embodiments of the present invention, including a method to select exposure times for specific protocols/chips.

As a fourth example, a real-time PCR thermal cycler run and data collection is performed according to embodiments of the present invention. Preferably, a number of initial conditions are provided prior to performing a real-time PCR thermal cycler run and data collection. These initial conditions may include the prior initiation of either or both of the processes described in relation to FIG. 36, 37, or 38. Additionally, initial conditions may include: Chip is loaded in instrument; Camera/Z-Stage are focused (off sets are established); Exposure times are configured; Excitation source is on and stable; Thermal Cycler is at "set up" temp; Assay/chip information and Thermal Cycler protocol information has been "transferred" to the computer (n number of cycles); and Command to run thermal cycler protocol has been initiated. Typically, a real-time PCR thermal cycler run and data collection is performed after the Gene Expression experiment is loaded in the instrument and ready to run. FIG. 39 is a simplified flowchart illustrating operations performed according to an exemplary embodiment of the present invention. Accordingly, the reference numerals in the following process flow refer to FIG. 39.

- 3910. Instrument collects base line images (see steps 3912, 3916(*g*), 3916(*i*), 3916(*j*), and 3916(*k*) below)
- 3912. Instrument configures hardware for next data acquisition point
    - 3912*a*. Instrument sets excitation filter position
    - 3912*b*. Instrument sets emission filter position
    - 3912*c*. Instrument sets Z stage height (offset)
- 3914. Instrument runs initial thermal cycler conditions (e.g. hot start)
    - 3914*a*. Instrument sets thermal cycler set point 1 and ramp power (e.g. 50° C.)
    - 3914*b*. Instrument queries thermal cycler for "chuck" temperature
    - 3914*c*. Once thermal cycler has reached set point temperature, instrument counts down hold time for set point 1
    - 3914*d*. Once hold time count has elapsed, Instrument sets thermal cycler set point 2 and ramp power (e.g. 95° C.)
    - 3914*e*. Once thermal cycler has reached set point temperature, instrument counts down hold time for set point 2
    - 3914*f*. Once hold time count has elapsed instrument runs PCR cycling method (Or runs further initial cycling condition set points)
- 3916. Instrument runs n PCR cycles
    - 3916*a*. Instrument sets thermal cycler initial cycling set point (e.g. annealing) and ramp power (e.g. 60° C.)
    - 3916*b*. Instrument queries thermal cycler for "chuck" temperature
    - 3916*c*. Once thermal cycler has reached set point temperature:
        - i. Instrument calculates required data acquisition time (i.e. total of all filter moves, exposure times and associated overhead)
        - ii. Instrument subtracts data acquisition time from total hold time (the result is the pre data acquisition hold time)
    - 3916*d*. Instrument counts down remaining pre data acquisition hold time
    - 3916*e*. Instrument verifies filter wheel positions and Z height (Runs step 3912)
    - 3916*f*. Once pre data acquisition time has elapsed Instrument requests CCD camera to "reset" and "arm"
    - 3916*g*. Instrument requests CCD to initiate integration and sends shutter task to NI card
        - i. NI waits 100 ms
        - ii. NI requests emission shutter to open
        - iii. NI waits 100 ms
        - iv. NI requests excitation shutter to open
        - v. NI waits predetermined exposure time (t ms)
        - vi. NI requests excitation shutter to close
        - vii. waits 100 ms
        - viii. NI requests emission shutter to close
    - 3916*h*. Instrument sets thermal cycler to second cycling set point (e.g. denature/95° C.) and ramp power (e.g. 10)
    - 3916*i*. Instrument requests CCD to transfer (reads out) data
    - 3916*j*. Instrument requests hardware status (e.g. filter positions, shutter times, array temp, CCD temp, Z position, # of data points, heat sink temp . . . )
    - 3916*k*. Instrument runs step 3912
    - 3916*l*. Data is saved to TIFF and log (csv) files (Data Analysis and Real-Time display are additional use cases, at this point)
    - 3916*m*. Instrument queries thermal cycler for "chuck" temperature
    - 3916*n*. Once thermal cycler has reached set point temperature, instrument counts down hold time for denature set point
    - 3916*o*. Once hold time count has elapsed go to step 3916(*a*) (Instrument repeats for n cycles)
- 3918. Once n cycles completes the method ends (See discussion related to process described with reference to FIG. 38)
- 3920. Perform other steps as necessary.

As shown, above, the above steps can be used to perform real-time PCR thermal cycling and data collection according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

According to embodiments of the present invention, after the real-time PCR method run is complete, and the data is collected, the data is saved and made ready for analysis of the present or future runs. Additionally, 24 hour walk away operation is provided by embodiments. Generally, the thermal cycler method run is based on current system architecture and two temperature PCR cycling is utilized. Alternatively, other alternatives are added as appropriate at step **3916(*o*)**. Moreover, sample temperature off set compensation is included in some embodiments. One of ordinary skill in the art would recognize many variations, modifications, and alternatives.

As a fifth example, a genotyping run and data collection is performed according to embodiments of the present invention. Preferably, a number of initial conditions are provided prior to performing a genotyping run and data collection. These initial conditions may include the prior initiation of either or both of the processes described in relation to FIG. 36, 37, or 38. Additionally, initial conditions may include: Chip is loaded in instrument; Camera/Z-Stage are focused (off sets are established); Exposure times are configured; Excitation source is on and stable; Thermal Cycler is at "set up" temp; Assay/chip information and Thermal Cycler protocol information has been "transferred" to the computer (n number of cycles); and Command to run thermal cycler protocol has been initiated. Typically, a genotyping run and data collection is performed after the Gene Expression experiment is loaded in the instrument and ready to run. FIG. 40 is a simplified flowchart illustrating operations performed according to an exemplary embodiment of the present invention. Accordingly, the reference numerals in the following process flow refer to FIG. 40.

4010. Instrument runs pre/post read thermal cycler condition
   **4010*a***. Instrument sets thermal cycler to data acquisition set point and ramp power (e.g. 60° C.)
   **4010*b***. Instrument queries thermal cycler for "chuck" temperature
   **4010*c***. Once thermal cycler has reached set point temperature, instrument counts down hold time for data acquisition stability
4012. Instrument configures hardware for next n data acquisition point
   **4012*a***. Instrument sets excitation filter position
   **4012*b***. Instrument sets emission filter position
   **4012*c***. Instrument sets Z stage height (offset)
4014. Instrument initiates data collection sequence
   **4014*a***. Instrument requests CCD camera to "reset" and "arm"
   **4014*b***. Instrument requests CCD to initiate integration and sends shutter task to NI card
     i. NI waits 100 ms
     ii. NI requests emission shutter to open
     iii. NI waits 100 ms
     iv. NI requests excitation shutter to open
     v. NI waits predetermined exposure time (t ms)
     vi. NI requests excitation shutter to close
     vii. NI waits 100 ms
     viii. NI requests emission shutter to close
   **4014*c***. Instrument requests CCD to transfer (reads out) data
   **4014*d***. Instrument requests hardware status (e.g., filter positions, shutter times, array temp, CCD temp, Z position, # of data points, heat sink temp, and the like)
   **4014*e***. Data is saved to TIFF and log (csv) files
4016. Instrument goes to step 4012 for next filter position/data point (Repeat steps 4012 through 4016 for n filter position/data points)
4018. Instrument runs initial thermal cycler conditions (e.g. hot start)
   **4018*a*. Instrument sets thermal cycler set point 1** and ramp power (e.g. 50° C.)
   **4018*b***. Instrument queries thermal cycler for "chuck" temperature
   **4018*c*. Once thermal cycler has reached set point temperature, instrument counts down hold time for set point 1**
   **4018*d*. Once hold time count has elapsed, Instrument sets thermal cycler set point 2** and ramp power (e.g. 95° C.)
   **4018*e*. Once thermal cycler has reached set point temperature, instrument counts down hold time for set point 2**
   **4018*f***. Once hold time count has elapsed instrument runs PCR cycling method (Or runs further initial cycling condition set points)
4020. Instrument runs n PCR cycles
   **4020*a***. Instrument sets thermal cycler initial cycling set point (e.g. annealing) and ramp power (e.g. 60° C.)
   **4020*b***. Instrument queries thermal cycler for "chuck" temperature
   **4020*c***. Once thermal cycler has reached set point temperature the instrument counts down hold time
   **4020*d***. Instrument sets thermal cycler to second cycling set point (e.g. denature/95° C.) and ramp power (e.g. 10)
   **4020*e***. Instrument queries thermal cycler for "chuck" temperature
   **4020*f***. Once thermal cycler has reached set point temperature, instrument counts down hold time for denature set point
   **4020*g*. Once hold time count has elapsed go to 4020(*a*)** (Instrument repeats for n cycles)
4022. Once n cycles completes the instrument collects the post PCR data (Run steps 4010 through 4016. Data analysis performed in an embodiment as described more fully throughout the present specification.
4024. Once the post run data is collected the method ends (See FIG. 38 and related description related to a generic instrument run)
4026. Perform other steps as necessary.

As shown, above, the above steps can be used to perform genotyping and data collection according to an embodiment of the present invention. Other alternatives can also be provided where steps are added, one or more steps are removed, or one or more steps are provided in a different sequence without departing from the scope of the claims herein. In certain embodiments, any of these steps may be combined with the others recited herein.

According to embodiments of the present invention, after the genotyping method run is complete, and the data is collected, the data is saved and made ready for analysis of the present or future runs. Additionally, 24 hour walk away operation is provided by embodiments. Generally, the thermal cycler method run is based on current system architecture and two temperature PCR cycling is utilized. Alternatively, other alternatives are added as appropriate at step **4020(*g*)**.

Moreover, sample temperature off set compensation is included in some embodiments. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 41A:
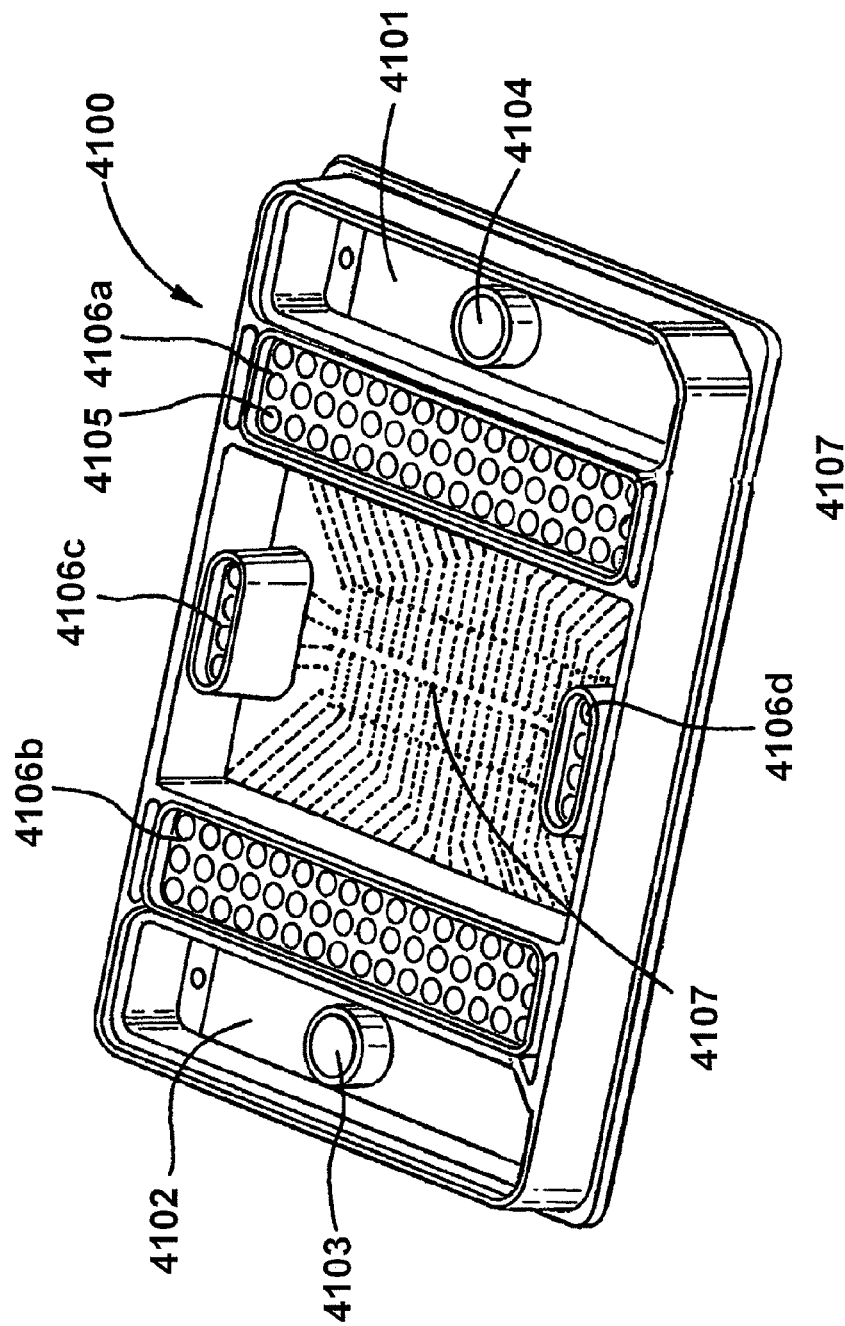
FIG. 41A depicts a substrate of a microfluidic device that has integrated pressure accumulator wells according to an embodiment of the present invention.
Figure 41B:
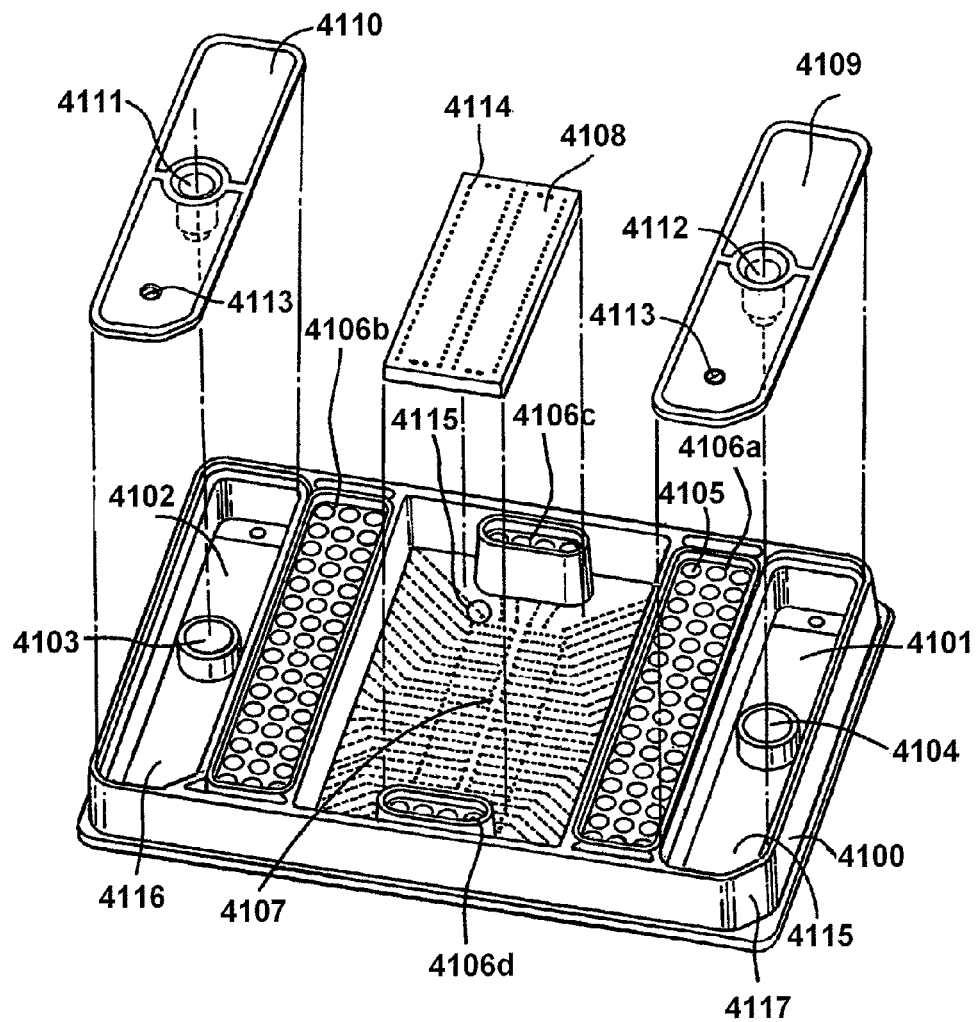
FIG. 41B depicts an exploded view of the microfluidic device shown in FIG. 41A, and further including an elastomeric block.

In an alternative embodiment of the present invention, FIG. 41A depicts a substrate 4100 of a microfluidic device that has integrated pressure accumulator wells 4101 and 4102, each having therein a drywell 4103, 4104 for receiving a valve, preferably a check valve attached to a cover (see FIG. 41B). Substrate 4100 further includes one or more well banks 4106*a, b, c*, and *d*, each having one or more wells 4105 located therein. Each of the wells 4105 of substrate 4100 have channels leading from well 4105 to elastomeric block location 4107 within substrate 4100 for attaching an elastomeric block, preferably an elastomeric block formed from two or more layers of elastomeric material having microfabricated recesses or channels formed therein.

Figure 41C:
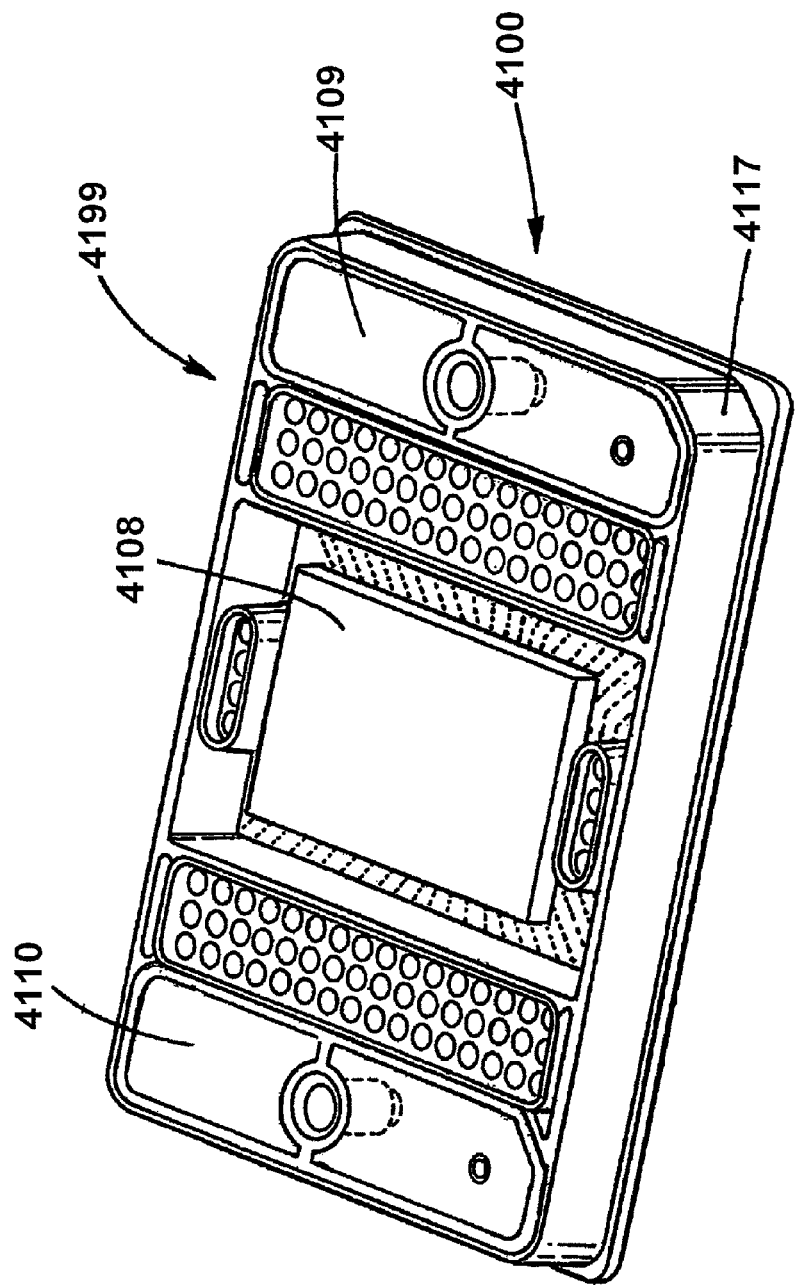
FIG. 41C is an overall view of the microfluidic device shown in FIG. 41B.

FIG. 41B depicts an exploded view of a complete microfluidic device 4199 comprising the components shown in FIG. 41A, and further comprising an elastomeric block 4108 which is attached, or more preferably bonded, and yet more preferably directly bonded, preferably without use of adhesives to the elastomeric block location 4107 of substrate 4100 to form the complete microfluidic device 4199 (FIG. 41C). Within elastomeric block 4108 are one or more channels in fluid communication with one or more vias 4114, which in turn provide fluid communication between the channels within the elastomeric block and channels within the substrate which then lead to wells 4105 within well rows 4106*a-d* to provide for fluid communication between wells 4105 of substrate 4100 and the channels within elastomeric block 4108. Accumulator well tops 4109 and 4110 are attached to accumulator wells 4101 and 4102 to form accumulator chambers 4115 and 4116. Accumulator well tops 4109 and 4110 include valves 4112 and 4111, respectively, which are preferably check valves for introducing and holding gas under pressure into accumulator chambers 4115 and 4116. Valves 4111 and 4112 are situated inside of drywells 4102 and 4104 to keep liquid, when present in accumulator chambers 4115 and 4116, from contacting valves 4111 and 4112. Valves 4111 and 4112 preferably may be mechanically opened by pressing a shave, pin or the like, within a preferred check valve to overcome the self closing force of the check valve to permit release of pressure from the accumulator chamber to reduce the pressure of the fluid contained within the accumulator chamber.

Figure 41D:
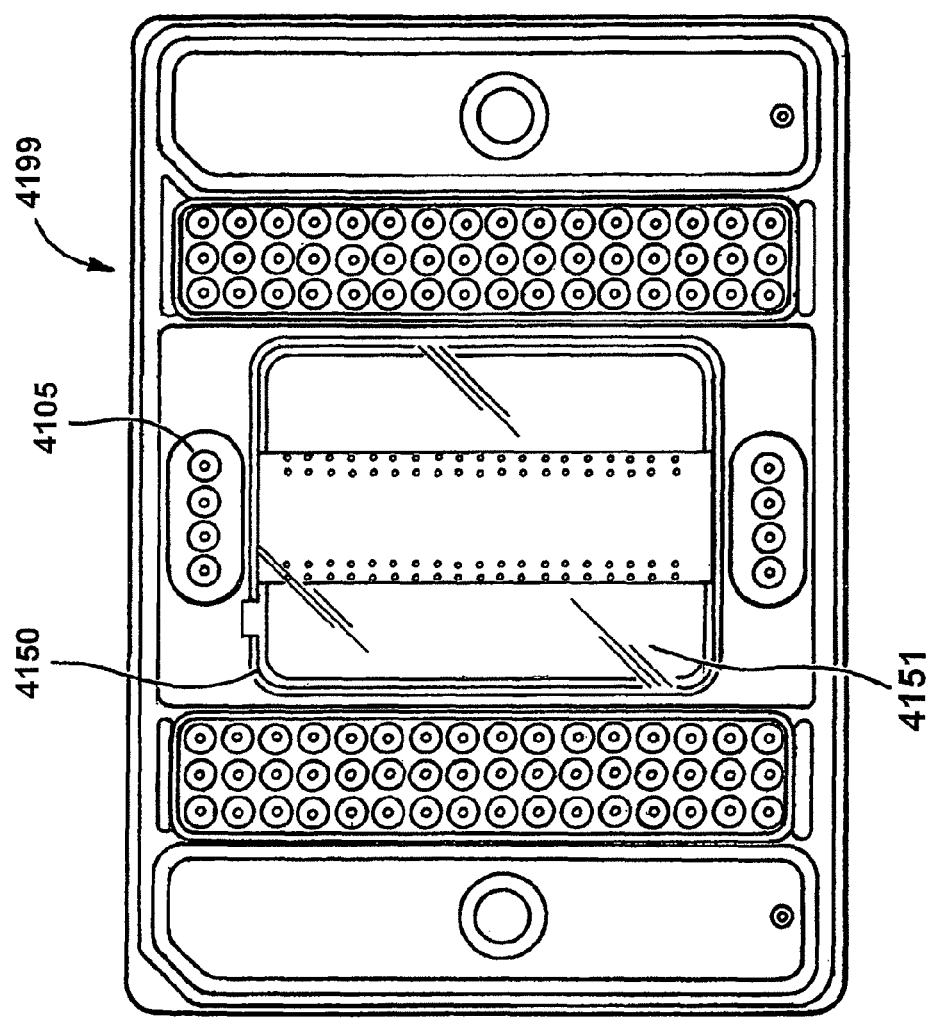
FIG. 41D is a plan view of the microfluidic device shown in FIG. 41B.

FIG. 41D depicts a plan view of microfluidic device 4199 and wells 4105, wherein a port is located adjacent the base of the well, preferably the bottom, or alternatively the side of well 4105 for passage of fluid from the well into a channel formed in substrate 4100, preferably on the side of substrate 4100 opposite of well 4105. In a particularly preferred embodiment, substrate 4100 is molded with recesses therein, the recesses being made into channels by a sealing layer, preferably an adhesive film or a sealing layer.

Substrate 4100 and its associated components may be fabricated from polymers, such as polypropylene, polyethylene, polycarbonate, high-density polyethylene, polytetrafluoroethylene PTFE or Teflon (R), glass, quartz, or a metal (for example, aluminum), transparent materials, polysilicon, or the like. Accumulator well tops 4109 and 4110 further may comprise access screws 4112 which can be removed to introduce or remove gas or liquid from accumulator chambers 4115 and 4116. Preferably, valves 4112 and 4111 can be actuated to release fluid pressure otherwise held inside of accumulator chambers 4115 and 4116. Notch 4117 is used to assist correct placement of the microfluidic device into other instrumentation, for example, instrumentation used to operate or analyze the microfluidic device or reactions carried out therein. FIG. 41D further depicts a hydration chamber 4150 surrounding elastomeric block region 4107, which can be covered with a hydration cover 4151 to form a humidification chamber to facilitate the control of humidity around the elastomeric block. Humidity can be increased by adding volatile liquid, for example water, to humidity chamber 4151, preferably by wetting a blotting material or sponge. Polyvinyl alcohol may preferably be used. Humidity control can be achieved by varying the ratio of polyvinyl alcohol and water, preferably used to wet a blotting material or sponge. Hydration can also be controlled by using a humidity control device such as a HUMIDIPAK™ humidification package which, for example, uses a water vapor permeable but liquid impermeable envelop to hold a salt solution having a salt concentration suitable for maintaining a desired humidity level. See U.S. Pat. No. 6,244,432 by Saari et al, which is herein incorporated by reference for all purposes including the specific purpose of humidity control devices and methods. Hydration cover 4150 is preferably transparent so as to not hinder visualization of events within the elastomeric block during use. Likewise, the portion of substrate 4100 beneath the elastomeric block region 4107 is preferably transparent, but may also be opaque or reflective.

Figure 41E:
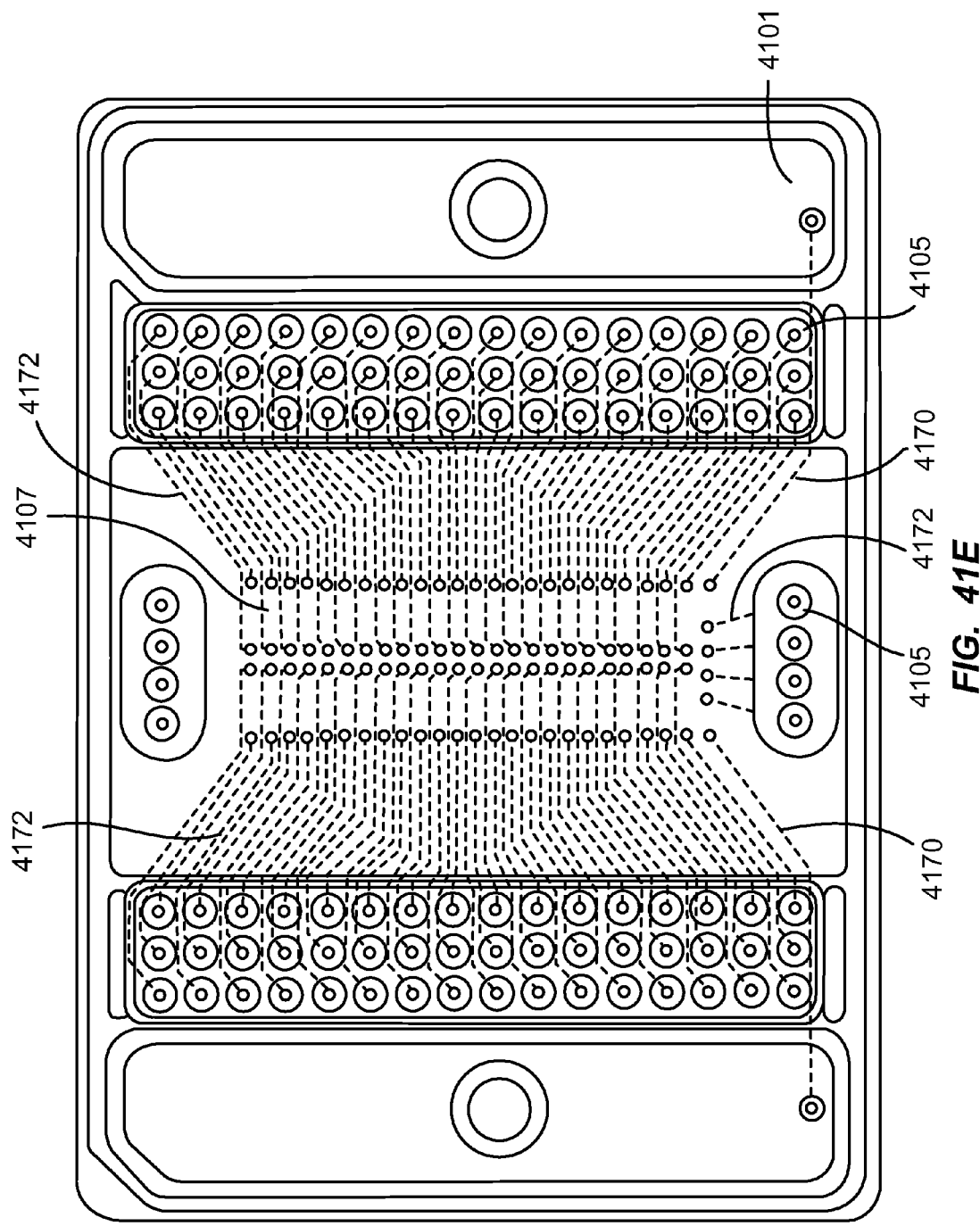
FIG. 41E depicts a plan view of the microfluidic device shown in FIG. 41B.

FIG. 41E depicts a plan view of substrate 4100 with its channels formed therein providing fluid communication between wells 4105 and elastomeric block 4108 (not shown) which is attached to substrate 4100 within elastomeric block region 4107, through channels 4172. Accumulator chambers 4101 and 4102 are in fluid communication with elastomeric block region 4107 and ultimately, elastomeric block 4108, through channels 4170.

Figure 41F:
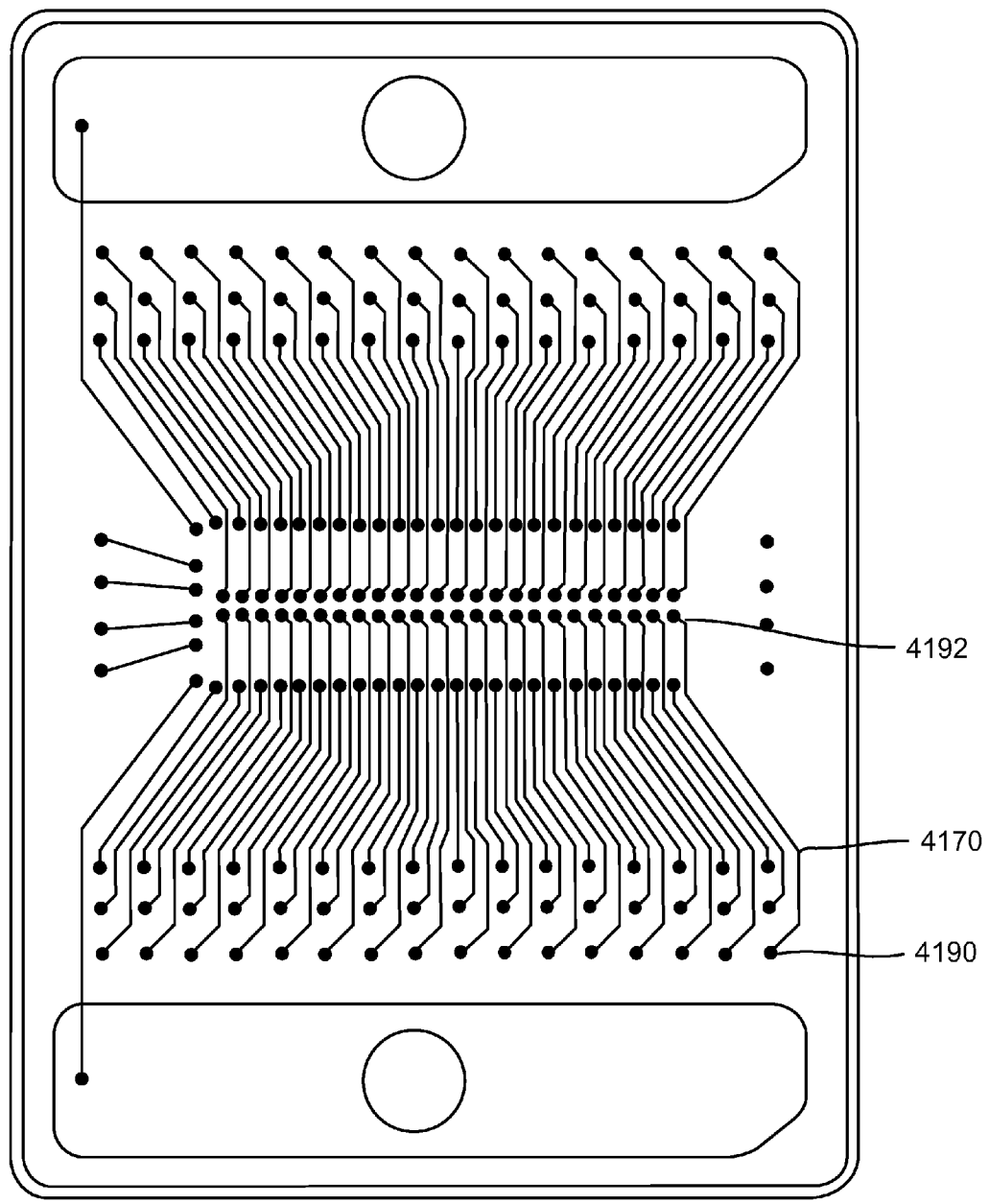
FIG. 41F depicts a bottom plan view of the microfluidic device shown in FIG. 41B.

FIG. 41F depicts a bottom plan view of substrate 4100. In a particularly preferred embodiment, recesses are formed in the bottom of substrate 4100 between a first port 4190 which passes through substrate 4100 to the opposite side where wells 4105 are formed and a second port 4192 which passes through substrate 4100 in fluid communication with a via in elastomeric block 4108 (not shown).

Figure 41G:
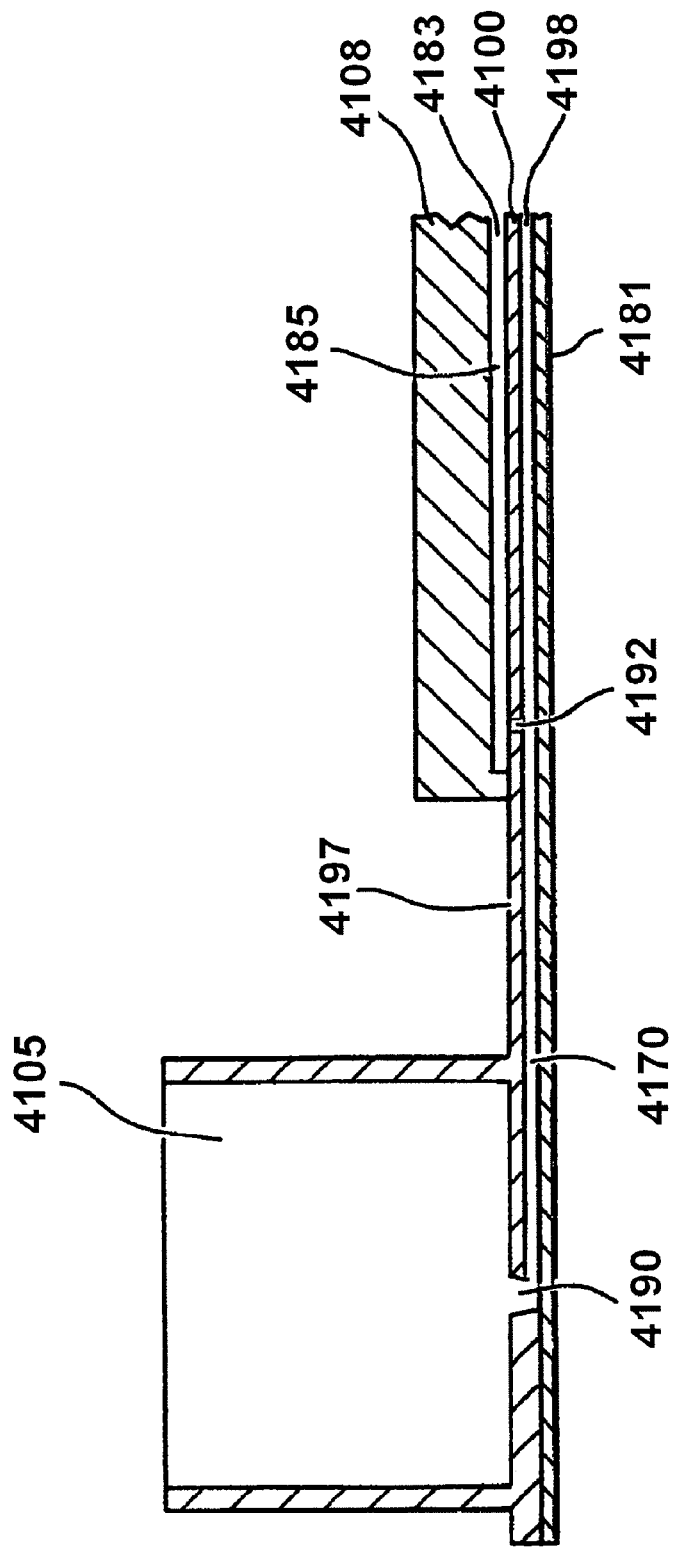
FIG. 41G depicts a cross-sectional view of the microfluidic device shown in FIG. 41B.

FIG. 41G depicts a cross-sectional view of substrate 4100 with elastomeric block 4108 situated in elastomeric block region 4107 along with sealing layer 4181 attached to the side of substrate 4100 opposite of elastomeric block 4108. Well 4105 is in fluid communication with elastomeric block 4108 through first port 4190, channel 4170, and second port 4192 and into a recess of elastomeric layer 4108, which is sealed by a top surface 4197 of substrate 4100 to form a channel 4185. Sealing layer 4181 forms channel 4170 from recesses molded or machined into a bottom surface 4198 substrate 4100. Sealing layer 4181 is preferably a transparent material, for example, polystyrene, polycarbonate, or polypropylene. In one embodiment, sealing layer 4181 is flexible such as in adhesive tape, and may be attached to substrate 4100 by bonding, such as with adhesive or heat sealing, or mechanically attached such as by compression. Preferably materials for sealing layer 4181 are compliant to form fluidic seals with each recess to form a fluidic channel with minimal leakage. Sealing layer 4181 may further be supported by an additional support layer that is rigid (not shown). In another embodiment, sealing layer 4181 is rigid.

Figure 42A:
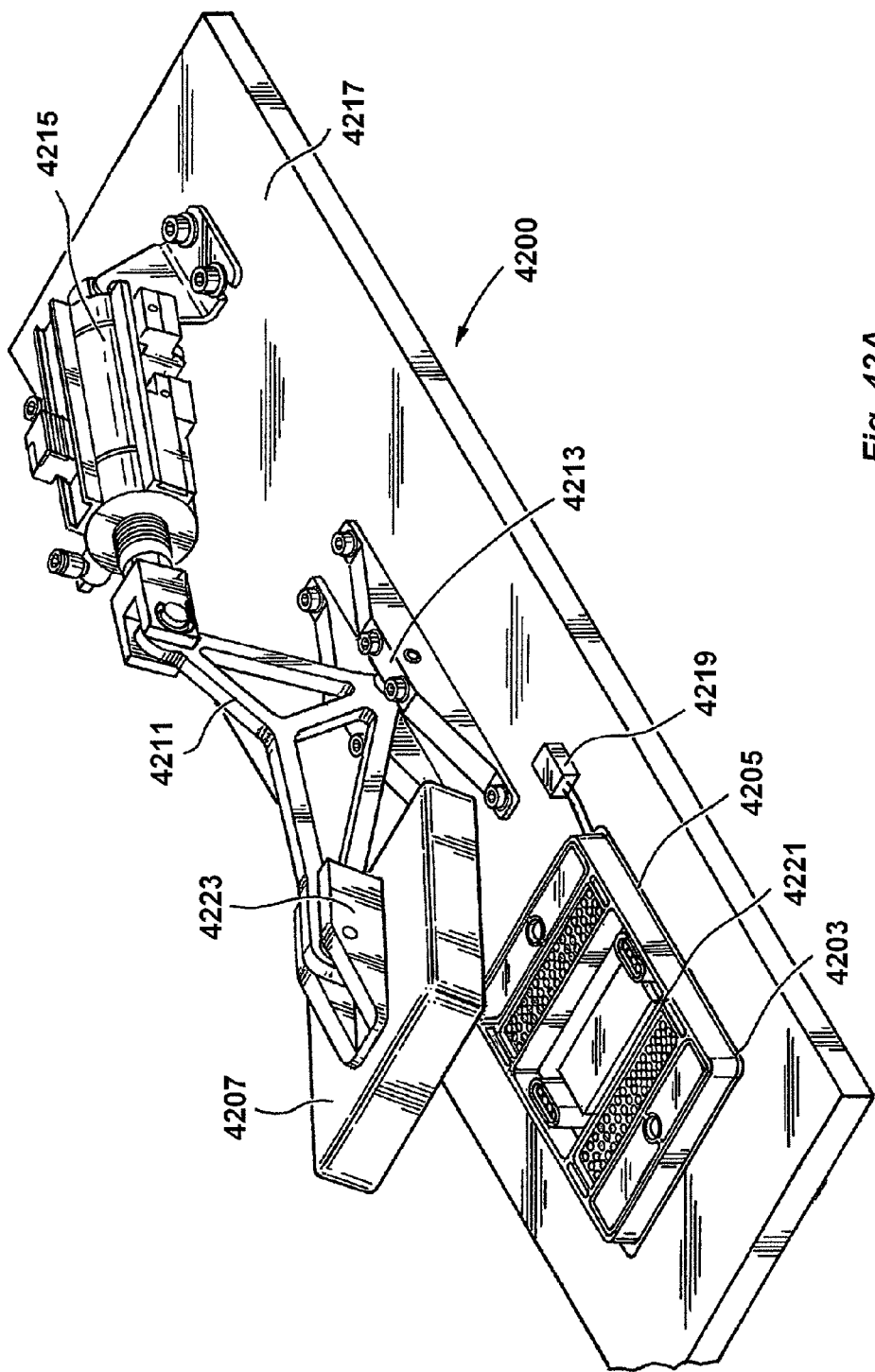
FIG. 42A is a perspective view of a station for actuating a microfluidic device according to an embodiment of the present invention.

The microfluidic devices of the present invention may be used as stand-alone devices, or preferably, may be used as part of a system as provided for by the present invention. FIG. 42A depicts a perspective view of a robotic station for actuating a microfluidic device. An automated pneumatic control and accumulator charging station 4200 includes a receiving bay 4203 for holding a microfluidic device 4205 of the present invention such as the type depicted in FIGS. 41A-G. A platen 4207 is adapted to contact an upper face 4209 of microfluidic device 4205. Platen 4207 has therein ports that align with microfluidic device 4205 to provide fluid pressure, preferably gas pressure, to wells and accumulators within microfluidic device 4205. In one embodiment, platen 4207 is urged against upper face 4221 of microfluidic device 4205 by movement of an arm 4211, which hinges upon a pivot 4213 and is motivated by a piston 4215 which is attached at one end to arm 4211 and at the other end to a platform 4217. Sensors along piston 4215 detect piston movement and relay information about piston position to a controller, preferably a controller under control of a computer (not shown) following a software script. A plate detector 4219 detects the presence of microfluidic device 4205 inside of receiving bay 4203, and preferably can detect proper orientation of microfluidic device 4205. This may occur, for example, by optically detecting the presence and orientation of microfluidic device 4205 by reflecting light off of the side of microfluidic device 4205. Platen 4207 may be lowered robotically, pneumatically, electrically, or the like. In some embodiments, platen 4207 is manually lowered to engage device 4205.

Figure 42B:
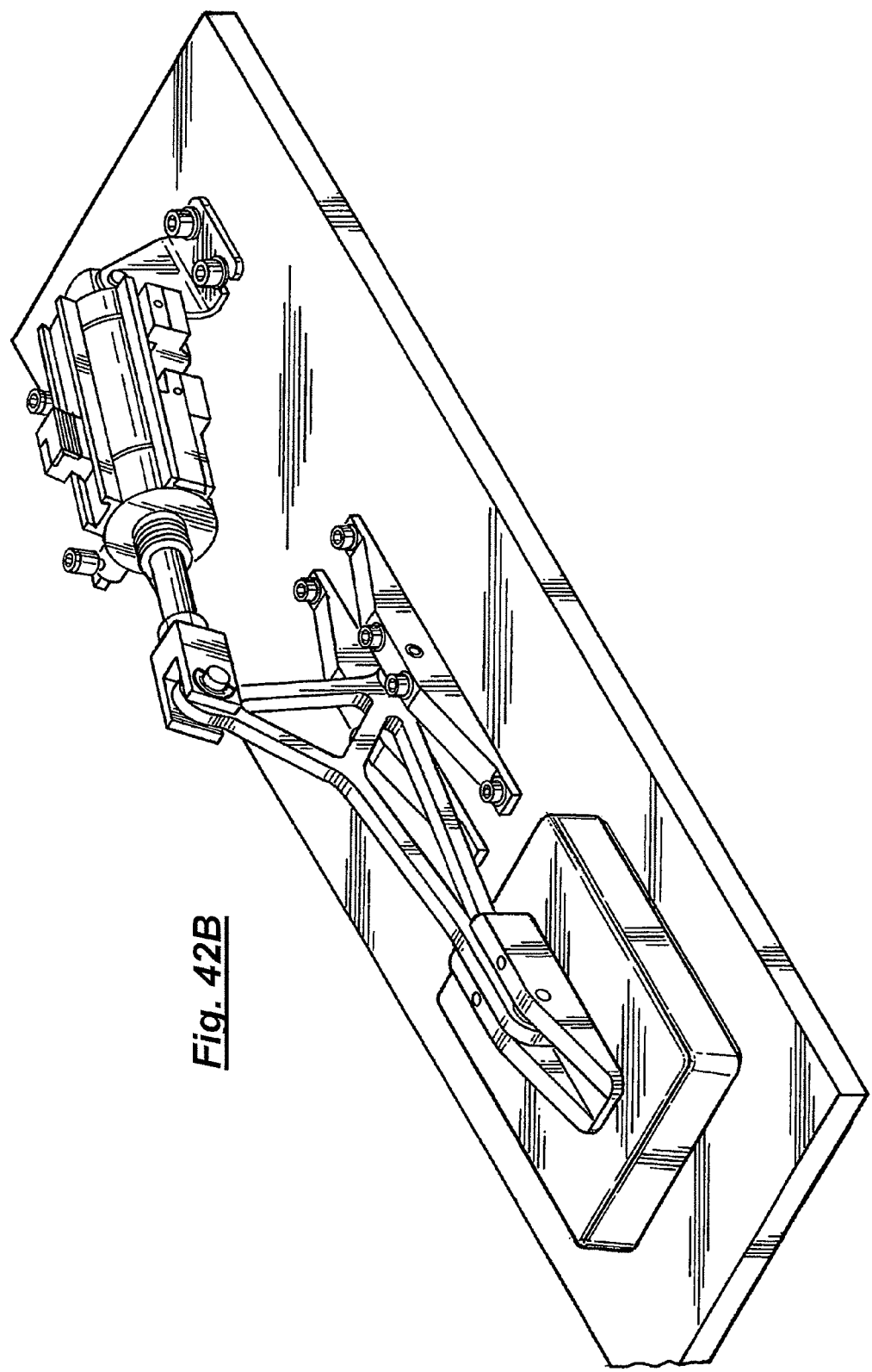
FIGS. 42B and 42D are perspective and side views, respectively, of the station of FIG. 42A with the platen in a down position.

FIG. 42B depicts charging station 4200 with platen 4207 in the down position urged against upper face 4221 of microfluidic device 4205, which is now covered by a shroud of platen 4207. In one embodiment, fluid lines leading to platen 4207 are located within arm 4211 and are connected to fluid pressure supplies, preferably automatic pneumatic pressure supplies under control of a controller. The pressure supplies provide controlled fluid pressure to ports within a platen face (not shown) of platen 4207, to supply controlled pressurized fluid to microfluidic device 4205. Fine positioning of platen 4207 is achieved, at least in-part, by employing a gimbal joint 4223 where platen 4207 attaches to arm 4211 so that platen 4207 may gimbal about an axis perpendicular to upper face 4221 of microfluidic device 4205.

Figure 42C:
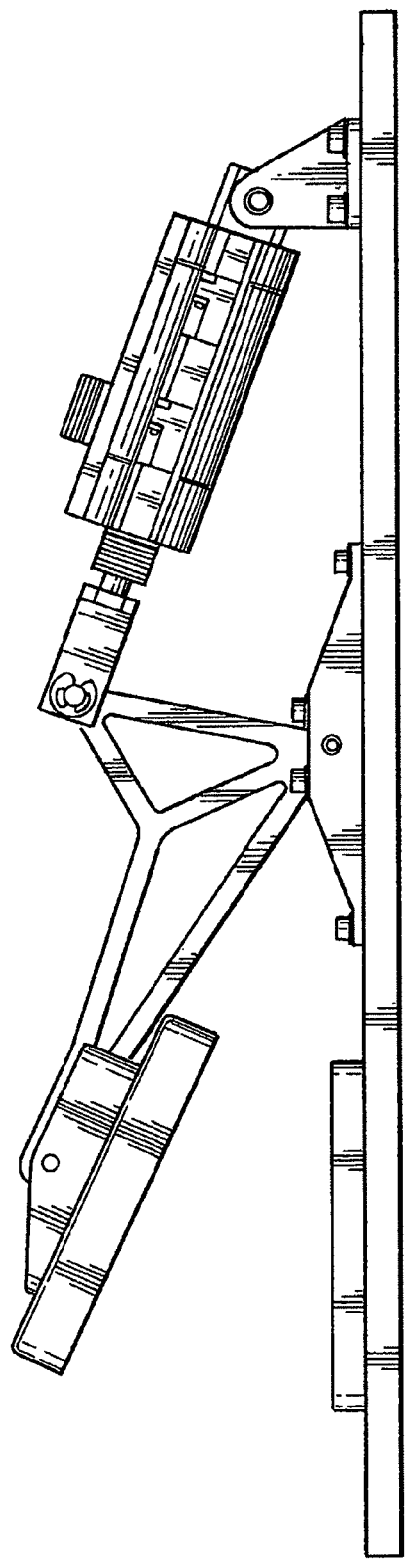
FIG. 42C is a side view of the station of FIG. 42A with the platen in an up position.
Figure 42D:
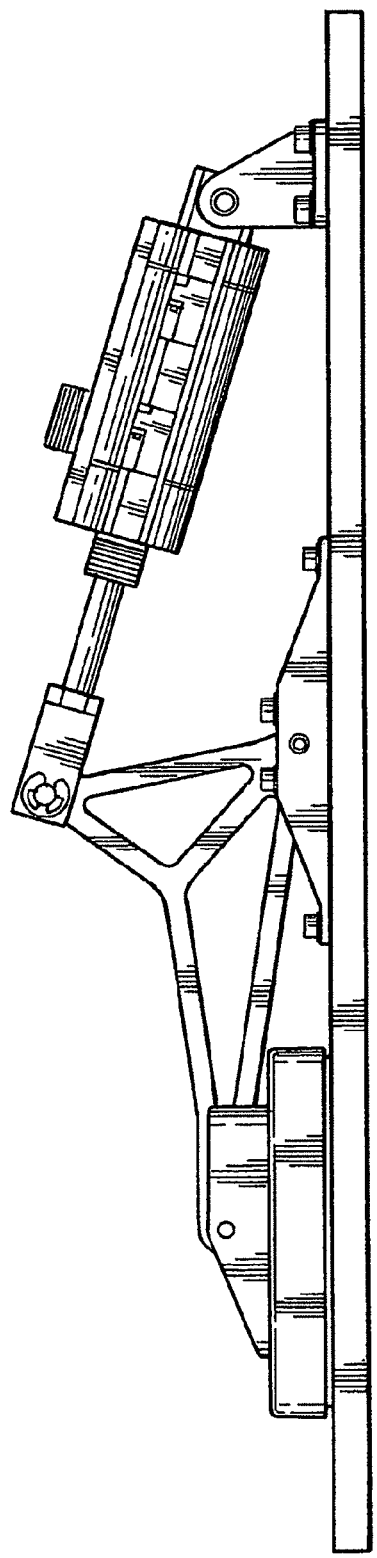
Figure 42E:
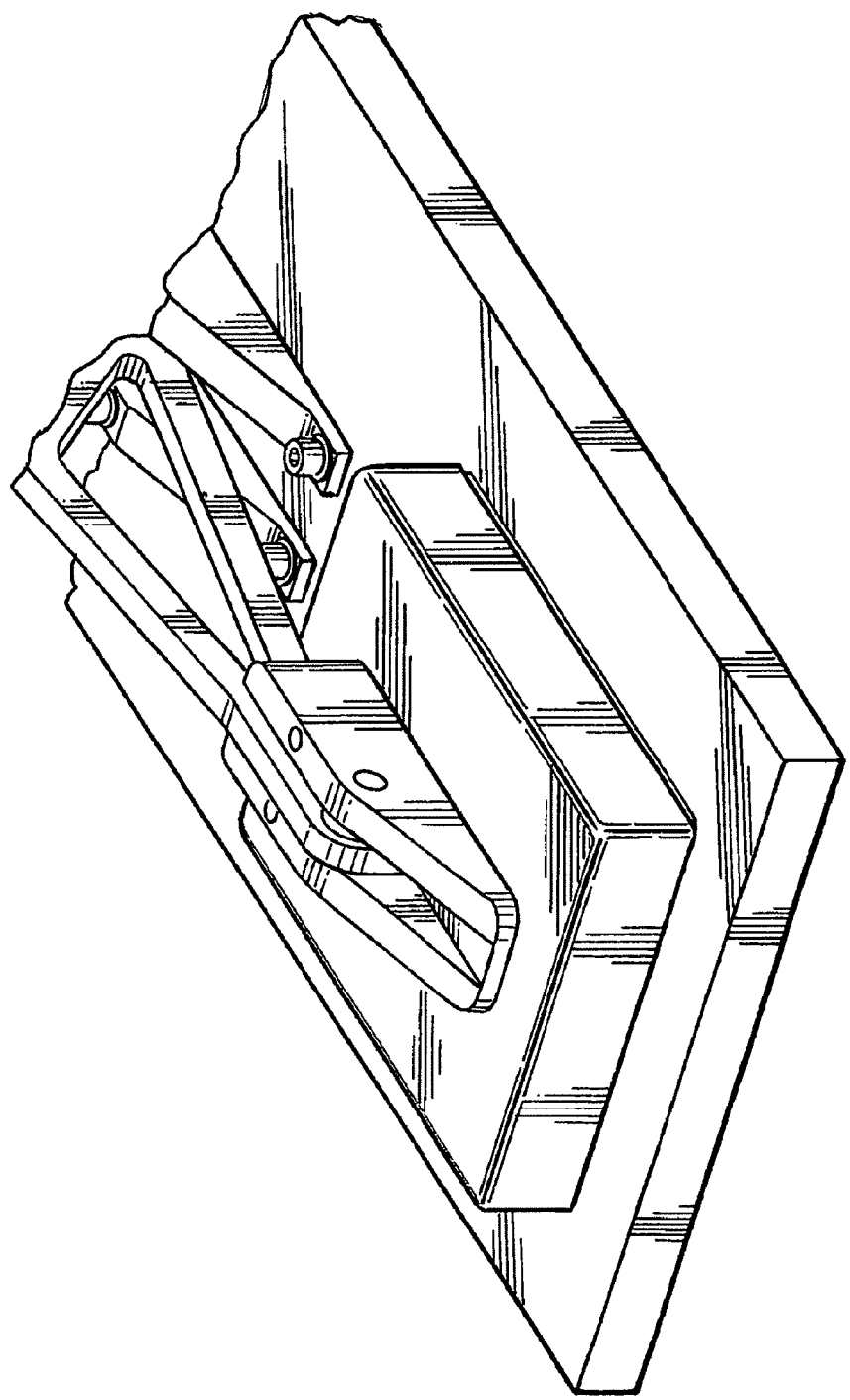
FIG. 42E depicts a close-up view of the platen of FIG. 42A.

FIGS. 42C and 42D provide side-views of charging station 4200 in both up and down positions, respectively. FIG. 42E depicts a close-up view of platen 4207 in a down position.

Figure 42F:
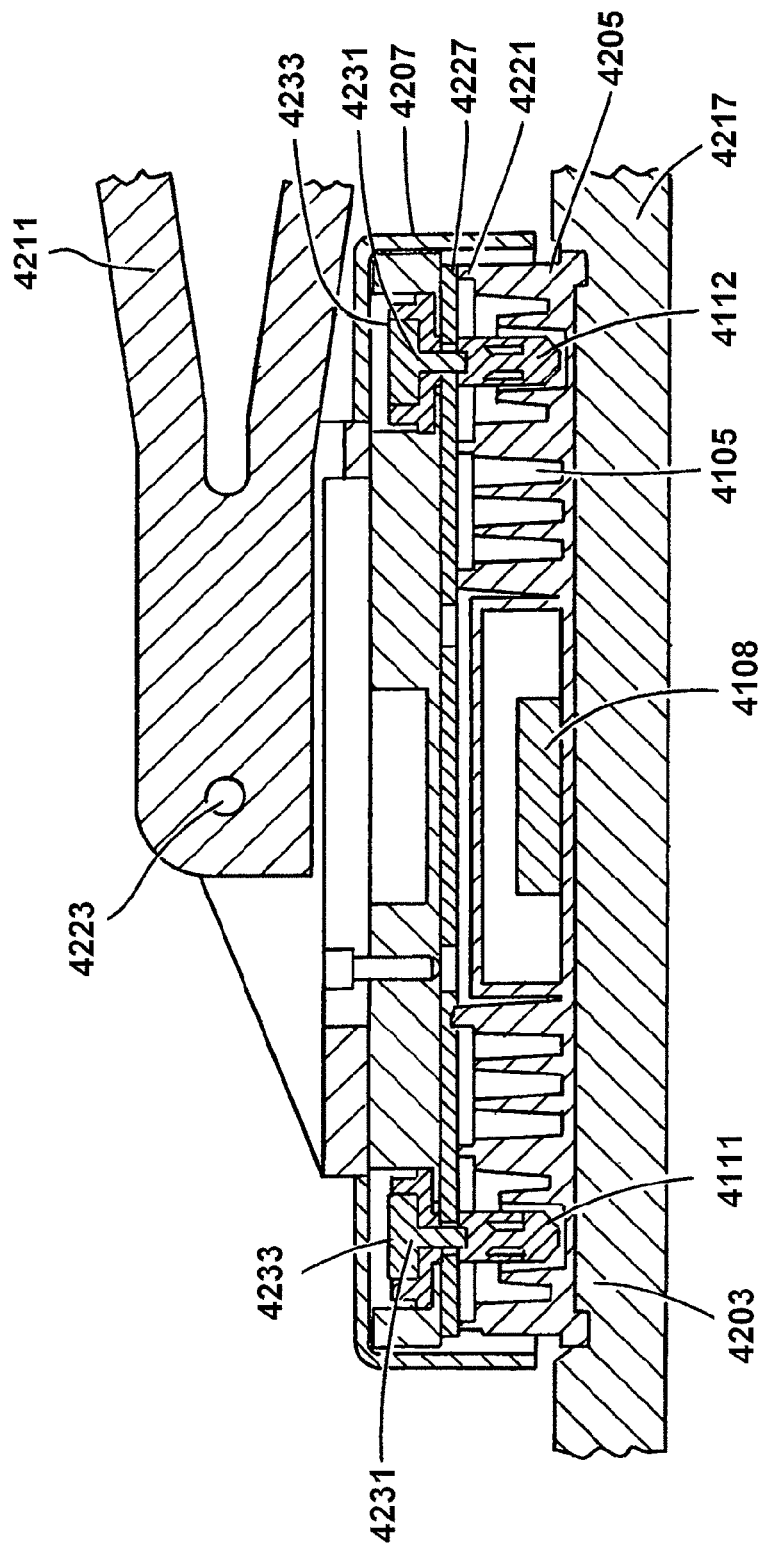
FIG. 42F depicts a cut-away side view of the platen of FIG. 42A.

FIG. 42F depicts a cut-away side-view of platen 4207 urged against upper face 4221 of microfluidic device 4205. Platen 4207 is urged against upper face 4221 of microfluidic device 4205 to form a fluid tight seal between microfluidic device 4205 and a platen face 4227, or between portions of device 4205 and face 4227. Platen face 4227, in one embodiment, includes or is made of a compliant material such as a resilient elastomer, preferably chemical resistant rubber or the like. Inside platen 4207 are separate fluid pressure lines, preferably gas pressure lines, which mate with various locations on upper face 4221 of microfluidic device 4205. Also shown are check valve purge actuators 4233 which are actuated, preferably pneumatically, and which when actuated, push a pin 4231 downward into check valve 4112 to open and relieve fluid pressure, or permit the introduction of fluid through check valve 4112 by overcoming its opening resistance. In one embodiment, platen 4207 has first and second purge actuators 4233 which engage check valves 4111 and 4112 (see FIG. 41B).

In another embodiment, chip or device 4205 is manufactured with normally closed containment and/or interface valves. In this embodiment, accumulators would not be necessary to hold valves shut during incubation. Pressure would be applied to carrier or device 4205 well regions when interface and/or containment valves are desired to be opened. For all or most other times, the valves would remain closed to separate the various chip experiments from one another, and/or to separate reagent and protein wells on the chip from one another.

Figure 42G:
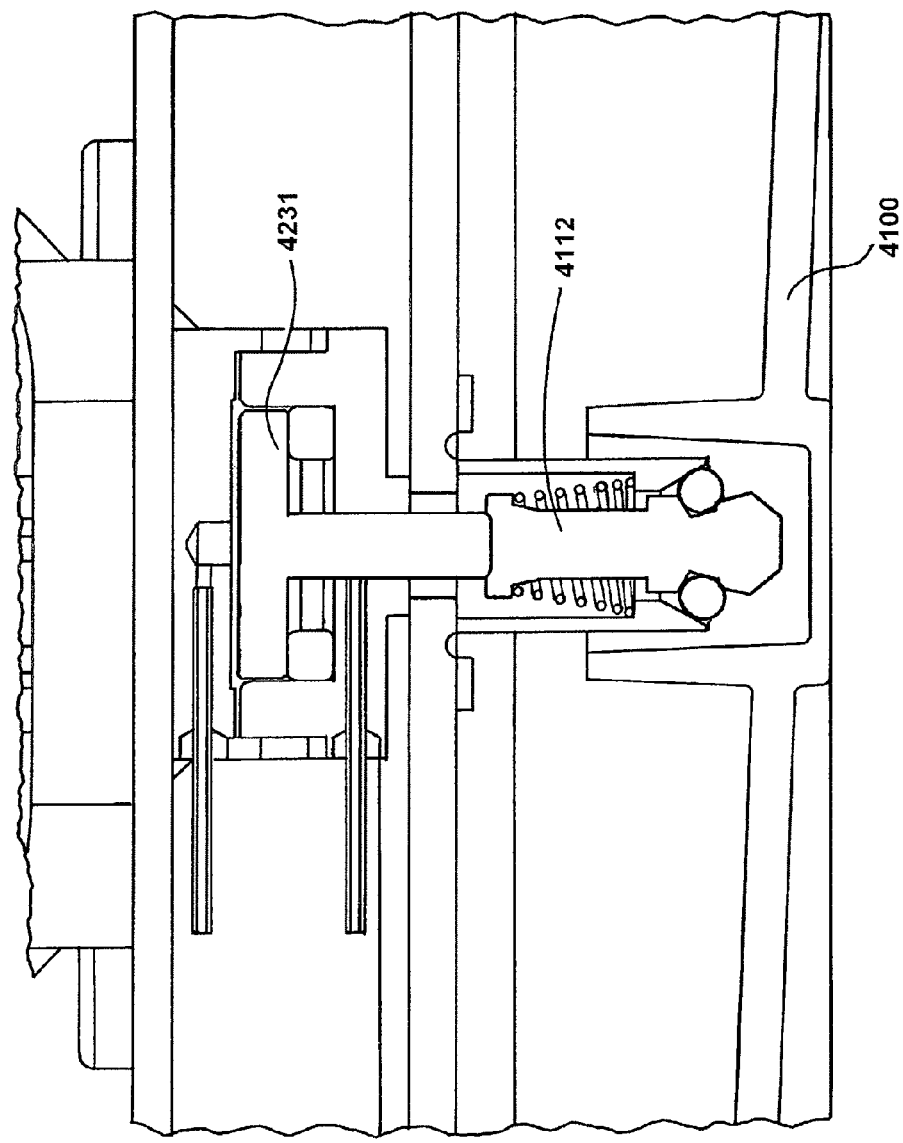
FIG. 42G is a close-up view of a purge actuator acting on a check valve according to an embodiment of the present invention.

FIG. 42G provides an extreme close-up view of purge actuator 4233 acting upon check valve 4112 located within substrate 4100 of microfluidic device 4205.

Figure 42H:
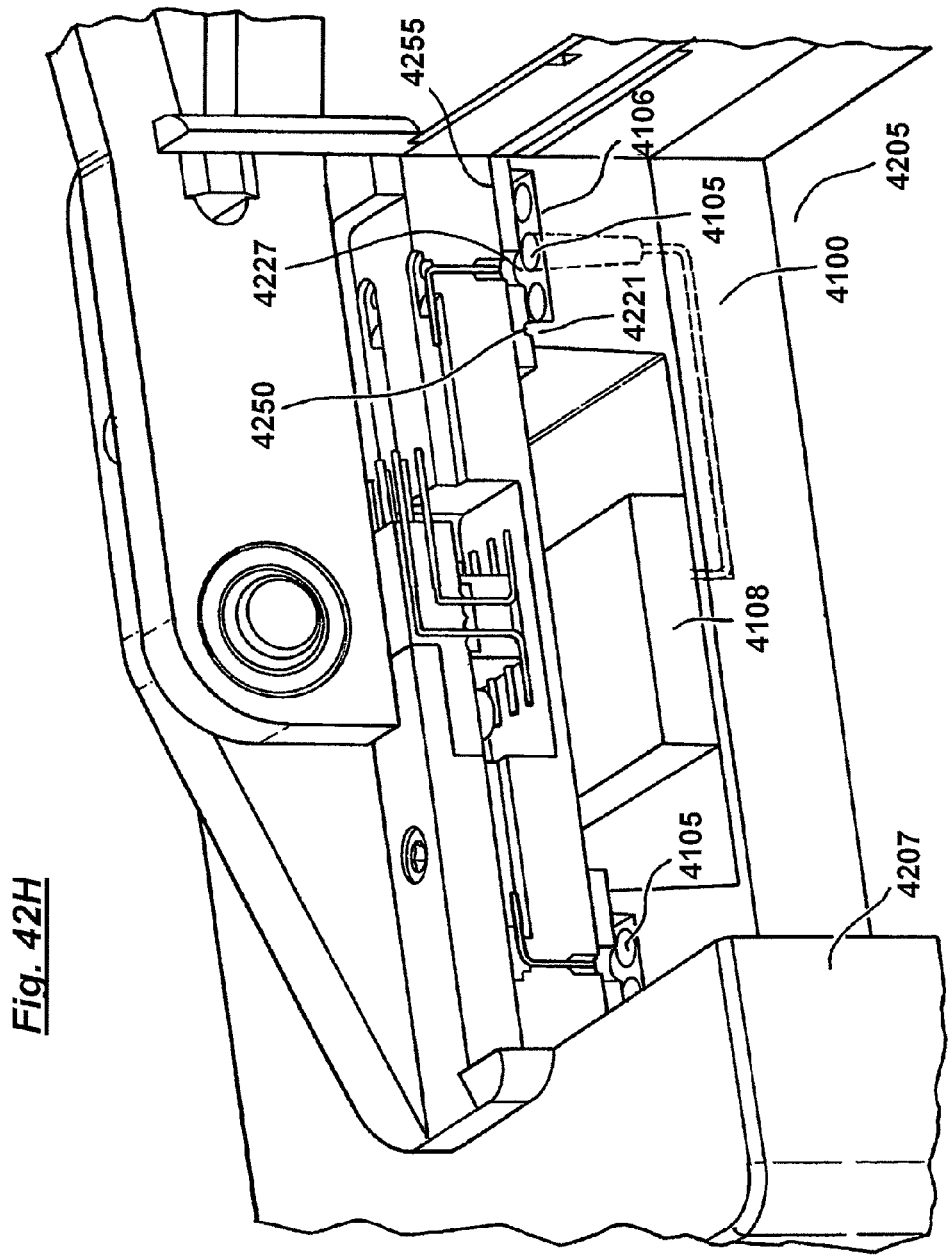
FIG. 42H depicts a cut-away view of a platen urged against the upper face of a microfluidic device according to an embodiment of the present invention.

FIG. 42H depicts a cut-away view of platen 4207 urged against upper face 4221 of microfluidic device 4205 wherein a pressure cavity 4255 is formed above well row 4106 by contacting platen face 4227 against a ridge 4250 of upper face 4221. Fluid pressure, preferably gas pressure, is then applied to pressure cavity 4255 by introducing a fluid into cavity 4255 from pressure lines running down arm 4211 of charging station 4200. Pressure is regulated by pressure regulators associated with charging station 4200, preferably by electronically controlled variable pressure regulators that can change output pressure in accordance with signals sent by a charging station controller, preferably under computer control. Fluid pressure inside of pressure cavity 4255 in turn drives liquid within well 4105 through the channels within substrate 4100 and into channels and/or chambers of elastomeric block 4108 to fill channels or chambers or to actuate a deflectable portion of elastomeric block 4108, preferably a deflectable membrane valve as previously described.

Figure 43A:
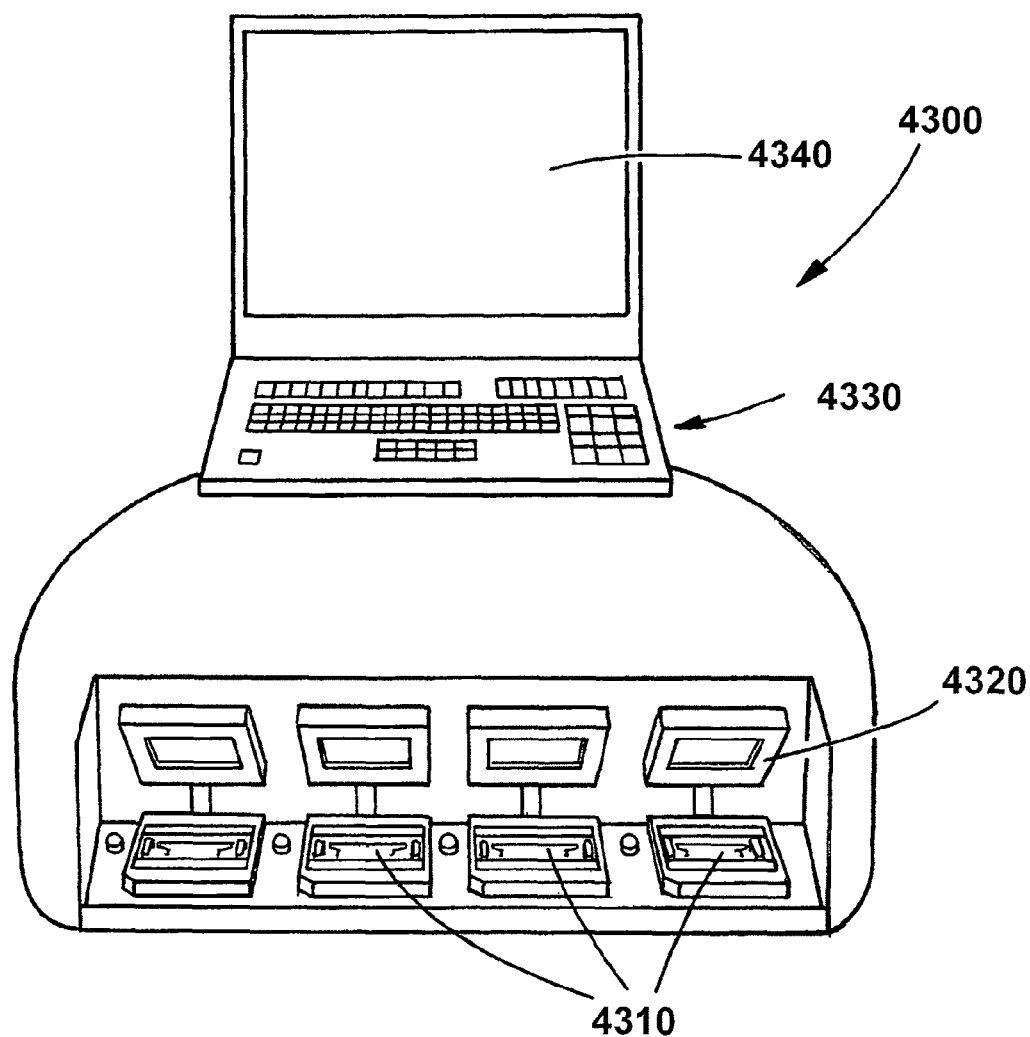
FIG. 43A is a simplified overall view of a system according to an embodiment of the present invention.
Figure 43B:
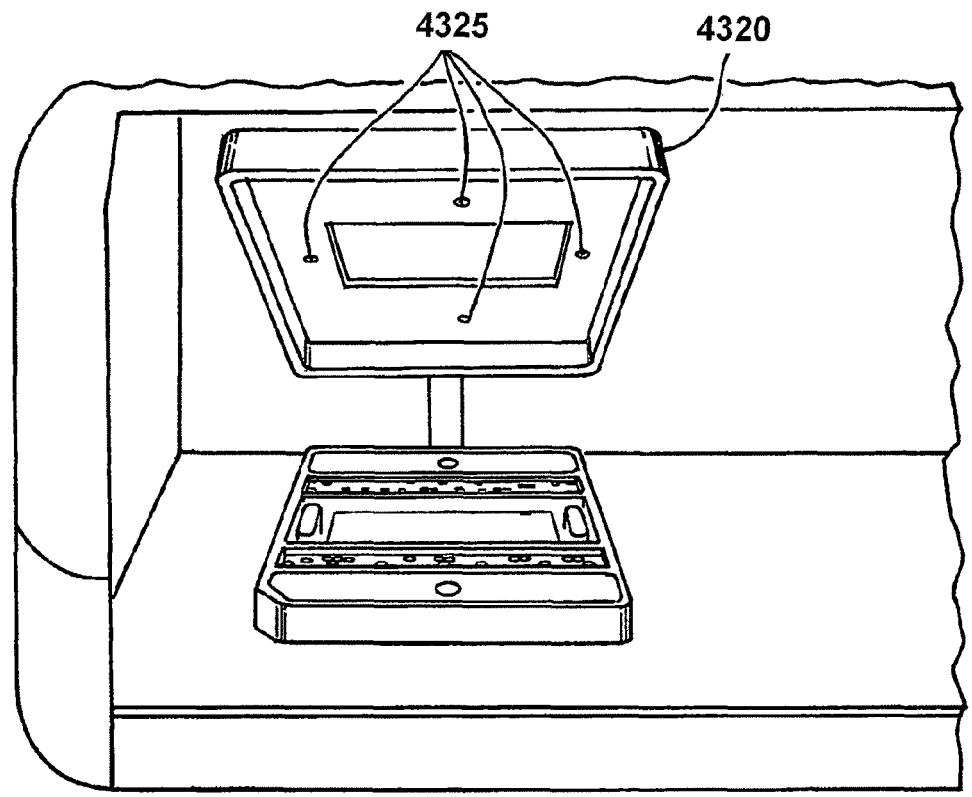
FIG. 43B is a perspective view of a receiving station in the system of FIG. 43A.

In a particular embodiment, the integrated carrier 4100 and microfluidic device are adapted for performing desired experiments according to embodiments of the present invention by using the systems of the present invention. More specifically, as shown in FIG. 43A, a system 4300 includes one or more receiving stations 4310 each adapted to receive a carrier 1400. In a particular embodiment, system 4300 includes four (4) receiving stations 4310, although fewer or a greater number of stations 4310 are provided in alternative embodiments of the present invention. FIG. 43B depicts carrier 4100 and a device in combination disposed in station 4310 under an interface plate 4320. Interface plate 4320 is adapted to translate downward in FIG. 43B so that interface plate 4320 engages the upper surface of carrier 4100 and its microfluidic device. In some embodiments, station 4310 and platen 4320 are similar to station 4200 and platen 4207. Interface plate 4320 includes one or more ports 4325 for coupling with regions in carrier 4100 which are adapted to receive fluids, pressure, or the like. In some embodiments, interface plate 4320 includes two ports, three ports, four ports, five ports, six ports, seven ports, eight ports, nine ports, ten ports, or the like. In a preferred embodiment, interface plate 4320 is coupled to six lines for providing pressure to desired regions of carrier 1400, and two lines for providing a mechanism for activating check valves 4111 and 4112.

Figure 43C:
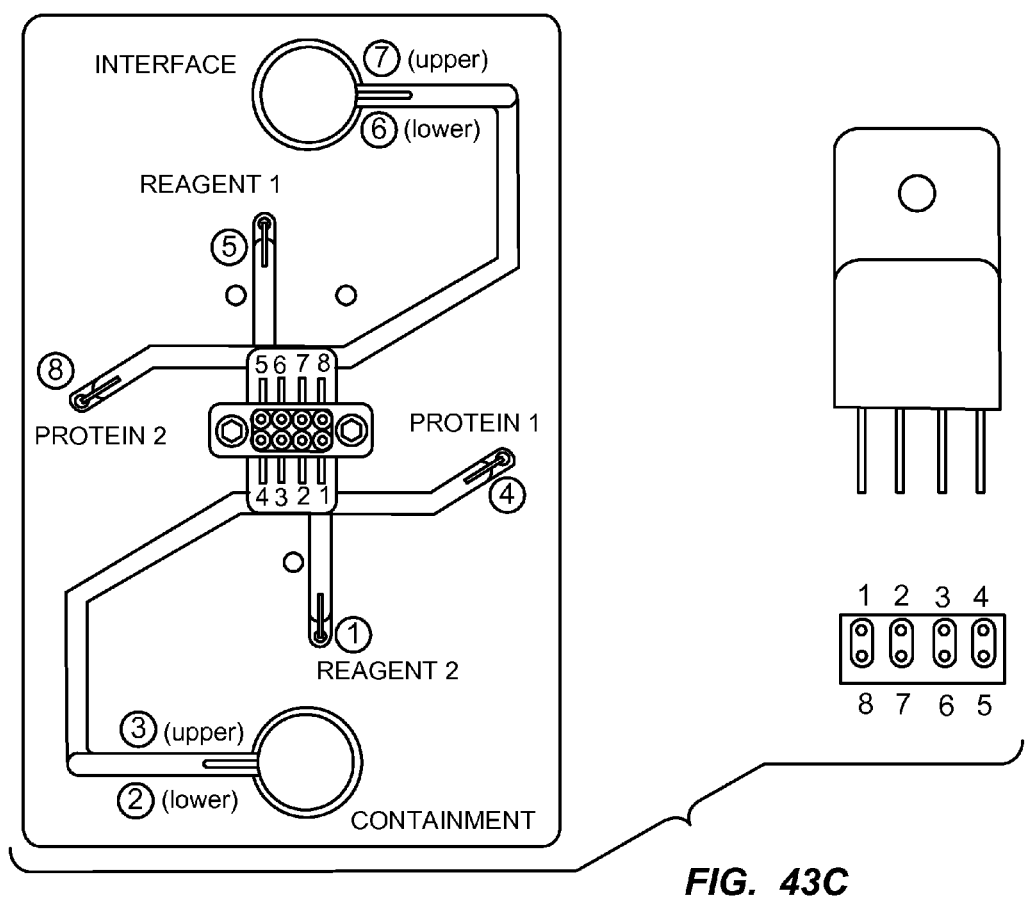
FIG. 43C is a rear plan view of fluidic routing within a plate interface or platen according to another embodiment of the present invention.

FIG. 43C depicts various regions of interface plate 4320 according to a particular embodiment of the present invention, similar to FIG. 43C. In alternative embodiments interface plate 4320 includes a different number or configuration of ports than those depicted in FIG. 43C.

As shown in FIG. 43A, system 4300 further includes a processor that, in one embodiment, is a processor associated with a laptop computer or other computing device 4330. Computing device 4330 includes memory adapted to maintain software, scripts, and the like for performing desired processes of the present invention. Further, computing device 4330 includes a screen 4340 for depicting results of studies and analyses of microfluidic devices. System 4300 is coupled to one or more pressure sources, such as a pressurized fluid, gas, or the like, for delivering same to the microfluidic devices which are fluidly coupled to interface plate(s) 4320.

Figure 44:
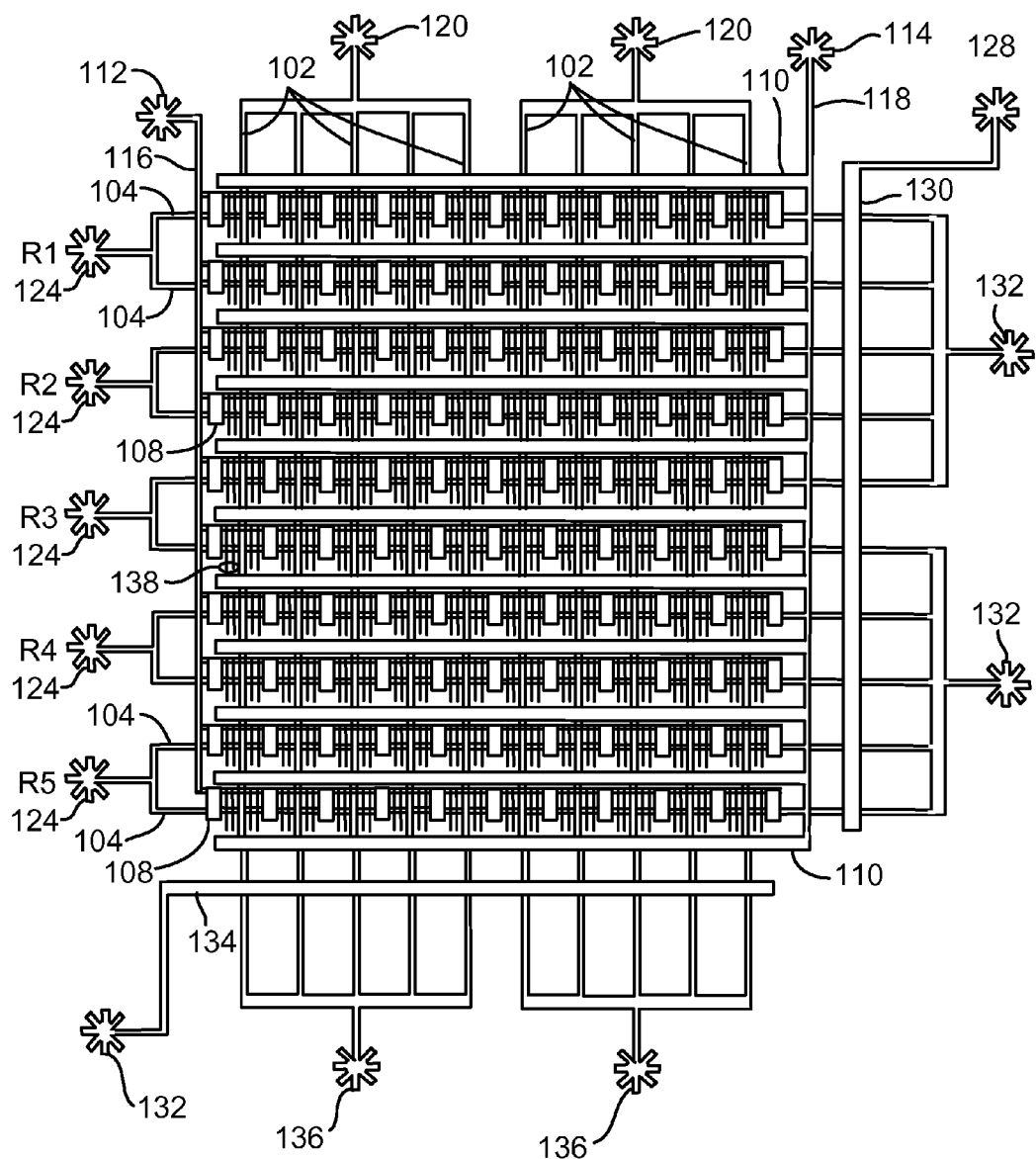
FIG. 44 is a schematic representation of another exemplary matrix design device that utilizes guard channels to reduce sample evaporation.

A modified version of the device shown in FIG. 27 is shown in FIG. 44. The general structure bears many similarities with that depicted in FIG. 27, and common elements in both figures share the same reference numbers. The device 150 illustrated in FIG. 44 differs in that pairs of horizontal flow channels 104 are joined to a common inlet 124. This essentially enables duplicate sets of reagents to be introduced into two adjacent flow channels with just a single injection into inlet 124. The use of a common inlet is further extended with respect to the vertical flow channels 102. In this particular example, each sample is introduced into five vertical flow channels 102 with a single injection into sample inlet 120. Thus, with this particular device, there are essentially ten replicate reactions for each particular combination of sample and reagent. Of course, the number of replicate reactions can be varied as desired by altering the number of vertical and/or horizontal flow channels 102, 104 that are joined to a common inlet 120, 124.

The device shown in FIG. 44 also includes a separate control channel inlet 128 that regulates control channel 130 that can be used to govern solution flow toward outlets 132 and another control channel inlet 132 that regulates control channel 134 that regulates solution flow to outlets 136. Additionally, device 150 incorporates guard channels 138. In this particular design, the guard channels 138 are formed as part of control channels 116. As indicated supra, the guard channels 138 are smaller than the row valves 108; consequently, the membranes of the guard channels 138 are not deflected into the underlying horizontal flow channels 104 such that solution flow is disrupted.

What is claimed is:

1. A database system for processing images provided in one or more well regions of a microfluidic device, each of the one or more well regions arranged in a spatial orientation, the database system comprising:
    a multi-pixel image capturing device coupled to the microfluidic device, the multi-pixel image capturing device being adapted to capture a plurality of multi-pixel images from at least one of the one or more well regions, each of the plurality of multi-pixel images being captured concurrently in a first format;
    an image processing device operably coupled to the multi-pixel image capturing device to provide the plurality of multi-pixel images to the image processing device and further including a data processor programmed to:
        derive at least a first image and a second image from the plurality of multi-pixel images, the first image and the second image being in a second format; and
        determine at least a first feature information from the first image; and
        determine a second feature information from the second image; and
    a database storage device coupled to the image processing device, the database storage device being adapted to store at least the first feature information and the second feature information.

2. The database system of claim 1 wherein the processor is further programmed to process multi-pixel images comprising images of at least one of a fluorescent species, a luminescent species, a colorometric species, or a radiometric species.

3. The database system of claim 1 wherein the one or more well regions comprise two or more well regions coupled together by one or more valves.

4. The database system of claim 1 further comprising a second chip device comprising at least one of multi-well plates for microbatch crystallization, sitting drop vapor diffusion crystallization, hanging drop vapor diffusion crystallization, or capillary plates for liquid-liquid diffusion.

5. The database system of claim 1 wherein the data processor is further programmed to transform the multi-pixel images in the first format into a second format comprising a transform domain.

6. The database system of claim 1 wherein the multi-pixel imaging capturing device is adapted to capture each of the plurality of multi-pixel images simultaneously.

7. A system for processing images, the system comprising:
    a microfluidic device comprising one or more well regions arranged in a spatial orientation;
    a multi-pixel image capturing device optically coupled to the microfluidic device, the multi-pixel image capturing device being adapted to concurrently capture a plurality of multi-pixel images in a first format from at least one of the one or more well regions;
    an image processing device including a data processor and operable to receive the plurality of multi-pixel images, the data processor being programmed to:
        derive at least a first image and a second image from the plurality of multi-pixel images, the first image and the second image being in a second format; and
        determine at least a first feature information from the first image; and
        determine a second feature information from the second image; and
    a database storage device coupled to the image processing device, the database storage device being adapted to store at least the first feature information and the second feature information.

8. The system of claim 7 wherein the data processor is further programmed to process multi-pixel images of at least one of a fluorescent species, a luminescent species, a colorometric species, or a radiometric species.

9. The system of claim 7 wherein the data processor is further programmed to transform the multi-pixel images in the first format into a second format comprising a transform domain.

10. The system of claim 7 wherein the multi-pixel image capturing device is adapted to simultaneously capture the multi-pixel images.

* * * * *